US011788087B2

(12) United States Patent
Bauer

(10) Patent No.: US 11,788,087 B2
(45) Date of Patent: Oct. 17, 2023

(54) BCL11A GUIDE DELIVERY

(71) Applicant: THE CHILDREN'S MEDICAL CENTER CORPORATION, Boston, MA (US)

(72) Inventor: Daniel Bauer, Cambridge, MA (US)

(73) Assignee: THE CHILDREN'S MEDICAL CENTER CORPORATION, Cambridge, MA (US)

( * ) Notice: Subject to any disclaimer, the term of this patent is extended or adjusted under 35 U.S.C. 154(b) by 764 days.

(21) Appl. No.: 16/616,224

(22) PCT Filed: May 25, 2018

(86) PCT No.: PCT/US2018/034618
§ 371 (c)(1),
(2) Date: Nov. 22, 2019

(87) PCT Pub. No.: WO2018/218135
PCT Pub. Date: Nov. 29, 2018

(65) Prior Publication Data
US 2020/0095582 A1 Mar. 26, 2020

Related U.S. Application Data

(60) Provisional application No. 62/511,115, filed on May 25, 2017.

(51) Int. Cl.
*C12N 15/113* (2010.01)
*A61K 31/7088* (2006.01)
*A61K 35/28* (2015.01)
*C12N 9/22* (2006.01)
*C12N 15/85* (2006.01)
*C12N 15/87* (2006.01)
*A61K 38/00* (2006.01)

(52) U.S. Cl.
CPC ........ *C12N 15/113* (2013.01); *A61K 31/7088* (2013.01); *A61K 35/28* (2013.01); *C12N 9/22* (2013.01); *C12N 15/85* (2013.01); *C12N 15/87* (2013.01); *A61K 38/00* (2013.01); *C12N 2310/20* (2017.05); *C12N 2310/315* (2013.01); *C12N 2310/346* (2013.01)

(58) Field of Classification Search
CPC ........ C12N 15/113; C12N 9/22; C12N 15/85; C12N 15/87; C12N 2310/20; C12N 2310/315; C12N 2310/346; A61K 31/7088; A61K 35/28; A61K 38/00
See application file for complete search history.

(56) References Cited

U.S. PATENT DOCUMENTS

| 5,460,964 A | 10/1995 | McGlave et al. |
| 5,635,387 A | 6/1997 | Fei et al. |
| 5,677,136 A | 10/1997 | Simmons et al. |
| 5,716,827 A | 2/1998 | Tsukamoto et al. |
| 5,750,397 A | 5/1998 | Tsukamoto et al. |
| 5,759,793 A | 6/1998 | Schwartz et al. |
| 5,928,638 A | 7/1999 | Uchida et al. |
| 6,682,907 B1 | 1/2004 | Charneau et al. |
| 8,383,604 B2 | 2/2013 | Orkin et al. |
| 9,228,185 B2 | 1/2016 | Orkin et al. |
| 9,822,355 B2 | 11/2017 | Orkin et al. |
| 9,885,041 B2 | 2/2018 | Orkin et al. |
| 10,287,588 B2 | 5/2019 | Milsom et al. |
| 10,662,429 B2 | 5/2020 | Milsom et al. |
| 2004/0259247 A1 | 12/2004 | Tuschl et al. |
| 2005/0227917 A1 | 10/2005 | Williams et al. |
| 2008/0051431 A1 | 2/2008 | Verhelle et al. |
| 2010/0273213 A1 | 10/2010 | Mineno et al. |
| 2011/0182867 A1 | 7/2011 | Orkin et al. |
| 2011/0294114 A1 | 12/2011 | Van Der Loo et al. |
| 2013/0004471 A1 | 1/2013 | Denaro et al. |
| 2013/0179999 A1 | 7/2013 | Hannon et al. |
| 2014/0018410 A1 | 1/2014 | Novobrantseva et al. |
| 2014/0068797 A1 | 3/2014 | Doudna et al. |

(Continued)

FOREIGN PATENT DOCUMENTS

| EP | 1752536 A1 | 2/2007 |
| EP | 2334794 B1 | 11/2016 |

(Continued)

OTHER PUBLICATIONS

Johari et al. (Biotech. Bioengin. (2015) 112; pp. 2527-2542). (Year: 2015).*
UCSC Genome Browser of Human Assembly, hg19. Feb. 2009. 1 Page.
Esrick et al. "Post-transcriptional genetic silencing of BCL11A to treat sickle ceil disease." New England Journal of Medicine 384(3): 205-215 (2021).
Yin et al. "BCL11A: a potential diagnostic biomarker and therapeutic target in human diseases." Bioscience Reports 39(11): 1-13 (2019).
Hendel et al., "Chemically modified guide RNAs enhance CRISPR-Cas genome editing in human primary cells." Nature Biotechnology 33(9):985-989 (2015).

(Continued)

*Primary Examiner* — J. E. Angell
(74) *Attorney, Agent, or Firm* — NIXON PEABODY LLP; David S. Resnick; Jeanne Jodoin

(57) ABSTRACT

Provided herein are 2'-O-methyl 3'phosphorothioate (MS)-modified synthetic nucleic acid molecules (single guide RNAs (sgRNAs)) for the use with a Cas9 nuclease in combination as a ribonucleoprotein (RNP) complex for an electroporation-based ex vivo targeted gene disruption of the BCL11A erythroid enhancer's +55, +58, or +62, functional regions. Additionally, provided herein are said RNP complexes (Cas9:MS-sgRNA), and compositions comprising the modified synthetic nucleic acid molecules or said RNP complexes, and methods for increasing fetal hemoglobin levels in a cell by disrupting BCL11A expression at the genomic level. Also provided herein are methods and compositions relating to the treatment of hemoglobinopathies by reinduction of fetal hemoglobin levels.

9 Claims, 32 Drawing Sheets
Specification includes a Sequence Listing.

(56) References Cited

U.S. PATENT DOCUMENTS

| | | |
|---|---|---|
| 2015/0056705 A1 | 2/2015 | Conway et al. |
| 2015/0132269 A1 | 5/2015 | Orkin et al. |
| 2015/0133528 A1 | 5/2015 | Krieg et al. |
| 2015/0232882 A1 | 8/2015 | Zheng et al. |
| 2017/0173184 A1 | 6/2017 | Gaspar et al. |
| 2017/0218372 A1 | 8/2017 | Milsom et al. |
| 2018/0119138 A1 | 5/2018 | Bauer et al. |
| 2018/0119175 A1 | 5/2018 | Conway et al. |

FOREIGN PATENT DOCUMENTS

| | | | |
|---|---|---|---|
| EP | 2334794 B8 | 4/2017 | |
| JP | 2006507841 A | 3/2006 | |
| WO | 2004054512 A2 | 7/2004 | |
| WO | 2009007685 A2 | 1/2009 | |
| WO | 2010030963 A2 | 3/2010 | |
| WO | 2011072086 A1 | 6/2011 | |
| WO | 2011133889 A2 | 10/2011 | |
| WO | 2012073047 A2 | 6/2012 | |
| WO | 2012079046 A2 | 6/2012 | |
| WO | 2013049615 A1 | 4/2013 | |
| WO | 2013126794 A1 | 8/2013 | |
| WO | 2013176772 A1 | 11/2013 | |
| WO | 2014085593 A1 | 6/2014 | |
| WO | 2014093965 A1 | 6/2014 | |
| WO | 2015065964 A1 | 5/2015 | |
| WO | 2015148863 A2 | 10/2015 | |
| WO | 2015164739 A1 | 10/2015 | |
| WO | 2015164750 A2 | 10/2015 | |
| WO | 2015164759 A2 | 10/2015 | |
| WO | 2015183667 A1 | 12/2015 | |
| WO | 2016094304 A2 | 6/2016 | |
| WO | 2016182893 A1 | 11/2016 | |
| WO | 2016183448 A1 | 11/2016 | |
| WO | 2017040529 A1 | 3/2017 | |
| WO | 2017115268 A1 | 7/2017 | |
| WO | WO-2017115268 A1 * | 7/2017 | ............ A61K 35/12 |
| WO | 2017139576 A1 | 8/2017 | |
| WO | 2017182881 A2 | 10/2017 | |
| WO | WO-2017173092 A1 * | 10/2017 | ............ C12N 15/11 |

OTHER PUBLICATIONS

Boden et al. "Enhanced gene silencing of HIV-1 specific siRNA using microRNA designed hairpins." Nucleic Acids Research 32(3): 1154-1158 (2004).

Brendel et al. "Lineage-specific BCL11A knockdown circumvents toxicities and reverses sickle phenotype." The Journal of Clinical Investigation 126(10): 3868-3878 (2016).

Brendel et al. "Optimization of Bci11a Knockdown by miRNA scaffold embedded shrnas leading to enhanced induction of fetal hemoglobin in erythroid cells for the treatment of beta-hemoglobinopathies." Blood 124(21): 2150-2150 (2014).

Calloni et al. "Scaffolds for artificial miRNA expression in animal cells." Human Gene Therapy Methods 26(5): 162-174 (2015).

Cante-Barrett et al. "Lentiviral gene transfer into human and murine hematopoietic stem ceils: size matters." BMC Research Notes 9(1): 1-6 (2016).

Cavazzana-Calvo et al. "Transfusion independence and HMGA2 activation after gene therapy of human β-thalassaemia." Nature 467(7313): 318-322 (2010).

Clever et al. "RNA secondary structure and binding sites for gag gene products in the 5' packaging signal of human immunodeficiency virus type 1." Journal of Virology 69(4): 2101-2109 (1995).

Cullen et al. "Regulatory pathways governing HIV-1 replication." Cell 58(3): 423-426 (1989).

Cullen. "Human immunodeficiency virus as a prototypic complex retrovirus." Journal of Virology 65(3): 1053-1056 (1991).

Database GenBank [Online] Mar. 3, 2015, Anonymous: "TPA: Homo sapiens microRNA hsa-mir-144 precursor", XP55876619, Database accession No. LM608500.

Extended European Search Report dated Jan. 12, 2021, for European Application No. 18775163.1, 11 pages.

Ginn et al. "Gene therapy clinical trials worldwide to 2012—an update." The Journal of Gene Medicine 15(2): 65-77 (2013).

Huang et al. "Role of the hepatitis B virus posttranscriptional regulatory element in export of intronless transcripts." Molecular and Cellular Biology 15(7): 3864-3869 (1995).

Imren et al. "Permanent and panerythroid correction of murine β thalassemia by multiple lentiviral integration in hematopoietic stem cells." Proceedings of the National Academy of Sciences 99(22): 14380-14385 (2002).

International Search Report and Written Opinion dated Jun. 25, 2018, for International Application No. PCT/US2018/025165, 10 paqes.

Kitowski, "A Lentiviral Vector Conferring Coregulated, Erythroid-Specific Expression of [gamma]-Globin and shRNA Sequences to BCL11A for the Treatment of Sickle Cell Disease," Aug. 1, 2016, 105 pages.

Kutner et al. "Production, concentration and titration of pseudotyped HIV-1-based lentiviral vectors." Nature Protocols 4(4): 495-505 (2009).

Kutner et al. "Simplified production and concentration of HIV-1-based lentiviral vectors using HYPERFlask vessels and anion exchange membrane chromatography," BMC Biotechnology 9(1): 1-7 (2009).

Landau et al. "Packaging system for rapid production of murine leukemia virus vectors with variable tropism." Journal of Virology 66(8): 5110-5113 (1992).

Liu et al. "HnRNP L binds a cis-acting RNA sequence element that enables intron-dependent gene expression." Genes & Development 9(14): 1766-1780 (1995).

Luc et al. "Bcl11a deficiency leads to hematopoietic stem cell defects with an aging-like phenotype." Cell Reports 16 (12): 3181-3194 (2016).

Mahajan et al. "Control of beta globin genes." Journal of Cellular Biochemistry 102(4): 801-810 (2007).

Malik et al. "Successful Correction of the Human Cooley's Anemia β-Thalassemia Major Phenotype Using a Lentiviral Vector Flanked by the Chicken Hypersensitive Site 4 Chromatin Insulator." Annals of the New York Academy of Sciences 1054(1): 238-249 (2005).

May et al. "Therapeutic haemoglobin synthesis in β-thalassaemic mice expressing lentivirus-encoded human β-globin." Nature 406(6791): 82-86 (2000).

Naldini. "Gene therapy returns to centre stage." Nature 526(7573): 351-360 (2015).

Negre et al. "Preclinical Evaluation of a Novel Lentiviral Vector Driving Lineage-Specific BCL11A Knockdown, β-Globin Induction and Simultaneous Repression of β-Globin for the Potential Treatment of Sickle Cell Disease." Blood 130(Supplement 1): 3557-3557 (2017).

Pawliuk et al. "Correction of sickle cell disease in transgenic mouse models by gene therapy." Science 294(5550): 2368-2371 (2001).

Pawliuk et al. "Correction of sickle cell disease in transgenic mouse models by gene therapy." Science 294(5550): 2368-2371 (2001) [Supplemental Material].

Rasmussen et al. "The miR-144/451 locus is required for erythroid homeostasis." Journal of Experimental Medicine 207(7): 1351-1358 (2010).

Soneoka et al. "A transient three-plasmid expression system for the production of high titer retroviral vectors." Nucleic Acids Research 23(4): 628-633 (1995).

Wang et al. "A 'suicide' CRISPR-Cas9 system to promote gene deletion and restoration by electroporation in Cryptococcus neoformans." Scientific Reports 6(1): 1-13 (2016).

Wu et al. "Highly efficient therapeutic gene editing of human hematopoietic stem cells." Nature Medicine 25(5): 776-783 (2019).

Yu et al. "Bcl11a is essential for lymphoid development and negatively regulates p53." Journal of Experimental Medicine 209(13): 2467-2483 (2012).

Zennou et al. "HIV-1 genome nuclear import is mediated by a central DNA flap." Cell 101(2): 173-185 (2000).

(56) References Cited

OTHER PUBLICATIONS

Zufferey et al. "Woodchuck hepatitis virus posttranscriptional regulatory element enhances expression of transgenes delivered by retroviral vectors." Journal of Virology 73(4): 2886-2892 (1999).
Bofill-De Ros et al. "Guidelines for the optimal design of miRNA-based shRNAs." Methods 103: 157-166 (2016).
Guda et al. "miRNA-embedded shRNAs for lineage-specific BCL11A knockdown and hemoglobin F induction." Molecular Therapy 23(9): 1465-1474 (2015).
Roggenkamp et al. "Tuning CRISPR-Cas9 gene drives in *Saccharomyces cerevisiae*." G3: Genes, Genomes, Genetics 8(3): 999-1018 (2018).
Win et al. "A modular and extensible RNA-based gene-regulatory platform for engineering cellular function." Proceedings of the National Academy of Sciences 104(36): 14283-14288 (2007).
Akinsheye et al., "Fetal hemoglobin in sickle cell anemia." Blood 118(1):19-27 (2011).
Amaya et al., "Mi2β-mediated silencing of the fetal γ-globin gene in adult erythroid cells." Blood 121(17):3493-501 (2013).
Amendah et al., "Sickle cell disease-related pediatric medical expenditures in the U.S." American Journal of Preventive Medicine 38(4 Suppl):S550-S556 (2010).
Atweh et al., "Pharmacological induction of fetal hemoglobin in sickle cell disease and beta-thalassemia." Seminars in Hematology 38(4):367-73 (2001).
Bauer et al., "An Erythroid Enhancer of BCL11A Subject to Genetic Variation Determines Fetal Hemoglobin Level." Science 342(6155):253-257 (2013).
Bauer et al., "HbF-Associated Genetic Variation Marks an Erythroid Regulatory Element Essential for BCL11A Transcription and Subsequent Stage-Specific Globin Expression." Blood 120:828 (2012).
Bauer et al., "Hemoglobin switching's surprise: the versatile transcription factor BCL11A is a master repressor of fetal hemoglobin" Current Opinion in Genetics & Development 33:62-70 (2015).
Bauer et al., "Reawakening fetal hemoglobin: prospects for new therapies for the B-globin disorders." Blood 120 (15):2945-2953 (2012).
Bauer et al., "Supplementary Material: An Erythroid Enhancer of BCL11A Subject to Genetic Variation Determines Fetal Hemoglobin Level." Science 342(6155):253-257 (2013).
Bjurström et al. "Reactivating fetal hemoglobin expression in human adult erythroblasts through BCL11A knockdown using targeted endonucleases." Molecular Therapy-Nucleic Acids 5:e351 (2016).
Boettcher et al., "Choosing the right tool for the job: RNAi, TALEN, or CRISPR." Molecular Cell 58(4):575-585 (2015).
Bohmer et al., "Identification of fetal nucleated red cells in co-cultures from fetal and adult peripheral blood: differential effects of serum on fetal and adult erythropoiesis." Prenatal Diagnosis 19(7):628-636 (1999).
Bunn "Reversing ontogeny." New Engl. J. Med. 328(2):129-131 (1993).
Canver et al., "BCL11A enhancer dissection by Cas9-mediated in situ saturating mutagenesis." Nature 527 (7577):192-197 (2015).
Cao et al., "Recent advances in B-thalassemias." Pediatric Reports 3(2):65-71 (2011).
Chabchoub et al., "The facial dysmorphy in the newly recognised microdeletion 2p15-p16.1 refined to a 570 kb region in 2p15." Journal of Medical Genetics 45(3):189-192 (2008).
Coleman et al., "Sickle cell anemia: targeting the role of fetal hemoglobin in therapy." Clinical Pediatrics 46 (5):386-391 (2007).
Cox et al., "Therapeutic genome editing: prospects and challenges" Nature Medicine 21(2):121-131 (2015).
Dixit et al., "Hydroxyurea in thalassemia intermedia—a promising therapy." Annals of Hematology 84(7):441-446 (2005).
Doench et al., "Rational design of highly active sgRNAs for CRISPR-Cas9-mediated gene inactivation." Nature Biotechnology 32(12):1262-1267 (2014).

Doench et al., "Supplementary Material: Rational design of highly active sgRNAs for CRISPR-Cas9-mediated gene inactivation." Nature Biotechnology 32(12):1262-1267 (2014).
Examination Search Report, dated May 11, 2018 in corresponding Canadian No. 2737180.
Fenaux "Inhibitors of DNA methylation: beyond myelodysplastic syndromes." Nature Reviews Clinical Oncology 2 (S21):S36-S44 (2005).
Fischer et al., "Pulmonary Passage is a Major Obstacle for Intravenous Stem Cell Delivery: The Pulmonary First-Pass Effect" Stem Cells and Development 18(5):683-91 (2009).
Flanagan et al., "Hydroxycarbamide alters erythroid gene expression in children with sickle cell anaemia." British Journal of Haematology 157(2):240-248 (2012).
GenBank Accession No. NM_022893.4. "*Homo sapiens* BAF chromatin remodeling complex subunit BCL11A (BCL11A), transcript variant 1, mRNA." https://www.ncbi.nlm.nih.gov/nuccore/NM_022893.4 (2019).
GeneCard for BCL11A, retrieved from http://www.genecards.org/cgi-bin/carddisp.pl?gene=BCL11A on Jun. 22, 2012.
Goffin et al., "DNA methyltransferase inhibitors-state of the art." Annals of Oncology 13(11):1699-716 (2002).
Goldberg et al., "Treatment of sickle cell anemia with hydroxyurea and erythropoietin." New England Journal of Medicine 323(6):366-372 (1990).
Hackam "Translating animal research into clinical benefit" BMJ 334:163-68 (2007).
Hancarova et al. "A patient with de novo 0.45 Mb deletion of 2p16.1: The role of BCL11A, PAPOLG, REL, and FLJ16341 in the 2p15-p16. 1 microdeletion syndrome." American Journal of Medical Genetics Part A 161(4):865-870 (2013).
Harding et al., "Large animal models for stem cell therapy", Stem Cell Research & Therapy 4(23):1-9 (2013).
Hebbel et al., "The HDAC inhibitors trichostatin A and suberoylanilide hydroxamic acid exhibit multiple modalities of benefit for the vascular pathobiology of sickle transgenic mice." Blood 115(12):2483-2490 (2010).
Higgs et al., "Genetic complexity in sickle cell disease." PNAS 105(33):11595-11596 (2008).
Ho et al., "In vitro induction of fetal hemoglobin in human erythroid progenitor cells." Experimental Hematology 31(7):586-591 (2003).
Hsieh et al., "Allogeneic hematopoietic stem-cell transplantation for sickle cell disease." New England Journal of Medicine 361(24):2309-2317 (2009).
Jane et al., "Understanding fetal globin gene expression: a step towards effective HbF reactivation in haemoglobinopathies." British Journal of Haematology 102(2):415-423 (1998).
Kauf et al., "The cost of health care for children and adults with sickle cell disease." American Journal of Hematology 84(6):323-327 (2009).
Kirschner et al., "Genomic mapping of chromosomal region 2p15-p21 (D2S378-D2S391): integration of Genemap'98 within a framework of yeast and bacterial artificial chromosomes" Genomics 62(1):21-33 (1999).
Koshy et al., "2-deoxy 5-azacytidine and fetal hemoglobin induction in sickle cell anemia." Blood 96(7):2379-2384 (2000).
Labie "Le contrôle en trans de la production d'hémoglobine fœtale: une recherche qui dure depuis 20 ans." Hématologie 14(2):165-166 (2008).
Lettre et al., "DNA polymorphisms at the BCL11A, HBS1L-MYB, and beta-globin loci associate with fetal hemoglobin levels and pain crises in sickle cell disease." PNAS 105(33):11869-11874 (2008).
Liu et al., "Bcl11a is essential for normal lymphoid development." Nature Immunology 4(6):525-532 (2003).
Knowles et al. "Palmitate diet-induced loss of cardiac caveolin-3: a novel mechanism for lipid-induced contractile dysfunction." PLoS One 8(4): e61369 pp. 1-11 (2013).
Liu et al., "Functional studies of BCL11A: characterization of the conserved BCL11A-XL splice variant and its interaction with BCL6 in nuclear paraspeckles of germinal center B cells." Molecular Cancer 5(18):1-6 (2006).

(56) References Cited

OTHER PUBLICATIONS

Lulli et al., "MicroRNA-486-3p regulates γ-globin expression in human erythroid cells by directly modulating BCL11A." PLoS One 8(4):e60436 (2013).
Makala et al., "Fetal Hemoglobin Induction to Treat b-Hemoglobinopathies: From Bench to Bedside" J Hematol Transfus 2(2):1-2 (2014).
Martin-Subero et al., "Recurrent involvement of the REL and BCL11Aloci in classical Hodgkin lymphoma." Blood 99(4):1474-1477 (2002).
Matsuda et al., "Transcription factors LRF and BCL11A independently repress expression of fetal hemoglobin" Science 351(6270):285-289 (2016).
Menzel et al., "A QTL influencing F cell production maps to a gene encoding a zinc-finger protein on chromosome 2p15." Nature Genetics 39(10):1197-1199 (2007).
Migliaccio et al., "Influence of recombinant hematopoietins and of fetal bovine serum on the globin synthetic pattern of human BFUe." Blood 76(6):1150-1157 (1990).
Moffat et al., "A lentiviral RNAi library for human and mouse genes applied to an arrayed viral high-content screen." Cell 124(6):1283-1298 (2006).
Nemudryi et al., "TALEN and CRISPR/Cas Genome Editing Systems: Tools of Discovery" Acta Naturae, 6(3):19-40 (2014).
Neven et al., "A Mendelian predisposition to B-cell lymphoma caused by IL-10R deficiency," Blood 3713-3722 (2013).
Orkin et al., "Recent advances in globin research using genome-wide association studies and gene editing." Annals of the New York Academy of Sciences 1368 (1):5-10 (2016).
Papayannopoulou et al., "Erythroid progenitors circulating in the blood of adult individuals produce fetal hemoglobin in culture." Science 199(4335):1349-1350 (1978).
Pauling et al., "Sickle cell anemia a molecular disease." Science 110(2865):543-548 (1949).
Pembrey et al., "Fetal haemoglobin production and the sickle gene in the oases of Eastern Saudi Arabia." British journal of haematology 40(3):415-429 (1978).
Perrine "Fetal globin induction—can it cure beta thalassemia?" American Society of Hematology Education Program Book pp. 38-44 (2005).
Platt et al., "Mortality in sickle cell disease. Life expectancy and risk factors for early death." New England Journal of Medicine 330(23):1639-1644 (1994).
Purton et al., "All-trans retinoic acid enhances the long-term repopulating activity of cultured hematopoietic stem cells." Blood 95(2):470-477 (2000).
Renella et al. "Hematopoietic SIN lentiviral micro RNA-mediated silencing of BCL11A: pre-clinical evidence for a sickle cell disease gene-therapy trial." 120(21):Abstract 753 (2012).
Ridley et al., "Erythropoietin: A Review" J Natl Med Assoc., 86(2):129-135 (1994).
Rodriguez et al., "A bioavailability and pharmacokinetic study of oral and intravenous hydroxyurea." Blood 9(5):1533-1541 (1998).
Rosenblum et al., "Peripheral blood erythroid progenitors from patients with sickle cell anemia: HPLC separation of hemoglobins and the effect of a HbF switching factor." Progress in Clinical and Biological Research 191:397-410 (1985).
Saiki et al., "Human EVI9, a homologue of the mouse myeloid leukemia gene, is expressed in the hematopoietic progenitors and down-regulated during myeloid differentiation of HL60 cells." Genomics 70(3):387-391 (2000).
Sankaran et al., "Developmental and species-divergent globin switching are driven by BCL11A." Nature 460 (7259):1093-1097 (2009).
Sankaran et al., "Human fetal hemoglobin expression is regulated by the developmental stage-specific repressor BCL11A." Science 322(5909):1839-1843 (2008).
Sankaran et al., "Targeted therapeutic strategies for fetal hemoglobin induction." American Society of Hematology Education Program Book 2011(1):459-465 (2011).
Satterwhite et al., "The BCL11 gene family: involvement of BCL11A in lymphoid malignancies." Blood, 98(12):3413-3420 (2001).
Schopman et al. "Optimization of shRNA inhibitors by variation of the terminal loop sequence." Antiviral Research 86(2):204-211 (2010).
Sebastian et al., "BCL11A enhancer haplotypes and fetal hemoglobin in sickle cell anemia." Blood Cells, Molecules, and Diseases 54(3):224-230 (2015).
Sedgewick et al., "BCL11A is a major HbF quantitative trait locus in three different populations with β-hemoglobinopathies." Blood Cells, Molecules, and Diseases 41(3):255-258 (2008).
Shen et al., "Modifcation of globin gene expression by RNA targeting strategies." Experimental Hematology, 35(8):1209-1218 (2007).
Takeuchi et al., "Redesign of extensive protein-DNA interfaces of meganucleases using iterative cycles of in vitro compartmentalization." PNAS 111(11):4061-4066 (2014).
Taymans et al., "Radiation hybrid mapping of chromosomal region 2p15-p16: integration of expressed and polymorphic sequences maps at the Carney complex (CNC) and Doyne honeycomb retinal dystrophy (DHRD) loci." Genomics 56(3):344-349 (1999).
Terasawa et al., "Synthetic pre-miRNA-based shRNA as potent RNAi triggers." Journal of Nucleic Acids (2011).
Thein "Genetic modifiers of the beta-haemoglobinopathies." British Journal of Hematology, 141(3):357-366 (2008).
Thein et al., "Discovering the genetics underlying foetal haemoglobin production in adults." British Journal of Haematology 145(4):455-467 (2009).
Thompson "Structure, Function, and Molecular Defects of Factor IX." Blood 67(3):565-72 (1986).
Uda et al., "Genome-wide association study shows BCL11A associated with persistent fetal hemoglobin and amelioration of the phenotype of β-thalassemia." PNAS 105(5):1620-1625 (2008).
Wang et al. "Genetic screens in human cells using the CRISPR/Cas9 system." Science 343(6166):80-84 (2013).
Wang et al. "Supplementary Material: Genetic screens in human cells using the CRISPR/Cas9 system." Science 343(6166):80-84 (2013).
Wang et al., "In Vivo Delivery Systems for Therapeutic Genome Editing" International Journal of Molecular Sciences 17(5):1-19 (2016).
Wang et al., "Selection of hyperfunctional siRNAs with improved potency and specificity." Nucleic Acids Research 37(22):e152 (2009).
White et al., "Factor VIII Gene and Hemophili A." Blood 73(1):1-12 (1989).
World Health Organization. "Sickle-cell anaemia. Report A59/9. Provisional agenda item 11.4." 59th World Health Assembly. www.who.int/gb/ebwha/pdf_files/WHA59/A59_9-en.pdf (2006).
Xu et al., "Correction of sickle cell disease in adult mice by interference with fetal hemoglobin silencing", Science 334(6058):993-996 (2011).
Xu et al., "Reactivation of silenced human HbF in adult mice by inactivation of BCL11A." Blood 116:Abstract 643 (2010).
Xu et al., "Transcriptional silencing of beta-globin by BCL11A involvs long-range interactions and cooperation with SOX6." Genes and Development 24(8):783-798 (2010).
Yin et al., "Bellia Causes p21 Cip1 Down-Regulation and Transplantable Leukemia in Nf1-Deficient Mice." Blood 110(11):2657-2657 (2007) [Abstract Only].

* cited by examiner

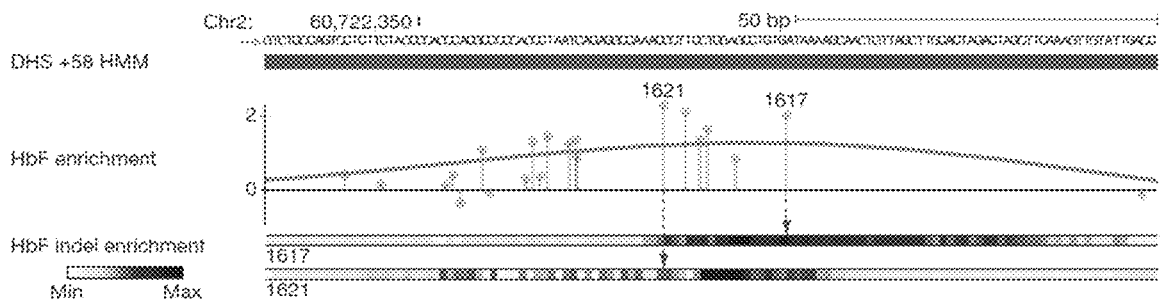
Figure 3.
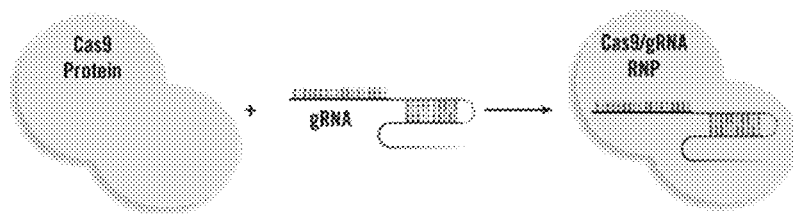
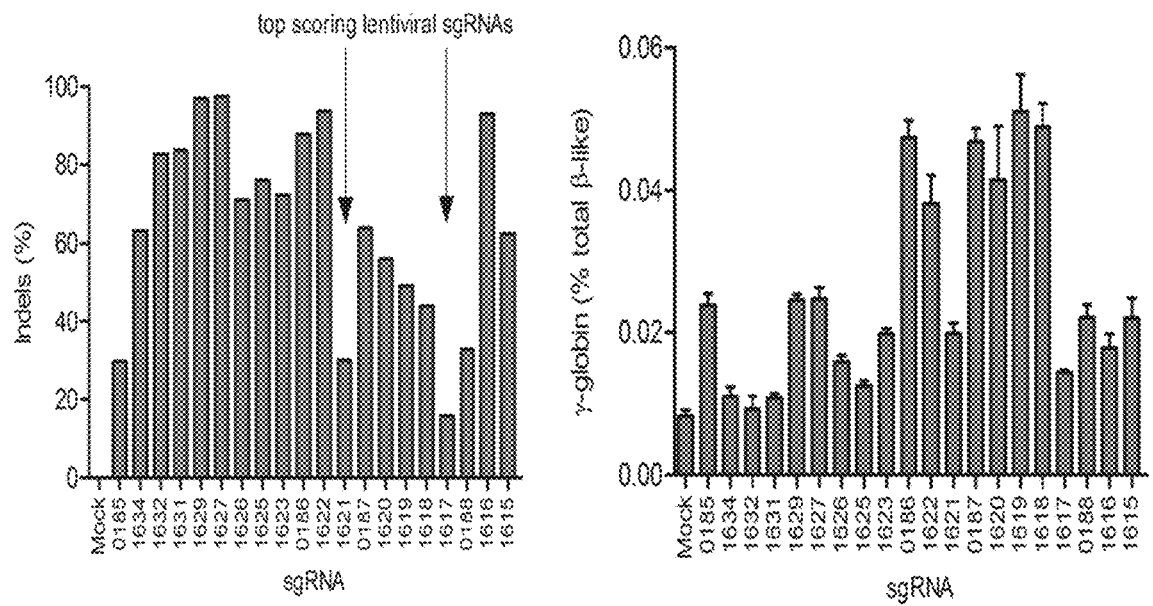
Figure 4.

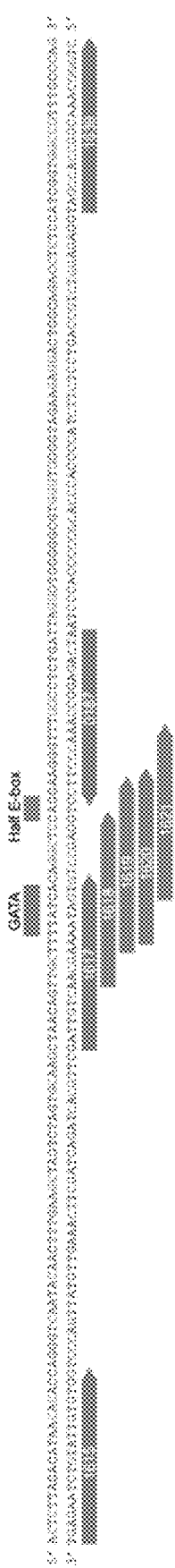
Figure 10A
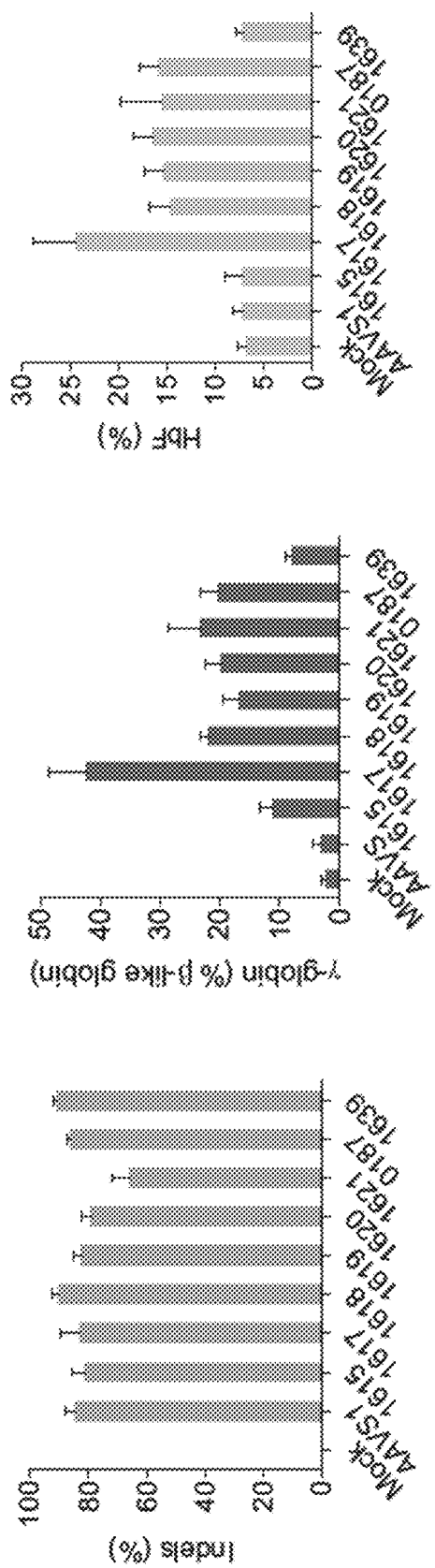
Figure 10D
Figure 10C
Figure 10B

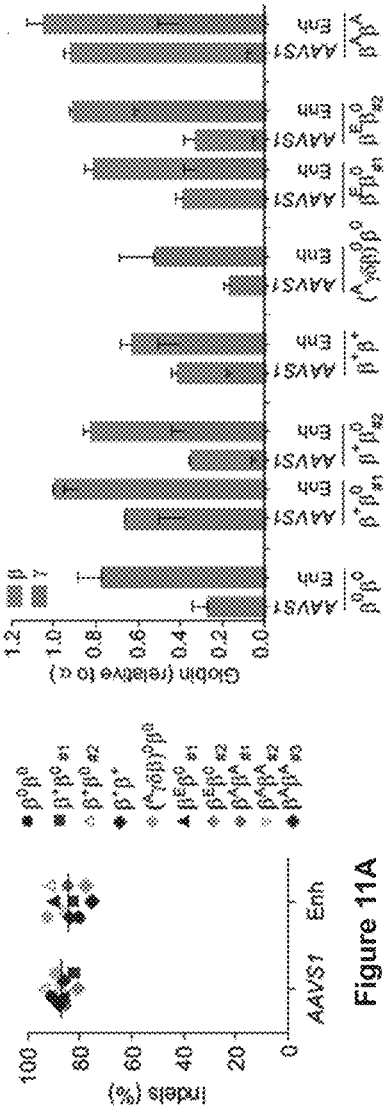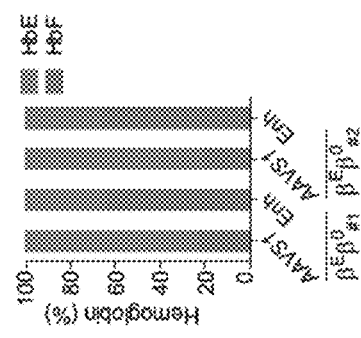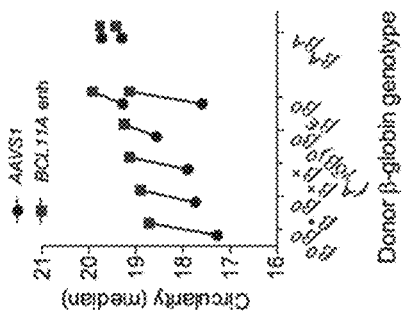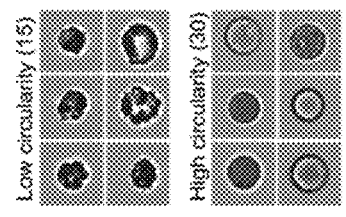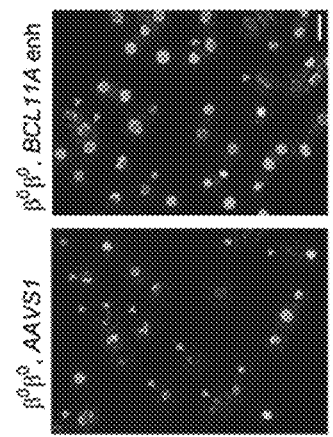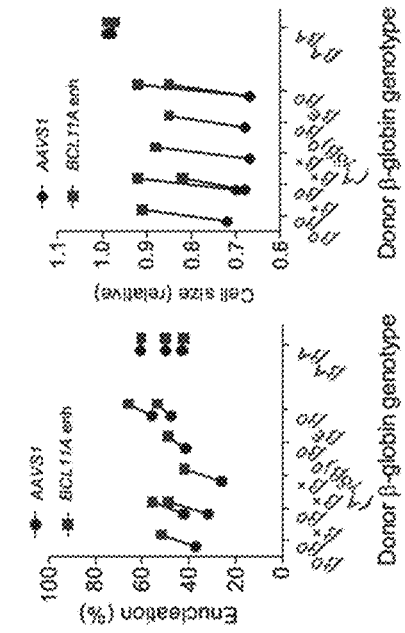
Figure 11A Figure 11B Figure 11C Figure 11D Figure 11E Figure 11F Figure 11G Figure 11H Figure 11I

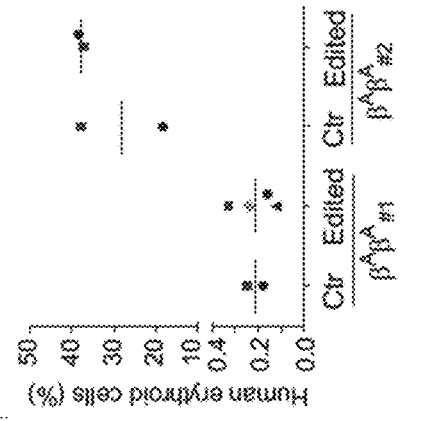
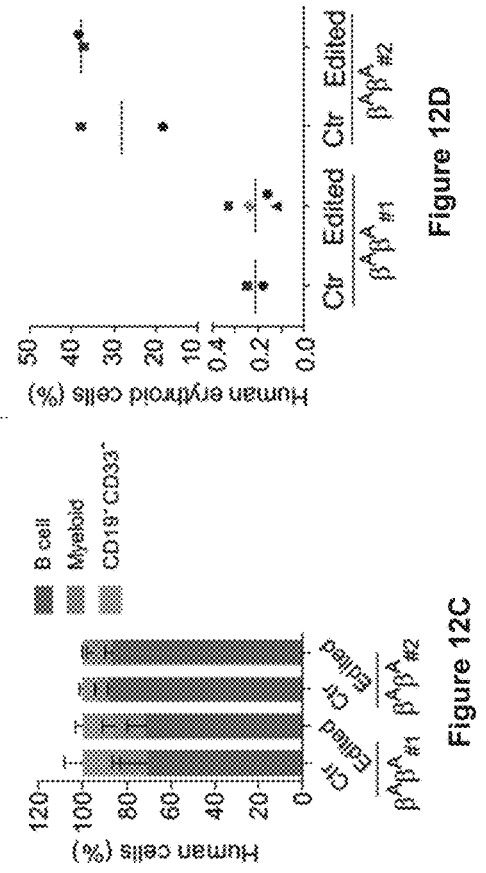
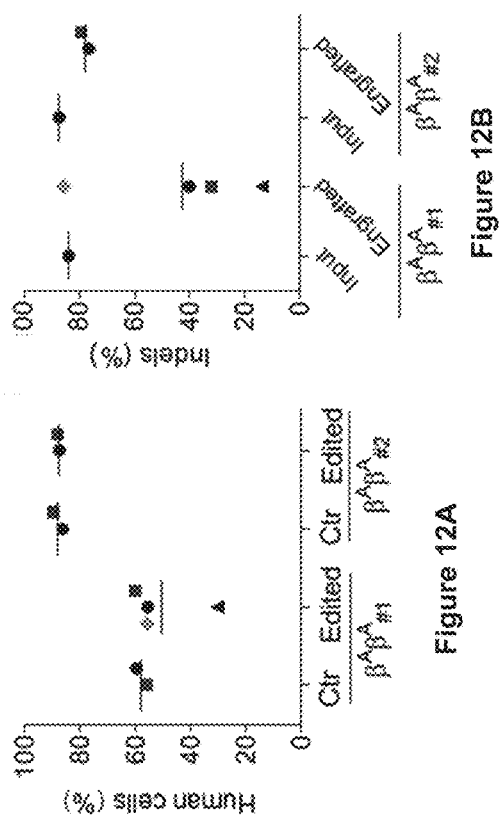
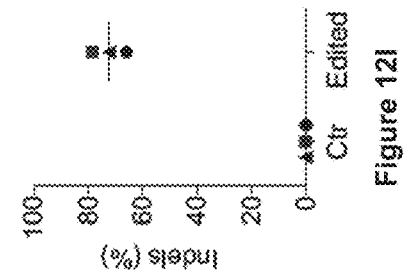
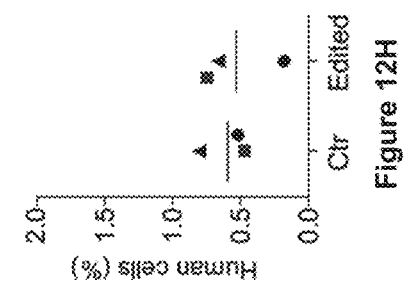
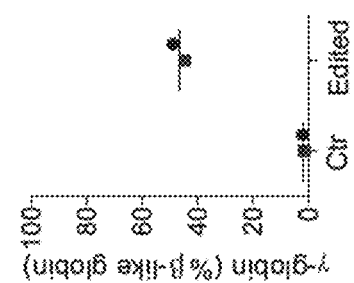
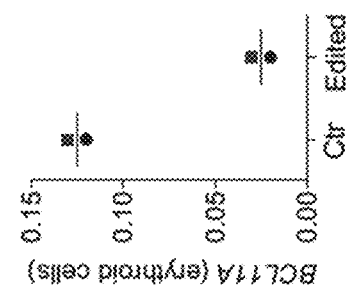
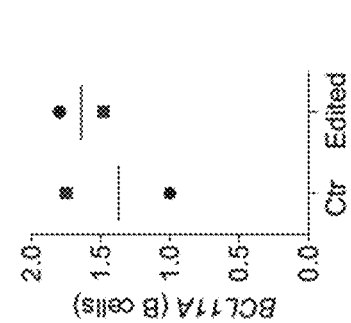

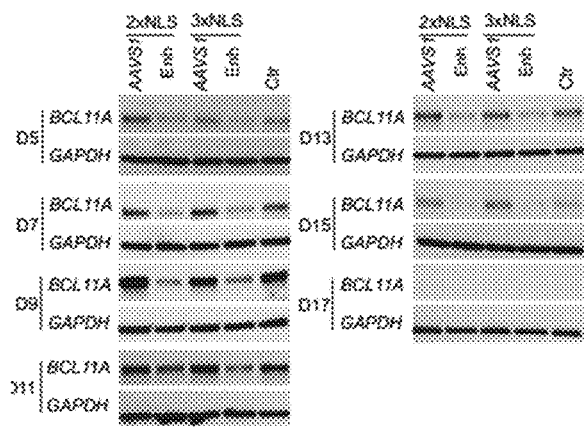
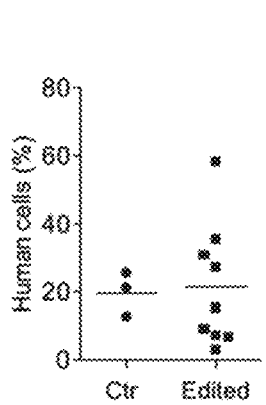
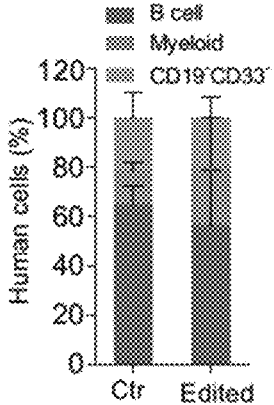
Figure 13G                Figure 13H                Figure 13I
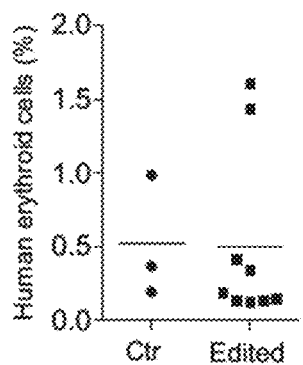
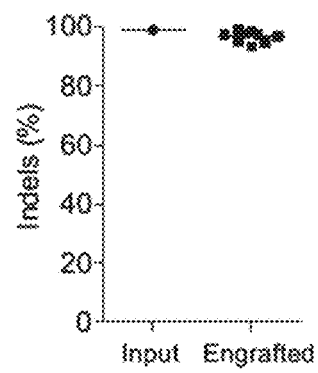
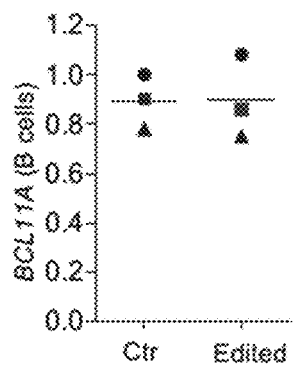
Figure 13J                Figure 13K                Figure 13L
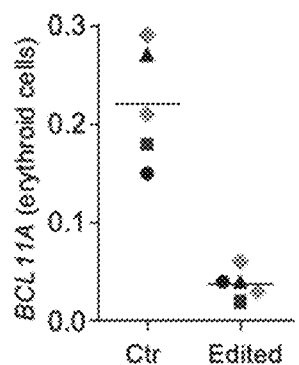
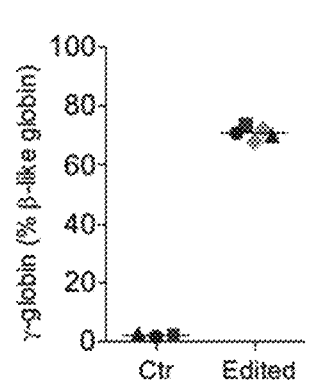
Figure 13M                Figure 13N

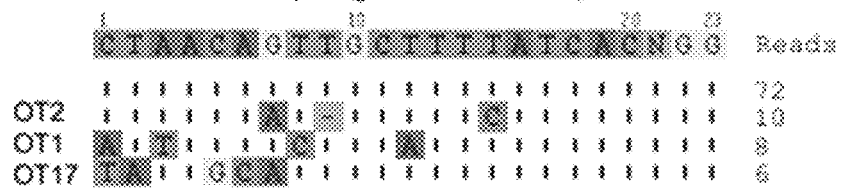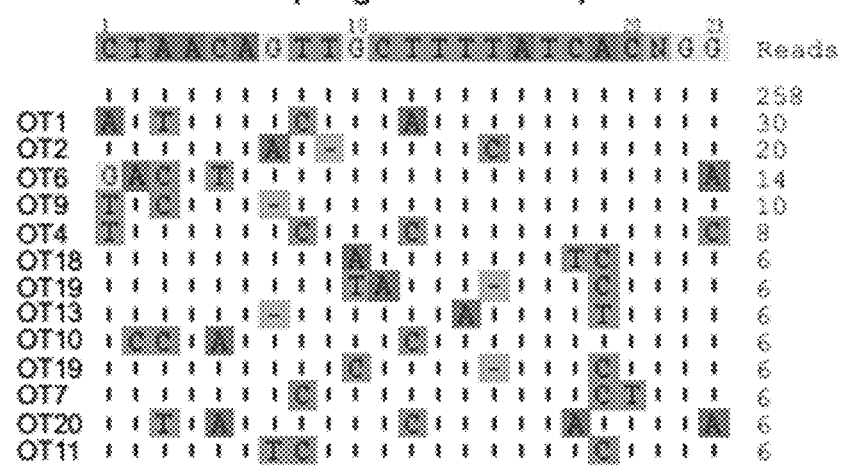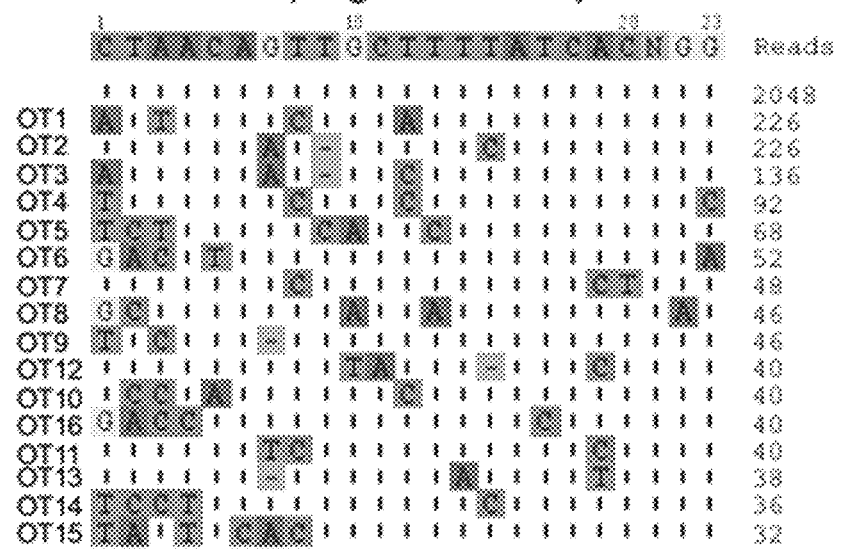
Figure 14A

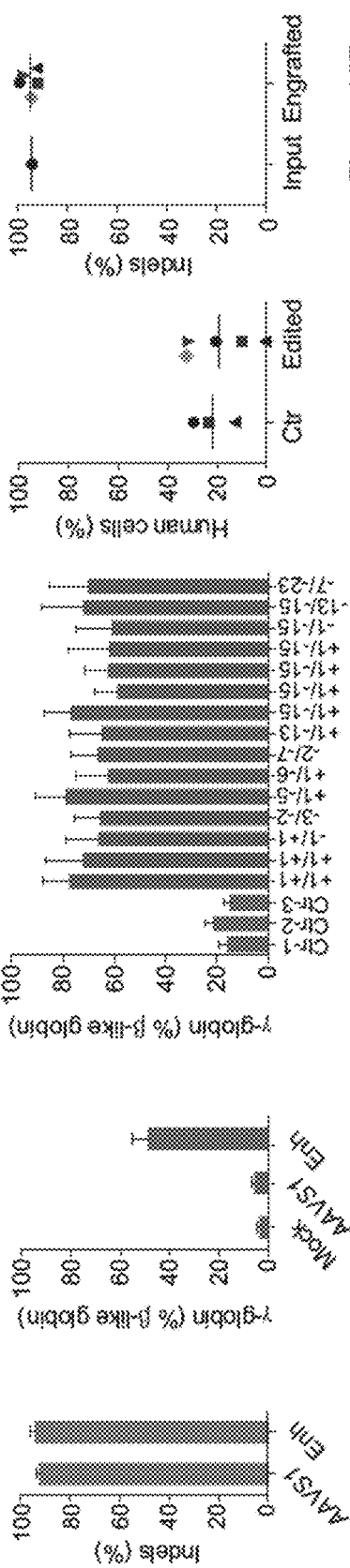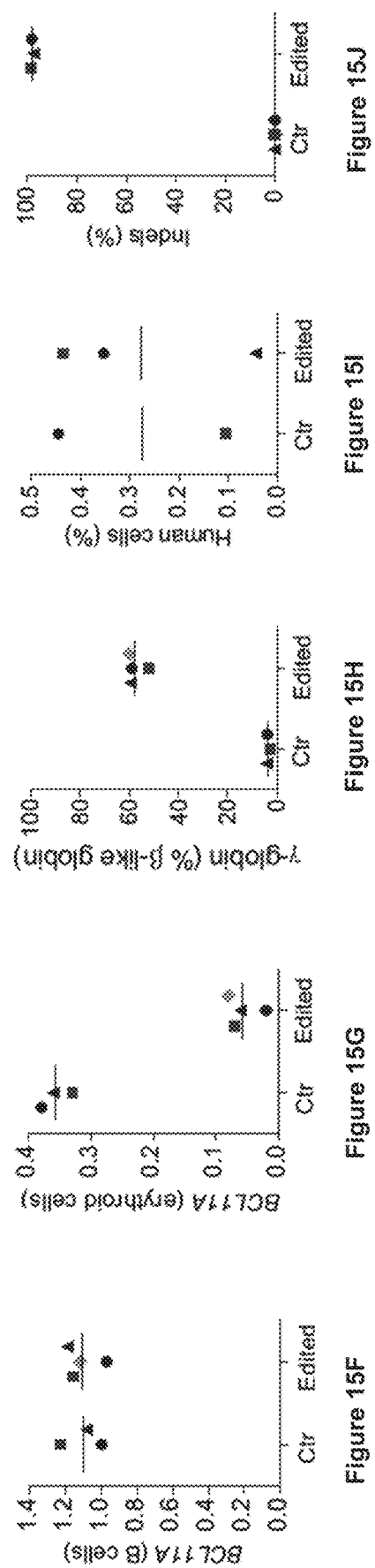

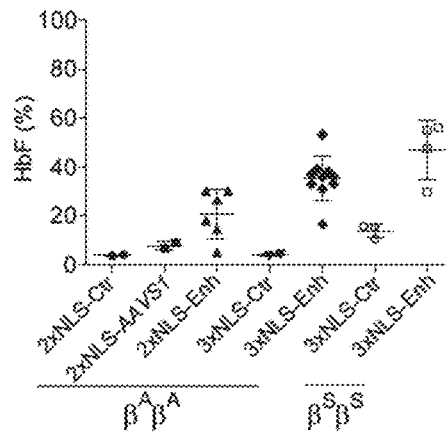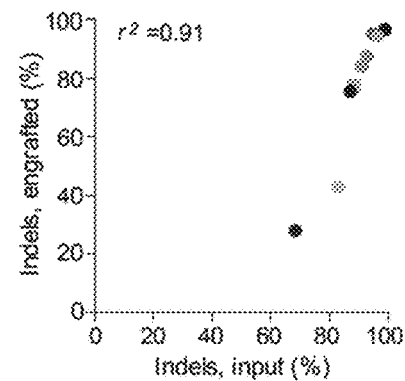
Figure 16A
Figure 16B
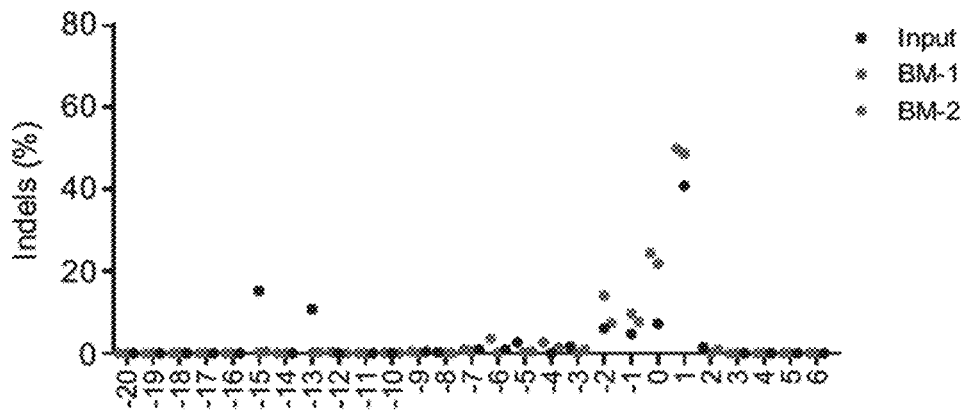
Figure 16C
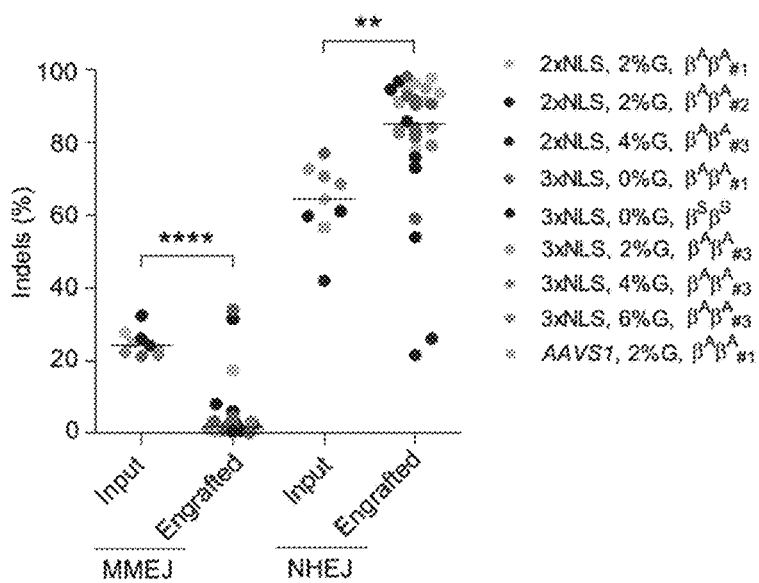
Figure 16D

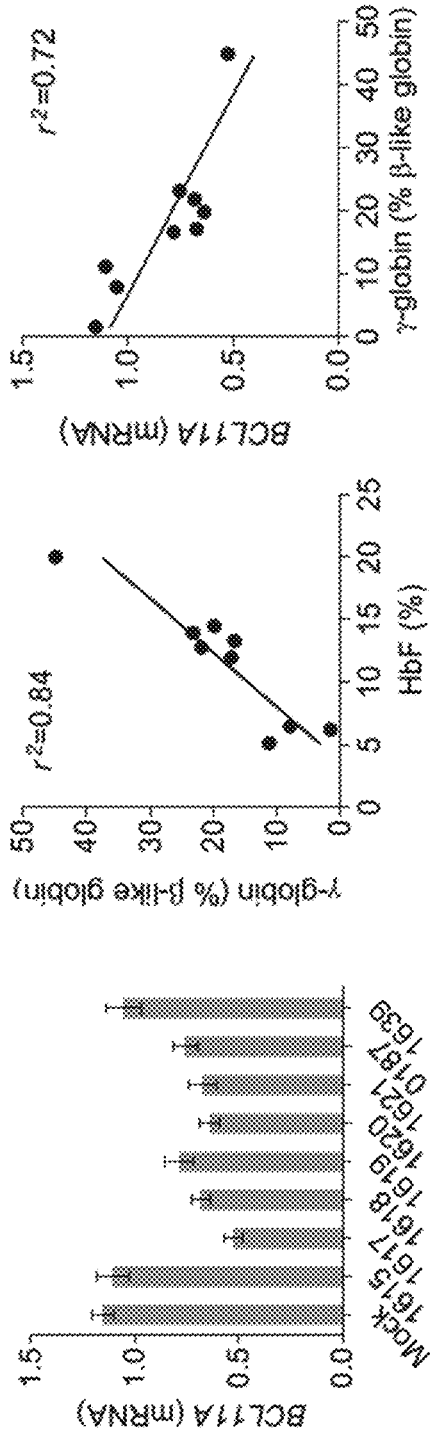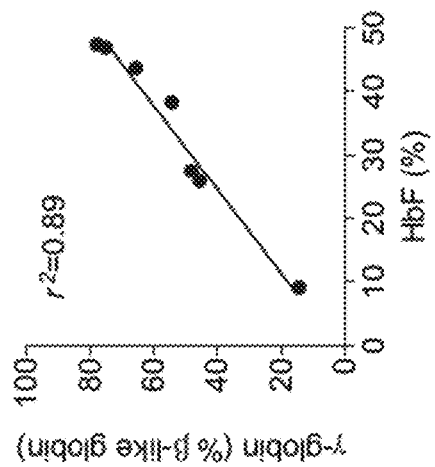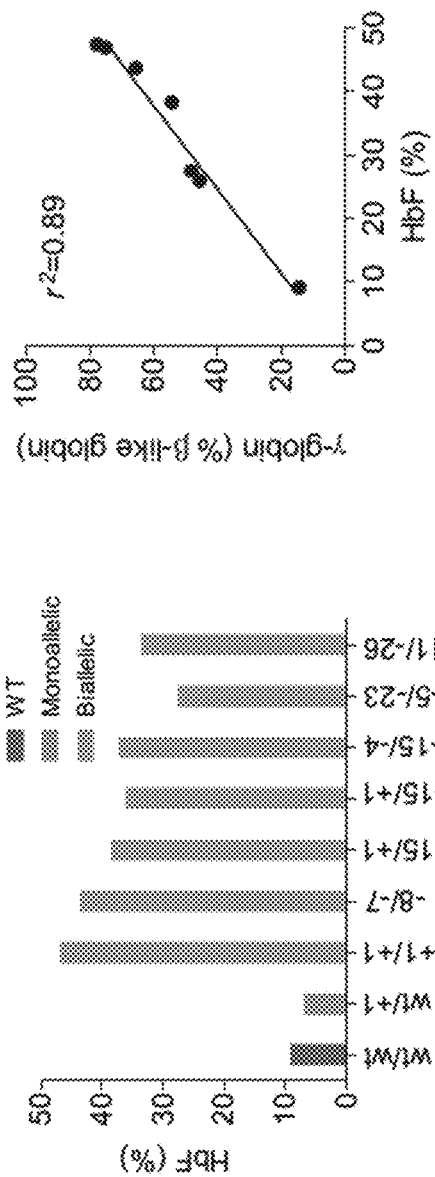

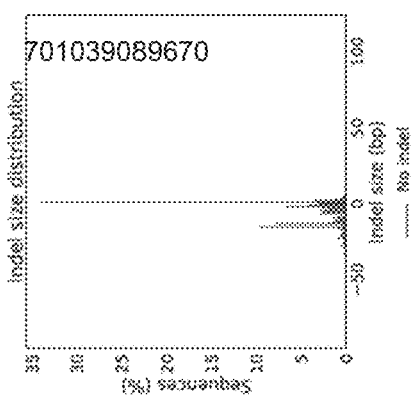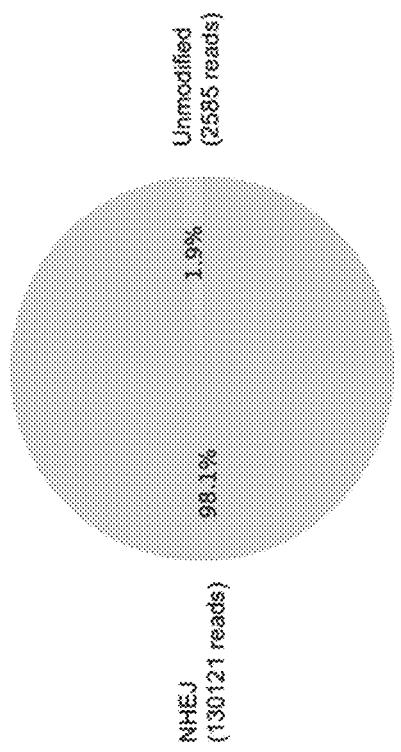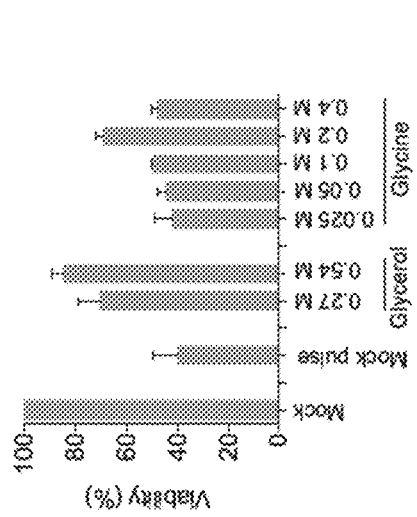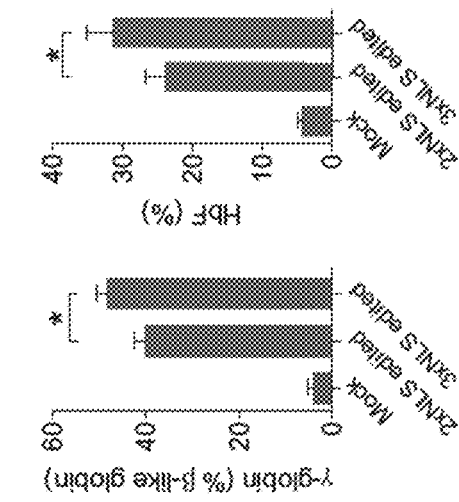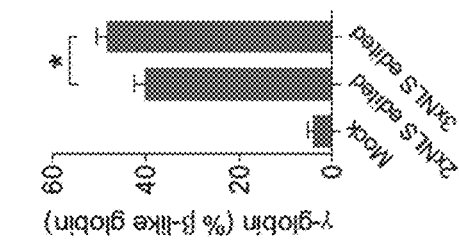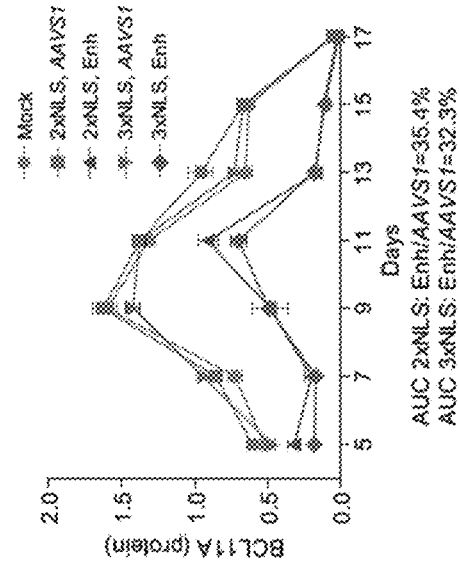
Figure 20A  Figure 20B  Figure 20C  Figure 20D  Figure 20E  Figure 20F  Figure 20G

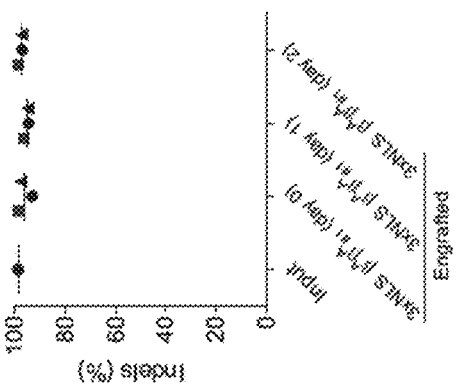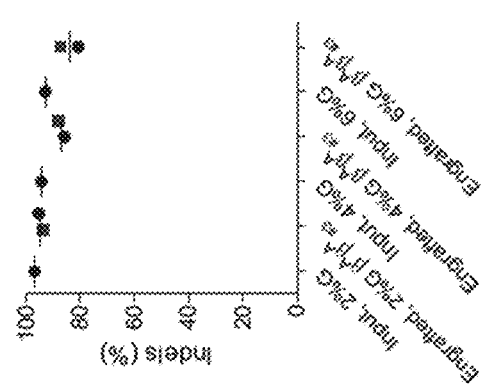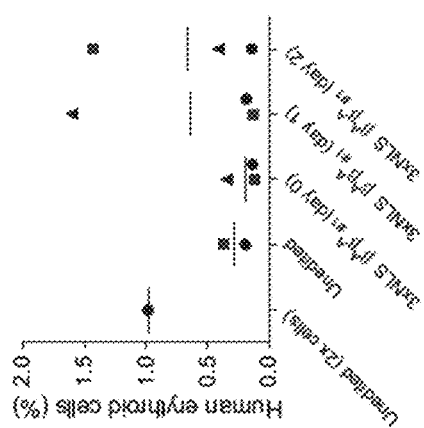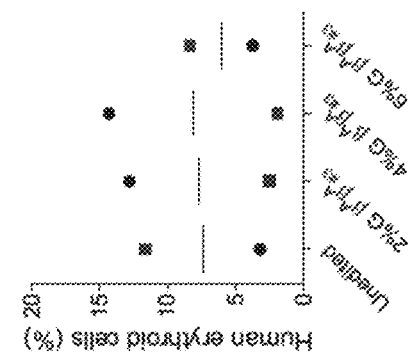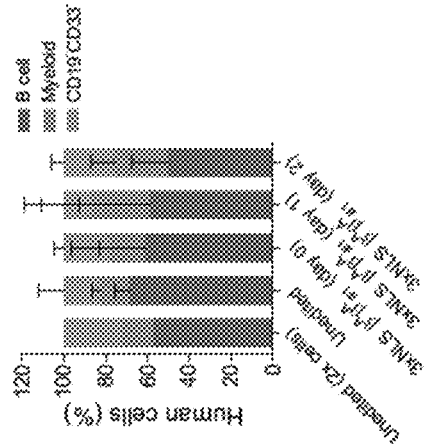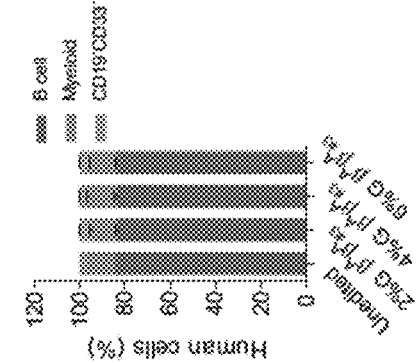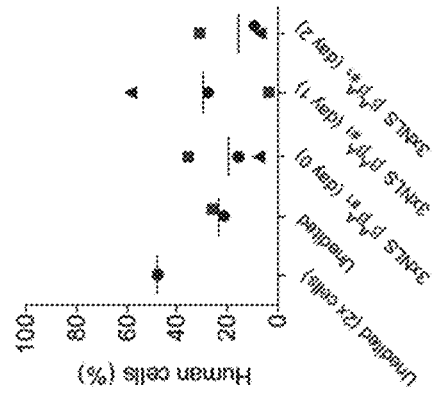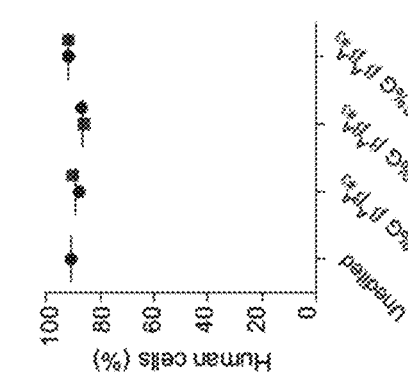

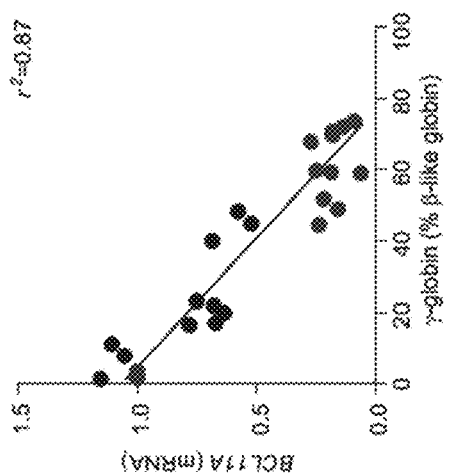
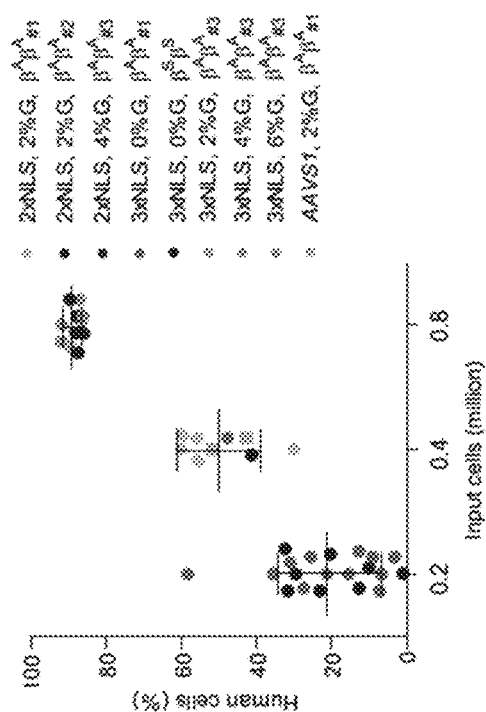
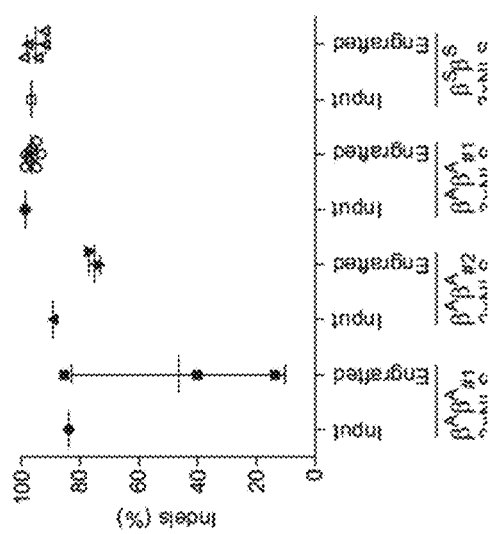
Figure 23A
Figure 23B
Figure 23C

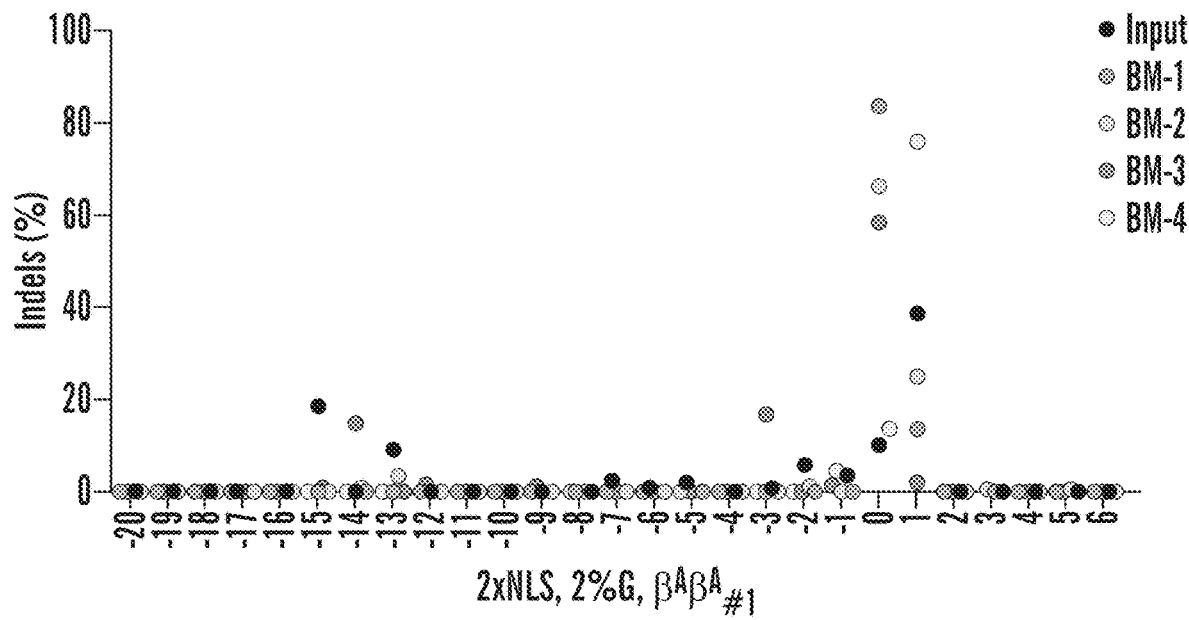
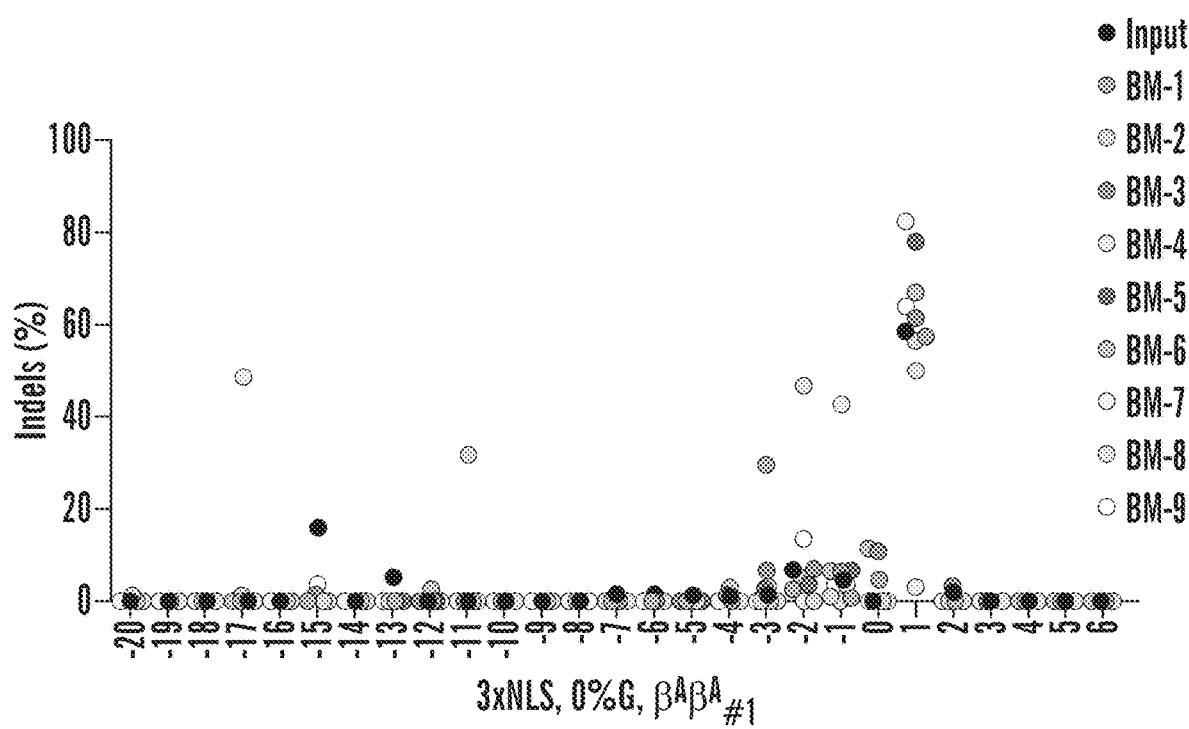
FIG. 24A

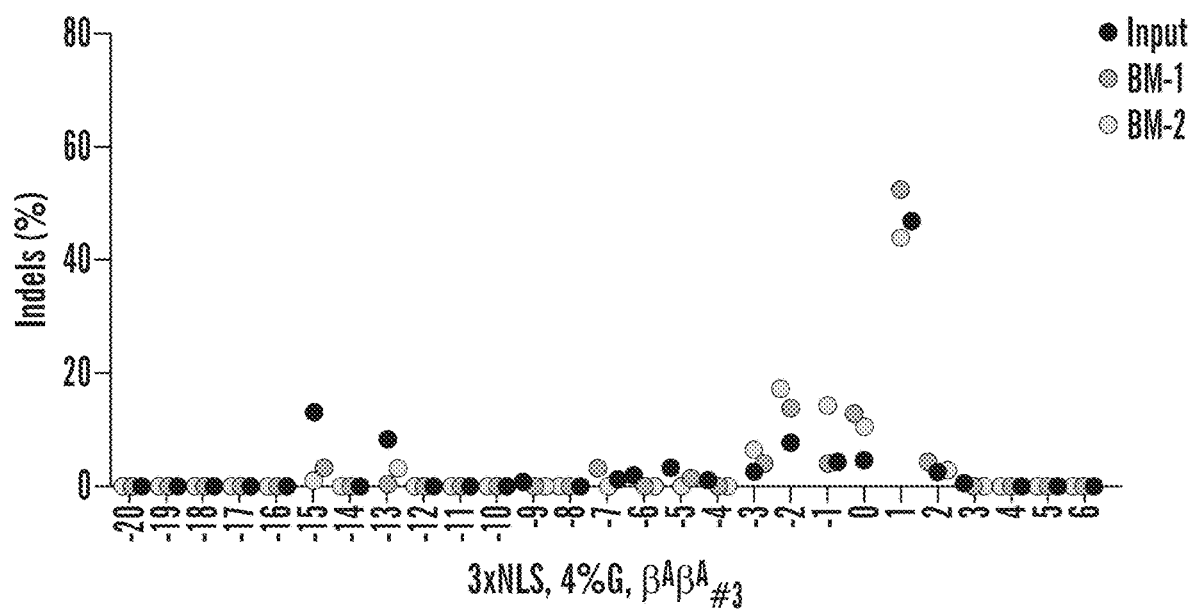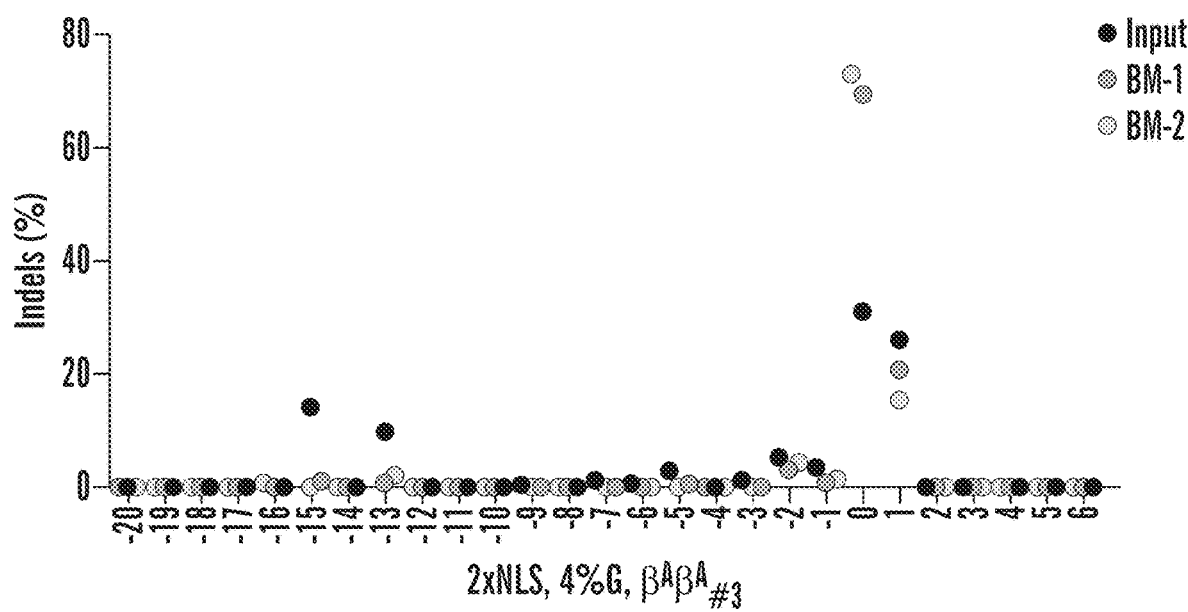
FIG. 24A (cont.)

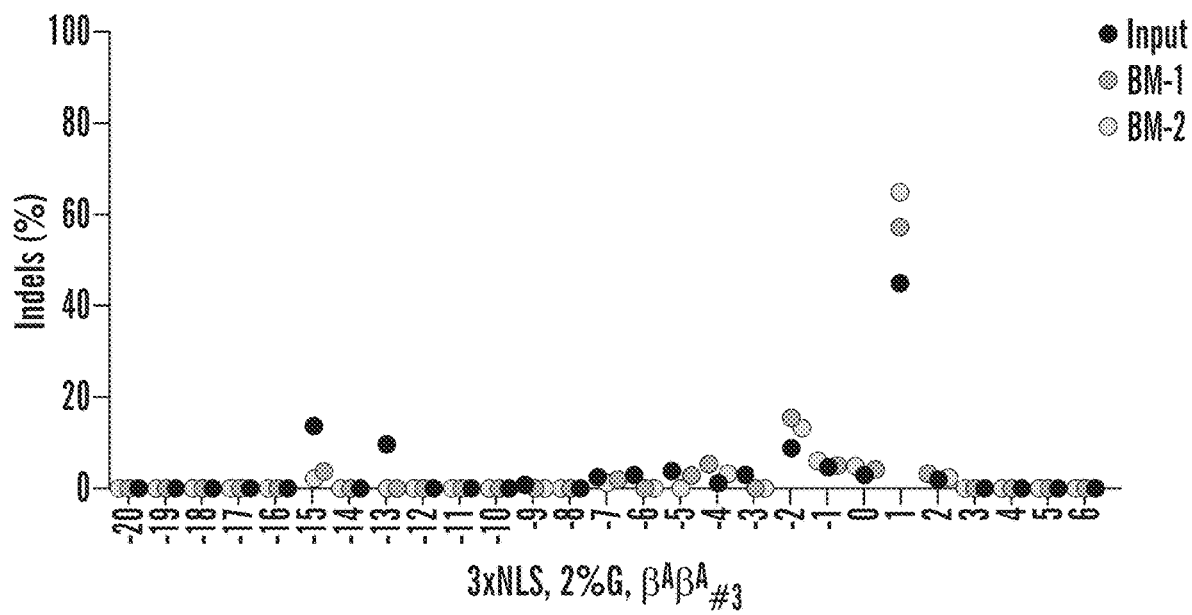
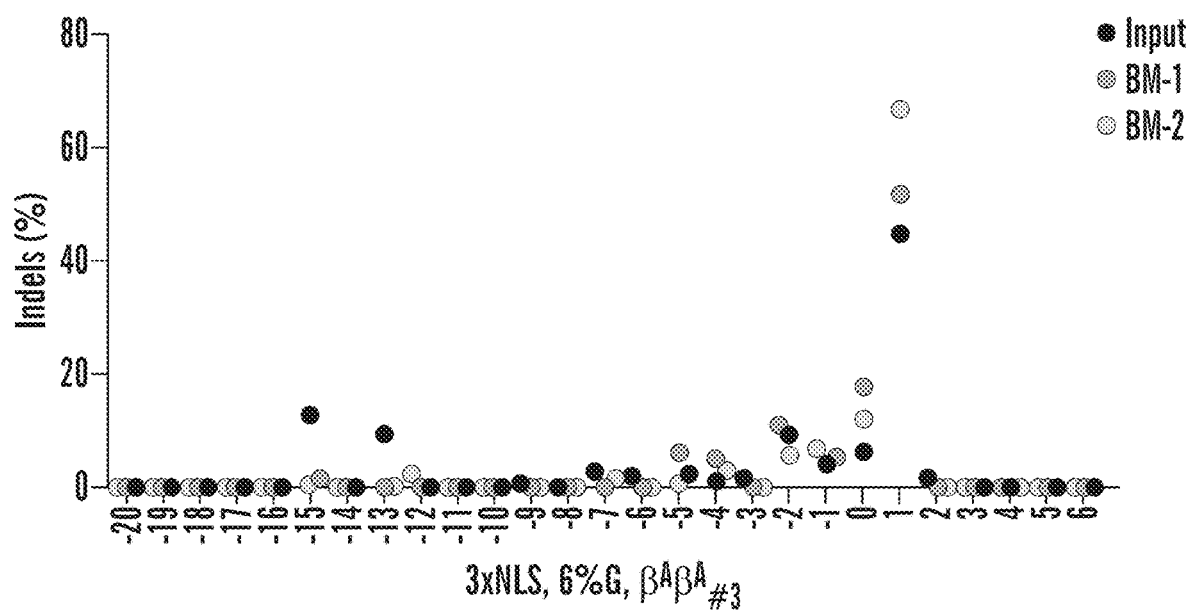
FIG. 24A (cont.)

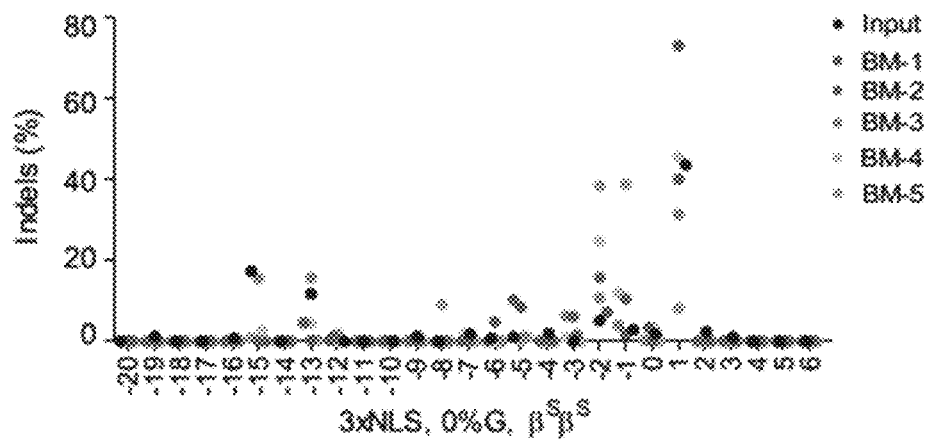
Figure 24A, CONT.
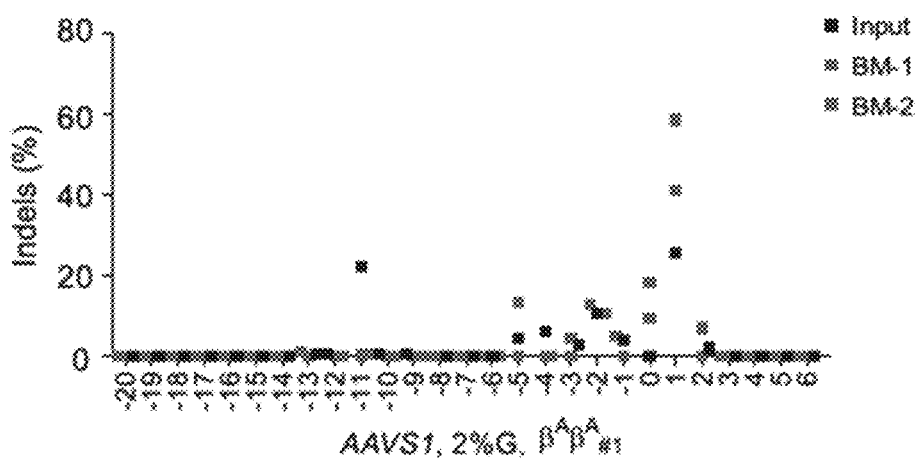
Figure 24B

SEQUENCE LISTING

<160> NUMBER OF SEQ ID NOS: 302

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tctgaggagc tagagacttg                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
agcaaatagg cttagtgtgc                                              20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ggctaaataa tgaatgtccc                                              20

```
<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tcccttccta gaattggcct                                                   20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ttcccttcct agaattggcc                                                   20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gaatgtccca ggccaattct                                                   20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
cccacttccc ttcctagaat                                                   20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
cctggtacca ggaaggcaat                                                   20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tcctggtacc aggaaggcaa                                                   20

<210> SEQ ID NO 10
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gcatcatcct ggtaccagga                                            20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
cattgcatca tcctggtacc                                            20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ctccaagcat tgcatcatcc                                            20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
taccaggatg atgcaatgct                                            20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gggtgtgccc tgagaaggtg                                            20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
agggtgtgcc ctgagaaggt                                            20

<210> SEQ ID NO 16
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tcacagggtg tgccctgaga                                                    20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ggcacaccct gtgatcttgt                                                    20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
agcacacaag atgcacaccc                                                    20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
tgtgcttggt cggcactgat                                                    20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gtgcttggtc ggcactgata                                                    20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tgcttggtcg gcactgatag                                                    20

<210> SEQ ID NO 22
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 22
gggtcgcggt agggagttgt                                              20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gccaacagtg ataaccagca                                              20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
tgccaacagt gataaccagc                                              20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gccctgctgg ttatcactgt                                              20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
agcagccctg ggcacagaag                                              20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
cctctatgta gacgggtgtg                                              20

<210> SEQ ID NO 28
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 28
ggaagggcct ctatgtagac                                                    20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ggaggtgtgg aggggataac                                                    20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ctggcagacc ctcaagagca                                                    20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
cccatggagg tggggagatg                                                    20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gtcatcctcg gccaatgaag                                                    20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
aagtgagcca ggtgatagaa                                                    20

<210> SEQ ID NO 34
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 34
tgaaaccaag cttcctctgc                                                   20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
agggagaaat gagacaaaag                                                   20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
aagaggccac tgagtccttt                                                   20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
actcttagac ataacacacc                                                   20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
ctcttagaca taacacacca                                                   20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ctaacagttg cttttatcac                                                   20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 40
ttgcttttat cacaggctcc                                               20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ttttatcaca ggctccagga                                               20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
tttatcacag gctccaggaa                                               20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
atcagaggcc aaacccttcc                                               20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
cttcaaagtt gtattgaccc                                               20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
cacaggctcc aggaagggtt                                               20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
cacgccccca ccctaatcag                                               20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
gaagggtttg gcctctgatt                                               20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
aagggtttgg cctctgatta                                               20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
ggtttggcct ctgattaggg                                               20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
gtttggcctc tgattagggt                                               20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
tttggcctct gattagggtg                                               20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 52
ttggcctctg attagggtgg                                                20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
tctgattagg gtgggggcgt                                                20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
attagggtgg gggcgtgggt                                                20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
ttagggtggg ggcgtgggtg                                                20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
tgggtggggt agaagaggac                                                20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
gcaaacggcc accgatggag                                                20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
```
cctgggcaaa cggccaccga                                              20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
aagaggcccc cctgggcaaa                                              20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
ccatcggtgg ccgtttgccc                                              20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
catcggtggc cgtttgccca                                              20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
atcggtggcc gtttgcccag                                              20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
tcggtggccg tttgcccagg                                              20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
cggtggccgt tgcccaggg                                                    20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
cttccgaaag aggccccct                                                    20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
ccttccgaaa gaggcccccc                                                   20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
tcaggggagg gcaagtcagt                                                   20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
agggaaaagg gagaggaaaa                                                   20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
tgtaactaat aaataccagg                                                   20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
ccagctgaag aaagaacatt                                                   20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
ccatctccct aatctccaat                                          20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
tggggagaga agagtggaaa                                          20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
ggagtatggg gagagaagag                                          20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
acaacctcct tgtttacaga                                          20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
gagatttact cttgttgccc                                          20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
ttgcccgggc tggaatgcaa                                          20

```
<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
ggagatcgct tgaacctggg                                                  20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
ctcagctact cgggaggctg                                                  20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
tgtaatctca gctactcggg                                                  20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
gcctgtaatc tcagctactc                                                  20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
tgcctgtaat ctcagctact                                                  20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
caggcatgta ttaccatgcc                                                  20
```

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
caggaggatc acctgaggtc                                                   20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
ctcaggtgat cctcctgccc                                                   20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
cccagcactt tgggaggccg                                                   20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
tcccagcact ttgggaggcc                                                   20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
atcccagcac tttgggaggc                                                   20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
acctgtaatc ccagcacttt                                                   20

<210> SEQ ID NO 89

<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
gccccggcct cccaaagtgc                                              20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
ccccggcctc ccaaagtgct                                              20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
atttgctctt ctccagggtg                                              20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
taaacagcca ccccacaccc                                              20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
tttgctcttc tccagggtgt                                              20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
ctcttctcca gggtgtgggg                                              20

<210> SEQ ID NO 95
<211> LENGTH: 20

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
tgtggggtgg ctgtttaaag                                               20

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
gggtggctgt ttaaagaggg                                               20

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
agttcaagta gatatcagaa                                               20

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
tatcagaagg gaactgtttg                                               20

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
aagaatggct tcaagaggct                                               20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
tctgtaagaa tggcttcaag                                               20

<210> SEQ ID NO 101
<211> LENGTH: 20
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 101
acagatgatg aaccagacca                                                   20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
tgaaccagac cacggcccgt                                                   20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
gaaccagacc acggcccgtt                                                   20

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
ggcccgttgg gagctccaga                                                   20

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
gcccgttggg agctccagaa                                                   20

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
cccgttggga gctccagaag                                                   20

<210> SEQ ID NO 107
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 107
ctggagctcc caacgggccg                                                    20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108 cccctctgg agctcccaac                                                     20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
tccccttctg gagctcccaa                                                    20

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
gatcatgacc tcctcacctg                                                    20

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
atcatgacct cctcacctgt                                                    20

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
aggaggtcat gatcccttc                                                     20

<210> SEQ ID NO 113
<211> LENGTH: 20
<212> TYPE: DNA
<213> ORGANISM: Artificial Sequence
<220> FEATURE:
```

<223> OTHER INFORMATION: Description of Artificial Sequence: Synthetic
oligonucleotide

<400> SEQUENCE: 113
ggcactgccc acaggtgagg                                               20

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 114
gtgccagatg aacttcccat                                               20

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 115
tgccagatga acttcccatt                                               20

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 116
gccagatgaa cttcccattg                                               20

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 117
tctggcactg cccacaggtg                                               20

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 118
ccagatgaac ttcccattgg                                               20

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 119
gttcatctgg cactgcccac                                              20

<210> SEQ ID NO 120
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
cccccaatgg gaagttcatc                                              20

<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
aaataagaat gtcccccaat                                              20

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
aaaataagaa tgtcccccaa                                              20

<210> SEQ ID NO 123
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
cacaaacgga aacaatgcaa                                              20

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
cctctgctta gaaaaagctg                                              20

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
ccacagcttt ttctaagcag						20

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
tcgattggtg aaggggaagg						20

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
atctcgattg gtgaagggga						20

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
tttcatctcg attggtgaag						20

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
gaaaaaagca tccaatcccg						20

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
aaaagcatcc aatcccgtgg						20

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 131
gcatccaatc ccgtggaggt                                              20

<210> SEQ ID NO 132
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
tcccgtggag gttggcatcc                                              20

<210> SEQ ID NO 133
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
tggcatccag gtcacgccag                                              20

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
gatgccaacc tccacgggat                                              20

<210> SEQ ID NO 135
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
acctggatgc caacctccac                                              20

<210> SEQ ID NO 136
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
gacctggatg ccaacctcca                                              20

<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
```
cgtcatcctc tggcgtgacc                                                    20

<210> SEQ ID NO 138
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
gataaacaat cgtcatcctc                                                    20

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
ctgctatgtg ttcctgtttg                                                    20

<210> SEQ ID NO 140
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
taatacgact cactataggg actcttagac ataacacacc gttttagagc tagaa            55

<210> SEQ ID NO 141
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
taatacgact cactataggg ctcttagaca taacacacca gttttagagc tagaa            55

<210> SEQ ID NO 142
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
taatacgact cactataggg tacagagccc cagtcctgga gttttagagc tagaa            55

<210> SEQ ID NO 143
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143

```
taatacgact cactataggg ttgcttttat cacaggctcc gttttagagc tagaa        55
```

<210> SEQ ID NO 144
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144

```
taatacgact cactataggg ttttatcaca ggctccagga gttttagagc tagaa        55
```

<210> SEQ ID NO 145
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145

```
taatacgact cactataggg tttatcacag gctccaggaa gttttagagc tagaa        55
```

<210> SEQ ID NO 146
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146

```
taatacgact cactataggg cacgccccca ccctaatcag gttttagagc tagaa        55
```

<210> SEQ ID NO 147
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147

```
taatacgact cactataggg atcagaggcc aaacccttcc gttttagagc tagaa        55
```

<210> SEQ ID NO 148
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148

```
taatacgact cactataggg cacaggctcc aggaagggtt gttttagagc tagaa        55
```

<210> SEQ ID NO 149
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149

```
taatacgact cactataggg gaagggtttg gcctctgatt gttttagagc tagaa        55
```

<210> SEQ ID NO 150
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
taatacgact cactataggg aagggtttgg cctctgatta gttttagagc tagaa          55

<210> SEQ ID NO 151
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
taatacgact cactataggg gtttggcctc tgattagggt gttttagagc tagaa          55

<210> SEQ ID NO 152
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
taatacgact cactataggg tttggcctct gattagggtg gttttagagc tagaa          55

<210> SEQ ID NO 153
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
taatacgact cactataggg ttggcctctg attagggtgg gttttagagc tagaa          55

<210> SEQ ID NO 154
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
taatacgact cactataggg tctgattagg gtgggggcgt gttttagagc tagaa          55

<210> SEQ ID NO 155
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
taatacgact cactataggg attagggtgg gggcgtgggt gttttagagc tagaa          55

```
<210> SEQ ID NO 156
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
taatacgact cactataggg ttagggtggg ggcgtgggtg gttttagagc tagaa      55

<210> SEQ ID NO 157
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
taatacgact cactataggg tgggtggggt agaagaggac gttttagagc tagaa      55

<210> SEQ ID NO 158
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
taatacgact cactataggg gcaaacggcc accgatggag gttttagagc tagaa      55

<210> SEQ ID NO 159
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
taatacgact cactataggg atcggtggcc gtttgcccag gttttagagc tagaa      55

<210> SEQ ID NO 160
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
taatacgact cactataggg ctccctccca ggatcctctc gttttagagc tagaa      55

<210> SEQ ID NO 161
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
gagagtgcag acaggggaag                                             20
```

```
<210> SEQ ID NO 162
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
accctggaaa acagcctgac                                                    20

<210> SEQ ID NO 163
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
cacacggcat ggcatacaaa                                                    20

<210> SEQ ID NO 164
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
caccctggaa aacagcctga                                                    20

<210> SEQ ID NO 165
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
caccttatat tcccagggcc g                                                  21

<210> SEQ ID NO 166
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
cctaggacgc accattctca c                                                  21

<210> SEQ ID NO 167
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
attgggtcta accccccacct                                                   20

<210> SEQ ID NO 168
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
tcagtgaaac gcaccagaca                                              20

<210> SEQ ID NO 169
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
aaccccagca cttaagcaaa                                              20

<210> SEQ ID NO 170
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
ggaggtcatg atcccttct                                               20

<210> SEQ ID NO 171
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
gccctggaga ggatgttc                                                18

<210> SEQ ID NO 172
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
ttcttgccgt ggccctta                                                18

<210> SEQ ID NO 173
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
cagtgcaggc tgcctatc                                                18

<210> SEQ ID NO 174
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
atacttgtgg gccagggcat                                                   20

<210> SEQ ID NO 175
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
tgggtcattt cacagaggag                                                   20

<210> SEQ ID NO 176
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
catcttccac attcaccttg c                                                 21

<210> SEQ ID NO 177
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
acccagaaga ctgtggatgg                                                   20

<210> SEQ ID NO 178
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
ttcagctcag ggatgaccct                                                   20

<210> SEQ ID NO 179
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
cttcgaccca agcaacatgc                                                   20

<210> SEQ ID NO 180
<211> LENGTH: 20
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 180
cggtgagtgt caggataggc					20

<210> SEQ ID NO 181
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 181
gccagaaaag agatatggca tc					22

<210> SEQ ID NO 182
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 182
agagagcctt ccgaaagagg					20

<210> SEQ ID NO 183
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 183
gttctctctt cttcctgaca gtg					23

<210> SEQ ID NO 184
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 184
gaggtcccta tgaaaagatg gct					23

<210> SEQ ID NO 185
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 185
gttgaatgcc aagtgcccaa					20

<210> SEQ ID NO 186
<211> LENGTH: 20
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 186
ggtctcagtt cagcccttc                                                     20

<210> SEQ ID NO 187
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
tgaacaatat tgcctttgt gct                                                 23

<210> SEQ ID NO 188
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
atgctgctgt aaggcactgt                                                    20

<210> SEQ ID NO 189
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
tccataaaac aatgttgagg tggg                                               24

<210> SEQ ID NO 190
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
gtcctccagt tgatcctgaa gt                                                 22

<210> SEQ ID NO 191
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
atccaggggc tttgagattg a                                                  21

<210> SEQ ID NO 192
<211> LENGTH: 23
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 192
tctccatccc cgttgttaag tga                                              23

<210> SEQ ID NO 193
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
cacacacaaa gcccttctgc                                                  20

<210> SEQ ID NO 194
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
caccatatcc agcctgtcgg                                                  20

<210> SEQ ID NO 195
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195
ctctggaaag cagggaccat                                                  20

<210> SEQ ID NO 196
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
gcatgctaac cagcacactg                                                  20

<210> SEQ ID NO 197
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 197
acagagctgg gccaataacc                                                  20

<210> SEQ ID NO 198
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 198
tgttcacatg ggaaagcctc a                                              21

<210> SEQ ID NO 199
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
gcttgtgtgc gtgtatggaa                                                20

<210> SEQ ID NO 200
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 200
gtagcacact aatacatgga aatga                                          25

<210> SEQ ID NO 201
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
taagatccaa acacccaatc acg                                            23

<210> SEQ ID NO 202
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
agtcttcagc tggtgatttc agg                                            23

<210> SEQ ID NO 203
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203
gtaccattcc tccaactaag gca                                            23

<210> SEQ ID NO 204
<211> LENGTH: 24
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 204
ctaagttctt ccacctcgag tcat                                            24

<210> SEQ ID NO 205
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205
agctgagatc acaccactgc                                                 20

<210> SEQ ID NO 206
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
tctagcccct ggtaacctcc                                                 20

<210> SEQ ID NO 207
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
acagaagatg aatagcggaa ca                                              22

<210> SEQ ID NO 208
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
tagtgacgcg aatagccctg                                                 20

<210> SEQ ID NO 209
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 209
atcagcctgg atccctaccc                                                 20

<210> SEQ ID NO 210
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 210
acctgagatt cctctgggct                                             20

<210> SEQ ID NO 211
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211
tctgtttcat ggtgatgctt ga                                          22

<210> SEQ ID NO 212
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 212 acaattttc actcttggta ctctt                                        25

<210> SEQ ID NO 213
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 213
tctctcctta gatttcttca tgtct                                       25

<210> SEQ ID NO 214
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214
cagaacaaag gcacagccac                                             20

<210> SEQ ID NO 215
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 215
acagaatgct atgagagacg tt                                          22

<210> SEQ ID NO 216
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 216
ggtaggaaaa acgcagaaaa ga        22

<210> SEQ ID NO 217
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
catgacttgg tgaagcccct        20

<210> SEQ ID NO 218
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218
atttgggcca ccaacttagg        20

<210> SEQ ID NO 219
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 219
gtgtagtgga ggagacagac aa        22

<210> SEQ ID NO 220
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 220
tttcaaactt gccagacccc a        21

<210> SEQ ID NO 221
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 221
gttcccagca tcccaaaaga ac        22

<210> SEQ ID NO 222
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 222
ggaggctctg agagaatgag g                                          21

<210> SEQ ID NO 223
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 223
gatgtgttca atgcaatgga gatta                                      25

<210> SEQ ID NO 224
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 224
ggctgcctct cattctcttg ta                                         22

<210> SEQ ID NO 225
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 225
agagtccaat aaattgaggt ttcac                                      25

<210> SEQ ID NO 226
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 226
ataactccat tccgggagcc                                            20

<210> SEQ ID NO 227
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 227
cagggcctca cttttgcctc                                            20

<210> SEQ ID NO 228
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 228
tgactgcata tccatgcacc at                                         22

<210> SEQ ID NO 229
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 229
cagctgaggc tactgctgtt                                              20

<210> SEQ ID NO 230
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 230
tcttctgttc actctttggc t                                            21

<210> SEQ ID NO 231
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 231
aaaaaagcac cgactcggtg                                              20

<210> SEQ ID NO 232
<211> LENGTH: 123
<212> TYPE: DNA
<213> ORGANISM: Homo sapiens

<400> SEQUENCE: 232
gtctgccagt cctcttctac cccacccacg cccccaccct aatcagaggc caaacccttc   60
ctggagcctg tgataaaagc aactgttagc ttgcactaga ctagcttcaa agttgtattg  120
acc                                                                123

<210> SEQ ID NO 233
<211> LENGTH: 171
<212> TYPE: DNA
<213> ORGANISM: Homo sapiens

<400> SEQUENCE: 233
actcttagac ataacacacc agggtcaata caactttgaa gctagtctag tgcaagctaa   60
cagttgcttt tatcacaggc tccaggaagg gtttggcctc tgattagggt ggggcgtgg   120 gtggggtaga agaggactgg cagacctctc catcggtggc cgtttgccca g            171

<210> SEQ ID NO 234
<211> LENGTH: 40
<212> TYPE: DNA
<213> ORGANISM: Homo sapiens

<400> SEQUENCE: 234
aagctaacag ttgcttttat cacaggctcc aggaagggtt                         40

```
<210> SEQ ID NO 235
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
aagctaacag ttgcttttat tcacaggctc caggaagggt                          40

<210> SEQ ID NO 236
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
aagctaacag gctccaggaa gggtt                                         25

<210> SEQ ID NO 237
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
aagctaacag ttgctccagg aagggtt                                       27

<210> SEQ ID NO 238
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
aagctaacac aggctccagg aagggtt                                       27

<210> SEQ ID NO 239
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
aagctaacag ttgcttttat caggctccag gaagggtt                           38

<210> SEQ ID NO 240
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240
aagctaacag ttgcttttca caggctccag gaagggtt                           38

<210> SEQ ID NO 241
```

```
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
aagctaacag ttgcacaggc tccaggaagg gtt                                  33

<210> SEQ ID NO 242
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
aagctaacag ttgctaacag gctccaggaa gggtt                                35

<210> SEQ ID NO 243
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
aagctaacag ttgcttttaa caggctccag gaagggtt                             38

<210> SEQ ID NO 244
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
aagctaacag ttgcttttat cacaggctcc aggaagggt                            39

<210> SEQ ID NO 245
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
aagctaacag ttgcttttat atcacaggct ccaggaaggg                           40

<210> SEQ ID NO 246
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
aagctaacag ttgcttttaa cacaggctcc aggaagggtt                           40

<210> SEQ ID NO 247
<211> LENGTH: 17
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
aagctccagg aagggtt                                                        17

<210> SEQ ID NO 248
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
aagctaacag gaagggtt                                                       18

<210> SEQ ID NO 249
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
aagctaacag ttgcttttat acaggctcca ggaagggtt                                39

<210> SEQ ID NO 250
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
aagctaacag ttgcttttac acaggctcca ggaagggtt                                39

<210> SEQ ID NO 251
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
aagctaacag ttgcttttc acaggctcca ggaagggtt                                 39

<210> SEQ ID NO 252
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252
agctaacagt tgcttttaat cacaggctcc aggaagggtt                               40

<210> SEQ ID NO 253
<211> LENGTH: 36
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 253
aagctaacag ttgcttcaca ggctccagga agggtt                                36

<210> SEQ ID NO 254
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
aagctaacag ttgctttcac aggctccagg aagggtt                               37

<210> SEQ ID NO 255
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
aagctaacag ttgcttttat ccacaggctc caggaagggt                            40

<210> SEQ ID NO 256
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
aagctaacag ttgtcacagg ctccaggaag ggtt                                  34

<210> SEQ ID NO 257
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 257
ctaacagttg cttttatcac ngg                                              23

<210> SEQ ID NO 258
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: a, c, t, g, unknown or other

<400> SEQUENCE: 258
ctaacaatgc tttcatcacn gg                                            22

<210> SEQ ID NO 259
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 259
attacagctg catttatcac ngg                                           23

<210> SEQ ID NO 260
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 260
taaagcattg cttttatcac ngg                                           23

<210> SEQ ID NO 261
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 261
gacatagttg cttttatcac nga                                           23

<210> SEQ ID NO 262
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: a, c, t, g, unknown or other

<400> SEQUENCE: 262
ttcacattgc ttttatcacn gg                                            22

<210> SEQ ID NO 263
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<221> NAME/KEY: modified_base
<222> LOCATION: (21)..(21)
<223> OTHER INFORMATION: a, c, t, g, unknown or other

<400> SEQUENCE: 263
ttaacagctg cctttatcac ngc                                              23

<210> SEQ ID NO 264
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 264
ctaacagtta cttttattcc ngg                                              23

<210> SEQ ID NO 265
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: a, c, t, g, unknown or other

<400> SEQUENCE: 265
ctaacagttt atttatcccn gg                                               22

<210> SEQ ID NO 266
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: a, c, t, g, unknown or other

<400> SEQUENCE: 266
ctaacattgc ttatatctcn gg                                               22

<210> SEQ ID NO 267
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 267
cccaaagttg cctttatcac ngg                                              23

<210> SEQ ID NO 268
```

```
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: a, c, t, g, unknown or other

<400> SEQUENCE: 268
ctaacagttc ctttatcccn gg                                              22

<210> SEQ ID NO 269
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 269
ctaacagctg cttttatcct ngg                                             23

<210> SEQ ID NO 270
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 270
cttaaagttg cctttataac nga                                             23

<210> SEQ ID NO 271
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 271
ctaacatctg cttttatccc ngg                                             23

<210> SEQ ID NO 272
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: a, c, t, g, unknown or other
```

```
<400> SEQUENCE: 272
ataacaatgc ctttatcacn gg                                              22

<210> SEQ ID NO 273
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 273
tctacagtca ctcttatcac ngg                                             23

<210> SEQ ID NO 274
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 274
gcaacagtta ctattatcac nag                                             23

<210> SEQ ID NO 275
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 275
gacccagttg cttttaccac ngg                                             23

<210> SEQ ID NO 276
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 276
tcctcagttg ctttcatcac ngg                                             23

<210> SEQ ID NO 277
<211> LENGTH: 23
<212> TYPE: DNA
<213> ORGANISM: Artificial Sequence
<220> FEATURE:
<223> OTHER INFORMATION: Description of Artificial Sequence: Synthetic
```

```
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 277
taatccactg cttttatcac ngg                                          23

<210> SEQ ID NO 278
<211> LENGTH: 23
<212> TYPE: DNA
<213> ORGANISM: Homo sapiens

<400> SEQUENCE: 278
ctaacagttg cttttatcac agg                                          23

<210> SEQ ID NO 279
<211> LENGTH: 23
<212> TYPE: DNA
<213> ORGANISM: Homo sapiens

<400> SEQUENCE: 279
attacagctg catttatcac agg                                          23

<210> SEQ ID NO 280
<211> LENGTH: 22
<212> TYPE: DNA
<213> ORGANISM: Homo sapiens

<400> SEQUENCE: 280
ctaacaatgc tttcatcacg gg                                           22

<210> SEQ ID NO 281
<211> LENGTH: 22
<212> TYPE: DNA
<213> ORGANISM: Homo sapiens

<400> SEQUENCE: 281
ataacaatgc ctttatcaca gg                                           22

<210> SEQ ID NO 282
<211> LENGTH: 23
<212> TYPE: DNA
<213> ORGANISM: Homo sapiens

<400> SEQUENCE: 282
ttaacagctg cctttatcac tgc                                          23

<210> SEQ ID NO 283
<211> LENGTH: 23
<212> TYPE: DNA
<213> ORGANISM: Homo sapiens

<400> SEQUENCE: 283
tctacagtca ctcttatcac tgg                                          23

<210> SEQ ID NO 284
<211> LENGTH: 23
<212> TYPE: DNA
<213> ORGANISM: Homo sapiens

<400> SEQUENCE: 284
gacatagttg cttttatcac aga                                          23
```

```
<210> SEQ ID NO 285
<211> LENGTH: 23
<212> TYPE: DNA
<213> ORGANISM: Homo sapiens

<400> SEQUENCE: 285
ctaacagctg cttttatcct ggg                                              23

<210> SEQ ID NO 286
<211> LENGTH: 23
<212> TYPE: DNA
<213> ORGANISM: Homo sapiens

<400> SEQUENCE: 286
gcaacagtta ctattatcac aag                                              23

<210> SEQ ID NO 287
<211> LENGTH: 22
<212> TYPE: DNA
<213> ORGANISM: Homo sapiens

<400> SEQUENCE: 287
ttcacattgc ttttatcact gg                                               22

<210> SEQ ID NO 288
<211> LENGTH: 23
<212> TYPE: DNA
<213> ORGANISM: Homo sapiens

<400> SEQUENCE: 288
cccaaagttg cctttatcac agg                                              23

<210> SEQ ID NO 289
<211> LENGTH: 23
<212> TYPE: DNA
<213> ORGANISM: Homo sapiens

<400> SEQUENCE: 289
ctaacatctg cttttatccc agg                                              23

<210> SEQ ID NO 290
<211> LENGTH: 22
<212> TYPE: DNA
<213> ORGANISM: Homo sapiens

<400> SEQUENCE: 290
ctaacagttt atttatccca gg                                               22

<210> SEQ ID NO 291
<211> LENGTH: 22
<212> TYPE: DNA
<213> ORGANISM: Homo sapiens

<400> SEQUENCE: 291
ctaacattgc ttatatctca gg                                               22

<210> SEQ ID NO 292
<211> LENGTH: 23
<212> TYPE: DNA
<213> ORGANISM: Homo sapiens

<400> SEQUENCE: 292
```
tcctcagttg ctttcatcac tgg                                                              23

<210> SEQ ID NO 293
<211> LENGTH: 23
<212> TYPE: DNA
<213> ORGANISM: Homo sapiens

<400> SEQUENCE: 293
taatccactg cttttatcac tgg                                                              23

<210> SEQ ID NO 294
<211> LENGTH: 23
<212> TYPE: DNA
<213> ORGANISM: Homo sapiens

<400> SEQUENCE: 294
gacccagttg cttttaccac agg                                                              23

<210> SEQ ID NO 295
<211> LENGTH: 23
<212> TYPE: DNA
<213> ORGANISM: Homo sapiens

<400> SEQUENCE: 295
taaagcattg cttttatcac agg                                                              23

<210> SEQ ID NO 296
<211> LENGTH: 23
<212> TYPE: DNA
<213> ORGANISM: Homo sapiens

<400> SEQUENCE: 296
ctaacagtta cttttattcc tgg                                                              23

<210> SEQ ID NO 297
<211> LENGTH: 22
<212> TYPE: DNA
<213> ORGANISM: Homo sapiens

<400> SEQUENCE: 297
ctaacagttc ctttatccct gg                                                               22

<210> SEQ ID NO 298
<211> LENGTH: 23
<212> TYPE: DNA
<213> ORGANISM: Homo sapiens

<400> SEQUENCE: 298
cttaaagttg cctttataac tga                                                              23

<210> SEQ ID NO 299
<211> LENGTH: 23
<212> TYPE: DNA
<213> ORGANISM: Homo sapiens

<400> SEQUENCE: 299
caaacagatt cttttatctc tgg                                                              23

<210> SEQ ID NO 300
<211> LENGTH: 23
<212> TYPE: DNA
<213> ORGANISM: Homo sapiens

<400> SEQUENCE: 300

```
gagacagtgg cttttatcac agg                                              23

<210> SEQ ID NO 301
<211> LENGTH: 23
<212> TYPE: DNA
<213> ORGANISM: Homo sapiens

<400> SEQUENCE: 301
ataacagtta ctttaaacac tgg                                              23

<210> SEQ ID NO 302
<211> LENGTH: 23
<212> TYPE: DNA
<213> ORGANISM: Homo sapiens

<400> SEQUENCE: 302
aaaaaagttt cttttatcac cag                                              23
```

BCL11A GUIDE DELIVERY

CROSS-REFERENCE TO RELATED APPLICATIONS

This application is a 35 U.S.C. § 371 National Phase Entry Application of International Application No. PCT/US2018/034618 filed May 25, 2018, which designated the U.S., and which claims the benefit under 35 U.S.C. § 119(e) of U.S. Provisional Application No. 62/511,115 filed on May 25, 2017, the contents of which are incorporated herein by reference in their entireties.

GOVERNMENT SUPPORT

This invention was made with Government support under Grant No. K08DK093705 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Jun. 25, 2018, is named 701039-089670WOPT_SL.txt and is 70,364 bytes in size.

BACKGROUND

Normal adult hemoglobin comprises four globin proteins, two of which are alpha (α) proteins and two of which are beta (β) proteins. During mammalian fetal development, particularly in humans, the fetus produces fetal hemoglobin, which comprises two gamma (γ)-globin proteins instead of the two β-globin proteins. During the neonatal period, a globin switch occurs, referred to as the "fetal switch", at which point, erythroid precursors switch from making predominantly γ-globin to making predominantly β-globin. The developmental switch from production of predominantly fetal hemoglobin or HbF ($\alpha_2\gamma_2$) to production of adult hemoglobin or HbA ($\alpha_2\beta_2$) begins at about 28 to 34 weeks of gestation and continues shortly after birth until HbA becomes predominant. This switch results primarily from decreased transcription of the gamma-globin genes and increased transcription of beta-globin genes. On average, the blood of a normal adult contains less than 1% HbF, though residual HbF levels have a variance of over 20 fold in healthy adults and are genetically controlled.

Hemoglobinopathies encompass a number of anemias of genetic origin in which there is a decreased production and/or increased destruction (hemolysis) of red blood cells (RBCs). These also include genetic defects that result in the production of abnormal hemoglobins with a concomitant impaired ability to maintain oxygen concentration. Some such disorders involve the failure to produce normal β-globin in sufficient amounts, while others involve the failure to produce normal β-globin entirely. These disorders associated with the β-globin protein are referred to generally as β-hemoglobinopathies. For example, β-thalassemias result from a partial or complete defect in the expression of the β-globin gene, leading to deficient or absent HbA. Sickle cell anemia results from a point mutation in the β-globin structural gene, leading to the production of an abnormal (sickle) hemoglobin (HbS). HbS is prone to polymerization, particularly under deoxygenated conditions. HbS RBCs are more fragile than normal RBCs and undergo hemolysis more readily, leading eventually to anemia.

Recently, the search for treatment aimed at reduction of globin chain imbalance or predisposition to hemoglobin polymerization in patients with β-hemoglobinopathies has focused on the pharmacologic manipulation of fetal hemoglobin ($\alpha 2\gamma 2$; HbF). The therapeutic potential of such approaches is indicated by observations of the mild phenotype of individuals with co-inheritance of both homozygous β-thalassemia and hereditary persistence of fetal hemoglobin (HPFH), as well as by those patients with homozygous β-thalassemia who synthesize no adult hemoglobin, but in whom a reduced requirement for transfusions is observed in the presence of increased concentrations of fetal hemoglobin. Furthermore, it has been observed that certain populations of adult patients with β chain abnormalities have higher than normal levels of fetal hemoglobin (HbF), and have been observed to have a milder clinical course of disease than patients with normal adult levels of HbF. For example, a group of Saudi Arabian sickle-cell anemia patients who express 20-30% HbF have only mild clinical manifestations of the disease. It is now accepted that hemoglobin disorders, such as sickle cell anemia and the β-thalassemias, are ameliorated by increased HbF production.

The switch from fetal hemoglobin to adult hemoglobin ($\alpha 2\gamma 2$; HbA) usually proceeds within six months after parturition. However, in the majority of patients with β-hemoglobinopathies, the upstream γ globin genes are intact and fully functional, so that if these genes become reactivated, functional hemoglobin synthesis could be maintained during adulthood, and thus ameliorate disease severity. Unfortunately, the in vivo molecular mechanisms underlying the globin switch are not well understood.

Evidence supporting the feasibility of reactivation of fetal hemoglobin production comes from experiments in which it was shown that peripheral blood, containing clonogenic cells, when given the appropriate combination of growth factors, produce erythroid colonies and bursts in semisolid culture. Individual cells in such colonies can accumulate fetal hemoglobin (HbF), adult hemoglobin (HbA) or a combination of both. In cultures from adult blood, nucleated red cells accumulate either HbA (F–A+) only, or a combination of HbF and HbA (F+A+). Importantly, individual colonies contain both F+ and F– cells, indicating that both types are progeny from the same circulating stem cells. Thus, during the early stages of development in culture, cells execute an option, through currently unknown mechanisms, whether or not to express HbF. The proportion of adult F+ cells developing in culture does not appear to be preprogrammed in vivo, but appears to depend on culture conditions: A shift into the combined HbF and HbA expression pathway can, for example, be achieved in vitro by high serum concentrations, due to the activity of an unidentified compound that can be absorbed on activated charcoal.

Genome editing of autologous hematopoietic stem cells (HSCs) is a promising strategy to enable cure of blood disorders like β-hemoglobinopathies. A distal regulatory region upstream of the BCL11A gene regulates the expression of the BCL11A protein. The BCL11A protein acts as a stage specific regulator of fetal hemoglobin expression by repressing γ-globin induction. This upstream distal regulatory region mapped to the human chromosome 2 at location 60,716,189-60,728,612 in the human genomic DNA according to UCSC Genome Browser hg 19 human genome assembly. Noticeably, this upstream distal regulatory region consistently contains three DNAse 1-hypersensitive sites (DHS) +62, +58, and +55. Identification of these specific functional regions within this ~12 kb molecules that play a role in the globin switch is important for the development of novel therapeutic strategies that interfere with adult hemoglobin and induce fetal hemoglobin synthesis. Previously it has shown that core sequences at the erythroid enhancer of BCL11A are required for repression of HbF in adult-stage erythroid cells but dispensable in non-erythroid cells. Prior efforts to use Cas9 and other programmable nucleases to edit human hematopoietic stem and progenitor cells (HSPCs) have shown variable efficiency, genotoxicity, requirement for HSC selection or expansion prior to infusion into recipient host, and limited ability to support long-term multilineage reconstitution with persistence of edited alleles. Provided here is an improved method of genome editing of the BCL11A's DHS +62, +58, and +55 functional regions, and the related reagents thereof. The improved method comprises selection-free conditions for Cas9:sgRNA ribonucleoprotein (RNP) electroporation of β-hemoglobinopathy patient-derived HSCs that induce highly efficient on-target editing, no off-target editing while lacking detectable genotoxicity.

SUMMARY

Embodiments described herein are based in part to the discovery of the following discoveries.

Firstly, electroporation turns out surprisingly to be an effective method for introducing the CRISPR gRNAs (also known as sgRNA) into primary human CD34+ HSPCs for efficient genome editing at the target site, with reduced or no detectable off-target editing. Moreover, the RNP electroporation is just as efficient if not better than the previously reported lentiviral-based delivery system of the CRISPR gRNAs, and provides efficient BCL11A enhancer editing and BCL11A silencing. The advantage of using electroporation is there is no lingering viral material in the engineered human CD34+ HSPC after genome editing and only a short pulse exposure to Cas9 nuclease thus minimizing potential for off-target effects. This electroporation method is optimized herein. Embodiments described herein provide a method of electroporating cells in a solution comprising glycerol. This method increases the yield of viable cells containing the RNPs following electroporation.

Secondly, chemically modified, synthesized sgRNAs yield high editing efficiencies in primary CD34+ HSPCs via electroporation. See FIG. 5. An example of a specific chemical modification of the guide RNA is 2'-O-methyl 3'phosphorothioate (MS) which was incorporated at three terminal nucleotides at both the 5' and 3' ends.

Thirdly, the combination of both chemically modified, synthesized sgRNAs and sgRNA delivery by electroporation provide efficient BCL11A enhancer editing and BCL11A silencing.

The inventors also found that both single and paired cleavages at the BCL11A enhancer result in dramatic elevation of fetal globin expression. See FIG. 7B. Genome editing of the BCL11A enhancer by paired guide RNAs increases erythroid γ-globin levels in CD34+ HSPCs. See FIG. 7B.

Accordingly, in one aspect, provided herein are chemically modified synthetic nucleic acid molecules that target the BCL11A enhancer functional region or BCL11A exon 2 region. Specifically, targeting the three BCL11A enhancer functional regions, +62, +58, and +55, or the exon 2 region. These chemically modified nucleic acid molecules are guide RNAs for use with a DNA-targeting endonuclease Cas (CRISPR-associated) protein in a ribonucleoprotein (RNP) complex via electroporation to edit the BCL11A genomic regions, at the BCL11A enhancer functional region or BCL11A exon 2 region, thereby causing a reduction of BCL11A expression in the edited cell, for example, a CD34+ hematopoietic progenitor cell or a hematopoietic stem cell. Upon decreased BCL11A mRNA and protein in such cells, as they differentiate into mature red blood cells, there would be an increase in erythroid γ-globin levels in these cells compared to cells that had not undergone targeting editing at the BCL11A locus. These resultant cells with increased erythroid γ-globin levels can be used to treat a hemoglobinopathy in a mammal, such as β-thalassemia and sickle cell anemia. In fact, edited BCL11A CD34+ hematopoietic progenitor cell or a hematopoietic stem cell can be transplanted into individuals with a hemoglobinopathy as a cell-based gene therapy treatment for the hemoglobinopathy.

Also in other aspects, provided herein compositions comprising the modified synthetic nucleic acid molecules, and methods for increasing fetal hemoglobin levels in a cell by disrupting BCL11A expression at the genomic level. Also provided herein are methods and compositions relating to the treatment of hemoglobinopathies by reinduction of fetal hemoglobin levels.

In one aspect, provided herein is a modified synthetic nucleic acid molecule comprising a nucleic acid sequence shown in Table 1, SEQ ID NOS: 1-139, wherein there is at least one chemical modification to a nucleotide in the nucleic acid molecule.

In one aspect, provided herein is a modified synthetic nucleic acid molecule described herein for use in the ex vivo targeted genome editing of the BCL11A erythroid enhancer DHS +62, +58, or +55 functional regions or the BCL11A exon 2 region in a progenitor cell. purpose In one aspect, provided herein is a modified synthetic nucleic acid molecule described herein for use in an ex vivo method of producing a progenitor cell or a population of progenitor cells wherein the cells or the differentiated progeny therefrom have decreased BCL11A mRNA or protein expression.

In one aspect, provided herein is a modified synthetic nucleic acid molecule described herein for use in an ex vivo method of producing an isolated genetic engineered human cell or a population of genetic engineered human cells having at least one genetic modification.

In one aspect, provided herein is a modified synthetic nucleic acid molecule described herein for use in an ex vivo method of increasing fetal hemoglobin levels in a cell or in a mammal.

In one aspect, provided herein is a composition comprising a modified synthetic nucleic acid molecule described herein, i.e., a modified synthetic nucleic acid molecule comprising a nucleic acid sequence shown in Table 1, SEQ ID NOS: 1-139, wherein there is at least one chemical modification to a nucleotide in the nucleic acid molecule.

In one aspect, provided herein is a composition comprising modified synthetic nucleic acid molecule described herein for use in the ex vivo targeted genome editing of the BCL11A erythroid enhancer DHS +62, +58, or +55 functional regions or the BCL11A exon 2 region in a progenitor cell. purpose In one aspect, provided herein is a composition comprising modified synthetic nucleic acid molecule described herein for use in an ex vivo method of producing a progenitor cell or a population of progenitor cells wherein the cells or the differentiated progeny therefrom have decreased BCL11A mRNA or protein expression.

In one aspect, provided herein is a composition comprising modified synthetic nucleic acid molecule described herein for use in an ex vivo method of producing an isolated genetic engineered human cell or a population of genetic engineered human cells having at least one genetic modification.

In one aspect, provided herein is a composition comprising modified synthetic nucleic acid molecule described herein for use in an ex vivo method of increasing fetal hemoglobin levels in a cell or in a mammal.

In one aspect, provided herein is a ribonucleoprotein (RNP) complex comprising a DNA-targeting endonuclease Cas (CRISPR-associated) protein and a modified synthetic nucleic acid molecule described herein, i.e., a modified synthetic nucleic acid molecule comprising a nucleic acid sequence shown in Table 1, SEQ ID NOS: 1-139, wherein there is at least one chemical modification to a nucleotide in the nucleic acid molecule.

In one aspect, provided herein is a RNP complex described herein for use in the ex vivo targeted genome editing of the BCL11A erythroid enhancer DHS +62, +58, or +55 functional regions or the BCL11A exon 2 region in a progenitor cell.

In one aspect, provided herein is a RNP complex described herein for use in an ex vivo method of producing a progenitor cell or a population of progenitor cells wherein the cells or the differentiated progeny therefrom have decreased BCL11A mRNA or protein expression.

In one aspect, provided herein is a RNP complex described herein for use in an ex vivo method of producing an isolated genetic engineered human cell or a population of genetic engineered human cells having at least one genetic modification.

In one aspect, provided herein is a RNP complex described herein for use in an ex vivo method of increasing fetal hemoglobin levels in a cell or in a mammal.

In one aspect, provided herein is a method for producing a progenitor cell or a population of progenitor cells having decreased BCL11A mRNA or protein expression, the method comprising contacting an isolated progenitor cell with an effective amount of a composition comprising a modified synthetic nucleic acid molecule described herein or a RNP complex described herein, whereby the contacted cells or the differentiated progeny cells therefrom have decreased BCL11A mRNA or protein expression.

In one aspect, provided herein is a method for producing an isolated genetic engineered human cell or a population of genetic engineered isolated human cells having at least one genetic modification, the method comprising contacting an isolated cell or a population of cells with an effective amount of a composition comprising a modified synthetic nucleic acid molecule described herein or a RNP complex described herein, wherein the at least one genetic modification produced is located in human chromosome 2 is that according to UCSC Genome Browser hg 19 human genome assembly.

In one aspect, provided herein is a method of increasing fetal hemoglobin levels in a cell, the method comprising the steps of: contacting an isolated cell with an effective amount of a composition comprising a modified synthetic nucleic acid molecule described herein or a RNP complex described herein, thereby causing at least one genetic modification at the human chromosome 2 is that according to UCSC Genome Browser hg 19 human genome assembly therein, whereby fetal hemoglobin expression is increased in said cell, or its progeny, relative to said cell prior to said contacting.

In one aspect, provided herein is an isolated genetic engineered human cell or a population of genetic engineered human cells having at least one genetic modification on chromosome 2 location 60725424 to 60725688 (+55 functional region), or at location 60722238 to 60722466 (+58 functional region), or at location 60718042 to 60718186 (+62 functional region), or at location 60773106 to 60773435 (exon 2) according to the methods described herein, wherein the genetic modification arise from the genomic editing made via said methods.

In one aspect, provided herein is a population of genetically edited progenitor cells having at least one genetic modification on chromosome 2 location 60725424 to 60725688 (+55 functional region), or at location 60722238 to 60722466 (+58 functional region), or at location 60718042 to 60718186 (+62 functional region), or at location 60773106 to 60773435 (exon 2) according to the methods described herein, wherein the genetic modification arise from the genomic editing made via said methods.

In one aspect, provided herein is a composition of genetic engineered human cells having at least one genetic modification on chromosome 2 location 60725424 to 60725688 (+55 functional region), or at location 60722238 to 60722466 (+58 functional region), or at location 60718042 to 60718186 (+62 functional region), or at location 60773106 to 60773435 (exon 2), according to the methods described herein, wherein the genetic modification arise from the genomic editing made via said methods.

In one aspect, provided herein is a composition of a population of genetically edited progenitor cells having at least one genetic modification on chromosome 2 location 60725424 to 60725688 (+55 functional region), or at location 60722238 to 60722466 (+58 functional region), or at location 60718042 to 60718186 (+62 functional region), or at location 60773106 to 60773435 (exon 2) according to the methods described herein, wherein the genetic modification arise from the genomic editing made via said methods.

In one aspect, provided herein is a method for increasing fetal hemoglobin levels in a mammal in need thereof, the method comprising the steps of (a) ex vivo contacting an isolated hematopoietic progenitor cell isolated from said mammal with an effective amount of a composition of comprising a modified synthetic nucleic acid molecule described herein or a RNP complex described herein whereby the DNA-targeting endonuclease cleaves the genomic DNA of the cell on chromosome 2 at location 60725424 to 60725688 (+55 functional region), at location 60722238 to 60722466 (+58 functional region), or at location 60718042 to 60718186 (+62 functional region), or at location 60773106 to 60773435 (exon 2), causing at least one genetic modification therein, whereby fetal hemoglobin expression is increased in said cell or the differentiated progeny cells therefrom, relative to expression prior to said contacting, and wherein the human chromosome 2 is that according to UCSC Genome Browser hg 19 human genome assembly; and (b) transplanting the contacted cells of (a) or culture-expanded cells therefrom into said mammal.

In one aspect, provided herein is a method for increasing fetal hemoglobin levels in a mammal in need thereof, the method comprising transplanting into the mammal: (a) an isolated genetic engineered human cell or a population of genetic engineered human cells having at least one genetic modification on chromosome 2 location 60725424 to 60725688 (+55 functional region), or at location 60722238 to 60722466 (+58 functional region), or at location 60718042 to 60718186 (+62 functional region), or at location 60773106 to 60773435 (exon 2) made according to the methods described herein, or (b) a population of genetically edited progenitor cells having at least one genetic modification on chromosome 2 location 60725424 to 60725688

(+55 functional region), or at location 60722238 to 60722466 (+58 functional region), or at location 60718042 to 60718186 (+62 functional region), or at location 60773106 to 60773435 (exon 2) made according to the methods described herein, or (c) a composition of genetic engineered human cells described in (a) or (d) a composition of genetically edited progenitor cells described in (b), or the progeny cells from of (a) or (b).

In one aspect, this disclosure provides a method of treatment of a hemoglobinopathy in a mammal (e.g. a human) comprising increasing fetal hemoglobin expression in the mammal by transplanting into the mammal: (a) an isolated genetic engineered human cell or a population of genetic engineered human cells having at least one genetic modification on chromosome 2 location 60725424 to 60725688 (+55 functional region), or at location 60722238 to 60722466 (+58 functional region), or at location 60718042 to 60718186 (+62 functional region), or at location 60773106 to 60773435 (exon 2) made according to the methods described herein, or (b) a population of genetically edited progenitor cells having at least one genetic modification on chromosome 2 location 60725424 to 60725688 (+55 functional region), or at location 60722238 to 60722466 (+58 functional region), or at location 60718042 to 60718186 (+62 functional region), or at location 60773106 to 60773435 (exon 2) made according the methods described herein, or (c) a composition of genetic engineered human cells described in (a) or (d) a composition of genetically edited progenitor cells described in (b), or the progeny cells from of (a) or (b).

In one aspect, this disclosure provides a method of treatment of a hemoglobinopathy in a mammal (e.g. a human) comprising (a) providing a population of hematopoietic progenitor cell or a hematopoietic stem cells from the mammal; (b) ex vivo contacting said isolated hematopoietic progenitor cell isolated from said mammal with an effective amount of a composition of comprising a modified synthetic nucleic acid molecule described herein or a RNP complex described herein whereby the DNA-targeting endonuclease cleaves the genomic DNA of the cell on chromosome 2 at location 60725424 to 60725688 (+55 functional region), at location 60722238 to 60722466 (+58 functional region), or at location 60718042 to 60718186 (+62 functional region), or at location 60773106 to 60773435 (exon 2), causing at least one genetic modification therein, whereby fetal hemoglobin expression is increased in said cell or the differentiated progeny cells therefrom, relative to expression prior to said contacting, and wherein the human chromosome 2 is that according to UCSC Genome Browser hg 19 human genome assembly; and (c) transplanting the contacted cells of (b) or culture-expanded cells therefrom into said mammal.

In one embodiment of this aspect and all other aspects described herein, the nucleic acid sequence of the modified synthetic nucleic acid molecule excludes the entire BCL11A enhancer functional regions.

In one embodiment of this aspect and all other aspects described herein, the nucleic acid sequence of the modified synthetic nucleic acid molecule excludes excludes the entire BCL11A coding region.

In one embodiment of this aspect and all other aspects described herein, the nucleic acid sequence of the modified synthetic nucleic acid molecule excludes excludes the entire BCL11A enhancer functional regions, that is excluding the entire region between the human chromosome 2 location 60725424 to 60725688 (DHS +55 functional region), or excludes the entire region at location 60722238 to 60722466 (DHS +58 functional region), or excludes the entire region at location 60718042 to 60718186 (DHS +62 functional region), or excludes the entire region at location 60773106 to 60773435 (exon 2) of the human chromosome 2 is that according to UCSC Genome Browser hg 19 human genome assembly.

In one embodiment of this aspect and all other aspects described herein, the modified synthetic nucleic acid molecule comprises a sequence selected from the group consisting of SEQ ID NOS: 1-139 or Table 1.

In one embodiment of this aspect and all other aspects described herein, the modified synthetic nucleic acid molecule comprises a sequence selected from the group consisting of SEQ ID NOS: 37, 38, 39, 40, 41, 42, 43, 44, 45, 46, 47, 48, 50, 51, 52, 53, 54, 55, 56, 57, and 62 as shown in Table 2.

In one embodiment of this aspect and all other aspects described herein, the chemical modifications on the modified synthetic nucleic acid molecule are located at one or more terminal nucleotides in nucleic acid molecule.

In one embodiment of this aspect and all other aspects described herein, the chemical modification is selected from the group consisting of 2'-O-methyl 3'phosphorothioate (MS), 2'-O-methyl-3'-phosphonoacetate (MP), 2'-0-Ci-4alkyl, 2'-H, 2'-0-Ci.3alkyl-0-Ci.3alkyl, 2'-F, 2'-NH2, 2'-arabino, 2'-F-arabino, 4'-thioribosyl, 2-thioU, 2-thioC, 4-thioU, 6-thioG, 2-aminoA, 2-aminopurine, pseudouracil, hypoxanthine, 7-deazaguanine, 7-deaza-8-azaguanine, 7-deazaadenine, 7-deaza-8-azaadenine, 5-methylC, 5-methylU, 5-hydroxymethylcytosine, 5-hydroxymethyluracil, 5,6-dehydrouracil, 5-propynylcytosine, 5-propynyluracil, 5-ethynylcytosine, 5-ethynyluracil, 5-allylU, 5-allylC, 5-aminoallyl-uracil, 5-aminoallyl-cytosine, an abasic nucleotide ("abN"), Z, P, UNA, isoC, isoG, 5-methyl-pyrimidine, x(A,G,C,T) and y(A,G,C,T), a phosphorothioate internucleotide linkage, a phosphonoacetate internucleotide linkage, a thiophosphonoacetate internucleotide linkage, a methylphosphonate internucleotide linkage, a boranophosphonate internucleotide linkage, a phosphorodithioate internucleotide linkage, 4'-thioribosyl nucleotide, a locked nucleic acid ("LNA") nucleotide, an unlocked nucleic acid ("ULNA") nucleotide, an alkyl spacer, a heteroalkyl (N, O, S) spacer, a 5'- and/or 3'-alkyl terminated nucleotide, a Unicap, a 5'-terminal cap known from nature, an xRNA base (analogous to "xDNA" base), an yRNA base (analogous to "yDNA" base), a PEG substituent, and a conjugated linker to a dye or non-fluorescent label (or tag).

In one embodiment of this aspect and all other aspects described herein, the chemical modification is located only at the 3' end, or added only at the 5' end, or added at both the 5' and 3' ends of the synthetic nucleic acid molecule.

In one embodiment of any one aspects described herein, the chemical modification is located to first three nucleotides and to the last three nucleotides of the synthetic nucleic acid molecule.

In one embodiment of any one aspects described herein, the nucleic acid sequence further comprising a crRNA/tracrRNA sequence. The crRNA/tracrRNA sequence is a hybrid sequence for the binding of DNA-targeting endonuclease is a Cas (CRISPR-associated) protein in forming the gene editing ribonucleoprotein (RNP) complex.

In one embodiment of any one aspects described herein, the nucleic acid molecule is a single guide RNA (sgRNA).

In one embodiment of any one aspects described herein, the modified synthetic nucleic acid molecule is used in combination with a DNA-targeting endonuclease Cas (CRISPR-associated) protein in a ribonucleoprotein (RNP) complex.

In one embodiment of any one aspects described herein, the RNP complex is used in the electroporation of cells.

In one embodiment of any one aspects described herein, the composition comprising a modified synthetic nucleic acid molecule further comprising a DNA-targeting endonuclease Cas (CRISPR-associated) protein.

In one embodiment of any one aspects described herein, the composition comprising a modified synthetic nucleic acid molecule is used in the electroporation of cells.

In one embodiment of any one aspects described herein, the contacted progenitor cell or contacted cell are further electroporated.

In one embodiment of any one aspects the step of electroporation is performed in a solution comprising glycerol.

In one embodiment of any one aspects described herein, the DNA-targeting endonuclease is a Cas (CRISPR-associated) protein.

In one embodiment of any one aspects described herein, the Cas protein is Cas 9.

Methods described herein can be used with any Cas 9 protein:sgRNA ribonucleoproteins (RNP) known in the art. Exemplary Cas 9 protein include, but are not limited to Cas 9 nickase, catalytic inactive Cas 9 alone, catalytic inactive Cas 9 linked to other effectors, such as methyltransferases, and Cas 9 base editors In one embodiment of this aspect and all other aspects described herein, the Cas 9 protein is a recombinant protein, a nickase, or a functional catalytic domain of a Cas 9 protein.

In one embodiment of this aspect and all other aspects described herein, the isolated progenitor cell or isolated cell is a hematopoietic progenitor cell or a hematopoietic stem cell.

In one embodiment of this aspect and all other aspects described herein, the hematopoietic progenitor is a cell of the erythroid lineage.

In one embodiment of this aspect and all other aspects described herein, the isolated progenitor cell or isolated cell is an induced pluripotent stem cell.

In one embodiment of this aspect and all other aspects described herein, the isolated progenitor cell or isolated cell is contacted ex vivo or in vitro.

In one embodiment of this aspect and all other aspects described herein, the contacted progenitor cell or contacted cell acquires at least one genetic modification.

In one embodiment of this aspect and all other aspects described herein, the at least one genetic modification is a deletion, insertion or substitution of the nucleic acid sequence.

In one embodiment of this aspect and all other aspects described herein, the at least one genetic modification is a deletion.

In one embodiment of this aspect and all other aspects described herein, the least one genetic modification is located between chromosome 2 location 60725424 to 60725688 (+55 functional region), or at location 60722238 to 60722466 (+58 functional region), or at location 60718042 to 60718186 (+62 functional region), or at location 60773106 to 60773435 (exon 2) of the human chromosome 2 is that according to UCSC Genome Browser hg 19 human genome assembly.

In one embodiment of this aspect and all other aspects described herein, the contacted progenitor cell or contacted cell acquires at least one epigenetic modification in the BCL11A enhancer functional region.

In one embodiment of this aspect and all other aspects described herein, the at least one epigenetic modification is selected from the group consisting of alteration of DNA methylation, histone tail modification, histone subunit composition and nucleosome positioning.

In one embodiment of this aspect and all other aspects described herein, the at least one epigenetic modification is located between chromosome 2 location 60725424 to 60725688 (+55 functional region), at location 60722238 to 60722466 (+58 functional region), and/or at location 60718042 to 60718186 (+62 functional region), or at location 60773106 to 60773435 (exon 2) of the human chromosome 2 is that according to UCSC Genome Browser hg 19 human genome assembly.

In one embodiment of any one aspects described herein, the contacted cells or the differentiated progeny cells therefrom further have increased fetal hemoglobin levels.

In one embodiment of any one aspects described herein, the contacted cells or the differentiated progeny cells therefrom further have decreased BCL11A mRNA or protein expression compared to non-contacted control cells.

In one embodiment of any one aspects described herein, the isolated genetic engineered human cell or a population of genetic engineered human cells described herein or the differentiated progeny cells therefrom have increased fetal hemoglobin levels.

In one embodiment of any one aspects described herein, the genetically edited progenitor cells described herein or the differentiated progeny cells therefrom have increased fetal hemoglobin levels.

In one embodiment of any one aspects described herein, the isolated genetic engineered human cell or a population of genetic engineered human cells described herein or the differentiated progeny cells therefrom have decreased BCL11A mRNA or protein expression compared to non-contacted control cells.

In one embodiment of any one aspects described herein, the genetically edited progenitor cells described herein or the differentiated progeny cells therefrom have decreased BCL11A mRNA or protein expression compared to non-contacted control cells.

In one embodiment of this aspect and all other aspects described herein, the isolated cell or isolated population of cells used in the contacting, the methods described herein, or electroporation described herein is/are human cell(s).

In one embodiment of this aspect and all other aspects described herein, the isolated cell or isolated population of cells used in the contacting, the methods described herein, or electroporation described herein is/are progenitor cell(s).

In one embodiment of this aspect and all other aspects described herein, the human cell is a hematopoietic progenitor cell.

In one embodiment of this aspect and all other aspects described herein, the human cell is an induced pluripotent stem cell.

In one embodiment of this aspect and all other aspects described herein, the induced pluripotent stem cell is hematopoietic progenitor cell.

In one embodiment of this aspect and all other aspects described herein, the hematopoietic progenitor is a cell of the erythroid lineage.

In one embodiment of this aspect and all other aspects described herein, the hematopoietic progenitor cell or isolated is contacted ex vivo or in vitro or in vivo.

In further embodiment of any one treatment method described, the method comprises chemotherapy and/or radiation therapy to remove or reduced the endogenous hematopoietic progenitor or stem cells in the mammal.

In one embodiment of any one method described herein, the contacted cells, targeted gene edited cells described herein having at least one genetic modification can be cryopreserved and stored until the cells are needed for administration into a mammal.

In one embodiment of any one method described herein, the contacted cells, targeted gene edited cells described herein having at least one genetic modification can be cultured ex vivo to expand or increase the number of cells prior to storage, eg. by cryopreservation, or prior to use, e.g., transplanted into a recipient mammal, e.g., a patient.

In one embodiment of any described method, the hematopoietic progenitor or stem cells or isolated cells can be substituted with an iPSCs described herein.

In one embodiment of any described method, the hematopoietic progenitor or stem cells or iPSCs or isolated cells are autologous to the mammal, meaning the cells are derived from the same mammal. In another of the embodiments of the described method, the hematopoietic progenitor or stem cells or iPSCs or isolated cells are non-autologous to the mammal, meaning the cells are not derived from the same mammal, but another mammal of the same species. For example, the mammal is a human.

In one embodiment of any treatment method described, the method further comprises selecting a mammal in need of increased fetal hemoglobin expression, such as a mammal having a hemoglobinopathy.

In one embodiment of any treatment method described, the method further comprises selecting a mammal in need of treatment of a hemoglobinopathy.

In any embodiment of any treatment method described, the hemoglobinopathy is α-hemoglobinopathy.

In any embodiment of any treatment method described, the hemoglobinopathy is β-thalassemia.

In any embodiment of any treatment method described, the hemoglobinopathy is sickle cell anemia.

BRIEF DESCRIPTION OF DRAWINGS

FIG. 3 discloses SEQ ID NO: 232.

FIG. 4 shows genome editing of the BCL11A enhancer increases erythroid expression of γ-globin in HUDEP-2 cells. Left panel: Cas9 RNP induces disruption of the BCL11A enhancer in HUDEP-2 cells. Right panel: Several guides targeting BCL11A erythroid enhancer dramatically induce the elevation of γ-globin.

FIGS. 10A-10G. show identification of efficient BCL11A enhancer guide RNAs for HbF induction. (FIG. 10A) Eight modified synthetic (MS) sgRNAs targeting BCL11A enhancer DHS h+58 functional core marked with blue arrows. GATA and Half E-box motifs marked respectively with red or green. FIG. 10A discloses SEQ ID NO: 233. (FIG. 10B) Editing efficiency of Cas9 coupled with various sgRNAs (each targeting BCL11A enhancer with exception of AAVS1) in CD34+ HSPCs measured by TIDE analysis. (FIGS. 10C and 10D) β-like globin expression by RT-qPCR, and HbF induction by HPLC analysis in erythroid cells in vitro differentiated from RNP edited CD34+ HSPCs. (FIG. 10E) Correlation of BCL11A mRNA expression determined by RT-qPCR versus HbF by HPLC. Black dots represent samples edited with Cas9 coupled with different sgRNAs. BCL11A expression normalized to CAT measured by RT-qPCR on day 11 of differentiation. HbF level was determined on day 18 of differentiation. The Pearson correlation coefficient ($r^2$) is shown. (FIG. 10F) Summary of deep sequencing data derived from the Cas9 RNP (coupled with MS-sgRNA-1617) edited CD34+ HSPCs. Asterisk indicates unedited allele. FIG. 10F discloses SEQ ID NOS 234-235, 234 and 236-248, respectively, in order of appearance. (FIG. 10G) Genotyping and β-like globin expression analysis of clonal erythroid cells derived from single CD34+ HSPCs. Error bars indicate standard deviation (n=3 replicates).

FIG. 11A-11I show amelioration of β-thalassemia pathophysiology by BCL11A enhancer editing. (FIG. 11A) Editing efficiency of Cas9:sgRNA RNP targeting AAVS1 or BCL11A DHS h+58 functional core (Enh) with MS-sgRNA-1617 in CD34+ HSPCs from β-thalassemia patients ($\beta^0\beta^0$, $\beta^+\beta^0$, $\beta^+\beta^+$, $(^A\gamma\delta\beta)^0\beta^0$ and $\beta^E\beta^0$) genotypes) as measured by TIDE analysis. (FIG. 11B-11D) β-like globin expression by RT-qPCR normalized by α-globin, and HbF induction by HPLC analysis in erythroid cells in vitro differentiated from RNP edited CD34+ HSPCs of indicated β-thalassemia β-globin genotype or healthy donors ($\beta^A\beta^A$). (FIG. 11E) Enucleation of in vitro differentiated erythroid cells from healthy donors or β-thalassemia patients as measured by flow cytometry in 7 β-thalassemia samples and 3 healthy controls. (FIG. 11F) Cell size measured by relative forward scatter intensity in 7 β-thalassemia samples and 3 healthy controls. (FIG. 11G) Representative microscopy image showing rounder and more uniform appearance of enucleated erythroid cells following BCL11A enhancer editing. Blue arrow indicates poikilocytes. (FIGS. 11H and 11I) Imaging flow cytometry was used to establish a circularity index (FIG. 11H) and then quantify (FIG. 11I) circularity of enucleated erythroid cells in 6 β-thalassemia samples and 2 healthy controls. Error bars indicate standard deviation (n=3 replicates).

FIG. 12A-12I show long-term multi-lineage engraftment of BCL11A enhancer edited HSPCs in immunodeficient mice. CD34$^+$ HSPCs from two healthy donors were electroporated with SpCas9 RNP (coupled with MS-sgRNA-1617) and transplanted into NBSGW mice. Non-electroporated cells were transplanted as controls. 0.4 million cells per mouse were infused for donor $β^Aβ^A_{\#1}$, and 0.8 million cells per mouse for donor $β^Aβ^A_{\#2}$. (FIG. 12A) Mouse bone marrow (BM) was analyzed for human cell chimerism by flow cytometry 16 weeks after transplantation, defined as % hCD45$^+$/(% hCD45$^+$+% mCD45$^+$) cells. Each symbol represents a mouse, and mean for each group is shown. (FIG. 12B) Indels at the human BCL11A enhancer were determined by TIDE analysis in the input HSPCs prior to transplant and in the mouse bone marrow 16 weeks after transplant. Each engrafted dot represents one mouse, and mean for each group is shown. (FIG. 12C) BM collected 16 weeks after transplantation was analyzed by flow cytometry for multilineage reconstitution (calculated as percentage of hCD45$^+$ cells). (FIG. 12D) BM collected 16 weeks after transplantation was analyzed by flow cytometry for CD235a$^+$ erythroid cells (calculated as percentage of mCD45$^-$hCD45$^-$ cells). (FIG. 12E-12G) Gene expression analysis by RT-qPCR in human cells (from donor $β^Aβ^A_{\#2}$) from BM of engrafted mice. BCL11A expression normalized by CAT in human B cells (FIG. 12E) or human erythroid cells (FIG. 12F) sorted from BM of engrafted mice, and β-like globin expression (FIG. 12G) by RT-qPCR in human erythroid cells sorted from BM. (FIG. 12H) BM from one engrafted mouse with unedited control or edited cells (from donor $β^Aβ^A_{\#1}$) were transplanted to three secondary NBSGW mice each (control mouse shown with black circle and edited mouse with green diamond symbol in (FIG. 12A, 12B, 12D). After 16 weeks, BM was analyzed for human cell chimerism by flow cytometry. (FIG. 12I) Indel frequencies within human BCL11A enhancer in BM 16 weeks after secondary transplantation. Each symbol represents an individual recipient mouse.

FIG. 13A-13N show highly efficient BCL11A enhancer editing in HSCs. (FIG. 13A) Schematic of 3×NLS-SpCas9 protein (1425 aa). SpCas9 was fused with a c-Myc nuclear localization signal (NLS) at the N-terminus and SV40 and Nucleoplasmin NLSs at the C-terminus. FIG. 13F discloses SEQ ID NOS 234-237, 240, 239, 234, 241, 249, 245, 250-251, 238 and 252-256, respectively, in order of appearance. (FIG. 13G) Western blot analysis showing reduction of BCL11A protein after editing of human BCL11A enhancer with 2×NLS-Cas9 or 3×NLS-Cas9 RNP (MS-sgRNA-AAVS1 or MS-sgRNA-1617) at indicated days of in vitro differentiation. (FIG. 13H-13K) NBSGW mice transplanted with 3×NLS-Cas9 RNP (coupled with MS-sgRNA-1617) edited CD34$^+$ HSPCs. BM collected 16 weeks after transplantation were analyzed by flow cytometry for human cell chimerism (FIG. 13H), multilineage reconstitution (FIG. 13I) or human erythroid cells (FIG. 13J) in BM, as well as the indel frequencies determined by TIDE analysis (FIG. 13K). Error bars indicate standard deviation. (FIG. 13L-13N) RT-qPCR analysis of BCL11A expression in sorted human B cells (FIG. 13 FIG. 13L) or human erythroid cells (FIG. 13M) and β-like globin expression in sorted human erythroid cells (FIG. 13N) from NBSGW mice transplanted with 3×NLS RNP edited CD34$^+$ HSPCs.

FIG. 14A-14B show off-target analysis of human CD34$^+$ HSPCs edited by SpCas9 RNP targeting BCL11A enhancer. FIG. 14A discloses SEQ ID NOS 257, 257-260, 257, 257, 259, 258, 261-271, 257, 257, 259, 258, 272, 263, 273, 261, 269, 274, 262, 265, 267, 275, 271, 266 and 276-277, respectively, in order of appearance. (FIG. 14A) Off-target sites detected by CIRCLE-seq for MS-sgRNA-1617 targeting human BCL11A enhancer. (FIG. 14B) Deep sequencing analysis of potential off-target sites detected by CIRCLE-seq or in silico computational prediction within human CD34$^+$ HSPCs edited by 2×NLS-Cas9 or 3×NLS-Cas9 RNP (coupled with MS-sgRNA-1617) targeting BCL11A enhancer. On-target sequence is at the BCL11A enhancer. Dotted line at 0.1% denotes sensitivity of deep sequencing to detect indels. FIG. 14B discloses SEQ ID NOS 278-302, respectively, in order of appearance.

FIG. 15A-15L show editing BCL11A enhancer in SCD patient HSCs prevents sickling. (FIG. 15A) Editing efficiency of 3×NLS-Cas9 coupled with MS-sgRNA-AAVS1 for control and -1617 for BCL11A enhancer editing in $β^Sβ^S$ CD34$^+$ HSPCs as measured by TIDE analysis. (FIG. 15B) β-like globin expression by RT-qPCR analysis in erythroid cells in vitro differentiated from RNP edited $β^Sβ^S$ CD34$^+$ HSPCs. Error bars indicate standard deviation (n=3 replicates). (FIG. 15C) Genotyping and β-like globin expression analysis of erythroid cells derived from single CD34$^+$ clones derived from unedited (ctr) or edited $β^Sβ^S$ CD34$^+$ HSPCs. (FIGS. 15D and 15E) NBSGW mice were transplanted with 3×NLS-Cas9 RNP (coupled with MS-sgRNA-1617) edited $β^Sβ^S$ CD34$^+$ HSPCs. BM were collected 16 weeks after transplantation and analyzed by flow cytometry for human cell chimerism (FIG. 15D) in BM, as well as the indel frequencies determined by TIDE analysis (FIG. 15E). Error bars indicate standard deviation. (FIGS. 15F-15H) RT-qPCR analysis of BCL11A expression in sorted human B cells (FIG. 15F) or human erythroid cells (FIG. 15G) and β-like globin expression in human erythroid cells sorted from BM (FIG. 15H). (FIG. 15I) BM from one mouse each engrafted with unedited control or edited cells (from donor $β^Sβ^S$, from control mouse shown with black circle and edited mouse with purple triangle symbols in (FIGS. 15D and 15E)) were transplanted to three secondary NBSGW mice. After 16 weeks, BM was analyzed for human cell chimerism by flow cytometry. (FIG. 15J) Indel frequencies within human BCL11A enhancer in BM 16 weeks after secondary transplantation. (FIG. 15K) Phase-contrast microscopy imaging of enucleated erythroid cells in vitro differentiated from BM of NBSGW mice transplanted with unedited or BCL11A enhancer edited $β^Sβ^S$ CD34$^+$ HSPCs with and without sodium metabisulfite (MBS) treatment. Cells with sickled cell morphology are indicated with red arrows. Bar=10 μm. (FIG. 15L) Analysis of in vitro sickling of unedited control or edited enucleated $\beta^S\beta^S$ erythroid cells. Images were taken every 1 minute after MBS treatment. Result shown as percent sickled cells at each time point.

FIG. 16A-16D show persistence of NHEJ repaired alleles in HSCs. (FIG. 16A) BM cells collected from engrafted mice were in vitro differentiated to human erythroid cells for HbF level analysis by HPLC. Each dot represents erythroid cells differentiated from BM of one mouse, and mean±SD for each group is shown. (FIG. 16B) Correlation of indel frequencies of input HSPCs to indel frequencies of engrafted human cells in mice BM after 16 weeks. Each dot represents average indel frequencies of mice transplanted with the same input HSPCs. Legend denoting transplant is same as in (FIG. 16D). The Pearson correlation coefficient ($r^2$) is shown. (FIG. 16C) Indel spectrum of input cells from $\beta^A\beta^A_{\#2}$ electroporated with 2×NLS-Cas9 (coupled with sgRNA-1617) supplemented with 2% glycerol and engrafted 16 week BM human cells. (FIG. 16D) Relative loss of edited alleles repaired by MMEJ and gain of edited alleles repaired by NHEJ in mice BM 16 weeks after transplant. The indel spectrum was determined by TIDE analysis and validated by deep sequencing. Indel length from −8 to +6 bp was calculated as NHEJ, and from −9 to −20 bp as MMEJ. These data comprise 28 mice transplanted with 8 BCL11A enhancer edited inputs and 2 mice transplanted with 1 AAVS1 edited input. Median of each group is shown as line, $P<0.005$, **$P<0.0001$ as determined by Kolmogorov-Smirnov test.

(FIG. 17A) Comparison of indel frequencies with in vitro transcribed (IVT), synthetic (syn) and modified synthetic (MS) sgRNAs in CD34+ HSPCs by TIDE analysis. (FIG. 17B) Dose dependent editing rates with Cas9 coupled with MS-sgRNA-1617 and -1639 targeting BCL11A enhancer and -e2 targeting BCL11A exon2 in CD34+ HSPCs by TIDE analysis. (FIG. 17C) Comparison of indel frequencies with different molar ratios of Cas9 to MS-sgRNA in CD34+ HSPCs by TIDE analysis. (FIG. 17D) Percent HbF cells by flow cytometry analysis in erythroid cells in vitro differentiated from CD34+ HSPCs edited by RNP coupled with various sgRNAs (each targeting BCL11A enhancer). Error bars indicate standard deviation (n=3 replicates).

(FIG. 18A) Frequency distribution of alleles with and without indels (shown in blue and red respectively) from deep sequencing of CD34+ HSPCs edited with 2×NLS-Cas9 RNP with indicated MS-sgRNAs targeting BCL11A enhancer. (FIG. 18B) Correlation of indel frequencies by deep sequencing versus indel frequencies by TIDE analysis. The Pearson correlation coefficient ($r^2$) is shown.

FIG. 19A-19E show correlation of BCL11A expression with HbF level. (FIG. 19A) BCL11A expression in CD34+ HSPCs edited with Cas9 coupled with various MS-sgRNAs targeting BCL11A enhancer. Expression normalized to CAT, measured by RT-qPCR on day 11 of in vitro differentiation. Error bars indicate standard deviation (n=3 replicates). (FIG. 19B) Correlation of γ-globin mRNA expression determined by RT-qPCR versus HbF by HPLC. Black dots represent samples edited with 2×NLS-Cas9 coupled with various MS-sgRNAs. (FIG. 19C) Correlation of BCL11A mRNA versus γ-globin mRNA determined by RT-qPCR. Black dots represent samples edited with 2×NLS-Cas9 coupled with various sgRNAs. (FIG. 19D) Genotyping and HbF level by HPLC of clonal erythroid cells derived from single CD34+ cells edited with MS-sgRNA-1617. (FIG. 19E) Correlation of percent γ-globin mRNA determined by RT-qPCR versus HbF by HPLC. Black dots represent single clones edited with 2×NLS-Cas9 coupled with MS-sgRNA-1617. The Pearson correlation coefficient ($r^2$) is shown.

FIG. 20A-20G show highly efficient editing of BCL11A enhancer in CD34+ HSPCs. (FIG. 20A) Dose dependent viability enhancement with glycerol or glycine after electroporation. 0.27 M=2% glycerol, 0.2 M=1.5% glycine. (FIG. 20B) Quantification of editing frequency from deep sequencing of CD34+ HSPCs edited with 3×NLS-Cas9 RNP with MS-sgRNA-1617. (FIG. 20C) Length distribution of alleles with and without indels (shown in blue and red respectively) from deep sequencing of the 2×NLS-Cas9 RNP with ms-sgRNA-1617. (FIGS. 20D and 20E) Reduction of BCL11A mRNA by RT-qPCR or protein by western blot after editing of human BCL11A enhancer with 2×NLS-Cas9 or 3×NLS-Cas9 RNP with MS-sgRNA-AAVS1 or -1617 on various days of in vitro differentiation. Relative areas under curve (AUCs) are indicated. (FIGS. 20F and 20G) β-like globin expression by RT-qPCR and HbF level by HPLC in erythroid cells in vitro differentiated from 3×NLS-Cas9 RNP coupled with MS-sgRNA-1617 edited CD34+ HSPCs. All data represent the mean±SD. Statistically significant differences are indicated as follows: *$P<0.05$ as determined by unpaired t test.

FIG. 21A-21H show long-term multi-lineage reconstituting HSCs edited with 3×NLS-Cas9. (FIG. 21A-21D) NBSGW mice were transplanted with 3×NLS-Cas9 RNP with MS-sgRNA-1617 edited CD34+ HSPCs 2 h (day 0), 24 h (day 1) or 48 h (day 2) after electroporation. BM were collected 16 weeks after transplantation and analyzed by flow cytometry for human cell chimerism (FIG. 21A), multilineage reconstitution (FIG. 21B) or human erythroid cells (FIG. 21C) in BM, as well as indel frequencies determined by TIDE analysis (FIG. 21D). (FIG. 21E-21H) NBSGW mice were transplanted with 3×NLS-Cas9 RNP with MS-sgRNA-1617 edited CD34+ HSPCs supplemented with 2%, 4% or 6% of glycerol for electroporation. BM were collected 16 weeks after transplantation and analyzed by flow cytometry for human cell chimerism (FIG. 21E), multilineage reconstitution (FIG. 21F) or human erythroid cells (FIG. 21G) in BM, as well as the indel frequencies determined by TIDE analysis (FIG. 21H). Error bars indicate standard deviation.

FIG. 23A-23C show summary of engraftment analysis. (FIG. 23A) Indel frequencies of indicated input HSPCs and engrafted human cells in 16 week BM. (FIG. 23B) Correlation between input cell number and human engraftment rates in 16 week BM. (FIG. 23C) Correlation of BCL11A mRNA versus γ-globin mRNA determined by RT-qPCR. Black dots represent erythroid cells from CD34+ HSPCs edited with SpCas9 coupled with various sgRNAs differentiated in vitro without engraftment; red dots represent erythroid cells sorted from mice BM engrafted from human CD34+ HSPCs edited with SpCas9 coupled with MS-sgRNA-1617. Error bars indicate standard deviation.

DETAILED DESCRIPTION

Figures 1, 2:
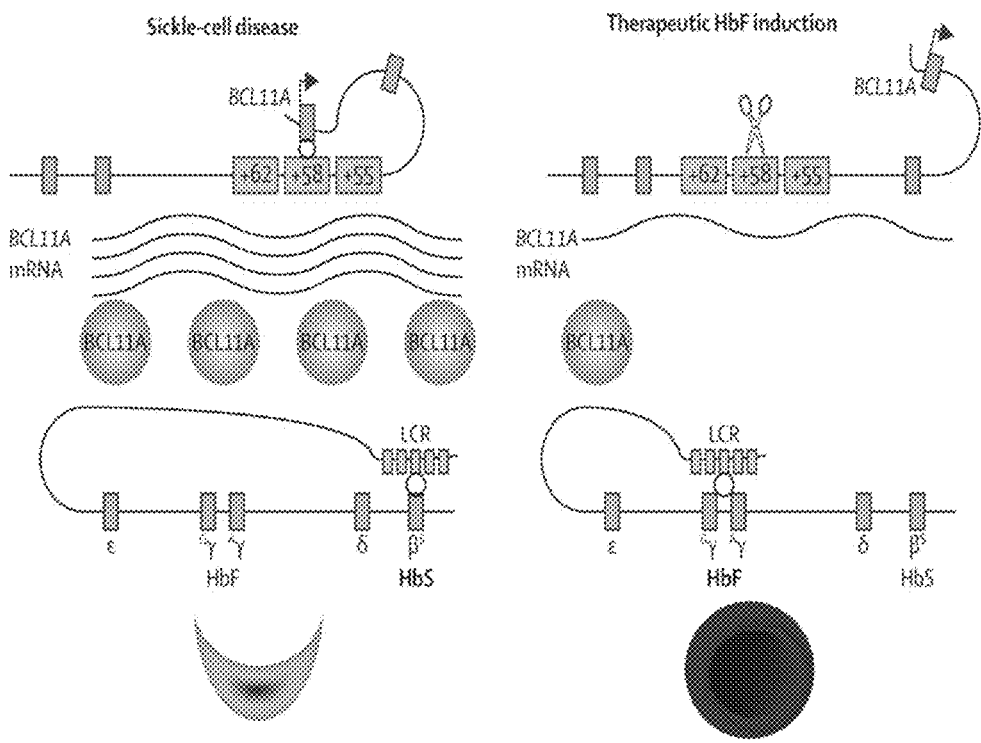
FIG. 1 shows curative approaches to sickle cell disease and β-thalassemia.
FIG. 2 shows therapeutic genome editing approach to induce fetal haemoglobin production in patients with sickle-cell disease FIG. 3. shows functional core of BCL11A +58 erythroid enhancer, with HbF enrichment score of individual sgRNAs depicted as gray circles and smoothed score as blue trace. Deep sequencing of HbF-high and HbF-low pools for cells exposed to indicated sgRNAs, with HbF indel enrichment shown as heatmap.

The methods and compositions described herein relate, in part, to the discovery that in vitro for Cas9:sgRNA ribonucleoprotein (RNP) electroporation of progenitor cells in a solution comprising glycerol is an effective method for producing viable edited progenitor cells that have (i) high on-target indel frequency (the result of targeted editing directed by the specific modified synthetic sgRNA), (ii) no detectable off-target editing, (iii) reduced BCL11A mRNA or protein expression, (iv) increased fetal hemoglobin expression, and (v) lack detectable genotoxicity. Furthermore, this electroporation approach eliminates the need for selection of the resultant cells after CRISPR-base gene editing. Importantly, Electroporation in the presence of glycerol increases the viability of cells now comprising RNP.

The BCL11A protein is a stage specific regulator of fetal hemoglobin expression by repressing γ-globin induction. Within the BCL11A locus, there are defined functional regions within the BCL11A ~12 kb enhancer region that regulate expression of the BCL11A protein. The functional regions are location 60725424 to 60725688 (+55 functional region), location 60722238 to 60722466 (+58 functional region), and location 60718042 to 60718186 (+62 functional region) on the human chromosome 2 according to UCSC Genome Browser hg 19 human genome assembly. Genome editing disruption at these regions have been shown to disrupt the expression of the BCL11A mRNA, expression of the BCL11A protein, and ultimately enriched the fetal hemoglobin (HbF) produced in the edited cells. The CRISPR/Cas9 technology using small single guide RNA (sgRNA or gRNA) sequences, introduced intracellularly by viral vectors, have been successful in targeted genomic targeting of these functional regions, and reduced BCL11A expression and increase HbF expression. However, the lentiviral delivery of Cas protein and sgRNA leaves the edited cells with viral genetic materials therein which may not be ideal for human therapy. Moreover, the levels of gene editing obtained by lentiviral delivery can be variable, and this can impede achieving therapeutically relevant level of gene editing for clinical applications in patients. The electroporation approach provides an alternative for BCL11A enhancer gene editing that give improved and high therapeutically relevant level for clinical uses.

In one aspect, provided herein are chemically modified synthetic nucleic acid molecules that target the BCL11A enhancer functional region or BCL11A exon 2 region. Specifically, targeting the three BCL11A enhancer functional regions, these three +62, +58, and +55, or the exon 2 region. These chemically modified nucleic acid molecules are guide RNAs for use with a DNA-targeting endonuclease Cas (CRISPR-associated) protein in a ribonucleoprotein (RNP) complex via electroporation to edit the BCL11A genomic regions, at the BCL11A enhancer functional region or BCL11A exon 2 region, thereby causing a reduction of BCL11A expression in the edited cell, for example, a CD 34+ hematopoietic progenitor cell or a hematopoietic stem cell. Upon decreased BCL11A mRNA and protein in such cells, as they differentiate into mature red blood cells, there would be an increase in erythroid γ-globin levels in these cells compared to cells that had not undergone targeting editing at the BCL11A locus. These resultant cells with increased erythroid γ-globin levels can be used to treatment a hemoglobinopathy in a mammal, such as β-thalassemia and sickle cell anemia. In fact, edited BCL11A CD 34+ hematopoietic progenitor cell or a hematopoietic stem cell can be transplanted into individuals with a hemoglobinopathy as a cell-based gene therapy treatment for the hemoglobinopathy.

Also in other aspects, provided herein compositions comprising the modified synthetic nucleic acid molecules, and methods for increasing fetal hemoglobin levels in a cell by disrupting BCL11A expression at the genomic level. Also provided herein are methods and compositions relating to the treatment of hemoglobinopathies by reinduction of fetal hemoglobin levels.

Accordingly, the methods and compositions provided herein are novel methods for the regulation of γ-globin expression in erythroid cells. More specifically, these activities can be harnessed in methods for the treatment of β-hemoglobinopathies by induction of γ-globin via inhibition of the BCL11A gene product.

The disclosure described herein, in one embodiment, does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

Accordingly, in one aspect, provided herein is a modified synthetic nucleic acid molecule comprising a nucleic acid sequence disclosed in Table 1, SEQ ID NOS: 1-139. In some embodiments, the modified synthetic nucleic acid molecule is chemically modified. In some embodiments, the modified synthetic nucleic acid molecule has at least one chemical modification to a nucleotide in the nucleic acid molecule.

In one aspect, provided herein is a modified synthetic nucleic acid molecule described herein for use in the ex vivo targeted genome editing of the BCL11A erythroid enhancer DHS +62, +58, or +55 functional regions or the BCL11A exon 2 region in a progenitor cell. The purpose of the modified synthetic nucleic acid molecule described herein is to direct DNA-targeting endonuclease Cas (CRISPR-associated) protein to edit the BCL11A locus at the enhancer DHS +62, +58, or +55 functional regions or the BCL11A exon 2 region.

In one aspect, provided herein is a modified synthetic nucleic acid molecule described herein for use in an ex vivo method of producing a progenitor cell or a population of progenitor cells wherein the cells or the differentiated progeny therefrom have decreased BCL11A mRNA or protein expression.

In one aspect, provided herein is a modified synthetic nucleic acid molecule described herein for use in an ex vivo method of producing an isolated genetic engineered human cell or a population of genetic engineered human cells having at least one genetic modification.

In one aspect, provided herein is a modified synthetic nucleic acid molecule described herein for use in an ex vivo method of increasing fetal hemoglobin levels in a cell or in a mammal.

In some embodiments, this disclosure provides compositions comprising the chemically modified synthetic nucleic acid molecules described supra. In one embodiment, the compositions are use in in vitro methods for producing an engineered cell (e.g. transfection with the nucleic acid described, or genetic modification described herein) so that the cell has reduced or decreased mRNA or protein expression of BCL11A compared to a similar cell that had not gone through the engineered process.

In one aspect, provided herein is a composition comprising a modified synthetic nucleic acid molecule described herein, i.e., a modified synthetic nucleic acid molecule comprising a nucleic acid sequence shown in Table 1, SEQ ID NOS: 1-139, wherein there is at least one chemical modification to a nucleotide in the nucleic acid molecule.

In one aspect, provided herein is a composition comprising modified synthetic nucleic acid molecule described herein for use in the ex vivo targeted genome editing of the BCL11A erythroid enhancer DHS +62, +58, or +55 functional regions or the BCL11A exon 2 region in a progenitor cell. purpose In one aspect, provided herein is a composition comprising modified synthetic nucleic acid molecule described herein for use in an ex vivo method of producing a progenitor cell or a population of progenitor cells wherein the cells or the differentiated progeny therefrom have decreased BCL11A mRNA or protein expression.

In one aspect, provided herein is a composition comprising modified synthetic nucleic acid molecule described herein for use in an ex vivo method of producing an isolated genetic engineered human cell or a population of genetic engineered human cells having at least one genetic modification.

In one aspect, provided herein is a composition comprising modified synthetic nucleic acid molecule described herein for use in an ex vivo method of increasing fetal hemoglobin levels in a cell or in a mammal.

In one aspect, provided herein is a ribonucleoprotein (RNP) complex comprising a DNA-targeting endonuclease Cas (CRISPR-associated) protein and a modified synthetic nucleic acid molecule described herein, i.e., a modified synthetic nucleic acid molecule comprising a nucleic acid sequence shown in Table 1, SEQ ID NOS: 1-139, wherein there is at least one chemical modification to a nucleotide in the nucleic acid molecule.

In one aspect, provided herein is a RNP complex described herein for use in the ex vivo targeted genome editing of the BCL11A erythroid enhancer DHS +62, +58, or +55 functional regions or the BCL11A exon 2 region in a progenitor cell. purpose In one aspect, provided herein is a RNP complex described herein for use in an ex vivo method of producing a progenitor cell or a population of progenitor cells wherein the cells or the differentiated progeny therefrom have decreased BCL11A mRNA or protein expression.

In one aspect, provided herein is a RNP complex described herein for use in an ex vivo method of producing an isolated genetic engineered human cell or a population of genetic engineered human cells having at least one genetic modification.

In one aspect, provided herein is a RNP complex described herein for use in an ex vivo method of increasing fetal hemoglobin levels in a cell or in a mammal.

In one aspect, provided herein is a method for producing a progenitor cell or a population of progenitor cells having decreased BCL11A mRNA or protein expression, the method comprising contacting an isolated progenitor cell with an effective amount of a composition comprising a modified synthetic nucleic acid molecule described herein or a RNP complex described herein, whereby the contacted cells or the differentiated progeny cells therefrom have decreased BCL11A mRNA or protein expression.

In one aspect, provided herein is a method for producing an isolated genetic engineered human cell or a population of genetic engineered isolated human cells having at least one genetic modification, the method comprising contacting an isolated cell or a population of cells with an effective amount of a composition comprising a modified synthetic nucleic acid molecule described herein or a RNP complex described herein, wherein the at least one genetic modification produced is located in human chromosome 2 is that according to UCSC Genome Browser hg 19 human genome assembly.

In one embodiment, this disclosure provides a method for producing an isolated genetic engineered human cell having at least one genetic modification comprising contacting an isolated cell with an effective amount of a composition comprising a modified synthetic nucleic acid molecule described herein, together with at least a DNA-targeting endonuclease whereby the DNA-targeting endonuclease cleaves the genomic DNA of the cell on chromosome 2 at location 60725424 to 60725688 (+55 functional region), or at location 60722238 to 60722466 (+58 functional region), and/or at location 60718042 to 60718186 (+62 functional region), or at location 60773106 to 60773435 (exon 2) causing at least one genetic modification therein, wherein the human chromosome 2 is that according to UCSC Genome Browser hg 19 human genome assembly. In one embodiment, the contacting is via electroporation.

It was found herein that electroporation of cells, as described herein, in a solution comprising glycerol increases the cell viability following electroporation, as compared to electroporation in a solution that does not comprise glycerol. Accordingly, in one embodiment, the step of electroporation is performed in a solution comprising glycerol. In one embodiment, the solution (e.g., a suitable buffer used for electroporation) comprises at least 1% glycerol. In one embodiment, the solution (e.g., a buffer used for electroporation) comprising less than 1%, at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more glycerol. In one embodiment, the amount of glycerol in the solution ranges from 2-4%. In one embodiment, the amount of glycerol in the solution ranges from 1-2%, 1-3%, 1-4%, 1-5%, 1-6%, 1-7%, 1-8%, 1-9%, 1-10%, 1-20%, 1-30%, 5-10%, 5-15%, 5-20%, 5-25%, 5-30%, 10-15%, 10-20%, 10-25%, 10-30%, 15-20%, 15-25%, 15-30%, 20-25%, 20-30%, 25-30%, 2-5%, 2-6%, 2-7%, 2-8%, 2-9%, 2-10%, 3-4%, 3-5%, 3-7%, 3-8%, 3-9%, 3-10%, 4-5%, 4-6%. 4-7%. 4-8%. 4-9%, 4-10%, 5-6%, 5-7%, 5-8%, 5-9%, 6-7%, 6-8%, 6-9%, 6-10%, -8%, 7-9%, 8-9%, 8-10%, or 9-10%. Glycerol can be purified glycerol or unpurified glycerol. Glycerol can be naturally occurring or synthesized. Glycerol can be derived from various processes known in the art, e.g., from plant or animal sources in which it occurs as triglerides, or propylene. In one embodiment, the solution comprises a glycerol derivative. Glycerol derivatives are further described in, e.g., U.S. Patent Application US2008/029360, which is incorporated herein by reference in its entirety.

In one aspect, provided herein is an isolated genetic engineered human cell or a population of genetic engineered human cells having at least one genetic modification on chromosome 2 location 60725424 to 60725688 (+55 functional region), or at location 60722238 to 60722466 (+58 functional region), or at location 60718042 to 60718186 (+62 functional region), or at location 60773106 to 60773435 (exon 2) according to the methods described herein, wherein the genetic modification arise from the genomic editing made via said methods. In one embodiment, the isolated genetic engineered human cell has reduced or decreased mRNA and/or protein expression of BCL11A compared to a control cell that has no one genetic modification on chromosome 2.

In one aspect, provided herein is a population of genetically edited progenitor cells having at least one genetic modification on chromosome 2 location 60725424 to 60725688 (+55 functional region), or at location 60722238 to 60722466 (+58 functional region), or at location 60718042 to 60718186 (+62 functional region), or at location 60773106 to 60773435 (exon 2) according to the methods described herein, wherein the genetic modification arise from the genomic editing made via said methods.

In one aspect, provided herein is a composition of genetic engineered human cells having at least one genetic modification on chromosome 2 location 60725424 to 60725688 (+55 functional region), or at location 60722238 to 60722466 (+58 functional region), or at location 60718042 to 60718186 (+62 functional region), or at location 60773106 to 60773435 (exon 2), according to the methods described herein, wherein the genetic modification arise from the genomic editing made via said methods.

In one aspect, provided herein is a composition of a population of genetically edited progenitor cells having at least one genetic modification on chromosome 2 location 60725424 to 60725688 (+55 functional region), or at location 60722238 to 60722466 (+58 functional region), or at location 60718042 to 60718186 (+62 functional region), or at location 60773106 to 60773435 (exon 2) according to the methods described herein, wherein the genetic modification arise from the genomic editing made via said methods.

In one embodiment of any one aspect described, the contacting of cells is via electroporation.

In one aspect, provided herein is a method of increasing fetal hemoglobin levels in a cell, the method comprising the steps of: contacting an isolated cell with an effective amount of a composition comprising a modified synthetic nucleic acid molecule described herein or a RNP complex described herein, thereby causing at least one genetic modification at the human chromosome 2 is that according to UCSC Genome Browser hg 19 human genome assembly therein, whereby fetal hemoglobin expression is increased in said cell, or its progeny, relative to said cell prior to said contacting.

In one embodiment, this disclosure provides a method of increasing fetal hemoglobin levels in a cell, the method comprising the steps of: contacting an isolated cell with an effective amount of a composition comprising a modified synthetic nucleic acid molecule described herein, together with at least a DNA-targeting endonuclease whereby the DNA-targeting endonuclease cleaves the genomic DNA of the cell on chromosome 2 at location 60725424 to 60725688 (+55 functional region), and/or at location 60722238 to 60722466 (+58 functional region), or at location 60718042 to 60718186 (+62 functional region), or at location 60773106 to 60773435 (exon 2) causing at least one genetic modification therein, whereby fetal hemoglobin expression is increased in said cell, or its progeny, relative to said cell prior to said contacting, and wherein the human chromosome 2 is that according to UCSC Genome Browser hg 19 human genome assembly. In one embodiment, the method is an in vitro or ex vivo method. In one embodiment, the contacting is via electroporation.

Another aspect provided herein relates to a method of increasing fetal hemoglobin levels in an isolated cell, the method comprising decreasing the BCL11A mRNA or protein expression in the cell. In one aspect, the decrease of BCL11A mRNA or protein expression is achieved by causing at least one genetic modification at the genomic DNA of the cell on chromosome 2 location 60725424 to 60725688 (+55 functional region), and/or at location 60722238 to 60722466 (+58 functional region), or at location 60718042 to 60718186 (+62 functional region), or at location 60773106 to 60773435 (exon 2) (according to UCSC Genome Browser hg 19 human genome assembly). In another aspect, the decrease of BCL11A mRNA or protein expression is achieved by causing at least one genetic modification at the genomic DNA of the cell on chromosome 2 location 60725424 to 60725688 (+55 functional region), and/or at location 60722238 to 60722466 (+58 functional region), or at location 60718042 to 60718186 (+62 functional region), or at location 60773106 to 60773435 (exon 2) that results in an epigenetic modification of the genetic function at chromosome 2.

By decrease in this aspect, the enhancer activity in enhancing BCL11A mRNA or protein expression in the cell is at least 5% lower is at least 10% lower, at least 20% lower, at least 30% lower, at least 40% lower, at least 50% lower, at least 60% lower, at least 70% lower, at least 80% lower, at least 90% lower, at least 1-fold lower, at least 2-fold lower, at least 5-fold lower, at least 10 fold lower, at least 100 fold lower, at least 1000-fold lower, or more compared to a control cell that is not treated in any method disclosed herein. By decrease of the BCL11A mRNA or protein expression in the cell means that protein expression is at least 5% lower is at least 10% lower, at least 20% lower, at least 30% lower, at least 40% lower, at least 50% lower, at least 60% lower, at least 70% lower, at least 80% lower, at least 90% lower, at least 1-fold lower, at least 2-fold lower, at least 5-fold lower, at least 10 fold lower, at least 100 fold lower, at least 1000-fold lower, or more compared to a control cell that is not treated in any method disclosed herein.

Another aspect provided herein relates to a method of increasing fetal hemoglobin levels in an isolated cell, the method comprising providing an isolated human cell or progenitor cell and decreasing the BCL11A mRNA or protein expression in the cell.

Another aspect provided herein relates to an ex vivo or in vitro method of increasing fetal hemoglobin levels in an isolated cell, the method comprising providing an isolated human cell or progenitor cell and decreasing the BCL11A mRNA or protein expression in the cell.

Another aspect described herein relates to a use of an isolated genetic engineered human cell described herein and produced according to a method described herein for the purpose of increasing the fetal hemoglobin levels in a mammal.

Another aspect described herein relates to a use of an isolated genetic engineered human cell described herein and produced according to a method described herein for the treatment a hemoglobinopathy in a mammal.

Another aspect described herein relates to a use of an isolated genetic engineered human cell described herein and produced according to a method described herein for the manufacturer of medicament for the treatment a hemoglobinopathy in a mammal whereby the fetal hemoglobin levels in a mammal is increased.

Another aspect described herein is a composition comprising isolated genetic engineered human cells described herein and produced according to a method described herein. In one embodiment, the composition further comprises a pharmaceutically acceptable carrier.

Another aspect described herein relates to a use of a composition comprising isolated genetic engineered human cells described herein and produced according to a method described herein for the purpose of increasing the fetal hemoglobin levels in a mammal.

Another aspect described herein relates to a use of a composition comprising isolated genetic engineered human cells described herein and produced according to a method described herein for the treatment a hemoglobinopathy in a mammal.

Another aspect described herein relates to a use of a composition comprising isolated genetic engineered human cells described herein and produced according to a method described herein for the manufacturer of medicament for the treatment a hemoglobinopathy in a mammal whereby the fetal hemoglobin levels in a mammal is increased.

Another aspect described herein is a composition comprising a modified synthetic nucleic acid molecule described herein, together with at least a DNA-targeting endonuclease whereby the DNA-targeting endonuclease cleaves the genomic DNA of a human cell on chromosome 2 location 60725424 to 60725688 (+55 functional region), and/or at location 60722238 to 60722466 (+58 functional region), or at location 60718042 to 60718186 (+62 functional region), or at location 60773106 to 60773435 (exon 2) causing at least one genetic modification therein. In one embodiment, the composition further comprises a pharmaceutically acceptable carrier. In some embodiments, the chemically modified nucleic acid molecule comprises the sequences disclosed in Table 1, or SEQ. ID. Nos: 1-139. In one embodiment, the compositions described herein has more than one modified synthetic nucleic acid molecule that targets the BCL11A enhancer region, particularly the human chromosome 2 location 60725424 to 60725688 (+55 functional region), or at location 60722238 to 60722466 (+58 functional region), or at location 60718042 to 60718186 (+62 functional region), or at location 60773106 to 60773435 (exon 2).

Another aspect described herein relates to a use of a composition comprising a modified synthetic nucleic acid molecule described herein together with at least a DNA-targeting endonuclease whereby the DNA-targeting endonuclease cleaves the genomic DNA of a human cell on chromosome 2 location 60725424 to 60725688 (+55 functional region), or at location 60722238 to 60722466 (+58 functional region), and/or at location 60718042 to 60718186 (+62 functional region), or at location 60773106 to 60773435 (exon 2) causing at least one genetic modification therein for the purpose of increasing the fetal hemoglobin levels in a mammal.

Another aspect described herein relates to a use of a composition comprising a modified synthetic nucleic acid molecule described herein, together with at least a DNA-targeting endonuclease whereby the DNA-targeting endonuclease cleaves the genomic DNA of a human cell on chromosome 2 location 60725424 to 60725688 (+55 functional region), or at location 60722238 to 60722466 (+58 functional region), or at location 60718042 to 60718186 (+62 functional region), or at location 60773106 to 60773435 (exon 2) causing at least one genetic modification therein for the treatment a hemoglobinopathy in a mammal.

In one embodiment, provided herein is a use of a modified synthetic nucleic acid molecule comprising a nucleic acid sequence described herein, for increasing the fetal hemoglobin in a mammal or for the treatment of a hemoglobinopathy in the mammal or for reducing the mRNA or expression of BCL11A, wherein the modified synthetic nucleic acid sequence excludes the entire human chromosome 2 and also excludes the entire genomic DNA sequence on the human chromosome 2 from location 60,716,189 to 60,728,612, and wherein the mRNA or protein expression of BCL11A is reduced.

In one embodiment, provided herein is a use of an effective amount of a composition comprising a modified synthetic nucleic acid molecule described herein together with at least a DNA-targeting endonuclease for increasing the fetal hemoglobin in a mammal or for the treatment of a hemoglobinopathy in the mammal or for reducing the mRNA or expression of BCL11A, whereby the DNA-targeting endonuclease cleaves the genomic DNA of a human cell on chromosome 2 location 60725424 to 60725688 (+55 functional region), and/or at location 60722238 to 60722466 (+58 functional region), or at location 60718042 to 60718186 (+62 functional region), or at location 60773106 to 60773435 (exon 2) causing at least one genetic modification therein.

In one embodiment, provided herein is a use of an effective amount of a composition comprising a modified synthetic nucleic acid molecule described herein together with at least a DNA-targeting enzyme for increasing the fetal hemoglobin in a mammal or for the treatment of a hemoglobinopathy in the mammal or for reducing the mRNA or expression of BCL11A, wherein the DNA-targeting enzyme produces at least one epigenetic modification in the genomic DNA of a human cell on chromosome 2, thereby affecting the mRNA or expression of BCL11A. In one embodiment, the at least one epigenetic modification is at location 60725424 to 60725688 (+55 functional region), and/or at location 60722238 to 60722466 (+58 functional region), or at location 60718042 to 60718186 (+62 functional region), or at location 60773106 to 60773435 (exon 2). In another embodiment, the effect of the one epigenetic modification is reducing the mRNA or protein expression of BCL11A. In one embodiment, the at least one epigenetic modification in the genomic DNA of the cell on chromosome 2 indirectly or directly affects the location 60725424 to 60725688 (+55 functional region), at location 60722238 to 60722466 (+58 functional region), or at location 60718042 to 60718186 (+62 functional region), or at location 60773106 to 60773435 (exon 2) of chromosome 2.

In one embodiment, provided herein is a composition comprising two or more modified synthetic nucleic acid molecules described herein that targets the BCL11A enhance region for use in generating modified, gene edited, engineered cells for increasing fetal hemoglobin in a mammal or for the treatment of a hemoglobinopathy in the mammal. In one embodiment, the modified, engineered cells are human CD34+ HSCPs. In one embodiment, the modified, gene edited engineered cells are produced by electroporation with a composition comprising two or more modified synthetic nucleic acid molecules.

In one embodiment, provided herein is a use of any isolated cells described herein for increasing the fetal hemoglobin in a mammal or for the treatment of a hemoglobinopathy in the mammal.

In one embodiment, provided herein is a use of a composition comprising isolated genetic engineered human cells for increasing the fetal hemoglobin in a mammal or for the treatment of a hemoglobinopathy in the mammal, wherein the cells have at least one genetic modification on chromosome 2 location 60725424 to 60725688 (+55 functional region), and/or at location 60722238 to 60722466 (+58 functional region), or at location 60718042 to 60718186 (+62 functional region), or at location 60773106 to 60773435 (exon 2) (according to UCSC Genome Browser hg 19 human genome assembly) made by the process of contacting the cells with an effective amount of a composition comprising a modified synthetic nucleic acid molecule described herein together with at least a DNA-targeting endonuclease whereby the DNA-targeting endonuclease cleaves the genomic DNA of the cell on chromosome 2 location 60725424 to 60725688 (+55 functional region), and/or at location 60722238 to 60722466 (+58 functional region), and/or at location 60718042 to 60718186 (+62 functional region), or at location 60773106 to 60773435 (exon 2) (according to UCSC Genome Browser hg 19 human genome assembly) causing at least one genetic modification therein.

In one embodiment, provided herein is a use of a composition comprising isolated genetic engineered human cells for increasing the fetal hemoglobin in a mammal or for the treatment of a hemoglobinopathy in the mammal, wherein the cells have at least one epigenetic modification on chromosome 2. In one embodiment, the at least one epigenetic modification on chromosome 2 is at location 60725424 to 60725688 (+55 functional region), and/or at location 60722238 to 60722466 (+58 functional region), or at location 60718042 to 60718186 (+62 functional region), or at location 60773106 to 60773435 (exon 2) (according to UCSC Genome Browser hg 19 human genome assembly). In another embodiment, at least one epigenetic modification on chromosome 2 is made by the process of contacting the cells with an effective amount of a composition comprising a modified synthetic nucleic acid molecule described herein, together with at least a DNA-targeting enzyme whereby the DNA-targeting enzyme produces at least one epigenetic modification in the genomic DNA of the cell on chromosome 2 which affects the location 60725424 to 60725688 (+55 functional region), or at location 60722238 to 60722466 (+58 functional region), and/or at location 60718042 to 60718186 (+62 functional region), or at location 60773106 to 60773435 (exon 2) (according to UCSC Genome Browser hg 19 human genome assembly) causing therein.

In one embodiment, provided herein is a use of any isolated cells described herein or any one of the compositions described herein for the manufacture of a medicament for increasing the fetal hemoglobin in a mammal in need thereof or for the treatment of a hemoglobinopathy in a mammal.

Another aspect described herein is a method of increasing fetal hemoglobin levels in a cell, the method comprising the steps of: contacting an isolated cell with an effective amount of a composition comprising one or more modified synthetic nucleic acid described herein, together with at least a DNA-targeting endonuclease whereby the DNA-targeting endonuclease cleaves the genomic DNA of the cell on chromosome 2 location 60725424 to 60725688 (+55 functional region), and/or at location 60722238 to 60722466 (+58 functional region), or at location 60718042 to 60718186 (+62 functional region), or at location 60773106 to 60773435 (exon 2) causing at least one genetic modification therein, whereby fetal hemoglobin expression is increased in said cell, or its progeny, relative to the cell prior to the contacting. In one embodiment, contacting is via electroporation.

In one aspect, provided herein is a method for increasing fetal hemoglobin levels in a mammal in need thereof, the method comprising the steps of (a) ex vivo contacting an isolated hematopoietic progenitor cell isolated from said mammal with an effective amount of a composition of comprising a modified synthetic nucleic acid molecule described herein or a RNP complex described herein whereby the DNA-targeting endonuclease cleaves the genomic DNA of the cell on chromosome 2 at location 60725424 to 60725688 (+55 functional region), at location 60722238 to 60722466 (+58 functional region), or at location 60718042 to 60718186 (+62 functional region), or at location 60773106 to 60773435 (exon 2), causing at least one genetic modification therein, whereby fetal hemoglobin expression is increased in said cell or the differentiated progeny cells therefrom, relative to expression prior to said contacting, and wherein the human chromosome 2 is that according to UCSC Genome Browser hg 19 human genome assembly; and (b) transplanting the contacted cells of (a) or culture-expanded cells therefrom into said mammal.

In one aspect, provided herein is a method for increasing fetal hemoglobin levels in a mammal in need thereof, the method comprising transplanting into the mammal: (a) an isolated genetic engineered human cell or a population of genetic engineered human cells having at least one genetic modification on chromosome 2 location 60725424 to 60725688 (+55 functional region), or at location 60722238 to 60722466 (+58 functional region), or at location 60718042 to 60718186 (+62 functional region), or at location 60773106 to 60773435 (exon 2) made according to the methods described herein, or (b) a population of genetically edited progenitor cells having at least one genetic modification on chromosome 2 location 60725424 to 60725688 (+55 functional region), or at location 60722238 to 60722466 (+58 functional region), or at location 60718042 to 60718186 (+62 functional region), or at location 60773106 to 60773435 (exon 2) made according the methods described herein, or (c) a composition of genetic engineered human cells described in (a) or (d) a composition of genetically edited progenitor cells described in (b), or the progeny cells from of (a) or (b).

In one embodiment, this disclosure provides a method for increasing fetal hemoglobin levels in a mammal in need thereof, the method comprising the steps of contacting an isolated hematopoietic progenitor cell in said mammal with an effective amount of a composition comprising a modified synthetic nucleic acid molecule described herein together with at least a DNA-targeting endonuclease whereby the DNA-targeting endonuclease cleaves the genomic DNA of the cell on chromosome 2 at location 60725424 to 60725688 (+55 functional region), at location 60722238 to 60722466 (+58 functional region), or at location 60718042 to 60718186 (+62 functional region), or at location 60773106 to 60773435 (exon 2) causing at least one genetic modification therein, whereby fetal hemoglobin expression is increased in said mammal, relative to expression prior to said contacting, and wherein the human chromosome 2 is that according to UCSC Genome Browser hg 19 human genome assembly. In one embodiment, the contacting is via electroporation. In some embodiments, the modified synthetic nucleic acid molecule comprises the sequences disclosed in Table 1, or SEQ. ID. NOS. 1-139.

In one embodiment, this disclosure provides a method for increasing fetal hemoglobin levels in a mammal in need thereof, the method comprising transplanting an isolated genetic engineered human cell described herein or a composition described herein into the mammal.

Another aspect described herein is a method for increasing fetal hemoglobin levels in a mammal in need thereof, the method comprising the steps of contacting an isolated hematopoietic progenitor cell in said mammal with an effective amount of a composition comprising one or more modified synthetic nucleic acid molecule described herein, together with at least a DNA-targeting endonuclease whereby the DNA-targeting endonuclease cleaves the genomic DNA of the cell on chromosome 2 location 60725424 to 60725688 (+55 functional region), or at location 60722238 to 60722466 (+58 functional region), and/or at location 60718042 to 60718186 (+62 functional region), or at location 60773106 to 60773435 (exon 2) causing at least one genetic modification therein, whereby fetal hemoglobin expression is increased in said mammal, relative to expression prior to said contacting. In one embodiment, contacting is via electroporation.

In one embodiment, this disclosure provides a method for increasing fetal hemoglobin levels in a mammal in need thereof, the method comprising the steps of providing an isolated population of hematopoietic progenitor cells or hematopoietic stem cells from the mammal in ex vivo, and contacting the population of hematopoietic progenitor or stem cells with an effective amount of a composition comprising one or more modified synthetic nucleic acid molecule described herein, together with at least a DNA-targeting endonuclease whereby the DNA-targeting endonuclease cleaves the genomic DNA of the cell on chromosome 2 location 60725424 to 60725688 (+55 functional region), and/or at location 60722238 to 60722466 (+58 functional region), or at location 60718042 to 60718186 (+62 functional region), or at location 60773106 to 60773435 (exon 2) causing at least one genetic modification therein, whereby fetal hemoglobin expression is increased in the mammal, relative to expression prior to the contacting.

In one embodiment, this disclosure provides a method for increasing fetal hemoglobin levels in a mammal in need thereof, the method comprising the steps of isolating a population of hematopoietic progenitor cells or hematopoietic stem cells from the mammal, and contacting in ex vivo the population of hematopoietic progenitor or stem cells with an effective amount of a composition comprising a modified synthetic nucleic acid molecule described herein together with at least a DNA-targeting endonuclease whereby the DNA-targeting endonuclease cleaves the genomic DNA of the cell on chromosome 2 location 60725424 to 60725688 (+55 functional region), and/or at location 60722238 to 60722466 (+58 functional region), or at location 60718042 to 60718186 (+62 functional region), or at location 60773106 to 60773435 (exon 2) causing at least one genetic modification therein, whereby fetal hemoglobin expression is increased in the mammal, relative to expression prior to the contacting.

In one embodiment, this disclosure provides a method for increasing fetal hemoglobin levels in a mammal in need thereof, the method comprising the steps of (a) providing isolating a population of hematopoietic progenitor cells or hematopoietic stem cells from the mammal and (b) deleting/adding/substituting the genomic DNA of the cells on chromosome 2 location 60725424 to 60725688 (+55 functional region), and/or at location 60722238 to 60722466 (+58 functional region), and/or at location 60718042 to 60718186 (+62 functional region), or at location 60773106 to 60773435 (exon 2) causing at least one genetic modification therein according to any one of the methods described herein, fetal hemoglobin expression is increased in the mammal, relative to expression prior to the contacting, and transplanting the resultant cells back to the mammal, whereby.

In one embodiment, this disclosure provides a method for increasing fetal hemoglobin levels in a mammal in need thereof, the method comprising the steps of isolating a population of hematopoietic progenitor cells or hematopoietic stem cells from the mammal and ex vivo deleting the genomic DNA of the cells on chromosome 2 location 60725424 to 60725688 (+55 functional region), and/or at location 60722238 to 60722466 (+58 functional region), and/or at location 60718042 to 60718186 (+62 functional region), or at location 60773106 to 60773435 (exon 2) causing at least one genetic modification therein according to any one methods described herein, whereby fetal hemoglobin expression is increased in the mammal, relative to expression prior to the cell contacting, and transplanting the resultant cells back to the mammal.

In one aspect, this disclosure provides a method of treatment of a hemoglobinopathy in a mammal (e.g. a human) comprising increasing fetal hemoglobin expression in the mammal by transplanting into the mammal: (a) an isolated genetic engineered human cell or a population of genetic engineered human cells having at least one genetic modification on chromosome 2 location 60725424 to 60725688 (+55 functional region), or at location 60722238 to 60722466 (+58 functional region), or at location 60718042 to 60718186 (+62 functional region), or at location 60773106 to 60773435 (exon 2) made according to the methods described herein, or (b) a population of genetically edited progenitor cells having at least one genetic modification on chromosome 2 location 60725424 to 60725688 (+55 functional region), or at location 60722238 to 60722466 (+58 functional region), or at location 60718042 to 60718186 (+62 functional region), or at location 60773106 to 60773435 (exon 2) made according the methods described herein, or (c) a composition of genetic engineered human cells described in (a) or (d) a composition of genetically edited progenitor cells described in (b), or the progeny cells from of (a) or (b).

In one aspect, this disclosure provides a method of treatment of a hemoglobinopathy in a mammal (e.g. a human) comprising (a) providing a population of hematopoietic progenitor cell or a hematopoietic stem cells from the mammal; (b) ex vivo contacting said isolated hematopoietic progenitor cell isolated from said mammal with an effective amount of a composition of comprising a modified synthetic nucleic acid molecule described herein or a RNP complex described herein whereby the DNA-targeting endonuclease cleaves the genomic DNA of the cell on chromosome 2 at location 60725424 to 60725688 (+55 functional region), at location 60722238 to 60722466 (+58 functional region), or at location 60718042 to 60718186 (+62 functional region), or at location 60773106 to 60773435 (exon 2), causing at least one genetic modification therein, whereby fetal hemoglobin expression is increased in said cell or the differentiated progeny cells therefrom, relative to expression prior to said contacting, and wherein the human chromosome 2 is that according to UCSC Genome Browser hg 19 human genome assembly; and (c) transplanting the contacted cells of (b) or culture-expanded cells therefrom into said mammal.

In one embodiment, this disclosure provides a method of treatment of a hemoglobinopathy in a mammal comprising the steps of (a) providing hematopoietic progenitor cells or hematopoietic stem cells or iPSCs; (b) contacting the cells ex vivo or in vitro with an effective amount of a composition comprising one or more modified synthetic nucleic acid described herein and a composition comprising at least a DNA-targeting endonuclease whereby the DNA-targeting endonuclease cleaves the genomic DNA of the cell on chromosome 2 location 60725424 to 60725688 (+55 functional region), and/or at location 60722238 to 60722466 (+58 functional region), or at location 60718042 to 60718186 (+62 functional region), or at location 60773106 to 60773435 (exon 2), causing at least one genetic modification therein, whereby fetal hemoglobin expression is increased in the mammal, relative to expression prior to the contacting; and (c) administering the cells of step (b) into the mammal.

In one embodiment, this disclosure provides a method of treatment of a hemoglobinopathy in a mammal (e.g. a human) comprising introducing a composition described herein comprising isolated genetic engineered cells having at least one genetic modification on chromosome 2 location 60725424 to 60725688 (+55 functional region), or at location 60722238 to 60722466 (+58 functional region), and/or at location 60718042 to 60718186 (+62 functional region), or at location 60773106 to 60773435 (exon 2), whereby fetal hemoglobin expression is increased in the mammal.

In one embodiment of this aspect and all other aspects described herein, the nucleic acid sequence of the modified synthetic nucleic acid molecule excludes the entire BCL11A enhancer functional regions.

In one embodiment of this aspect and all other aspects described herein, the nucleic acid sequence of the modified synthetic nucleic acid molecule excludes excludes the entire BCL11A coding region.

In one embodiment of this aspect and all other aspects described herein, the nucleic acid sequence of the modified synthetic nucleic acid molecule excludes excludes the entire BCL11A enhancer functional regions, that is excluding the entire region between the human chromosome 2 location 60725424 to 60725688 (DHS +55 functional region), or excludes the entire region at location 60722238 to 60722466 (DHS +58 functional region), or excludes the entire region at location 60718042 to 60718186 (DHS +62 functional region), or excludes the entire region at location 60773106 to 60773435 (exon 2) of the human chromosome 2 is that according to UCSC Genome Browser hg 19 human genome assembly.

In one embodiment of this aspect and all other aspects described herein, the modified synthetic nucleic acid molecule comprises a sequence selected from the group consisting of SEQ ID NOS: 1-139 or Table 1.

In one embodiment of this aspect and all other aspects described herein, the modified synthetic nucleic acid molecule comprises a sequence selected from the group consisting of SEQ ID NOS: 37, 38, 39, 40, 41, 42, 43, 44, 45, 46, 47, 48, 50, 51, 52, 53, 54, 55, 56, 57, and 62 as shown in Table 2.

In one embodiment of this aspect and all other aspects described herein, the chemical modifications on the modified synthetic nucleic acid molecule are located at one or more terminal nucleotides in the nucleic acid molecule.

In one embodiment, the chemical modification is only found on the 5' end of the modified synthetic nucleic acid molecule. In another embodiment, the chemical modification is found only on the 3'-end. Methods of chemical modification are known in the art. MS-based modifications produces efficient BCL11A enhancer targeting guide RNAs. For example, as described in Hendel et al., 2015, Nature Biotechnology, the reference is incorporated herein in its entirety. Chemically modified guide RNAs can purchased from Synthego.

In one embodiment of this aspect and all other aspects described herein, the chemical modification is selected from the group consisting of 2'-O-methyl 3'phosphorothioate (MS), 2'-O-methyl-3'-phosphonoacetate (MP), 2'-0-Ci-4alkyl, 2'-H, 2'-0-Ci.3alkyl-0-Ci.3alkyl, 2'-F, 2'-NH2, 2'-arabino, 2'-F-arabino, 4'-thioribosyl, 2-thioU, 2-thioC, 4-thioU, 6-thioG, 2-aminoA, 2-aminopurine, pseudouracil, hypoxanthine, 7-deazaguanine, 7-deaza-8-azaguanine, 7-deazaadenine, 7-deaza-8-azaadenine, 5-methylC, 5-methylU, 5-hydroxymethylcytosine, 5-hydroxymethyluracil, 5,6-dehydrouracil, 5-propynylcytosine, 5-propynyluracil, 5-ethynylcytosine, 5-ethynyluracil, 5-allylU, 5-allylC, 5-aminoallyl-uracil, 5-aminoallyl-cytosine, an abasic nucleotide ("abN"), Z, P, UNA, isoC, isoG, 5-methyl-pyrimidine, x(A,G,C,T) and y(A,G,C,T), a phosphorothioate internucleotide linkage, a phosphonoacetate internucleotide linkage, a thiophosphonoacetate internucleotide linkage, a methylphosphonate internucleotide linkage, a boranophosphonate internucleotide linkage, a phosphorodithioate internucleotide linkage, 4'-thioribosyl nucleotide, a locked nucleic acid ("LNA") nucleotide, an unlocked nucleic acid ("ULNA") nucleotide, an alkyl spacer, a heteroalkyl (N, O, S) spacer, a 5'- and/or 3'-alkyl terminated nucleotide, a Unicap, a 5'-terminal cap known from nature, an xRNA base (analogous to "xDNA" base), an yRNA base (analogous to "yDNA" base), a PEG substituent, and a conjugated linker to a dye or non-fluorescent label (or tag). Chemical modifications of gRNA are further described in, e.g., Hendel A, et al. Nat Biotechnol. 2015 September; 33(9): 985-989, which is incorporated herein by reference in its entirety. Methods for generating chemical modifications on gRNA are further reviewed in, e.g., Patent Application WO2016/089433, which is incorporated herein by reference in its entirety.

In one embodiment of this aspect and all other aspects described herein, the chemical modification is located only at the 3' end, or added only at the 5' end, or added at both the 5' and 3' ends of the modified synthetic nucleic acid molecule.

In one embodiment of any one aspects described herein, the chemical modification is located to first three nucleotides and to the last three nucleotides of the modified synthetic nucleic acid molecule.

In one embodiment of any one aspects described herein, the nucleic acid sequence further comprising a crRNA/tracrRNA sequence. The crRNA/tracrRNA sequence is a hybrid sequence for the binding of DNA-targeting endonuclease is a Cas (CRISPR-associated) protein in forming the gene editing ribonucleoprotein (RNP) complex.

In one embodiment of any one aspects described herein, the nucleic acid molecule is a single guide RNA (sgRNA).

In one embodiment of any one aspects described herein, the modified synthetic nucleic acid molecule is used in combination with a DNA-targeting endonuclease Cas (CRISPR-associated) protein in a ribonucleoprotein (RNP) complex.

In one embodiment of any one aspects described herein, the RNP complex is used in the electroporation of cells.

In one embodiment of any one aspects described herein, the composition comprising a modified synthetic nucleic acid molecule further comprising a DNA-targeting endonuclease Cas (CRISPR-associated) protein.

In one embodiment of any one aspects described herein, the composition comprising a modified synthetic nucleic acid molecule is used in the electroporation of cells.

In one embodiment of any one aspects described herein, the contacted progenitor cell or contacted cell are further electroporated.

In one embodiment of any one aspects described herein, the DNA-targeting endonuclease is a Cas (CRISPR-associated) protein.

In one embodiment of any one aspects described herein, the Cas protein is Cas 9.

In one embodiment of this aspect and all other aspects described herein, the Cas 9 protein is a recombinant protein, a nickase, or a functional catalytic domain of a Cas 9 protein.

In some embodiments of any of the ex vivo or in vitro methods described herein, the isolated progenitor cell or isolated cell is a hematopoietic progenitor cell.

In some embodiments of any of the ex vivo or in vitro methods described herein, the hematopoietic progenitor is a cell of the erythroid lineage.

In some embodiments of any of the ex vivo or in vitro methods described herein, wherein the isolated progenitor cell or isolated cell is an induced pluripotent stem cell.

In one embodiment of this aspect and all other aspects described herein, the isolated progenitor cell or isolated cell is a hematopoietic progenitor cell or a hematopoietic stem cell.

In one embodiment of this aspect and all other aspects described herein, the hematopoietic progenitor is a cell of the erythroid lineage.

In one embodiment of this aspect and all other aspects described herein, the isolated progenitor cell or isolated cell is an induced pluripotent stem cell.

In one embodiment of this aspect and all other aspects described herein, the isolated progenitor cell or isolated cell is contacted ex vivo or in vitro.

In one embodiment of this aspect and all other aspects described herein, the contacted progenitor cell or contacted cell acquires at least one genetic modification.

In one embodiment of this aspect and all other aspects described herein, the at least one genetic modification is a deletion, insertion or substitution of the nucleic acid sequence.

In one embodiment of this aspect and all other aspects described herein, the at least one genetic modification is a deletion.

In one embodiment of this aspect and all other aspects described herein, the least one genetic modification is located between chromosome 2 location 60725424 to 60725688 (+55 functional region), or at location 60722238 to 60722466 (+58 functional region), or at location 60718042 to 60718186 (+62 functional region), or at location 60773106 to 60773435 (exon 2) of the human chromosome 2 is that according to UCSC Genome Browser hg 19 human genome assembly.

In one embodiment of this aspect and all other aspects described herein, the method further comprises selecting a mammal in need of increasing fetal hemoglobin levels therein.

In one embodiment of this aspect and all other aspects described herein, the method further comprises providing an isolated cell or an isolated progenitor cell or an isolated population of cells which can be progenitor cell or hematopoietic progenitor cell or an iPSCs.

In one embodiment of this aspect and all other aspects described herein, the isolated cell is an isolated progenitor cell.

In one embodiment of this aspect and all other aspects described herein, the isolated progenitor cell is an isolated human cell.

In one embodiment of this aspect and all other aspects described herein, the isolated human cell is a hematopoietic progenitor cell or a hematopoietic stem cell. In other embodiment, the isolated human cell is an embryonic stem cell, a somatic stem cell, a progenitor cell, or a bone marrow cell.

In one embodiment of this aspect and all other aspects described herein, the method described herein comprises contacting an embryonic stem cell, a somatic stem cell, a progenitor cell, a bone marrow cell, a hematopoietic stem cell, or a hematopoietic progenitor cell with an effective amount of a composition described herein or an effective amount of at least isolated nucleic acid molecule described herein.

In another embodiment of this aspect and all other aspects described herein, the hematopoietic cell is a cell of the erythroid lineage. Methods of isolating hematopoietic progenitor cell are well known in the art, e.g., by flow cytometric purification of CD34+ or CD133+ cells, microbeads conjugated with antibodies against CD34 or CD133, markers of hematopoietic progenitor cell. Commercial kits are also available, e.g., MACS® Technology CD34 MicroBead Kit, human, and CD34 MultiSort Kit, human, and STEMCELL™ Technology EasySep™ Mouse Hematopoietic Progenitor Cell Enrichment Kit.

In another embodiment of this aspect and all other aspects described herein, the hematopoietic stem cells, hematopoietic progenitor cells, embryonic stem cells, somatic stem cells, or progenitor cells are collected from peripheral blood, cord blood, chorionic villi, amniotic fluid, placental blood, or bone marrow.

In one embodiment of any described method, the hematopoietic progenitor or stem cells or isolated cells can be substituted with an iPSCs described herein.

In one embodiment of any described method, the hematopoietic progenitor or stem cells or iPSCs or isolated cells are autologous to the mammal, meaning the cells are derived from the same mammal. In another of the embodiments of the described method, the hematopoietic progenitor or stem cells or iPSCs or isolated cells are non-autologous to the mammal, meaning the cells are not derived from the same mammal, but another mammal of the same species. For example, the mammal is a human.

In one embodiment of this aspect and all other aspects described herein, the human cell is a hematopoietic progenitor cell.

In one embodiment of this aspect and all other aspects described herein, the human cell is an induced pluripotent stem cell (iPSC).

In one embodiment of this aspect and all other aspects described herein, the induced pluripotent stem cell is hematopoietic progenitor cell.

In one embodiment of this aspect and all other aspects described herein, the hematopoietic progenitor is a cell of the erythroid lineage.

In one embodiment of this aspect and all other aspects described herein, the hematopoietic progenitor cell or isolated is contacted ex vivo or in vitro or in vivo.

In another embodiment of this aspect and all other aspects described herein, the contacting of any cell described herein can be ex vivo or in vitro or in vivo.

In one embodiment of this aspect and all other aspects described herein, the contacted progenitor cell or contacted cell acquires at least one epigenetic modification in the BCL11A enhancer functional region.

In one embodiment of this aspect and all other aspects described herein, the at least one epigenetic modification is selected from the group consisting of alteration of DNA methylation, histone tail modification, histone subunit composition and nucleosome positioning.

In one embodiment of this aspect and all other aspects described herein, the at least one epigenetic modification in the genomic DNA of the cell on chromosome 2 indirectly or directly affects the location 60725424 to 60725688 (+55 functional region), and/or at location 60722238 to 60722466 (+58 functional region), and/or at location 60718042 to 60718186 (+62 functional region), or at location 60773106 to 60773435 (exon 2) of chromosome 2.

In one embodiment of this aspect and all other aspects described herein, the at least one epigenetic modification is located between chromosome 2 location 60725424 to 60725688 (+55 functional region), at location 60722238 to 60722466 (+58 functional region), and/or at location 60718042 to 60718186 (+62 functional region), or at location 60773106 to 60773435 (exon 2) of the human chromosome 2 is that according to UCSC Genome Browser hg 19 human genome assembly.

As used herein, "indirectly affecting the location 60725424 to 60725688 (+55 functional region), at location 60722238 to 60722466 (+58 functional region), and/or at location 60718042 to 60718186 (+62 functional region) of chromosome 2" refers to long distance effects of epigenetic modification in the genomic DNA of the cell on chromosome 2 the location 60725424 to 60725688 (+55 functional region), at location 60722238 to 60722466 (+58 functional region), or at location 60718042 to 60718186 (+62 functional region), or at location 60773106 to 60773435 (exon 2) of chromosome 2.

In one embodiment of any one aspects described herein, the contacted cells or the differentiated progeny cells therefrom further have increased fetal hemoglobin levels.

In one embodiment of any one aspects described herein, the contacted cells or the differentiated progeny cells therefrom further have decreased BCL11A mRNA or protein expression compared to non-contacted control cells.

In one embodiment of any one aspects described herein, the isolated genetic engineered human cell or a population of genetic engineered human cells described herein or the differentiated progeny cells therefrom have increased fetal hemoglobin levels.

In one embodiment of any one aspects described herein, the genetically edited progenitor cells described herein or the differentiated progeny cells therefrom have increased fetal hemoglobin levels.

In one embodiment of any one aspects described herein, the isolated genetic engineered human cell or a population of genetic engineered human cells described herein or the differentiated progeny cells therefrom have decreased BCL11A mRNA or protein expression compared to non-contacted control cells.

In one embodiment of any one aspects described herein, the genetically edited progenitor cells described herein or the differentiated progeny cells therefrom have decreased BCL11A mRNA or protein expression compared to non-contacted control cells.

In one embodiment of this aspect and all other aspects described herein, the isolated cell or isolated population of cells used in the contacting, the methods described herein, or electroporation described herein is/are human cell(s).

In one embodiment of this aspect and all other aspects described herein, the isolated cell or isolated population of cells used in the contacting, the methods described herein, or electroporation described herein is/are progenitor cell(s).

In another embodiment of this aspect and all other aspects described herein, the hematopoietic progenitor cell, the isolated human cell, or isolated cell is contacted ex vivo or in vitro.

In another embodiment of this aspect and all other aspects described herein, the at least one genetic modification is a deletion. In another embodiment of this aspect and all other aspects described herein, the at least one epigenetic modification.

In another embodiment of this aspect and all other aspects described herein, the deletion comprises one or more of the DNAse 1-hypersensitive sites (DHS) +62, +58, or +55, or exon 2.

In another embodiment of this aspect and all other aspects described herein, the epigenetic modification comprises or affects one or more of the DNAse 1-hypersensitive sites (DHS) +62, +58, and +55. As used herein, the phrase "affects one or more of the DNAse 1-hypersensitive sites" means natural function of these DNAse 1-hypersensitive sites (DHS) +62, +58, and +55 are reduce, for example, access to transcription factors or DNA degradation enzymes such as DNase I. In general, DNase I hypersensitive sites (DHSs) are regions of chromatin which are sensitive to cleavage by the DNase I enzyme. In these specific regions of the genome, chromatin has lost its condensed structure, exposing the DNA, and making it accessible. This raises the availability of DNA to degradation by enzymes, like DNase I. These accessible chromatin zones are functionally related to transcriptional activity, since this remodeled state is necessary for the binding of proteins such as transcription factors. Accordingly, the epigenetic modification contemplated herein results in reduced access to DNA degradation enzymes that is at least 5% lower is at least 10% lower, at least 20% lower, at least 30% lower, at least 40% lower, at least 50% lower, at least 60% lower, at least 70% lower, at least 80% lower, at least 90% lower, at least 1-fold lower, at least 2-fold lower, at least 5-fold lower, at least 10 fold lower, at least 100 fold lower, at least 1000-fold lower, or more compared to a control cell that is not treated in any method disclosed herein.

In another embodiment of this aspect and all other aspects described herein, the epigenetic modification is from 60,716, 189 to 60,728,612, from 60,716,189 to 60,723,870, from 60,722,992 to 60,728,612, from 60,717,236 to 60,719,036, from 60,722,006 to 60,723,058, from 60,724,917 to 60,726, 282, from 60,616,396 to 60,618,032, from 60,623,536 to 60,624,989, from 60,626,565 to 60,628,177, from 60,717, 236 to 60,719,036, from 60,721,212 to 60,722,958, from 60,724,780 to 60,726,471, from 60,739,075 to 60,740,154, from 60,748,003 to 60,749,009, from 60,826,438 to 60,827, 601, or from 60,831,589 to 60,833,556.

In another embodiment of this aspect and all other aspects described herein, the epigenetic modification that interferes with the establishment and/or maintenance of the epigenetic signature at the enhancer region on chromosome 2 location 60725424 to 60725688 (+55 functional region), and/or at location 60722238 to 60722466 (+58 functional region), and/or at location 60718042 to 60718186 (+62 functional region) (according to UCSC Genome Browser hg 19 human genome assembly) thereby leading to reduced mRNA or protein expression of BCL11A, and increasing fetal hemoglobin expression in the mammal.

In one embodiment of this aspect and all other aspects described herein, the epigenetic modification that interferes with the establishment and/or maintenance of the epigenetic signature at the enhancer region on chromosome 2 location 60725424 to 60725688 (+55 functional region), and/or at location 60722238 to 60722466 (+58 functional region), and/or at location 60718042 to 60718186 (+62 functional region) (according to UCSC Genome Browser hg 19 human genome assembly) includes but is not limited to epigenetic modifications that affects DNase I sensitivity, epigenetic modifications that affects histone modifications, epigenetic modifications that affects GATA1/TAL1 binding, and epigenetic modifications that affects long-range promoter interaction of the promoter of BCL11A.

For example, an epigenetic modification that interferes with the establishment and/or maintenance of the epigenetic signature at the enhancer region on chromosome 2 location functional regions described include but is not limited to at least one deletion within chromosome 2 location 60,716,189-60,728,612 such that the overall function of this region is affected whereby the mRNA and expression of BCL11A is reduced or decreased. For example, the deletion is at the DNaseI sensitivity regions chromosome 2 location 60,716,189-60,728,612, e.g., +62, +58, and +55. The deletion could be at +62 or +58 or +55 or combination thereof. For examples, at +62 and +58, +58 and +55, +62 and +55, or at all three +62, +58, and +55.

As another example, an epigenetic modification that interferes with the establishment and/or maintenance of the epigenetic signature at the enhancer region on chromosome 2 location +55, +58 and +62 functional regions include but is not limited to changes in the histone modifications on chromosome 2 that is not at location functional regions or changes in the histone modifications on chromosome 2 at location functional regions, or both histone modifications on chromosome 2 not at location 60,716,189-60,728,612 as well as at location 60,716,189-60,728,612 such that the overall function of this region is affected whereby the mRNA and expression of BCL11A is reduced or decreased.

In another embodiment, an epigenetic modification that interferes with the establishment and/or maintenance of the epigenetic signature at the enhancer region on chromosome 2 location 60,716,189-60,728,612 include but is not limited to an insertion of at least one engineered specific-repressor sequence that change the epigenetic features of noncoding elements at chromosome 2, +55, +58 and +62 functional regions, and thus result in repression of target gene expression. The first is specifically focused on epigenetically repressing individual enhancers. In other words, insertion of engineered specific-repressor sequences into chromosome 2 would prospectively interfering with epigenetic modification at the BCL11A erythroid enhancer which eventually leads to reduced BCL11A gene expression.

Any methods known in the art can be used to produce the epigenetic modification contemplated. For example, as described in Mendenhall E M. et al., Nat. Biotechnol. 8 Sep. 2013, and Maeder M L et al., Nat Biotechnol. 9 Oct. 2013 2013.

In one embodiment of this aspect and all other aspects described herein, the insertion of at least one engineered specific-repressor sequence on any location chromosome 2 results in but is not limited to reduced DNaseI sensitivity regions at chromosome 2 location +55, +58 and +62 functional regions; increased histone modifications on chromosome 2 location 60,716,189-60,728,612 or at the +55, +58 and +62 functional regions; reduced transcription factors binding to the GATA1/TAL1 of the enhancer region on chromosome 2 +55, +58 and +62 functional regions; and reduced or weakened interaction between the chromosome 2 location +55, +58 and +62 functional regions with the BCL11A promoter.

In one embodiment of this aspect and all other aspects described herein, the overall effects of the insertion of at least one engineered specific-repressor sequence on any location chromosome 2 is reduced or decreased mRNA and expression of BCL11A.

In some embodiments, as used in the context of mRNA and expression of BCL11A, interaction between the chromosome 2 location 60,716,189-60,728,612, at the +55, +58 and +62 functional regions, or BCL11A enhancer with the BCL11A promoter, and transcription factors binding to the GATA1/TAL1 of the enhancer region, the term "reduced" or "decreased" refers to at least 5% lower is at least 10% lower, at least 20% lower, at least 30% lower, at least 40% lower, at least 50% lower, at least 60% lower, at least 70% lower, at least 80% lower, at least 90% lower, at least 1-fold lower, at least 2-fold lower, at least 5-fold lower, at least 10 fold lower, at least 100 fold lower, at least 1000-fold lower, or more compared to the control situation that is in the absence of the epigenetic modification or genetic modification or insertion of engineered sequences disclosed herein. By decrease of the BCL11A mRNA or protein expression in the cell means that protein expression is at least 5% lower is at least 10% lower, at least 20% lower, at least 30% lower, at least 40% lower, at least 50% lower, at least 60% lower, at least 70% lower, at least 80% lower, at least 90% lower, at least 1-fold lower, at least 2-fold lower, at least 5-fold lower, at least 10 fold lower, at least 100 fold lower, at least 1000-fold lower, or more compared to a control cell that does not have the epigenetic modification or genetic modification or insertion of engineered sequences disclosed herein.

In one embodiment of this aspect and all other aspects described herein, the insertion of at least one engineered specific-repressor sequence occurs within the DNaseI sensitivity regions of chromosome 2 at location 60,716,189-60,728,612, or at the +55, +58 and +62 functional regions or at exon 2. The insertion could be at the 5' end of +62 or +58 or +55 or at the 3'end of +62 or +58 or +55, or between +62 and +58, or between +58 and +55, or between +55 and +62.

In one embodiment of this aspect and all other aspects described herein, the insertion of at least one engineered specific-repressor sequence changes the DNaseI sensitivity regions of chromosome 2 at location +55, +58 and +62 functional regions.

In one embodiment of this aspect and all other aspects described herein, the epigenetic modifications change the DNaseI sensitivity regions of chromosome 2 at location 60,716,189-60,728,612 or at the +55, +58 and +62 functional regions.

In one embodiment of this aspect and all other aspects described herein, the epigenetic modifications change the histone modifications on chromosome 2 location 60,716,189-60,728,612, or at the +55, +58 and +62 functional regions.

In one embodiment of this aspect and all other aspects described herein, the insertion of at least one engineered specific-repressor sequence changes the histone modifications on chromosome 2 location 60,716,189-60,728,612 or at the +55, +58 and +62 functional regions.

In one embodiment of this aspect and all other aspects described herein, the epigenetic modifications change the GATA1/TAL1 binding of the enhancer region on chromosome +55, +58 and +62 functional regions, such that the overall function of this region is affected whereby the mRNA and expression of BCL11A is reduced or decreased. For example, the binding of transcription factors to the GATA1/TAL1.

In one embodiment of this aspect and all other aspects described herein, the genetic modification such as an insertion or deletion or substitution occurs within the GATA1/TAL1 as described herein. The insertion can be at the 5' end or 3'end of GATA1 or TALL The genetic modification can be between GATA1 and TAL1. The genetic modification changes the GATA1/TAL1 binding of the enhancer region on chromosome 2 +55, +58 and +62 functional regions, such that the overall function of this region is affected whereby the mRNA and expression of BCL11A is reduced or decreased. For example, the binding of transcription factors to the GATA1/TAL1.

In one embodiment of this aspect and all other aspects described herein, the epigenetic modification and/or genetic modification changes the interaction between the BCL11A enhancer and the BCL11A promoter. In one embodiment, the interaction is reduced or weakened such that the overall function of this region is affected whereby the mRNA and expression of BCL11A is reduced or decreased.

In one embodiment of this aspect and all other aspects described herein, the epigenetic modifications and/or genetic modification change the interaction between the chromosome 2 location 60,716,189-60,728,612 and/or the +55, +58 and +62 functional regions with the BCL11A promoter. In one embodiment, the interaction is reduced or weakened such that the overall function of this region is affected whereby the mRNA and expression of BCL11A is reduced or decreased.

In one embodiment of this aspect and all other aspects described herein, the isolated genetic engineered human cell has at least one epigenetic modification at the genomic DNA of the cell on chromosome 2. In another of this aspect and all other aspects described herein, the isolated genetic engineered human cell has at least one epigenetic modification at the genomic DNA of the cell on chromosome 2 location 60725424 to 60725688 (+55 functional region), and/or at location 60722238 to 60722466 (+58 functional region), and/or at location 60718042 to 60718186 (+62 functional region) or at the BCL11A exon2.

In some aspects of any of these isolated genetic engineered human cells having at least one epigenetic modification or genetic modification, the cells are transplanted into a mammal for use in increasing the fetal hemoglobin in the mammal.

In one embodiment of this aspect and all other aspects described herein, the isolated genetic engineered human cell having at least one genetic modification at the genomic DNA of the cell on chromosome 2 location 60725424 to 60725688 (+55 functional region), and/or at location 60722238 to 60722466 (+58 functional region), and/or at location 60718042 to 60718186 (+62 functional region) or at the BCL11A exon 2 is transplanted into a mammal for use in increasing the fetal hemoglobin in the mammal.

In one embodiment of this aspect and all other aspects described herein, the isolated genetic engineered human cell having at least one genetic modification at the genomic DNA of the cell on chromosome 2 location 60725424 to 60725688 (+55 functional region), and/or at location 60722238 to 60722466 (+58 functional region), and/or at location 60718042 to 60718186 (+62 functional region) or at the BCL11A exon 2 is stored for later use by cryopreservation.

In some aspects of any of those isolated genetic engineered human cells having at least one epigenetic modification or genetic modification, the cells are stored for later use by cryopreservation.

In one embodiment of this aspect and all other aspects described herein, the isolated genetic engineered human cell having at least one genetic modification at the genomic DNA of the cell on chromosome 2 location 60725424 to 60725688 (+55 functional region), and/or at location 60722238 to 60722466 (+58 functional region), and/or at location 60718042 to 60718186 (+62 functional region) or at the BCL11A exon 2 is cryopreserved, thawed and transplanted into mammal for use in increasing the fetal hemoglobin in the mammal.

In some aspects of any of those isolated genetic engineered human cells having at least one epigenetic modification or genetic modification, cryopreserved, thawed and transplanted into mammal for use in increasing the fetal hemoglobin in the mammal.

In one embodiment of this aspect and all other aspects described herein, the composition causes an increase in fetal hemoglobin mRNA or protein expression in the contact cell.

In one embodiment of this aspect and all other aspects described herein, the cells of any compositions described are autologous, to the mammal who is the recipient of the cells in a transplantation procedure, i.e., the cells of the composition are derived or harvested from the mammal prior to any described genetic modification or targeted gene editing.

In one embodiment of this aspect and all other aspects described herein, the cells of any compositions described are non-autologous to the mammal who is the recipient of the cells in a transplantation procedure, i.e., the cells of the composition are not derived or harvested from the mammal prior to any described genetic modification or targeted gene editing.

In one embodiment of this aspect and all other aspects described herein, the cells of any compositions described are at the minimum HLA type matched with to the mammal who is the recipient of the cells in a transplantation procedure.

In one embodiment of this aspect and all other aspects described herein, the cells of any compositions described are isolated progenitor cells prior to any described genetic modification or targeted gene editing.

In one embodiment of this aspect and all other aspects described herein, the cells of any compositions described are isolated hematopoietic progenitor cells prior to any described genetic modification or targeted gene editing.

In one embodiment of this aspect and all other aspects described herein, the cells of any compositions described are isolated induced pluripotent stem cells prior to any described genetic modification or targeted gene editing.

In another embodiment of this aspect and all other aspects described herein, the deletion comprises one or more of the DNAse 1-hypersensitive sites (DHS) +62, +58, and +55. In another embodiment of this aspect and all other aspects described herein, the deletion consists essentially of one or more of the DNAse 1-hypersensitive sites (DHS) +62, +58, and +55. In another embodiment, the deletion consists of one or more of the DNAse 1-hypersensitive sites (DHS) +62, +58, and +55. In one embodiment, as used herein, the term "portion" in the context of genomic deletion is at least 10% to about 100% of the specified region. In other embodiments, the portion deleted is at least 20%, at least 30%, at least 40%, at least 50%, at least 60%, at least 70%, at least 80%, at least 90%, at least 95%, at least 99% or even 100% of the specified region.

In one embodiment of this aspect and all other aspects described herein, the method further comprises selecting a mammal in need of increasing fetal hemoglobin, such as a mammal having a hemoglobinopathy.

In one embodiment of this aspect and all other aspects described herein, the mammal has been diagnosed with a hemoglobinopathy.

In one embodiment of this aspect and all other aspects described herein, the mammal in need of increasing fetal hemoglobin has been diagnosed with a hemoglobinopathy.

In one embodiment of this aspect and all other aspects described herein, the hemoglobinopathy is a β-hemoglobinopathy.

In one embodiment of this aspect and all other aspects described herein, the hemoglobinopathy is sickle cell disease.

In one embodiment of this aspect and all other aspects described herein, the hemoglobinopathy is β-thalassemia.

In one embodiment of this aspect and all other aspects described herein, the contacted cell, human cell, hematopoietic progenitor cell or its progeny is administered to the mammal.

In further embodiment of any one treatment method described, the method comprises chemotherapy and/or radiation therapy to remove or reduced the endogenous hematopoietic progenitor or stem cells in the mammal.

In one embodiment of any one method described herein, the contacted cells, targeted gene edited cells described herein having at least one genetic modification can be cryopreserved and stored until the cells are needed for administration into a mammal.

In one embodiment of any one method described herein, the contacted cells, targeted gene edited cells described herein having at least one genetic modification can be cultured ex vivo to expand or increase the number of cells prior to storage, eg. by cryopreservation, or prior to use, e.g., transplanted into a recipient mammal, e.g., a patient.

In one embodiment of this aspect and all other aspects described herein, the contacted population of hematopoietic progenitor or stem cells having increased fetal hemoglobin expression is cryopreserved and stored or reintroduced into the mammal. In another embodiment, the cryopreserved population of hematopoietic progenitor or stem cells having increased fetal hemoglobin expression is thawed and then reintroduced into the mammal. In further embodiment of this method, the method comprises chemotherapy and/or radiation therapy to remove or reduced the endogenous hematopoietic progenitor or stem cells in the mammal. In any of the embodiment of the described method, the hematopoietic progenitor or stem cells can be substituted with an iPSCs described herein.

In another embodiment, the cryopreserved population of hematopoietic progenitor or stem cells having increased fetal hemoglobin expression is thawed and then reintroduced into the mammal. In further embodiment of this method, the method comprises chemotherapy and/or radiation therapy to remove or reduced the endogenous hematopoietic progenitor or stem cells in the mammal. In any of the embodiment of the described method, the hematopoietic progenitor or stem cells can be substituted with an iPSCs derived from the mammal. In any embodiment of the method, the method further comprises selecting a mammal in need of increased fetal hemoglobin expression.

In further embodiment of this method, the population of hematopoietic progenitor or stem cells with genetic modification or targeted gene editing in the genomic DNA and having increased fetal hemoglobin expression is cryopreserved and stored or reintroduced into the mammal. In another embodiment, the population of hematopoietic progenitor or stem cells with deleted genomic DNA and having increased fetal hemoglobin expression is thawed and then reintroduced into the mammal. In further embodiment of this method, the method comprises chemotherapy and/or radiation therapy to remove or reduced the endogenous hematopoietic progenitor or stem cells in the mammal. In any of the embodiment of the described method, the hematopoietic progenitor or stem cells can be substituted with an iPSCs described herein. In any of the embodiment of the described method, the hematopoietic progenitor or stem cells or iPSCs are analogous to the mammal, meaning the cells are derived from the same mammal. In another of the embodiment of the described method, the hematopoietic progenitor or stem cells or iPSCs are non-analogous to the mammal, meaning the cells are not derived from the same mammal, but another mammal of the same species. For example, the mammal is a human. In any embodiment of the method, the method further comprises selecting a mammal in need of increased fetal hemoglobin expression.

In further embodiment of this method, the population of hematopoietic progenitor or stem cells with genetic modification or targeted gene editing in the genomic DNA and having increased fetal hemoglobin expression is cryopreserved and stored or reintroduced into the mammal. In another embodiment, the cryopreserved population of hematopoietic progenitor or stem cells having increased fetal hemoglobin expression is thawed and then reintroduced into the mammal. In further embodiment of this method, the method comprises chemotherapy and/or radiation therapy to remove or reduced the endogenous hematopoietic progenitor or stem cells in the mammal. In any of the embodiment of the described method, the hematopoietic progenitor or stem cells can be substituted with an iPSCs derived from the mammal. In any embodiment of the method, the method further comprises selecting a mammal in need of increased fetal hemoglobin expression.

In one embodiment of any method described, the method further comprises selecting a mammal in need of increased fetal hemoglobin expression. Exemplary mammal in need of increased fetal hemoglobin expression is one that has been diagnosed with a hemoglobinopathy.

In one embodiment of any method, the cells obtained after electroporation the compositions described herein can be cryopreserved till they are needed for administration into the mammal. In further embodiment of this method, the method comprises chemotherapy and/or radiation therapy to remove or reduced the endogenous hematopoietic progenitor or stem cells in the mammal. In any of the embodiment of the described method, the hematopoietic progenitor or stem cells or iPSCs are autologous to the mammal, meaning the cells are derived from the same mammal. In another of the embodiment of the described method, the hematopoietic progenitor or stem cells or iPSCs are non-autologous to the mammal, meaning the cells are not derived from the same mammal, but another mammal of the same species. For example, the mammal is a human.

In one embodiment of any method described, the method further comprises selecting a mammal in need of treatment of a hemoglobinopathy.

In one embodiment, the cells obtained after the contacting step can be cryopreserved till they are needed for administration into the mammal. In any embodiment of the method, the method further comprises selecting a mammal in need of treatment of a hemoglobinopathy.

In one embodiment of any method described, the method further comprises administering the cells obtained after the contacting step into the mammal.

In one aspect of any method, the method further comprises of selecting a subject diagnosed with a hemoglobinopathy or a subject at risk of developing a hemoglobinopathy.

In one aspect of any method, the hemoglobinopathy is sickle cell disease (SCD) or thalassemia (THAL). For example, β-thalassemias.

In one aspect of the method, the method further comprising administering to the subject a therapy comprising oxygen, hydroxyurea, folic acid, or a blood transfusion.

In one aspect, the present specification provides a method of treating, or reducing a risk of developing, a hemoglobinopathy in a subject In any embodiment of any treatment method described, the hemoglobinopathy is a β-hemoglobinopathy.

In any embodiment of any treatment method described, the hemoglobinopathy is β-thalassemia.

In any embodiment of any treatment method described, the hemoglobinopathy is sickle cell anemia.

In one of embodiment of any described method, the hematopoietic progenitor or stem cells or iPSCs are autologous to the mammal, meaning the cells are derived from the same mammal. In another of the embodiment of any described method, the hematopoietic progenitor or stem cells or iPSCs are non-autologous to the mammal, meaning the cells are not derived from the same mammal, but another mammal of the same species. For example, the mammal is a human.

In one of embodiment of any described method, the contacting of any cell described herein can be ex vivo or in vitro or in vivo.

In one aspect, fetal hemoglobin expression is increased in the mammal, relative to expression prior to the contacting.

In another embodiment of any described method, the hematopoietic progenitor cell, the isolated human cell, or isolated cell is contacted ex vivo or in vitro.

In another embodiment of any described method, the at least one genetic modification is a deletion. In another embodiment of this aspect and all other aspects described herein, the at least one epigenetic modification.

In one embodiment of use of the composition described herein, the composition causes an increase in fetal hemoglobin mRNA or protein expression in the contact cell.

In one embodiment of use of the composition described herein, the cells of any compositions described are autologous, to the mammal who is the recipient of the cells in a transplantation procedure, i.e., the cells of the composition are derived or harvested from the mammal prior to any described modification.

In one embodiment of use of the composition described herein, the cells of any compositions described are non-autologous to the mammal who is the recipient of the cells in a transplantation procedure, i.e., the cells of the composition are not derived or harvested from the mammal prior to any described modification.

In one embodiment of use of the composition described herein, the cells of any compositions described are at the minimum HLA type matched with to the mammal who is the recipient of the cells in a transplantation procedure.

In one embodiment of use of the composition described herein, the cells of any compositions described are isolated progenitor cells prior to any described genetic modification by targeted editing using the methods described herein.

In one embodiment of use of the composition described herein, the cells of any compositions described are isolated hematopoietic progenitor cells prior to any described genetic modification by targeted editing using the methods described herein.

In one embodiment of use of the composition described herein, the cells of any compositions described are isolated induced pluripotent stem cells prior to any described genetic modification by targeted editing using the methods described herein.

In one embodiment of use of the composition described herein, the cells of any compositions described are cryopreserved prior to use.

In one embodiment of any one method described, the method is used to treat, prevent, or ameliorate a hemoglobinopathy is selected from the group consisting of: hemoglobin C disease, hemoglobin sickle cell disease (SCD), sickle cell anemia, hereditary anemia, thalassemia, β-thalassemia, thalassemia major, thalassemia intermedia, α-thalassemia, and hemoglobin H disease.

The contacted or electroporated cells described herein are then administered to a subject in need of gene therapy.

In one embodiment of any one method described, the method further comprises selecting a subject in need of the gene therapy described. For example, a subject exhibiting symptoms or cytology of a hemoglobinopathy is selected from the group consisting of hemoglobin C disease, hemoglobin sickle cell disease (SCD), sickle cell anemia, hereditary anemia, thalassemia, β-thalassemia, thalassemia major, thalassemia intermedia, α-thalassemia, and hemoglobin H disease. Alternatively, the subject carries a genetic mutation that is associated with a hemoglobinopathy, a genetic mutation described herein. For example, a subject diagnosis of SCD with genotype HbSS, HbS/β0 thalassemia, HbSD, or HbSO, and/or with HbF<10% by electrophoresis.

In a particular embodiment, a method of preventing, ameliorating, or treating a hemoglobinopathy in a subject is provided. The method comprises administering a population of cells comprising engineered/genetically modified hematopoietic stem cells or hematopoietic progenitor cells described herein.

In particular embodiments of any methods described, a population of engineered/genetically modified cells administered to a subject comprises hematopoietic stem or progenitor cells, proerythroblasts, basophilic erythroblasts, polychromatic erythroblasts, orthochromatic erythroblasts, polychromatic erythrocytes, and erythrocytes (RBCs), or any combination thereof.

In some embodiments of any methods described, the population of engineered/genetically modified cells can be culture expanded in vitro or ex vivo prior to implantation/engraftment into a subject or prior to cryopreservation for storage.

In some embodiments of any methods described, the population of engineered/genetically modified cells can be culture expanded in vitro or ex vivo after cryopreservation prior to implantation/engraftment into a subject.

In some embodiments of any methods described, the population of engineered/genetically modified cells can be differentiated in vitro or ex vivo prior to implantation into a subject.

The genetically modified cells may be administered as part of a bone marrow or cord blood transplant in an individual that has or has not undergone bone marrow ablative therapy. In one embodiment, genetically modified cells contemplated herein are administered in a bone marrow transplant to an individual that has undergone chemoablative or radioablative bone marrow therapy.

In one embodiment of any method described, a dose of genetically modified cells is delivered to a subject intravenously. In one embodiment, genetically modified hematopoietic cells are intravenously administered to a subject.

In particular embodiments, patients receive a dose of genetically modified cells, e.g., hematopoietic stem cells, of about $1 \times 10^5$ cells/kg, about $5 \times 10^5$ cells/kg, about $1 \times 10^6$ cells/kg, about $2 \times 10^6$ cells/kg, about $3 \times 10^6$ cells/kg, about $4 \times 10^6$ cells/kg, about $5 \times 10^6$ cells/kg, about $6 \times 10^6$ cells/kg, about $7 \times 10^6$ cells/kg, about $8 \times 10^6$ cells/kg, about $9 \times 10^6$ cells/kg, about $1 \times 10^7$ cells/kg, about $5 \times 10^7$ cells/kg, about $1 \times 10^8$ cells/kg, or more in one single intravenous dose. In certain embodiments, patients receive a dose of genetically modified cells, e.g., hematopoietic stem cells described herein or genetic engineered cells described herein or progeny thereof, of at least $1 \times 10^5$ cells/kg, at least $5 \times 10^5$ cells/kg, at least $1 \times 10^6$ cells/kg, at least $2 \times 10^6$ cells/kg, at least $3 \times 10^6$ cells/kg, at least $4 \times 10^6$ cells/kg, at least $5 \times 10^6$ cells/kg, at least $6 \times 10^6$ cells/kg, at least $7 \times 10^6$ cells/kg, at least $8 \times 10^6$ cells/kg, at least $9 \times 10^6$ cells/kg, at least $1 \times 10^7$ cells/kg, at least $5 \times 10^7$ cells/kg, at least $1 \times 10^8$ cells/kg, or more in one single intravenous dose.

In an additional embodiment, patients receive a dose of genetically modified cells, e.g., hematopoietic stem cells, of about $1 \times 10^5$ cells/kg to about $1 \times 10^8$ cells/kg, about $1 \times 10^6$ cells/kg to about $1 \times 10^8$ cells/kg, about $1 \times 10^6$ cells/kg to about $9 \times 10^6$ cells/kg, about $2 \times 10^6$ cells/kg to about $8 \times 10^6$ cells/kg, about $2 \times 10^6$ cells/kg to about $8 \times 10^6$ cells/kg, about $2 \times 10^6$ cells/kg to about $5 \times 10^6$ cells/kg, about $3 \times 10^6$ cells/kg to about $5 \times 10^6$ cells/kg, about $3 \times 10^6$ cells/kg to about $4 \times 10^8$ cells/kg, or any intervening dose of cells/kg.

In various embodiments, the methods described here provide more robust and safe gene therapy than existing methods and comprise administering a population or dose of cells comprising about 5% transduced/genetically modified cells, about 10% transduced/genetically modified cells, about 15% transduced/genetically modified cells, about 20% transduce/genetically modified d cells, about 25% transduced/genetically modified cells, about 30% transduced/genetically modified cells, about 35% transduced/genetically modified cells, about 40% transduced/genetically modified cells, about 45% transduced/genetically modified cells, or about 50% transduce/genetically modified cells, to a subject.

In one embodiment, the invention provides genetically modified cells, such as a stem cell, e.g., hematopoietic stem cell, with the potential to expand or increase a population of erythroid cells. Hematopoietic stem cells are the origin of erythroid cells and thus, are preferred.

In one embodiment, the contacted hematopoietic stem cells described herein or genetic engineered cells described herein or the the progeny cells thereof are implanted with prostaglandin E2 and/or antioxidant N-acetyl-L-cysteine (NAC) to promote the engraftments of the respective cells.

In a further embodiment of any methods described herein, the hematopoietic stem cell or hematopoietic progenitor cell being contacted is of the erythroid lineage.

In one embodiment of any methods described herein, the hematopoietic stem cell or hematopoietic progenitor cell is collected from peripheral blood, cord blood, chorionic villi, amniotic fluid, placental blood, or bone marrow.

In a further embodiment of any methods described herein, the recipient subject is treated with chemotherapy and/or radiation prior to implantation of the contacted or transfected cells (ie. the contacted hematopoietic stem cells described herein or genetic engineered cells described herein or the the progeny cells thereof).

In one embodiment, the chemotherapy and/or radiation is to reduce endogenous stem cells to facilitate engraftment of the implanted cells.

In one aspect of any method, the contacted hematopoietic stem cells described herein or genetic engineered cells described herein or the the progeny cells thereof are treated ex vivo with prostaglandin E2 and/or antioxidant N-acetyl-L-cysteine (NAC) to promote subsequent engraftment in a recipient subject.

Engraftment analysis was performed 4, 8 and 12 weeks post transplantation in peripheral blood and bone marrow. For example, harvest a sample of blood from these locations and determine the BCL11A expression by any method known in the art.

In one aspect of any one method described herein, the method comprises obtaining a sample or a population of embryonic stem cells, somatic stem cells, progenitor cells, bone marrow cells, hematopoietic stem cells, or hematopoietic progenitor cells from the subject.

In one embodiment of any one method described herein, the cells that is contacted with a nucleic acid molecule describe herein, or a composition describe herein comprising a nucleic acid molecule.

In one embodiment, the embryonic stem cells, somatic stem cells, progenitor cells, bone marrow cells, hematopoietic stem cells, hematopoietic progenitor cells are isolated from the host subject, transfected, cultured (optional), and transplanted back into the same host, i. e. an autologous cell transplant. In another embodiment, the embryonic stem cells, somatic stem cells, progenitor cells, bone marrow cells, hematopoietic stem cells, or hematopoietic progenitor cells are isolated from a donor who is an HLA-type match with a host (recipient) who is diagnosed with or at risk of developing a hemoglobinopathy. Donor-recipient antigen type-matching is well known in the art. The HLA-types include HLA-A, HLA-B, HLA-C, and HLA-D. These represent the minimum number of cell surface antigen matching required for transplantation. That is the transfected cells are transplanted into a different host, i.e., allogeneic to the recipient host subject. The donor's or subject's embryonic stem cells, somatic stem cells, progenitor cells, bone marrow cells, hematopoietic stem cells, or hematopoietic progenitor cells can be contacted (electroporated) with a nucleic acid molecule described herein, the contacted cells are culture expanded, and then transplanted into the host subject. In one embodiment, the transplanted cells engraft in the host subject. The transfected cells can also be cryopreserved after transfected and stored, or cryopreserved after cell expansion and stored.

In one aspect of any method, the embryonic stem cell, somatic stem cell, progenitor cell, bone marrow cell, hema-

Definitions

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

As used herein, the phrase "agent that binds the genomic DNA of the cell on chromosome 2 location 60725424 to 60725688 (+55 functional region), at location 60722238 to 60722466 (+58 functional region), and/or at location 60718042 to 60718186 (+62 functional region)" refers to small molecules, nucleic acids, proteins, peptides or oligonucleotides that can bind to the location within the genomic DNA (e.g., chromosome 2 location 60725424 to 60725688 (+55 functional region), at location 60722238 to 60722466 (+58 functional region), and/or at location 60718042 to 60718186 (+62 functional region)) and represses mRNA or protein expression of BCL11A in a cell by at least 20% compared to the mRNA or protein level of BCL11A in a cell not treated with such an agent. In one embodiment, the agent "interferes with BCL11A interactions with BCL11A binding partners," as that phrase is used herein.

As used herein, the term "small molecule" refers to a chemical agent including, but not limited to, peptides, peptidomimetics, amino acids, amino acid analogs, polynucleotides, polynucleotide analogs, aptamers, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

A "nucleic acid", as described herein, can be RNA or DNA, and can be single or double stranded, and can be selected, for example, from a group including: nucleic acid encoding a protein of interest, oligonucleotides, nucleic acid analogues, for example peptide-nucleic acid (PNA), pseudo-complementary PNA (pc-PNA), locked nucleic acid (LNA) etc. Such nucleic acid sequences include, for example, but are not limited to, nucleic acid sequence encoding proteins, for example that act as transcriptional repressors, antisense molecules, ribozymes, small inhibitory nucleic acid sequences, for example but are not limited to RNAi, shRNAi, siRNA, micro RNAi (mRNAi), antisense oligonucleotides etc.

By "interferes with BCL11A interactions with BCL11A binding partners" is meant that the amount of interaction of BCL11A with the BCL11A binding partner is at least 5% lower in populations treated with a BCL11A inhibitor, than a comparable, control population, wherein no BCL11A inhibitor is present. It is preferred that the amount of interaction of BCL11A with the BCL11A binding partner in a BCL11A-inhibitor treated population is at least 10% lower, at least 20% lower, at least 30% lower, at least 40% lower, at least 50% lower, at least 60% lower, at least 70% lower, at least 80% lower, at least 90% lower, at least 1-fold lower, at least 2-fold lower, at least 5-fold lower, at least 10 fold lower, at least 100 fold lower, at least 1000-fold lower, or more than a comparable control treated population in which no BCL11A inhibitor is added. At a minimum, BCL11A interaction can be assayed by determining the amount of BCL11A binding to the BCL11A binding partner using techniques standard in the art, including, but not limited to, mass spectrometry, immunoprecipitation, or gel filtration assays. Alternatively, or in addition, BCL11A activity can be assayed by measuring fetal hemoglobin expression at the mRNA or protein level following treatment with a candidate BCL11A inhibitor.

In one embodiment, BCL11A activity is the interaction of BCL11A with its binding partners: GATA-1, FOG-1, components of the NuRD complex, matrin-3, MTA2 and RBBP7. Accordingly, any antibody or fragment thereof, small molecule, chemical or compound that can block this interaction is considered an inhibitor of BCL11A activity.

As used herein, the term "genetic engineered cell" refers to a cell that comprises at least one genetic modification, as that term is used herein.

As used herein, the term "genetic modification" refers to a disruption at the genomic level resulting in a decrease in BCL11A expression or activity in a cell. Exemplary genetic modifications can include deletions, frame shift mutations, point mutations, exon removal, removal of one or more DNAse 1-hypersensitive sites (DHS) (e.g., 2, 3, 4 or more DHS regions), etc.

By "inhibits BCL11A expression" is meant that the amount of expression of BCL11A is at least 5% lower in a cell or cell population treated with a DNA-targeting endonuclease, than a comparable, control cell or cell population, wherein no DNA-targeting endonuclease is present. It is preferred that the percentage of BCL11A expression in a treated population is at least 10% lower, at least 20% lower, at least 30% lower, at least 40% lower, at least 50% lower, at least 60% lower, at least 70% lower, at least 80% lower, at least 90% lower, at least 1-fold lower, at least 2-fold lower, at least 5-fold lower, at least 10 fold lower, at least 100 fold lower, at least 1000-fold lower, or more than a comparable control treated population in which no DNA-targeting endonuclease is added.

By "inhibits BCL11A activity" is meant that the amount of functional activity of BCL11A is at least 5% lower in a cell or cell population treated with the methods described herein, than a comparable, control cell or population, wherein no DNA-targeting endonuclease is present. It is preferred that the percentage of BCL11A activity in a BCL11A-inhibitor treated population is at least 10% lower, at least 20% lower, at least 30% lower, at least 40% lower, at least 50% lower, at least 60% lower, at least 70% lower, at least 80% lower, at least 90% lower, at least 1-fold lower, at least 2-fold lower, at least 5-fold lower, at least 10 fold lower, at least 100 fold lower, at least 1000-fold lower, or more than a comparable control treated population in which no DNA-targeting endonuclease is added. At a minimum, BCL11A activity can be assayed by determining the amount of BCL11A expression at the protein or mRNA levels, using techniques standard in the art. Alternatively, or in addition, BCL11A activity can be determined using a reporter construct, wherein the reporter construct is sensitive to BCL11A activity. The γ-globin locus sequence is recognizable by the nucleic acid-binding motif of the BCL11A construct.

In one embodiment, as used herein, the term "DNA targeting endonuclease" refers to an endonuclease that generates a double-stranded break at a desired position in the genome (e.g., chromosome 2 location 60,716,189-60,728, 612) without producing undesired off-target double-stranded breaks. The DNA targeting endonuclease can be a naturally occurring endonuclease (e.g., a bacterial meganuclease) or it can be artificially generated.

In another embodiment, as used herein, the term "DNA targeting endonuclease" refers to an endonuclease that generates a single-stranded break or a "nick" or break on one strand of the DNA phosphate sugar backbone at a desired position in the genome (e.g., chromosome 2 location 60725424 to 60725688 (+55 functional region), at location 60722238 to 60722466 (+58 functional region), and/or at location 60718042 to 60718186 (+62 functional region)) without producing undesired off-target DNA stranded breaks.

As used herein the term "cleaves" generally refers to the generation of a double-stranded break in the DNA genome at a desired location.

As used herein, the term "effective amount of a composition comprising at least a DNA-targeting endonuclease" refers to an amount of a DNA-targeting endonuclease that yields sufficient endonuclease activity to generate a double-stranded break in the desired location of the genome. In one embodiment, the effective amount of a DNA-targeting endonuclease generates a double-stranded break at the desired genetic locus in at least 20% of the cells in a population contacted with the composition (e.g., at least 30%, at least 40%, at least 50%, at least 60%, at least 70%, at least 80%, at least 90%, at least 95%, at least 99%, or even 100% of the cells in the population comprise a genetic modification produced by the DNA-targeting endonuclease composition).

As used herein the term "increasing the fetal hemoglobin levels" in a cell indicates that fetal hemoglobin is at least 5% higher in populations treated with an agent that disrupts BCL11A mRNA or protein expression (e.g., a DNA-targeting endonuclease) by binding to genomic DNA at chromosome 2 location 60,716,189-60,728,612, than in a comparable, control population, wherein no agent is present. It is preferred that the percentage of fetal hemoglobin expression in a population treated with such an agent that binds the genomic DNA at chromosome 2 location 60,716,189-60,728,612 is at least 10% higher, at least 20% higher, at least 30% higher, at least 40% higher, at least 50% higher, at least 60% higher, at least 70% higher, at least 80% higher, at least 90% higher, at least 1-fold higher, at least 2-fold higher, at least 5-fold higher, at least 10 fold higher, at least 100 fold higher, at least 1000-fold higher, or more than a control treated population of comparable size and culture conditions. The term "control treated population" is used herein to describe a population of cells that has been treated with identical media, viral induction, nucleic acid sequences, temperature, confluency, flask size, pH, etc., with the exception of the addition of the agent that binds genomic DNA at chromosome 2 location 60,716,189-60,728,612. In one embodiment, any method known in the art can be used to measure an increase in fetal hemoglobin expression, e. g. Western Blot analysis of fetal γ-globin protein and quantifying mRNA of fetal γ-globin.

The term "isolated cell" as used herein refers to a cell that has been removed from an organism in which it was originally found, or a descendant of such a cell. Optionally the cell has been cultured in vitro, e.g., in the presence of other cells. Optionally the cell is later introduced into a second organism or re-introduced into the organism from which it (or the cell from which it is descended) was isolated.

The term "isolated population" with respect to an isolated population of cells as used herein refers to a population of cells that has been removed and separated from a mixed or heterogeneous population of cells. In some embodiments, an isolated population is a substantially pure population of cells as compared to the heterogeneous population from which the cells were isolated or enriched. In some embodiments, the isolated population is an isolated population of human hematopoietic progenitor cells, e.g., a substantially pure population of human hematopoietic progenitor cells as compared to a heterogeneous population of cells comprising human hematopoietic progenitor cells and cells from which the human hematopoietic progenitor cells were derived.

The term "substantially pure," with respect to a particular cell population, refers to a population of cells that is at least about 75%, preferably at least about 85%, more preferably at least about 90%, and most preferably at least about 95% pure, with respect to the cells making up a total cell population. That is, the terms "substantially pure" or "essentially purified," with regard to a population of hematopoietic progenitor cells, refers to a population of cells that contain fewer than about 20%, more preferably fewer than about 15%, 10%, 8%, 7%, most preferably fewer than about 5%, 4%, 3%, 2%, 1%, or less than 1%, of cells that are not hematopoietic progenitor cells as defined by the terms herein.

A "subject," as used herein, includes any animal that exhibits a symptom of a monogenic disease, disorder, or condition that can be treated with the cell-based therapeutics, and methods disclosed elsewhere herein. In preferred embodiments, a subject includes any animal that exhibits symptoms of a disease, disorder, or condition of the hematopoietic system, e.g., a hemoglobinopathy, that can be treated with the gene therapy/cell-based therapeutics, and methods contemplated herein. Suitable subjects (e.g., patients) include laboratory animals (such as mouse, rat, rabbit, or guinea pig), farm animals, and domestic animals or pets (such as a cat or dog). Non-human primates and, preferably, human patients, are included. Typical subjects include animals that exhibit aberrant amounts (lower or higher amounts than a "normal" or "healthy" subject) of one or more physiological activities that can be modulated by gene therapy.

In one embodiment, as used herein, "prevent," and similar words such as "prevented," "preventing" etc., indicate an approach for preventing, inhibiting, or reducing the likelihood of the occurrence or recurrence of, a disease or condition. In another embodiment, the term refers to delaying the onset or recurrence of a disease or condition or delaying the occurrence or recurrence of the symptoms of a disease or condition. In another embodiment, as used herein, "prevention" and similar words includes reducing the intensity, effect, symptoms and/or burden of a disease or condition prior to onset or recurrence of the disease or condition.

As used herein, the term "treating" includes reducing or alleviating at least one adverse effect or symptom of a condition, disease or disorder. For example, the term "treating" and "treatment" refers to administering to a subject an effective amount of a composition, e.g., an effective amount of a composition comprising a population of hematopoietic progenitor cells so that the subject has a reduction in at least one symptom of the disease or an improvement in the disease, for example, beneficial or desired clinical results. For purposes of this disclosure, beneficial or desired clinical results include, but are not limited to, alleviation of one or more symptoms, diminishment of extent of disease, disease stabilization (e.g., not worsening), delay or slowing of disease progression, amelioration or palliation of the disease state, and remission (whether partial or total), whether detectable or undetectable. In some embodiments, treating can refer to prolonging survival as compared to expected survival if not receiving treatment. Thus, one of skill in the art realizes that a treatment can improve the disease condition, but may not be a complete cure for the disease. In some embodiments, treatment can include prophylaxis. However, in alternative embodiments, treatment does not include prophylaxis.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. Typically, such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used with the methods described herein that will be effective in the treatment of a particular disorder or condition will depend on the nature of the disorder or condition, and can be determined by standard clinical techniques.

As used herein, "prevention" or "preventing," when used in reference to a disease, disorder or symptoms thereof, refers to a reduction in the likelihood that an individual will develop a disease or disorder, e.g., a hemoglobinopathy. The likelihood of developing a disease or disorder is reduced, for example, when an individual having one or more risk factors for a disease or disorder either fails to develop the disorder or develops such disease or disorder at a later time or with less severity, statistically speaking, relative to a population having the same risk factors and not receiving treatment as described herein. The failure to develop symptoms of a disease, or the development of reduced (e.g., by at least 10% on a clinically accepted scale for that disease or disorder) or delayed (e.g., by days, weeks, months or years) symptoms is considered effective prevention.

In connection with contacting a cell with a DNA-targeting endonuclease to decrease BCL11A expression, the phrase "increasing fetal hemoglobin levels in a cell" indicates that fetal hemoglobin in a cell or population of cells is at least 5% higher in the cell or population of cells treated with the DNA-targeting endonuclease, than a comparable, control population, wherein no DNA-targeting endonuclease is present. It is preferred that the fetal hemoglobin expression in a DNA-targeting endonuclease treated cell is at least 10% higher, at least 20% higher, at least 30% higher, at least 40% higher, at least 50% higher, at least 60% higher, at least 70% higher, at least 80% higher, at least 90% higher, at least 1-fold higher, at least 2-fold higher, at least 5-fold higher, at least 10 fold higher, at least 100 fold higher, at least 1000-fold higher, or more than a comparable control treated population. The term "control treated population" is used herein to describe a population of cells that has been treated with identical media, viral induction, nucleic acid sequences, temperature, confluency, flask size, pH, etc., with the exception of the addition of the BCL11A inhibitor.

The term "mammal" is intended to encompass a singular "mammal" and plural "mammals," and includes, but is not limited to humans; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and bears. In some preferred embodiments, a mammal is a human.

Accordingly, in one embodiment, the mammal has been diagnosed with a hemoglobinopathy. In a further embodiment, the hemoglobinopathy is a β-hemoglobinopathy. In one preferred embodiment, the hemoglobinopathy is a sickle cell disease. As used herein, "sickle cell disease" can be sickle cell anemia, sickle-hemoglobin C disease (HbSC), sickle beta-plus-thalassemia (HbS/β+), or sickle beta-zero-thalassaemia (HbS/β0). In another preferred embodiment, the hemoglobinopathy is a β-thalassemia.

As used herein, the term "hemoglobinopathy" means any defect in the structure or function of any hemoglobin of an individual, and includes defects in the primary, secondary, tertiary or quaternary structure of hemoglobin caused by any mutation, such as deletion mutations or substitution mutations in the coding regions of the β-globin gene, or mutations in, or deletions of, the promoters or enhancers of such genes that cause a reduction in the amount of hemoglobin produced as compared to a normal or standard condition. The term further includes any decrease in the amount or effectiveness of hemoglobin, whether normal or abnormal, caused by external factors such as disease, chemotherapy, toxins, poisons, or the like.

In one embodiment, the term "effective amount", as used herein, refers to the amount of a cell composition that is safe and sufficient to treat, lesson the likelihood of, or delay the development of a hemoglobinopathy. The amount can thus cure or result in amelioration of the symptoms of the hemoglobinopathy, slow the course of hemoglobinopathy disease progression, slow or inhibit a symptom of a hemoglobinopathy, slow or inhibit the establishment of secondary symptoms of a hemoglobinopathy or inhibit the development of a secondary symptom of a hemoglobinopathy. The effective amount for the treatment of the hemoglobinopathy depends on the type of hemoglobinopathy to be treated, the severity of the symptoms, the subject being treated, the age and general condition of the subject, the mode of administration and so forth. Thus, it is not possible or prudent to specify an exact "effective amount". However, for any given case, an appropriate "effective amount" can be determined by one of ordinary skill in the art using only routine experimentation.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth. It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

Hemoglobinopathies

Fetal hemoglobin (HbF) is a tetramer of two adult α-globin polypeptides and two fetal β-like γ-globin polypeptides. During gestation, the duplicated γ-globin genes constitute the predominant genes transcribed from the β-globin locus. Following birth, γ-globin becomes progressively replaced by adult β-globin, a process referred to as the "fetal switch" (3). The molecular mechanisms underlying this switch have remained largely undefined and have been a subject of intense research. The developmental switch from production of predominantly fetal hemoglobin or HbF ($\alpha_2\gamma_2$) to production of adult hemoglobin or HbA ($\alpha 2\beta 2$) begins at about 28 to 34 weeks of gestation and continues shortly after birth at which point HbA becomes predominant. This switch results primarily from decreased transcription of the gamma-globin genes and increased transcription of beta-globin genes. On average, the blood of a normal adult contains only about 2% HbF, though residual HbF levels have a variance of over 20 fold in healthy adults (Atweh, Semin. Hematol. 38(4):367-73 (2001)).

Hemoglobinopathies encompass a number of anemias of genetic origin in which there is a decreased production and/or increased destruction (hemolysis) of red blood cells (RBCs). These disorders also include genetic defects that result in the production of abnormal hemoglobins with a concomitant impaired ability to maintain oxygen concentration. Some such disorders involve the failure to produce normal β-globin in sufficient amounts, while others involve the failure to produce normal β-globin entirely. These disorders specifically associated with the β-globin protein are referred to generally as β-hemoglobinopathies. For example, β-thalassemias result from a partial or complete defect in the expression of the β-globin gene, leading to deficient or absent HbA. Sickle cell anemia results from a point mutation in the β-globin structural gene, leading to the production of an abnormal (sickled) hemoglobin (HbS). HbS RBCs are more fragile than normal RBCs and undergo hemolysis more readily, leading eventually to anemia (Atweh, Semin. Hematol. 38(4):367-73 (2001)). Moreover, the presence of a BCL11A genetic variant, HBS11L-MYB variation, ameliorates the clinical severity in beta-thalassemia. This variant has been shown to be associated with HbF levels. It has been shown that there is an odds ratio of 5 for having a less severe form of beta-thalassemia with the high-HbF variant (Galanello S. et al., 2009, Blood, in press).

The search for treatment aimed at reduction of globin chain imbalance in patients with β-hemoglobinopathies has focused on the pharmacologic manipulation of fetal hemoglobin (α2γ2; HbF). The important therapeutic potential of such approaches is indicated by observations of the mild phenotype of individuals with co-inheritance of both homozygous β-thalassemia and hereditary persistence of fetal hemoglobin (HPFH), as well as by those patients with homozygous β-thalassemia who synthesize no adult hemoglobin, but in whom a reduced requirement for transfusions is observed in the presence of increased concentrations of fetal hemoglobin. Furthermore, it has been observed that certain populations of adult patients with β chain abnormalities have higher than normal levels of fetal hemoglobin (HbF), and have been observed to have a milder clinical course of disease than patients with normal adult levels of HbF. For example, a group of Saudi Arabian sickle-cell anemia patients who express 20-30% HbF have only mild clinical manifestations of the disease (Pembrey, et al., Br. J. Haematol. 40: 415-429 (1978)). It is now accepted that β-hemoglobinopathies, such as sickle cell anemia and the β-thalassemias, are ameliorated by increased HbF production. (Reviewed in Jane and Cunningham Br. J. Haematol. 102: 415-422 (1998) and Bunn, N. Engl. J. Med. 328: 129-131 (1993)).

While the molecular mechanisms controlling the in vivo developmental switch from γ- to β-globin gene expression are currently unknown, there is accumulating evidence that external factors can influence γ-globin gene expression. The first group of compounds discovered having HbF reactivation activity were cytotoxic drugs. The ability to cause de novo synthesis of HbF by pharmacological manipulation was first shown using 5-azacytidine in experimental animals (DeSimone, Proc Natl Acad Sci USA. 79(14):4428-31 (1982)). Subsequent studies confirmed the ability of 5-azacytidine to increase HbF in patients with β-thalassemia and sickle cell disease (Ley, et al., N. Engl. J. Medicine, 307: 1469-1475 (1982), and Ley, et al., Blood 62: 370-380 (1983)). Additional experiments demonstrated that baboons treated with cytotoxic doses of arabinosylcytosine (ara-C) responded with striking elevations of F-reticulocytes (Papayannopoulou et al., Science. 224(4649):617-9 (1984)), and that treatment with hydroxyurea led to induction of γ-globin in monkeys or baboons (Letvin et. al., N Engl J Med. 310(14):869-73 (1984)).

The second group of compounds investigated for the ability to cause HbF reactivation activity was short chain fatty acids. The initial observation in fetal cord blood progenitor cells led to the discovery that γ-aminobutyric acid can act as a fetal hemoglobin inducer (Perrine et al., Biochem Biophys Res Commun. 148(2):694-700 (1987)). Subsequent studies showed that butyrate stimulated globin production in adult baboons (Constantoulakis et al., Blood. December; 72(6):1961-7 (1988)), and it induced γ-globin in erythroid progenitors in adult animals or patients with sickle cell anemia (Perrine et al., Blood. 74(1):454-9 (1989)). Derivatives of short chain fatty acids such as phenylbutyrate (Dover et al., Br J Haematol. 88(3):555-61 (1994)) and valproic acid (Liakopoulou et al., 1: Blood. 186(8):3227-35 (1995)) also have been shown to induce HbF in vivo. Given the large number of short chain fatty acid analogs or derivatives of this family, there are a number of potential compounds of this family more potent than butyrate. Phenylacetic and phenylalkyl acids (Torkelson et al., Blood Cells Mol Dis. 22(2):150-8. (1996)), which were discovered during subsequent studies, were considered potential HbF inducers as they belonged to this family of compounds. Presently, however, the use of butyrate or its analogs in sickle cell anemia and β-thalassemia remains experimental and cannot be recommended for treatment outside of clinical trials.

Clinical trials aimed at reactivation of fetal hemoglobin synthesis in sickle cell anemia and β-thalassemia have included short term and long term administration of such compounds as 5-azacytidine, hydroxyurea, recombinant human erythropoietin, and butyric acid analogs, as well as combinations of these agents. Following these studies, hydroxyurea was used for induction of HbF in humans and later became the first and only drug approved by the Food and Drug Administration (FDA) for the treatment of hemoglobinopathies. However, varying drawbacks have contraindicated the long term use of such agents or therapies, including unwanted side effects and variability in patient responses. For example, while hydroxyurea stimulates HbF production and has been shown to clinically reduce sickling crisis, it is potentially limited by myelotoxicity and the risk of carcinogenesis. Potential long term carcinogenicity would also exist in 5-azacytidine-based therapies. Erythropoietin-based therapies have not proved consistent among a range of patient populations. The short half-lives of butyric acid in vivo have been viewed as a potential obstacle in adapting these compounds for use in therapeutic interventions. Furthermore, very high dosages of butyric acid are necessary for inducing γ-globin gene expression, requiring catheterization for continuous infusion of the compound. Moreover, these high dosages of butyric acid can be associated with neurotoxicity and multiorgan damage (Blau, et al., Blood 81: 529-537 (1993)). While even minimal increases in HbF levels are helpful in sickle cell disease, β-thalassemias require a much higher increase that is not reliably, or safely, achieved by any of the currently used agents (Olivieri, Seminars in Hematology 33: 24-42 (1996)).

Identifying natural regulators of HbF induction and production could provide a means to devise therapeutic interventions that overcome the various drawbacks of the compounds described above. Recent genome-wide association studies have yielded insights into the genetic basis of numerous complex diseases and traits (McCarthy et al., Nat Rev Genet 9, 356 (2008) and Manolio et. al. J Clin Invest 118, 1590 (2008)). However, in the vast majority of instances, the functional link between a genetic association and the underlying pathophysiology remains to be uncovered. The level of fetal hemoglobin (HbF) is inherited as a quantitative trait and clinically important, given its above-mentioned and well-characterized role in ameliorating the severity of the principal β-hemoglobinopathies, sickle cell disease and β-thalassemia (Nathan et. al., Nathan and Oski's hematology of infancy and childhood ed. 6th, pp. 2 v. (xiv, 1864, xli p.) 2003)). Two genome-wide association studies have identified three major loci containing a set of five common single nucleotide polymorphisms (SNPs) that account for ~20% of the variation in HbF levels (Lettre et al., Proc Natl Acad Sci USA (2008); Uda et al., Proc Natl Acad Sci USA 105, 1620 (2008); Menzel et al., Nat Genet 39, 1197 (2007)). Moreover, several of these variants appear to predict the clinical severity of sickle cell disease (Lettre et al., Proc Natl Acad Sci USA (2008)) and at least one of these SNPs may also affect clinical outcome in β-thalassemia (Uda et al., Proc Natl Acad Sci USA 105, 1620 (2008)). The SNP with the largest effect size, explaining over 10% of the variation in HbF, is located in the second intron of a gene on chromosome 2, BCL11A. Whereas BCL11A, a C2H2-type zinc finger transcription factor, has been investigated for its role in lymphocyte development (Liu et al., Nat Immunol 4, 525 (2003) and Liu et al., Mol Cancer 5, 18 (2006)), its role in red blood cell production or globin gene regulation has not been previously assessed.

At the onset of the recombinant DNA era, studies of globin gene structure provided a strong molecular foundation for interrogating the fetal globin switch. Considerable effort has focused on delineating the cis-elements within the β-globin locus necessary for proper regulation of the genes within the β-like globin cluster. These studies relied on naturally occurring mutations and deletions that dramatically influence HbF levels in adults, and have been complemented by generation of transgenic mice harboring portions of the cluster (Nathan et. al., Nathan and Oski's hematology of infancy and childhood ed. 6th, pp. 2 v. (xiv, 1864, xli p.) 2003) and G. Stamatoyannopoulos, Exp Hematol 33, 259 (2005)). Although the precise cis-elements required for globin switching remain ill-defined, findings in transgenic mice have strongly indicated that the γ-globin genes are autonomously silenced in the adult stage, a finding that is most compatible with the absence of fetal-stage specific activators or the presence of a stage-specific repressor. The results of recent genetic association studies provide candidate genes to interrogate for their involvement in control of the γ-globin genes, such as BCL11A.

As used herein, treating or reducing a risk of developing a hemoglobinopathy in a subject means to ameliorate at least one symptom of hemoglobinopathy. In one aspect, the invention features methods of treating, e.g., reducing severity or progression of, a hemoglobinopathy in a subject. In another aspect, the methods can also be used to reduce a risk of developing a hemoglobinopathy in a subject, delaying the onset of symptoms of a hemoglobinopathy in a subject, or increasing the longevity of a subject having a hemoglobinopathy. In one aspect, the methods can include selecting a subject on the basis that they have, or are at risk of developing, a hemoglobinopathy, but do not yet have a hemoglobinopathy, or a subject with an underlying hemoglobinopathy. Selection of a subject can include detecting symptoms of a hemoglobinopathy, a blood test, genetic testing, or clinical recordings. If the results of the test(s) indicate that the subject has a hemoglobinopathy, the methods also include administering the compositions described herein, thereby treating, or reducing the risk of developing, a hemoglobinopathy in the subject. For example, a subject who is diagnosis of SCD with genotype HbSS, HbS/β0 thalassemia, HbSD, or HbSO, and/or HbF<10% by electrophoresis.

As used herein, the term "hemoglobinopathy" refers to a condition involving the presence of an abnormal hemoglobin molecule in the blood. Examples of hemoglobinopathies include, but are not limited to, SCD and THAL. Also included are hemoglobinopathies in which a combination of abnormal hemoglobins is present in the blood (e.g., sickle cell/Hb-C disease). An exemplary example of such a disease includes, but is not limited to, SCD and THAL. SCD and THAL and their symptoms are well-known in the art and are described in further detail below. Subjects can be diagnosed as having a hemoglobinopathy by a health care provider, medical caregiver, physician, nurse, family member, or acquaintance, who recognizes, appreciates, acknowledges, determines, concludes, opines, or decides that the subject has a hemoglobinopathy.

The term "SCD" is defined herein to include any symptomatic anemic condition which results from sickling of red blood cells. Manifestations of SCD include: anemia; pain; and/or organ dysfunction, such as renal failure, retinopathy, acute-chest syndrome, ischemia, priapism, and stroke. As used herein the term "SCD" refers to a variety of clinical problems attendant upon SCD, especially in those subjects who are homozygotes for the sickle cell substitution in HbS. Among the constitutional manifestations referred to herein by use of the term of SCD are delay of growth and development, an increased tendency to develop serious infections, particularly due to pneumococcus, marked impairment of splenic function, preventing effective clearance of circulating bacteria, with recurrent infarcts and eventual destruction of splenic tissue. Also included in the term "SCD" are acute episodes of musculoskeletal pain, which affect primarily the lumbar spine, abdomen, and femoral shaft, and which are similar in mechanism and in severity. In adults, such attacks commonly manifest as mild or moderate bouts of short duration every few weeks or months interspersed with agonizing attacks lasting 5 to 7 days that strike on average about once a year. Among events known to trigger such crises are acidosis, hypoxia, and dehydration, all of which potentiate intracellular polymerization of HbS (J. H. Jandl, Blood: Textbook of Hematology, 2nd Ed., Little, Brown and Company, Boston, 1996, pages 544-545).

As used herein, "THAL" refers to a hereditary disorder characterized by defective production of hemoglobin. In one embodiment, the term encompasses hereditary anemias that occur due to mutations affecting the synthesis of hemoglobins. In other embodiments, the term includes any symptomatic anemia resulting from thalassemic conditions such as severe or β-thalassemia, thalassemia major, thalassemia intermedia, α-thalassemias such as hemoglobin H disease. β-thalassemias are caused by a mutation in the β-globin chain, and can occur in a major or minor form. In the major form of β-thalassemia, children are normal at birth, but develop anemia during the first year of life. The mild form of β-thalassemia produces small red blood cells. Alpha-thalassemias are caused by deletion of a gene or genes from the globin chain.

By the phrase "risk of developing disease" is meant the relative probability that a subject will develop a hemoglobinopathy in the future as compared to a control subject or population (e.g., a healthy subject or population). For example, an individual carrying the genetic mutation associated with SCD, an A to T mutation of the β-globin gene, and whether the individual in heterozygous or homozygous for that mutation increases that individual's risk.

As used herein, the term "genome editing" refers to a reverse genetics method using artificially engineered nucleases to cut and create specific double-stranded breaks at a desired location(s) in the genome, which are then repaired by cellular endogenous processes such as, homologous recombination (HR), homology directed repair (HDR) and non-homologous end-joining (NHEJ). NHEJ directly joins the DNA ends in a double-stranded break, while HDR utilizes a homologous sequence as a template for regenerating the missing DNA sequence at the break point.

It is contemplated herein that the Cas9/CRISPR system of genome editing be employed with the methods and compositions described herein. Clustered regularly interspaced short palindromic repeats (CRISPR)/CRISPR-associated (Cas) systems is useful for RNA-programmable genome editing (see e.g., Jinek, M. et al. Science (2012) 337(6096): 816-821).

Trans-activating crRNA (tracrRNA) is a small trans-encoded RNA. It was first discovered in the human pathogen *Streptococcus pyogenes*. (see Deltcheva E, et al. (2011). Nature 471 (7340): 602-7). In bacteria and archaea, CRISPR/Cas (clustered, regularly interspaced short palindromic repeats/CRISPR-associated proteins) constitute an RNA-mediated defense system which protects against viruses and plasmids. This defensive pathway has three steps. First a copy of the invading nucleic acid is integrated into the CRISPR locus. Next, CRISPR RNAs (crRNAs) are transcribed from this CRISPR locus. The crRNAs are then incorporated into effector complexes, where the crRNA guides the complex to the invading nucleic acid and the Cas proteins degrade this nucleic acid. (See Terns M P and Terns R M (2011). Curr Opin Microbiol 14 (3): 321-7). There are several pathways of CRISPR activation, one of which requires a tracrRNA which plays a role in the maturation of crRNA. TracrRNA is complementary to and base pairs with a pre-crRNA forming an RNA duplex. This is cleaved by RNase III, an RNA-specific ribonuclease, to form a crRNA/tracrRNA hybrid. This hybrid acts as a guide for the endonuclease Cas9, which cleaves the invading nucleic acid. (see Deltcheva E, et al. supra; Jinek M, et al. (2012), Science 337 (6096): 816-21; and Brouns S J (2012), Science 337 (6096): 808-9).

Hematopoietic Progenitor Cells

In one embodiment, the hematopoietic progenitor cell is contacted ex vivo or in vitro. In a specific embodiment, the cell being contacted is a cell of the erythroid lineage. In one embodiment, the cell composition comprises cells having decreased BCL11A expression.

"Hematopoietic progenitor cell" as the term is used herein, refers to cells of a stem cell lineage that give rise to all the blood cell types including the myeloid (monocytes and macrophages, neutrophils, basophils, eosinophils, erythrocytes, megakaryocytes/platelets, dendritic cells), and the lymphoid lineages (T-cells, B-cells, NK-cells). A "cell of the erythroid lineage" indicates that the cell being contacted is a cell that undergoes erythropoiesis such that upon final differentiation it forms an erythrocyte or red blood cell (RBC). Such cells belong to one of three lineages, erythroid, lymphoid, and myeloid, originating from bone marrow hematopoietic progenitor cells. Upon exposure to specific growth factors and other components of the hematopoietic microenvironment, hematopoietic progenitor cells can mature through a series of intermediate differentiation cellular types, all intermediates of the erythroid lineage, into RBCs. Thus, cells of the "erythroid lineage", as the term is used herein, comprise hematopoietic progenitor cells, rubriblasts, prorubricytes, erythroblasts, metarubricytes, reticulocytes, and erythrocytes.

In some embodiment, the hematopoietic progenitor cell has at least one of the cell surface marker characteristic of hematopoietic progenitor cells: CD34+, CD59+, Thy1/CD90+, CD38lo/−, and C-kit/CD117+. Preferably, the hematopoietic progenitor cells have several of these markers.

In some embodiments, the hematopoietic progenitor cells of the erythroid lineage have the cell surface marker characteristic of the erythroid lineage: CD71 and Ter119.

Stem cells, such as hematopoietic progenitor cells, are capable of proliferation and giving rise to more progenitor cells having the ability to generate a large number of mother cells that can in turn give rise to differentiated or differentiable daughter cells. The daughter cells themselves can be induced to proliferate and produce progeny that subsequently differentiate into one or more mature cell types, while also retaining one or more cells with parental developmental potential. The term "stem cell" refers then, to a cell with the capacity or potential, under particular circumstances, to differentiate to a more specialized or differentiated phenotype, and which retains the capacity, under certain circumstances, to proliferate without substantially differentiating. In one embodiment, the term progenitor or stem cell refers to a generalized mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell which itself is derived from a multipotent cell, and so on. While each of these multipotent cells may be considered stem cells, the range of cell types each can give rise to may vary considerably. Some differentiated cells also have the capacity to give rise to cells of greater developmental potential. Such capacity may be natural or may be induced artificially upon treatment with various factors. In many biological instances, stem cells are also "multipotent" because they can produce progeny of more than one distinct cell type, but this is not required for "stem-ness." Self-renewal is the other classical part of the stem cell definition, and it is essential as used in this document. In theory, self-renewal can occur by either of two major mechanisms. Stem cells may divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only. Generally, "progenitor cells" have a cellular phenotype that is more primitive (i.e., is at an earlier step along a developmental pathway or progression than is a fully differentiated cell). Often, progenitor cells also have significant or very high proliferative potential. Progenitor cells can give rise to multiple distinct differentiated cell types or to a single differentiated cell type, depending on the developmental pathway and on the environment in which the cells develop and differentiate.

In the context of cell ontogeny, the adjective "differentiated", or "differentiating" is a relative term. A "differentiated cell" is a cell that has progressed further down the developmental pathway than the cell it is being compared with. Thus, stem cells can differentiate to lineage-restricted precursor cells (such as a hematopoietic progenitor cell), which in turn can differentiate into other types of precursor cells further down the pathway (such as an erythrocyte precursor), and then to an end-stage differentiated cell, such as an erythrocyte, which plays a characteristic role in a certain tissue type, and may or may not retain the capacity to proliferate further.

Induced Pluripotent Stem Cells

In some embodiments, the genetic engineered human cells described herein are derived from isolated pluripotent stem cells. An advantage of using iPSCs is that the cells can be derived from the same subject to which the progenitor cells are to be administered. That is, a somatic cell can be obtained from a subject, reprogrammed to an induced pluripotent stem cell, and then re-differentiated into a hematopoietic progenitor cell to be administered to the subject (e.g., autologous cells). Since the progenitors are essentially derived from an autologous source, the risk of engraftment rejection or allergic responses is reduced compared to the use of cells from another subject or group of subjects. In some embodiments, the hematopoietic progenitors are derived from non-autologous sources. In addition, the use of iPSCs negates the need for cells obtained from an embryonic source. Thus, in one embodiment, the stem cells used in the disclosed methods are not embryonic stem cells.

Although differentiation is generally irreversible under physiological contexts, several methods have been recently developed to reprogram somatic cells to induced pluripotent stem cells. Exemplary methods are known to those of skill in the art and are described briefly herein below.

As used herein, the term "reprogramming" refers to a process that alters or reverses the differentiation state of a differentiated cell (e.g., a somatic cell). Stated another way, reprogramming refers to a process of driving the differentiation of a cell backwards to a more undifferentiated or more primitive type of cell. It should be noted that placing many primary cells in culture can lead to some loss of fully differentiated characteristics. Thus, simply culturing such cells included in the term differentiated cells does not render these cells non-differentiated cells (e.g., undifferentiated cells) or pluripotent cells. The transition of a differentiated cell to pluripotency requires a reprogramming stimulus beyond the stimuli that lead to partial loss of differentiated character in culture. Reprogrammed cells also have the characteristic of the capacity of extended passaging without loss of growth potential, relative to primary cell parents, which generally have capacity for only a limited number of divisions in culture.

The cell to be reprogrammed can be either partially or terminally differentiated prior to reprogramming. In some embodiments, reprogramming encompasses complete reversion of the differentiation state of a differentiated cell (e.g., a somatic cell) to a pluripotent state or a multipotent state. In some embodiments, reprogramming encompasses complete or partial reversion of the differentiation state of a differentiated cell (e.g., a somatic cell) to an undifferentiated cell (e.g., an embryonic-like cell). Reprogramming can result in expression of particular genes by the cells, the expression of which further contributes to reprogramming. In certain embodiments described herein, reprogramming of a differentiated cell (e.g., a somatic cell) causes the differentiated cell to assume an undifferentiated state (e.g., is an undifferentiated cell). The resulting cells are referred to as "reprogrammed cells," or "induced pluripotent stem cells (iPSCs or iPS cells)."

Reprogramming can involve alteration, e.g., reversal, of at least some of the heritable patterns of nucleic acid modification (e.g., methylation), chromatin condensation, epigenetic changes, genomic imprinting, etc., that occur during cellular differentiation. Reprogramming is distinct from simply maintaining the existing undifferentiated state of a cell that is already pluripotent or maintaining the existing less than fully differentiated state of a cell that is already a multipotent cell (e.g., a hematopoietic stem cell). Reprogramming is also distinct from promoting the self-renewal or proliferation of cells that are already pluripotent or multipotent, although the compositions and methods described herein can also be of use for such purposes, in some embodiments.

The specific approach or method used to generate pluripotent stem cells from somatic cells (broadly referred to as "reprogramming") is not critical to the claimed invention. Thus, any method that re-programs a somatic cell to the pluripotent phenotype would be appropriate for use in the methods described herein.

Reprogramming methodologies for generating pluripotent cells using defined combinations of transcription factors have been described induced pluripotent stem cells. Yamanaka and Takahashi converted mouse somatic cells to ES cell-like cells with expanded developmental potential by the direct transduction of Oct4, Sox2, Klf4, and c-Myc (Takahashi and Yamanaka, 2006). iPSCs resemble ES cells as they restore the pluripotency-associated transcriptional circuitry and muc of the epigenetic landscape. In addition, mouse iPSCs satisfy all the standard assays for pluripotency: specifically, in vitro differentiation into cell types of the three germ layers, teratoma formation, contribution to chimeras, germline transmission (Maherali and Hochedlinger, 2008), and tetraploid complementation (Woltjen et al., 2009).

Subsequent studies have shown that human iPS cells can be obtained using similar transduction methods (Lowry et al., 2008; Park et al., 2008; Takahashi et al., 2007; Yu et al., 2007b), and the transcription factor trio, OCT4, SOX2, and NANOG, has been established as the core set of transcription factors that govern pluripotency (Jaenisch and Young, 2008). The production of iPS cells can be achieved by the introduction of nucleic acid sequences encoding stem cell-associated genes into an adult, somatic cell, historically using viral vectors.

iPS cells can be generated or derived from terminally differentiated somatic cells, as well as from adult stem cells, or somatic stem cells. That is, a non-pluripotent progenitor cell can be rendered pluripotent or multipotent by reprogramming. In such instances, it may not be necessary to include as many reprogramming factors as required to reprogram a terminally differentiated cell. Further, reprogramming can be induced by the non-viral introduction of reprogramming factors, e.g., by introducing the proteins themselves, or by introducing nucleic acids that encode the reprogramming factors, or by introducing messenger RNAs that upon translation produce the reprogramming factors (see e.g., Warren et al., Cell Stem Cell, 2010 Nov. 5; 7(5):618-30). Reprogramming can be achieved by introducing a combination of nucleic acids encoding stem cell-associated genes including, for example Oct-4 (also known as Oct-3/4 or Pouf51), Sox1, Sox2, Sox3, Sox 15, Sox 18, NANOG, Klf1, Klf2, Klf4, Klf5, NR5A2, c-Myc, 1-Myc, n-Myc, Rem2, Tert, and LIN28. In one embodiment, reprogramming using the methods and compositions described herein can further comprise introducing one or more of Oct-3/4, a member of the Sox family, a member of the Klf family, and a member of the Myc family to a somatic cell. In one embodiment, the methods and compositions described herein further comprise introducing one or more of each of Oct 4, Sox2, Nanog, c-MYC and Klf4 for reprogramming. As noted above, the exact method used for reprogramming is not necessarily critical to the methods and compositions described herein. However, where cells differentiated from the reprogrammed cells are to be used in, e.g., human therapy, in one embodiment the reprogramming is not effected by a method that alters the genome. Thus, in such embodiments, reprogramming is achieved, e.g., without the use of viral or plasmid vectors.

The efficiency of reprogramming (i.e., the number of reprogrammed cells) derived from a population of starting cells can be enhanced by the addition of various small molecules as shown by Shi, Y., et al (2008) Cell-Stem Cell 2:525-528, Huangfu, D., et al (2008) Nature Biotechnology 26(7):795-797, and Marson, A., et al (2008) Cell-Stem Cell 3:132-135. Thus, an agent or combination of agents that enhance the efficiency or rate of induced pluripotent stem cell production can be used in the production of patient-specific or disease-specific iPSCs. Some non-limiting examples of agents that enhance reprogramming efficiency include soluble Wnt, Wnt conditioned media, BIX-01294 (a G9a histone methyltransferase), PD0325901 (a MEK inhibitor), DNA methyltransferase inhibitors, histone deacetylase (HDAC) inhibitors, valproic acid, 5'-azacytidine, dexamethasone, suberoylanilide, hydroxamic acid (SAHA), vitamin C, and trichostatin (TSA), among others.

Other non-limiting examples of reprogramming enhancing agents include: Suberoylanilide Hydroxamic Acid (SAHA (e.g., MK0683, vorinostat) and other hydroxamic acids), BML-210, Depudecin (e.g., (−)-Depudecin), HC Toxin, Nullscript (4-(1,3-Dioxo-1H,3H-benzo[de]isoquinolin-2-yl)-N-hydroxybutanamide), Phenylbutyrate (e.g., sodium phenylbutyrate) and Valproic Acid ((VPA) and other short chain fatty acids), Scriptaid, Suramin Sodium, Trichostatin A (TSA), APHA Compound 8, Apicidin, Sodium Butyrate, pivaloyloxymethyl butyrate (Pivanex, AN-9), Trapoxin B, Chlamydocin, Depsipeptide (also known as FR901228 or FK228), benzamides (e.g., CI-994 (e.g., N-acetyl dinaline) and MS-27-275), MGCD0103, NVP-LAQ-824, CBHA (m-carboxycinnaminic acid bishydroxamic acid), JNJ16241199, Tubacin, A-161906, proxamide, oxamflatin, 3-Cl-UCHA (e.g., 6-(3-chlorophenylureido) caproic hydroxamic acid), AOE (2-amino-8-oxo-9,10-epoxydecanoic acid), CHAP31 and CHAP 50. Other reprogramming enhancing agents include, for example, dominant negative forms of the HDACs (e.g., catalytically inactive forms), siRNA inhibitors of the HDACs, and antibodies that specifically bind to the HDACs. Such inhibitors are available, e.g., from BIOMOL International, Fukasawa, Merck Biosciences, Novartis, Gloucester Pharmaceuticals, Aton Pharma, Titan Pharmaceuticals, Schering AG, Pharmion, MethylGene, and Sigma Aldrich.

To confirm the induction of pluripotent stem cells for use with the methods described herein, isolated clones can be tested for the expression of a stem cell marker. Such expression in a cell derived from a somatic cell identifies the cells as induced pluripotent stem cells. Stem cell markers can be selected from the non-limiting group including SSEA3, SSEA4, CD9, Nanog, Fbx15, Ecat1, Esg1, Eras, Gdf3, Fgf4, Cripto, Dax1, Zpf296, Slc2a3, Rex1, Utf1, and Nat1. In one embodiment, a cell that expresses Oct4 or Nanog is identified as pluripotent. Methods for detecting the expression of such markers can include, for example, RT-PCR and immunological methods that detect the presence of the encoded polypeptides, such as Western blots or flow cytometric analyses. In some embodiments, detection does not involve only RT-PCR, but also includes detection of protein markers. Intracellular markers may be best identified via RT-PCR, while cell surface markers are readily identified, e.g., by immunocytochemistry.

The pluripotent stem cell character of isolated cells can be confirmed by tests evaluating the ability of the iPSCs to differentiate to cells of each of the three germ layers. As one example, teratoma formation in nude mice can be used to evaluate the pluripotent character of the isolated clones. The cells are introduced to nude mice and histology and/or immunohistochemistry is performed on a tumor arising from the cells. The growth of a tumor comprising cells from all three germ layers, for example, further indicates that the cells are pluripotent stem cells.

Somatic Cells for Reprogramming

Somatic cells, as that term is used herein, refer to any cells forming the body of an organism, excluding germline cells. Every cell type in the mammalian body—apart from the sperm and ova, the cells from which they are made (gametocytes) and undifferentiated stem cells—is a differentiated somatic cell. For example, internal organs, skin, bones, blood, and connective tissue are all made up of differentiated somatic cells.

Additional somatic cell types for use with the compositions and methods described herein include: a fibroblast (e.g., a primary fibroblast), a muscle cell (e.g., a myocyte), a cumulus cell, a neural cell, a mammary cell, a hepatocyte and a pancreatic islet cell. In some embodiments, the somatic cell is a primary cell line or is the progeny of a primary or secondary cell line. In some embodiments, the somatic cell is obtained from a human sample, e.g., a hair follicle, a blood sample, a biopsy (e.g., a skin biopsy or an adipose biopsy), a swab sample (e.g., an oral swab sample), and is thus a human somatic cell.

Some non-limiting examples of differentiated somatic cells include, but are not limited to, epithelial, endothelial, neuronal, adipose, cardiac, skeletal muscle, immune cells, hepatic, splenic, lung, circulating blood cells, gastrointestinal, renal, bone marrow, and pancreatic cells. In some embodiments, a somatic cell can be a primary cell isolated from any somatic tissue including, but not limited to brain, liver, gut, stomach, intestine, fat, muscle, uterus, skin, spleen, endocrine organ, bone, etc. Further, the somatic cell can be from any mammalian species, with non-limiting examples including a murine, bovine, simian, porcine, equine, ovine, or human cell. In some embodiments, the somatic cell is a human somatic cell.

When reprogrammed cells are used for generation of hematopoietic progenitor cells to be used in the therapeutic treatment of disease, it is desirable, but not required, to use somatic cells isolated from the patient being treated. For example, somatic cells involved in diseases, and somatic cells participating in therapeutic treatment of diseases and the like can be used. In some embodiments, a method for selecting the reprogrammed cells from a heterogeneous population comprising reprogrammed cells and somatic cells they were derived or generated from can be performed by any known means. For example, a drug resistance gene or the like, such as a selectable marker gene can be used to isolate the reprogrammed cells using the selectable marker as an index.

Reprogrammed somatic cells as disclosed herein can express any number of pluripotent cell markers, including: alkaline phosphatase (AP); ABCG2; stage specific embryonic antigen-1 (SSEA-1); SSEA-3; SSEA-4; TRA-1-60; TRA-1-81; Tra-2-49/6E; ERas/ECAT5, E-cadherin; β-III-tubulin; α-smooth muscle actin (α-SMA); fibroblast growth factor 4 (Fgf4), Cripto, Dax1; zinc finger protein 296 (Zfp296); N-acetyltransferase-1 (Nat1); (ES cell associated transcript 1 (ECAT1); ESG1/DPPA5/ECAT2; ECAT3; ECAT6; ECAT7; ECAT8; ECAT9; ECAT10; ECAT15-1; ECAT15-2; Fthl17; Sal14; undifferentiated embryonic cell transcription factor (Utf1); Rex1; p53; G3PDH; telomerase, including TERT; silent X chromosome genes; Dnmt3a; Dnmt3b; TRIM28; F-box containing protein 15 (Fbx15); Nanog/ECAT4; Oct3/4; Sox2; Klf4; c-Myc; Esrrb; TDGF1; GABRB3; Zfp42, FoxD3; GDF3; CYP25A1; developmental pluripotency-associated 2 (DPPA2); T-cell lymphoma breakpoint 1 (Tcl1); DPPA3/Stella; DPPA4; other general markers for pluripotency, etc. Other markers can include Dnmt3L; Sox15; Stat3; Grb2; β-catenin, and Bmi1. Such cells can also be characterized by the down-regulation of markers characteristic of the somatic cell from which the induced pluripotent stem cell is derived.

Pharmaceutically Acceptable Carriers

The methods of administering human hematopoietic progenitor cells or genetic engineered cells described herein or their progeny to a subject as described herein involve the use of therapeutic compositions comprising hematopoietic progenitor cells. Therapeutic compositions contain a physiologically tolerable carrier together with the cell composition and optionally at least one additional bioactive agent as described herein, dissolved or dispersed therein as an active ingredient. In a preferred embodiment, the therapeutic composition is not substantially immunogenic when administered to a mammal or human patient for therapeutic purposes, unless so desired.

In general, the hematopoietic progenitor cells described herein or genetic engineered cells described herein or their progeny are administered as a suspension with a pharmaceutically acceptable carrier. One of skill in the art will recognize that a pharmaceutically acceptable carrier to be used in a cell composition will not include buffers, compounds, cryopreservation agents, preservatives, or other agents in amounts that substantially interfere with the viability of the cells to be delivered to the subject. A formulation comprising cells can include e.g., osmotic buffers that permit cell membrane integrity to be maintained, and optionally, nutrients to maintain cell viability or enhance engraftment upon administration. Such formulations and suspensions are known to those of skill in the art and/or can be adapted for use with the hematopoietic progenitor cells as described herein using routine experimentation.

A cell composition can also be emulsified or presented as a liposome composition, provided that the emulsification procedure does not adversely affect cell viability. The cells and any other active ingredient can be mixed with excipients which are pharmaceutically acceptable and compatible with the active ingredient and in amounts suitable for use in the therapeutic methods described herein.

Additional agents included in a cell composition as described herein can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active compound used in the cell compositions as described herein that is effective in the treatment of a particular disorder or condition will depend on the nature of the disorder or condition, and can be determined by standard clinical techniques.

In some embodiments, the compositions of isolated genetic engineered cells described further comprises a pharmaceutically acceptable carrier. In one embodiment, the pharmaceutically acceptable carrier does not include tissue or cell culture media.

In some embodiments, the compositions of modified synthetic nucleic acid molecules described further comprises a pharmaceutically acceptable carrier. In one embodiment, the pharmaceutically acceptable carrier does not include tissue or cell culture media.

In some embodiments, the compositions comprising the nucleic acid molecules described further comprises a pharmaceutically acceptable carrier. In one embodiment, the pharmaceutically acceptable carrier does not include tissue or cell culture media.

Administration & Efficacy

As used herein, the terms "administering," "introducing" and "transplanting" are used interchangeably in the context of the placement of cells, e.g. hematopoietic progenitor cells, as described herein into a subject, by a method or route which results in at least partial localization of the introduced cells at a desired site, such as a site of injury or repair, such that a desired effect(s) is produced. The cells e.g. hematopoietic progenitor cells, or their differentiated progeny can be administered by any appropriate route which results in delivery to a desired location in the subject where at least a portion of the implanted cells or components of the cells remain viable. The period of viability of the cells after administration to a subject can be as short as a few hours, e.g., twenty-four hours, to a few days, to as long as several years, i.e., long-term engraftment. For example, in some embodiments of the aspects described herein, an effective amount of hematopoietic progenitor cells or engineered cells with reduced BCL11A expression is administered via a systemic route of administration, such as an intraperitoneal or intravenous route.

When provided prophylactically, hematopoietic progenitor cells or engineered cells with reduced BCL11A expression described herein can be administered to a subject in advance of any symptom of a hemoglobinopathy, e.g., prior to the switch from fetal γ-globin to predominantly β-globin. Accordingly, the prophylactic administration of a hematopoietic progenitor cell population serves to prevent a hemoglobinopathy, as disclosed herein.

When provided therapeutically, hematopoietic progenitor cells are provided at (or after) the onset of a symptom or indication of a hemoglobinopathy, e.g., upon the onset of sickle cell disease.

In some embodiments of the aspects described herein, the hematopoietic progenitor cell population or engineered cells with reduced BCL11A expression being administered according to the methods described herein comprises allogeneic hematopoietic progenitor cells obtained from one or more donors. As used herein, "allogeneic" refers to a hematopoietic progenitor cell or biological samples comprising hematopoietic progenitor cells obtained from one or more different donors of the same species, where the genes at one or more loci are not identical. For example, a hematopoietic progenitor cell population or engineered cells with reduced BCL11A expression being administered to a subject can be derived from umbilical cord blood obtained from one more unrelated donor subjects, or from one or more non-identical siblings. In some embodiments, syngeneic hematopoietic progenitor cell populations can be used, such as those obtained from genetically identical animals, or from identical twins. In other embodiments of this aspect, the hematopoietic progenitor cells are autologous cells; that is, the hematopoietic progenitor cells are obtained or isolated from a subject and administered to the same subject, i.e., the donor and recipient are the same.

For use in the various aspects described herein, an effective amount of hematopoietic progenitor cells or engineered cells with reduced BCL11A expression, comprises at least $10^2$ cells, at least $5\times10^2$ cells, at least $10^3$ cells, at least $5\times10^3$ cells, at least $10^4$ cells, at least $5\times10^4$ cells, at least $10^5$ cells, at least $2\times10^5$ cells, at least $3\times10^5$ cells, at least $4\times10^5$ cells, at least $5\times10^5$ cells, at least $6\times10^5$ hematopoietic progenitor cells, at least $7\times10^5$ cells, at least $8\times10^5$ cells, at least $9\times10^5$ cells, at least $1\times10^6$ cells, at least $2\times10^6$ cells, at least $3\times10^6$ cells, at least $4\times10^6$ cells, at least $5\times10^6$ cells, at least $6\times10^6$ cells, at least $7\times10^6$ cells, at least $8\times10^6$ cells, at least $9\times10^6$ cells, or multiples thereof. The hematopoietic progenitor cells or engineered cells with reduced BCL11A expression can be derived from one or more donors, or can be obtained from an autologous source. In some embodiments of the aspects described herein, the hematopoietic progenitor cells are expanded in culture prior to administration to a subject in need thereof.

In one embodiment, the term "effective amount" as used herein refers to the amount of a population of human hematopoietic progenitor cells or their progeny needed to alleviate at least one or more symptom of a hemoglobinopathy, and relates to a sufficient amount of a composition to provide the desired effect, e.g., treat a subject having a hemoglobinopathy. The term "therapeutically effective amount" therefore refers to an amount of hematopoietic progenitor cells, or genetic engineered cells described herein or their progeny or a composition comprising hematopoietic progenitor cells, or genetic engineered cells described herein or their progeny that is sufficient to promote a particular effect when administered to a typical subject, such as one who has or is at risk for a hemoglobinopathy. An effective amount as used herein would also include an amount sufficient to prevent or delay the development of a symptom of the disease, alter the course of a symptom disease (for example but not limited to, slow the progression of a symptom of the disease), or reverse a symptom of the disease. It is understood that for any given case, an appropriate "effective amount" can be determined by one of ordinary skill in the art using routine experimentation.

As used herein, "administered" refers to the delivery of a hematopoietic stem cell composition as described herein into a subject by a method or route which results in at least partial localization of the cell composition at a desired site. A cell composition can be administered by any appropriate route which results in effective treatment in the subject, i.e. administration results in delivery to a desired location in the subject where at least a portion of the composition delivered, i.e. at least $1\times10^4$ cells are delivered to the desired site for a period of time. Modes of administration include injection, infusion, instillation, or ingestion. "Injection" includes, without limitation, intravenous, intramuscular, intra-arterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. For the delivery of cells, administration by injection or infusion is generally preferred.

In one embodiment, the cells as described herein are administered systemically. The phrases "systemic administration," "administered systemically", "peripheral administration" and "administered peripherally" as used herein refer to the administration of a population of hematopoietic progenitor cells other than directly into a target site, tissue, or organ, such that it enters, instead, the subject's circulatory system and, thus, is subject to metabolism and other like processes.

The efficacy of a treatment comprising a composition as described herein for the treatment of a hemoglobinopathy can be determined by the skilled clinician. However, a treatment is considered "effective treatment," as the term is used herein, if any one or all of the signs or symptoms of, as but one example, levels of fetal β-globin are altered in a beneficial manner, other clinically accepted symptoms or markers of disease are improved or ameliorated, e.g., by at least 10% following treatment with an inhibitor. Efficacy can also be measured by failure of an individual to worsen as assessed by hospitalization or need for medical interventions (e.g., progression of the disease is halted or at least slowed). Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting, or slowing the progression of sepsis; or (2) relieving the disease, e.g., causing regression of symptoms; and (3) preventing or reducing the likelihood of the development of infection or sepsis.

The treatment according to the present invention ameliorates one or more symptoms associated with a β-globin disorder by increasing the amount of fetal hemoglobin in the individual. Symptoms typically associated with a hemoglobinopathy, include for example, anemia, tissue hypoxia, organ dysfunction, abnormal hematocrit values, ineffective erythropoiesis, abnormal reticulocyte (erythrocyte) count, abnormal iron load, the presence of ring sideroblasts, splenomegaly, hepatomegaly, impaired peripheral blood flow, dyspnea, increased hemolysis, jaundice, anemic pain crises, acute chest syndrome, splenic sequestration, priapism, stroke, hand-foot syndrome, and pain such as angina pectoris.

In one embodiment, the hematopoietic progenitor cell is contacted ex vivo or in vitro with a DNA targeting endonuclease, and the cell or its progeny is administered to the mammal (e.g., human). In a further embodiment, the hematopoietic progenitor cell is a cell of the erythroid lineage. In one embodiment, a composition comprising a hematopoietic progenitor cell that was previously contacted with a DNA-targeting endonuclease and a pharmaceutically acceptable carrier and is administered to a mammal.

In one embodiment, any method known in the art can be used to measure an increase in fetal hemoglobin expression, e.g., Western Blot analysis of fetal hemoglobin protein and quantifying mRNA of fetal γ-globin.

In one embodiment, the hematopoietic progenitor cell is contacted with a DNA-targeting endonuclease in vitro, or ex vivo. In one embodiment, the cell is of human origin (e.g., an autologous or heterologous cell). In one embodiment, the composition causes an increase in fetal hemoglobin expression.

The disclosure described herein, in a preferred embodiment, does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

The disclosure described herein, in a preferred embodiment, does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

Furthermore, the disclosure described herein does not concern the destruction of a human embryo.

This invention is further illustrated by the following example which should not be construed as limiting. The contents of all references cited throughout this application, as well as the figures and table are incorporated herein by reference.

Some embodiments of the invention described herein can be defined according to any of the following numbered paragraphs:

1) A modified synthetic nucleic acid molecule comprising a nucleic acid sequence shown in Table 1, SEQ ID NOS: 1-139, wherein there is at least one chemical modification to a nucleotide in the nucleic acid molecule.
2) The modified synthetic nucleic acid molecule of paragraph 1, wherein the nucleic acid sequence excludes the entire BCL11A enhancer functional regions and excludes the entire BCL11A coding region.
3) The modified synthetic nucleic acid molecule of paragraph 1 or 2, wherein the nucleic acid sequence is selected from the group consisting of SEQ ID NOS: 37, 38, 39, 40, 41, 42, 43, 44, 45, 46, 47, 48, 50, 51, 52, 53, 54, 55, 56, 57, and 62 as shown in Table 2.

4) The modified synthetic nucleic acid molecule of any one of paragraphs 1-3, wherein the chemical modifications is located at one or more terminal nucleotides in nucleic acid molecule.
5) The modified synthetic nucleic acid molecule of paragraph 4, wherein the chemical modification is selected from the group consisting of 2'-O-methyl 3'phosphorothioate (MS), 2'-O-methyl-3'-phosphonoacetate (MP), 2'-0-Ci-4alkyl, 2'-H, 2'-0-Ci.3alky]-0-Ci.3alkyl, 2'-F, 2'-NH2, 2'-arabino, 2'-F-arabino, 4'-thioribosyl, 2-thioU, 2-thioC, 4-thioU, 6-thioG, 2-aminoA, 2-aminopurine, pseudouracil, hypoxanthine, 7-deazaguanine, 7-deaza-8-azaguanine, 7-deazadenine, 7-deaza-8-azaadenine, 5-methylC, 5-methylU, 5-hydroxymethylcytosine, 5-hydroxymethyluracil, 5,6-dehydrouracil, 5-propynylcytosine, 5-propynyluracil, 5-ethynylcytosine, 5-ethynyluracil, 5-allylU, 5-allylC, 5-aminoallyl-uracil, 5-aminoallyl-cytosine, an abasic nucleotide ("abN"), Z, P, UNA, isoC, isoG, 5-methyl-pyrimidine, x(A,G,C,T) and y(A,G,C,T), a phosphorothioate internucleotide linkage, a phosphonoacetate internucleotide linkage, a thiophosphonoacetate internucleotide linkage, a methylphosphonate internucleotide linkage, a boranophosphonate internucleotide linkage, a phosphorodithioate internucleotide linkage, 4'-thioribosyl nucleotide, a locked nucleic acid ("LNA") nucleotide, an unlocked nucleic acid ("ULNA") nucleotide, an alkyl spacer, a heteroalkyl (N, O, S) spacer, a 5'- and/or 3'-alkyl terminated nucleotide, a Unicap, a 5'-terminal cap known from nature, an xRNA base (analogous to "xDNA" base), an yRNA base (analogous to "yDNA" base), a PEG substituent, and a conjugated linker to a dye or non-fluorescent label (or tag).
6) The modified synthetic nucleic acid molecule of any one of paragraphs 1-5, wherein the chemical modification is located only at the 3' end, or added only at the 5' end, or added at both the 5' and 3' ends of the synthetic nucleic acid molecule.
7) The modified synthetic nucleic acid molecule of any one of paragraphs 1-6, wherein the chemical modification is located to first three nucleotides and to the last three nucleotides of the synthetic nucleic acid molecule.
8) The modified synthetic nucleic acid molecule of any one of paragraphs 1-7, wherein the nucleic acid sequence further comprising a crRNA/tracrRNA sequence.
9) The modified synthetic nucleic acid molecule of any one of paragraphs 1-8, wherein the nucleic acid molecule is a single guide RNA (sgRNA).
10) The modified synthetic nucleic acid molecule of any one of paragraphs 1-9, wherein the synthetic nucleic acid molecule excludes the entire region between the human chromosome 2 location 60725424 to 60725688 (DHS +55 functional region), or excludes the entire region at location 60722238 to 60722466 (DHS +58 functional region), or excludes the entire region at location 60718042 to 60718186 (DHS +62 functional region), or excludes the entire region at location 60773106 to 60773435 (exon 2) of the human chromosome 2 is that according to UCSC Genome Browser hg 19 human genome assembly.
11) The modified synthetic nucleic acid molecule of any one of paragraphs 1-10 for use in the ex vivo targeted genome editing of the BCL11A erythroid enhancer DHS +62, +58, or +55 functional regions or the BCL11A exon 2 region in a progenitor cell purpose.
12) The modified synthetic nucleic acid molecule of any one of paragraphs 1-10 for use in an ex vivo method of producing a progenitor cell or a population of progenitor cells wherein the cells or the differentiated progeny therefrom have decreased BCL11A mRNA or protein expression.
13) The modified synthetic nucleic acid molecule of any one of paragraphs 1-10 for use in an ex vivo method of producing an isolated genetic engineered human cell or a population of genetic engineered human cells having at least one genetic modification.
14) The modified synthetic nucleic acid molecule of any one of paragraphs 1-10 for use in an ex vivo method of increasing fetal hemoglobin levels in a cell or in a mammal.
15) The modified synthetic nucleic acid molecule of any one of paragraphs 11-14, wherein the modified synthetic nucleic acid molecule is used in combination with a DNA-targeting endonuclease Cas (CRISPR-associated) protein in a ribonucleoprotein (RNP) complex.
16) The modified synthetic nucleic acid molecule of paragraph 15, wherein the Cas protein is Cas 9.
17) The modified synthetic nucleic acid molecule of paragraph 15 or 16, wherein the RNP complex is used in the electroporation of cells.
18) The modified synthetic nucleic acid molecule of any one of paragraphs 11-17, wherein the isolated progenitor cell or isolated cell is a hematopoietic progenitor cell or a hematopoietic stem cell.
19) The modified synthetic nucleic acid molecule of paragraph 18, wherein the hematopoietic progenitor is a cell of the erythroid lineage.
20) The modified synthetic nucleic acid molecule of any one of paragraphs 11-17, wherein the isolated progenitor cell or isolated cell is an induced pluripotent stem cell.
21) The modified synthetic nucleic acid molecule of any one of paragraphs 11-20, wherein the progenitor cell or human cell acquires at least one genetic modification.
22) The modified synthetic nucleic acid molecule of paragraph 21, wherein the at least one genetic modification is a deletion, insertion or substitution of the genetic sequence of the cell.
23) The modified synthetic nucleic acid molecule of paragraph 22, wherein the least one genetic modification is located between chromosome 2 location 60725424 to 60725688 (+55 functional region), or at location 60722238 to 60722466 (+58 functional region), or at location 60718042 to 60718186 (+62 functional region), or at location 60773106 to 60773435 (exon 2) of the human chromosome 2 is that according to UCSC Genome Browser hg 19 human genome assembly.
24) A composition comprising a modified synthetic nucleic acid molecule of any one of paragraphs 1-10.
25) The composition of paragraph 24, further comprising a DNA-targeting endonuclease Cas (CRISPR-associated) protein.
26) The composition of paragraph 25, wherein the Cas protein is Cas 9.
27) The composition of any one of paragraphs 24-26 for use in the ex vivo targeted genome editing of the BCL11A erythroid enhancer DHS +62, +58, or +55 functional regions or the BCL11A exon 2 in a progenitor cell.

28) The composition of any one of paragraphs 24-26 for use in an ex vivo method of producing a progenitor cell or a population of progenitor cells wherein the cells or the differentiated progeny therefrom have decreased BCL11A mRNA or protein expression.
29) The composition of any one of paragraphs 24-26 for use in an ex vivo method of producing an isolated genetic engineered human cell or a population of progenitor cells having at least one genetic modification.
30) The composition of any one of paragraphs 24-26 for use in an ex vivo method for increasing fetal hemoglobin levels in a cell or in a mammal.
31) The composition of any one of paragraphs 24-30, wherein the composition is used in the electroporation of cells.
32) The method of paragraph 31, wherein the step of electroporation is performed in a solution comprising glycerol.
33) A ribonucleoprotein (RNP) complex comprising a DNA-targeting endonuclease Cas (CRISPR-associated) protein and a modified synthetic nucleic acid molecule of any one of paragraphs 1-10.
34) The RNP complex of paragraph 33 for use in the ex vivo targeted genome editing of the BCL11A erythroid enhancer DHS +62, +58, and +55 functional regions or the BCL11A exon 2 in a progenitor cell.
35) The RNP complex of paragraph 33 for use in an ex vivo method of producing a progenitor cell or a population of progenitor cell wherein the cells or the differentiated progeny thereof have decreased BCL11A mRNA or protein expression.
36) The RNP complex of paragraph 33 for use in an ex vivo method of producing an isolated genetic engineered human cell or a population of genetic engineered human cells having at least one genetic modification.
37) The RNP complex of paragraph 33 for use in an ex vivo method for increasing fetal hemoglobin levels in a cell or in a mammal.
38) The RNP complex of any one of paragraphs 33-37, wherein the RNP complex is used in the electroporation of cells.
39) A method for producing a progenitor cell or a population of progenitor cells having decreased BCL11A mRNA or protein expression, the method comprising contacting an isolated progenitor cell with an effective amount of a composition of any one of paragraphs 24-26 or a ribonucleoprotein (RNP) complex of paragraph 33, whereby the contacted cells or the differentiated progeny cells therefrom have decreased BCL11A mRNA or protein expression.
40) The method of paragraph 39, wherein the contacted progenitor cell acquires at least one genetic modification in the human chromosome 2 is that according to UCSC Genome Browser hg 19 human genome assembly.
41) The method of paragraph 40, wherein the at least one genetic modification is a deletion, insertion or substitution of the genetic sequence of the cell.
42) The method of paragraph 39-41, wherein the least one genetic modification is located between chromosome 2 location 60725424 to 60725688 (+55 functional region), or at location 60722238 to 60722466 (+58 functional region), or at location 60718042 to 60718186 (+62 functional region), or at location 60773106 to 60773435 (exon 2) of the human chromosome 2 is that according to UCSC Genome Browser hg 19 human genome assembly.
43) The method of any one of paragraphs 39-42, wherein the contacted cells or the differentiated progeny cells therefrom further have increased fetal hemoglobin levels.
44) A method for producing an isolated genetic engineered human cell or a population of genetic engineered isolated human cells having at least one genetic modification, the method comprising contacting an isolated cell or a population of cells with an effective amount of a composition of any one of paragraphs 24-26 or a ribonucleoprotein (RNP) complex of paragraph 33, wherein the at least one genetic modification produced is located in human chromosome 2 is that according to UCSC Genome Browser hg 19 human genome assembly.
45) A method of increasing fetal hemoglobin levels in a cell, the method comprising the steps of: contacting an isolated cell with an effective amount of a composition of any one of paragraphs 24-26 or a ribonucleoprotein (RNP) complex of paragraph 33, thereby causing at least one genetic modification at the human chromosome 2 is that according to UCSC Genome Browser hg 19 human genome assembly therein, whereby fetal hemoglobin expression is increased in said cell, or its progeny, relative to said cell prior to said contacting.
46) The method of any one of paragraphs 39-45, wherein the isolated progenitor cell or isolated cell is a hematopoietic progenitor cell or a hematopoietic stem cell.
47) The method of paragraph 45, wherein the hematopoietic progenitor is a cell of the erythroid lineage.
48) The method of any one of paragraphs 39-45, wherein the isolated progenitor cell or isolated cell is an induced pluripotent stem cell.
49) The method of any one of paragraphs 39-48, wherein the isolated progenitor cell or isolated cell is contacted ex vivo or in vitro.
50) The method of any one of paragraphs 39-49, wherein the contacted progenitor cell or contacted cell acquires at least one genetic modification.
51) The method of paragraph 50, wherein the at least one genetic modification is a deletion, insertion or substitution of the nucleic acid sequence of chromosome 2.
52) The method of any one of paragraphs 38-50, wherein the least one genetic modification is located between chromosome 2 location 60725424 to 60725688 (+55 functional region), at location 60722238 to 60722466 (+58 functional region), or at location 60718042 to 60718186 (+62 functional region), or at location 60773106 to 60773435 (exon 2).
53) The method of any one of paragraphs 39-52, wherein the contacted progenitor cell or contacted cell are further electroporated.
54) The method of paragraph 52, wherein the step of electroporation is performed in a solution comprising glycerol.
55) An isolated genetic engineered human cell or a population of genetic engineered human cells having at least one genetic modification on chromosome 2 location 60725424 to 60725688 (+55 functional region), or at location 60722238 to 60722466 (+58 functional region), or at location 60718042 to 60718186 (+62 functional region), or at location 60773106 to 60773435 (exon 2) according to paragraphs 43, 45-52.
56) A population of genetically edited progenitor cells having at least one genetic modification on chromosome 2 location 60725424 to 60725688 (+55 functional region), or at location 60722238 to 60722466 (+58 functional region), or at location 60718042 to 60718186 (+62 functional region), or at location 60773106 to 60773435 (exon 2) according to paragraphs 38-52.
57) The cells of any one of paragraphs 55-56 have reduced BCL11A mRNA or protein expression.
58) A composition comprising isolated genetic edited human cells of paragraphs 56-57.
59) A composition comprising genetically edited progenitor cells of paragraphs 56-57.
60) A method for increasing fetal hemoglobin levels in a mammal in need thereof, the method comprising the steps of:
   a. ex vivo contacting an isolated hematopoietic progenitor cell isolated from said mammal with an effective amount of a composition of any one of paragraph 24-26 or a ribonucleoprotein (RNP) complex of paragraph 33 whereby the DNA-targeting endonuclease cleaves the genomic DNA of the cell on chromosome 2 at location 60725424 to 60725688 (+55 functional region), at location 60722238 to 60722466 (+58 functional region), or at location 60718042 to 60718186 (+62 functional region), or at location 60773106 to 60773435 (exon 2), causing at least one genetic modification therein, whereby fetal hemoglobin expression is increased in said cell or the differentiated progeny cells therefrom, relative to expression prior to said contacting, and wherein the human chromosome 2 is that according to UCSC Genome Browser hg 19 human genome assembly; and
   b. transplanting the contacted cells of (a) or culture expanded cells therefrom into said mammal.
61) A method for increasing fetal hemoglobin levels in a mammal in need thereof, the method comprising transplanting into the mammal:
   a. an isolated genetic engineered human cell of paragraph 55 or 57, or
   b. a population of genetically edited progenitor cells of paragraphs 56 or 57, or
   c. a composition of paragraph 58, or
   d. a composition of paragraph 59, or the progeny cells from of (a) or (b).

EXAMPLES

Example 1

Sickle cell disease (SCD) and β-thalassemia are severe disorders affecting hemoglobin, the critical oxygen carrying protein of the blood. Despite the fact that these diseases are somewhat simple at a molecular level, adequate treatment options remain sorely lacking. However, some patients have a much less severe forms of disease due to the presence of elevated levels of fetal hemoglobin (HbF), an alternative type of hemoglobin which can replace the defective hemoglobin but is typically silenced after birth. Therapies which substantially increased HbF levels could provide a functional cure for hemoglobin disorders. See FIG. 1. Normally the HbF level is turned off after birth by a repressor called BCL11A. The inventor's strategy is to block this repressor to result in increased HbF. Specifically, they propose to block a switch that turns on BCL11A in red blood cells (known as an erythroid enhancer) since this would have the advantage of not altering BCL11A in other cells in the body.

See FIG. 2. Gene therapy approaches to the hemoglobin disorders focus on a patient's own blood stem cells (i.e., autologous cells), since by targeting these, lifelong beneficial effects may be maintained in continuously turning over red blood cells. See FIG. 1. Using the genome editing technology called CRISPR, very precise modifications can be made in DNA sequences in blood stem cells or their progenitor cells. Here the inventors tested the use of Cas9 protein in combination with single chimeric guide RNAs (sgRNA) as a ribonucleoprotein (RNP) complex for the ex vivo targeting of the BCL11A erythroid enhancer in HSCs from patients with β-thalassemia and SCD, using electroporation. See FIG. 4. The inventors were able to optimized efficient and non-toxic means of CRISPR delivery to primary human CD34+ HSPCs by RNP electroporation using specially chemically modified guide RNAs.

Materials and Methods

Erythroid differentiation medium (EDM) consists of IMDM supplemented with 330 μg/mL holo-human transferrin (Sigma), 10 μg/mL recombinant human insulin (Sigma), 2 IU/mL heparin (Sigma), 5% human solvent detergent pooled plasma AB (Rhode Island Blood Center), 3 IU/mL erythropoietin (Amgen), 1% L-glutamine (Life Technologies), and 2% penicillin/streptomycin (Life Technologies). During days 0-7 of culture, EDM was further supplemented with $10^{-6}$ M hydrocortisone (Sigma), 100 ng/mL human SCF (R&D), and human IL-3 (R&D). During days 7-11 of culture, EDM was supplemented with 100 ng/mL SCF only. During days 11-18 of culture, EDM had no additional supplements.

Cell culture—Human primary human CD34+ hematopoietic stem and progenitor cells (HSPCs) from mobilized peripheral blood of deidentified healthy donors were obtained from Fred Hutchinson Cancer Research Center, Seattle, Wash. CD34+ HSPCs were thawed on day 0 into X-VIVO 15 (Lonza, 04-418Q) supplemented with 100 ng $ml^{-1}$ human SCF, 100 ng $ml^{-1}$ human thrombopoietin (TPO) and 100 ng $ml^{-1}$ recombinant human Flt3-ligand (Flt3-L). HSPCs were electroporated with Cas9 RNP 24 h after thawing and maintained in X-VIVO media with cytokines. For in vitro erythroid maturation experiments, 24 h after electroporation, HSPCs were transferred into erythroid differentiation medium (EDM) consisting of IMDM supplemented with 330 μg ml-holo-human transferrin, 10 μg ml-recombinant human insulin, 2 IU ml-heparin, 5% human solvent detergent pooled plasma AB, 3 IU ml-erythropoietin, 1% L-glutamine, and 1% penicillin/streptomycin. During days 0-7 of culture, EDM was further supplemented with $10^{-6}$ M hydrocortisone (Sigma), 100 ng $ml^{-1}$ human SCF, and 5 ng $ml^{-1}$ human IL-3 (R&D) as EDM-1. During days 7-11 of culture, EDM was supplemented with 100 ng $ml^{-1}$ human SCF only as EDM-2. During days 11-18 of culture, EDM had no additional supplements as EDM-3. Globin gene expression was assessed on day 18 of erythroid culture. HUDEP-2 cells were cultured and differentiated in vitro as previously described[1]. Enucleation percentage and γ-globin induction were assessed on day 18 of erythroid culture.

In vitro transcription of sgRNAs—Firstly, sgRNAs with T7 promoter were amplified by PCR from pX458 plasmid with specific primers (data S6) and in vitro transcribed using MEGAshortscript T7 kit (Life Technologies). After transcription, the sgRNAs were purified with MEGAclear kit (Life Technologies) according to manufacturer's instructions.

RNP electroporation—Electroporation was performed using Lonza 4D Nucleofector (V4XP-3032 for 20 μl Nucleocuvette Strips) as the manufacturer's instructions. 2×NLS- Cas9 was obtained from QB3 MacroLab of University of California, Berkeley. The modified synthetic sgRNA (2'-O-methyl 3' phosphorothioate modifications in the first and last 3 nucleotides) was from Synthego. sgRNA concentration is calculated using the full-length product reporting method, which is 3-fold lower than the OD reporting method. CD34+ HSPCs were thawed 24 h before electroporation. For 20 μl Nucleocuvette Strips, the RNP complex was prepared by mixing Cas9 (200 pmol) and sgRNA (200 pmol, OD reporting method) and incubating for 15 min at room temperature immediately before electroporation. 50 K HSPCs resuspended in 20 μl P3 solution were mixed with RNP and transferred to a cuvette for electroporation with program EO-100. The electroporated cells were resuspended with X-VIVO media with cytokines and changed into EDM 24 h later for in vitro differentiation.

Measurement of indel frequencies—Indel frequencies were measured with cells cultured in EDM 5 days after electroporation. Briefly, genomic DNA was extracted using the Qiagen Blood and Tissue kit. BCL11A enhancer DHS h+58 functional core was amplified with KOD Hot Start DNA Polymerase and corresponding primers using the following cycling conditions: 95 degrees for 3 min; 35 cycles of 95 degrees for 20 s, 60 degrees for 10 s, and 70 degrees for 10 s; 70 degrees for 5 min.

RT-qPCR quantification of γ-globin induction—RNA isolation with RNeasy columns (Qiagen, 74106), reverse transcription with iScript cDNA synthesis kit (Bio-Rad, 170-8890), RT-qPCR with iQ SYBR Green Supermix (Bio-Rad, 170-8880) was subject to determine γ-globin induction using primers amplifying HBG1/2, HBB or HBA1/2 cDNA.

Hemoglobin HPLC—Hemolysates were prepared from erythroid cells after 18 days of differentiation using Hemolysate reagent (5125, Helena Laboratories) and analyzed with D-10 Hemoglobin Analyzer (Bio-Rad) or high-performance liquid chromatography (HPLC) in the clinical laboratory of the Brigham and Women's Hospital using clinically calibrated standards for the human hemoglobins.

Determination of BCL11A mRNA and protein level—Cells was directly lysed into the RLT plus buffer (Qiagen) for total RNA extraction according to manufacturer's instructions provided in the RNeasy Plus Mini Kit. BCL11A mRNA expression was determined by primers amplifying BCL11A or CAT as internal control (data S6). All gene expression data represent the mean of at least three technical replicates. BCL11A protein level was measured by western blot analysis as described previously with following antibodies: BCL11A (Abcam, ab19487), GAPDH (Cell Signaling, 5174S). The western blot results were quantified with ImageJ software.

Clonal culture of CD34+ HSPCs—Edited CD34+ HSPCs were sorted into 150 μl EDM$^{-1}$ in 96-well round bottom plates (Nunc) at one cell per well using FACSAria II. The cells were changed into EDM-2 media 7 days later in 96-well flat bottom plates (Nunc). After additional 4 days of culture, 1/10 of cells in each well was harvested for genotyping analysis, the remaining cells were changed into 150 μl-500 μl EDM-3 at 1M ml-1 for further differentiation. After additional 7 days of culture, 1/10 of the cells were stained with Hoechst 33342 for enucleation analysis, the remaining cells were harvested for RNA isolation with RNeasy Micro Kit (74004, Qiagen).

Human CD34+ HSPC transplant and flow cytometry analysis—All animal experiments were approved by the Boston Children's Hospital Institutional Animal Care and Use Committee. NOD.Cg-Kit$^{W-41J}$ Tyr$^+$ Prkdc$^{scid}$ Il2rg$^{tm1Wjl}$ (NBSGW) mice were obtained from Jackson Laboratory (Stock 026622). Non-irradiated NBSGW female mice (4-5 weeks of age) were infused by retro-orbital injection with 0.2-0.8M CD34$^+$ HSPCs (resuspended in 200 μl DPBS) derived from healthy donors or SCD patients. Equal numbers of pre-electroporation CD34+ HSPCs were used for experiments comparing in vitro culture for 0, 1, or 2 days following electroporation. Bone marrow was isolated for human xenograft analysis 16 weeks post engraftment. Serial transplants were conducted using retro-orbital injection of bone marrow cells from the primary recipients. For flow cytometry analysis of bone marrow, BM cells were first incubated with Human TruStain FcX (422302, BioLegend) and TruStain fcX ((anti-mouse CD16/32, 101320, BioLegend) blocking antibodies for 10 min, followed by the incubation with V450 Mouse Anti-Human CD45 Clone HI30 (560367, BD Biosciences), PE-eFluor 610 mCD45 Monoclonal Antibody (30-F11) (61-0451-82, Thermo Fisher), FITC anti-human CD235a Antibody (349104, BioLegend), PE anti-human CD33 Antibody (366608, BioLegend), APC anti-human CD19 Antibody (302212, BioLegend) and Fixable Viability Dye eFluor 780 for live/dead staining (65-0865-14, Thermo Fisher). Percentage human engraftment was calculated as hCD45+ cells/(hCD45+ cells+mCD45+ cells)×100. B cells (CD19+) and myeloid (CD33+) lineages were gated on the hCD45+ population. Human erythroid cells (CD235a+) were gated on mCD45-hCD45-population. Cell sorting was performed on a FACSAria II machine (BD Biosciences).

Amplicon deep sequencing—For indel frequencies or off-target analysis with deep sequencing, BCL11A enhancer loci or potential off-target loci were amplified with corresponding primers firstly (data S6). After another round of PCR with primers containing sample-specific barcodes and adaptor, amplicons were sequenced for 2×150 paired-end reads with MiSeq Sequencing System (Illumina). The deep sequencing data was analyzed by CRISPResso software. In particular, we used a minimum alignment identity of 75%, window size of 2 bp around the cleavage site to quantify indels, an average PHRED quality score of 30 and excluded substitutions to limit potential false positives. For OT10, in which the amplicon includes homologous genomic sequences, we used a minimum alignment identity of 90%.

Figure 5:
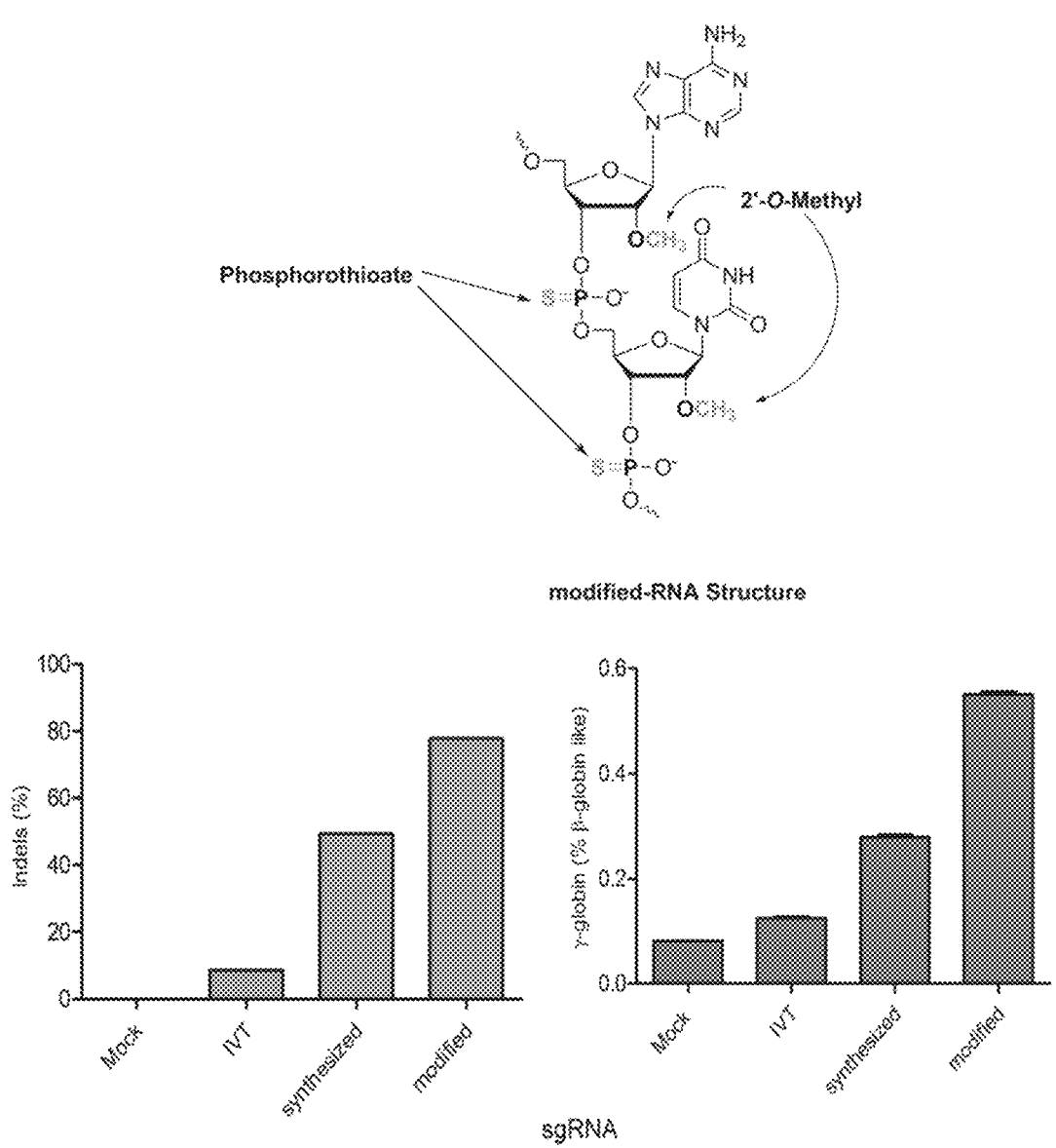
FIG. 5 shows modified synthesized guides were highly active in CD34+ HSPCs. Cas9 protein with synthesized modified guides targeting the BCL11A enhancer produce much higher mutation rates and elevation of γ-globin than with in vitro transcribed (IVT) guides.

CIRCLE-seq library preparation and data analysis—CIRCLE-seq experiments were performed as described previously. In brief, purified genomic DNA was sheared to an average length of 300 bp, end repaired, A tailed, and ligated to uracil-containing stem-loop adaptor. Adaptor-ligated DNA was treated with Lambda Exonuclease (NEB) and *E. coli* Exonuclease I (NEB), followed by treatment with USER enzyme (NEB) and T4 polynucleotide kinase (NEB), then circularized with T4 DNA ligase, and treated with Plasmid-Safe ATP-dependent DNase (Epicentre) to degrade linear DNA. The circularized DNA was in vitro cleaved by SpCas9 RNP coupled with sgRNA-1617. Cleaved products were A tailed, ligated with a hairpin adaptor, treated with USER enzyme (NEB), and amplified by Kapa HiFi polymerase (Kapa Biosystems). The libraries were sequenced with 150 bp paired-end reads on an Illumina MiSeq instrument. The CIRCLE-seq sequencing data was analyzed by open-source Python package circleseq Results Identification of a potent and specific RNP complex—Electroporation of Cas9 and sgRNA RNP complexes enables delivery of a transient pulse of genome editing material to human cells. Previously employed lentiviral pooled sgRNA screening had identify a set of sgRNAs that target the core of the +58 erythroid enhancer of BCL11A resulting in potent HbF derepression[1]. See FIG. 3. In vitro transcription was used to produce sgRNAs targeting the BCL11A enhancer and electroporated RNP complexes to healthy donor CD34+ HSPCs. In the electroporated healthy donor CD34+ HSPCs, there were variability in editing, ranging from 9.5-87.0% indels (FIG. 4). Of note, several sgRNAs such as sgRNA-1621 and -1617 that were among the top performing in the lentiviral screen context were associated with relatively low indel frequencies. To improve indel frequencies, the sgRNAs were synthesized with specific chemical modifications. Specifically, 2'-O-methyl 3'phosphorothioate was added to the terminal nucleotides of the sgRNAs. Consistent with prior observations, it was found that chemically modified synthetic (MS) sgRNAs produced more efficient editing as compared to in vitro transcribed sgRNAs following RNP electroporation of CD34+ HSPCs[5]. See FIG. 5. We observed a dose-dependent relationship between RNP concentration and indel frequency and similar editing efficiency at Cas9:sgRNA molar ratios ranging from 1:1 to 1:2.5 (data not shown).

Figure 6:
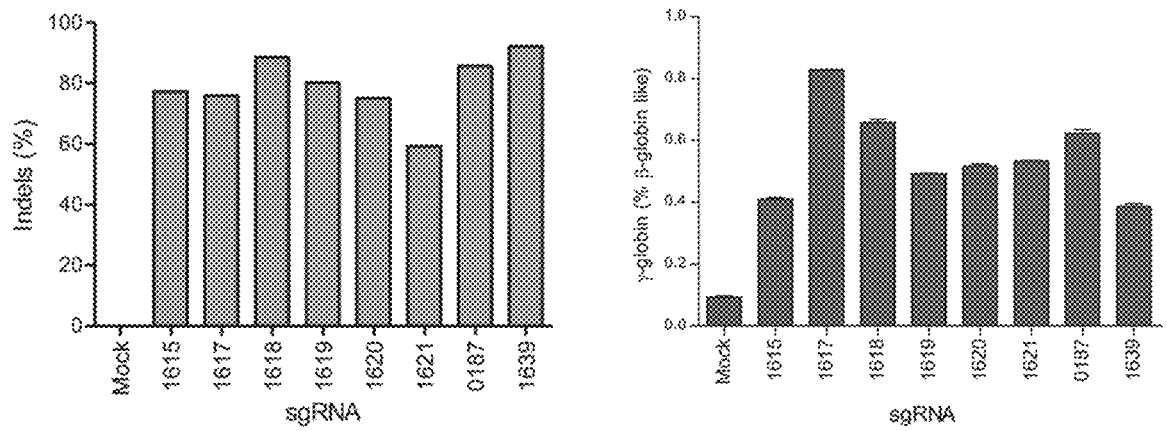
FIG. 6 shows genome editing of the BCL11A enhancer increases erythroid γ-globin levels in CD34+ HSPCs. Left panel: Cas9 RNP induced disruption of the BCL11A enhancer with synthetic modified guides in CD34+ primary cells. Right panel: Characterization of genome-edited CD34+ HSPCs for γ-globin mRNA level.
Figure 7A:
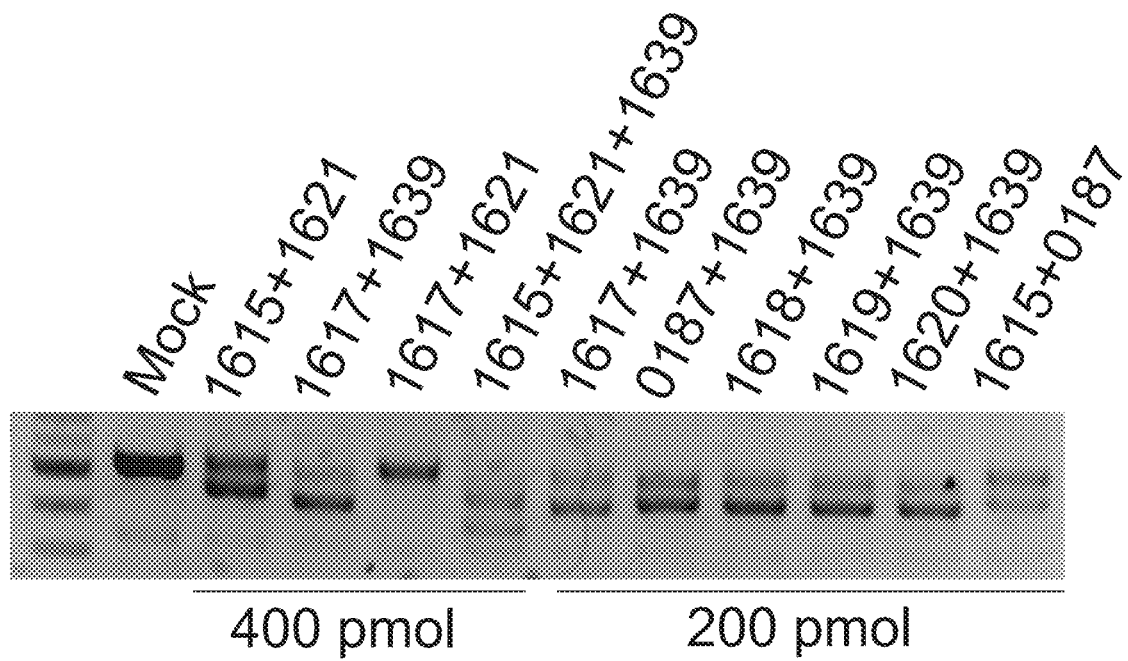
FIG. 7A shows genome editing of the BCL11A enhancer by paired guides increases erythroid γ-globin levels in CD34+ HSPCs. Cas9 RNP induced disruption of the BCL11A enhancer with paired synthetic modified guides in CD34+ HSPCs.
Figure 7B:
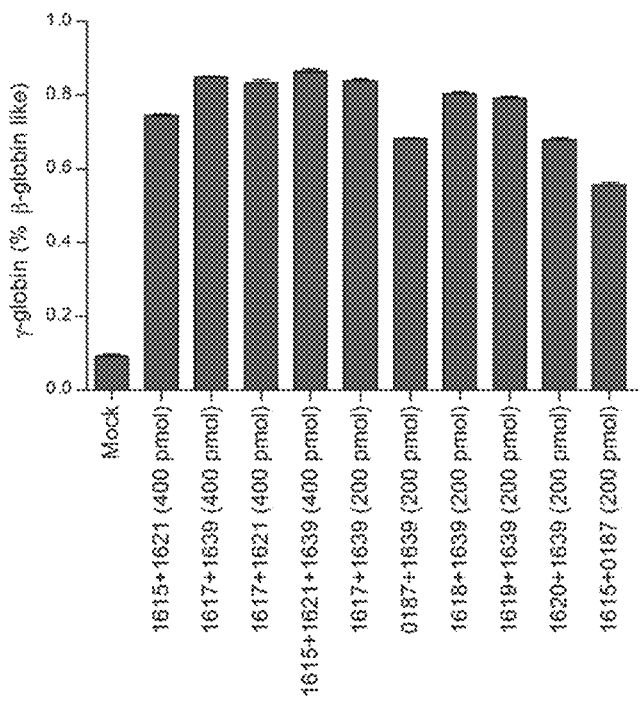
FIG. 7B shows genome editing of the BCL11A enhancer by paired guides increases erythroid γ-globin levels in CD34+ HSPCs. Characterization of genome-edited CD34+ HSPCs for γ-globin mRNA level.
Figure 8:
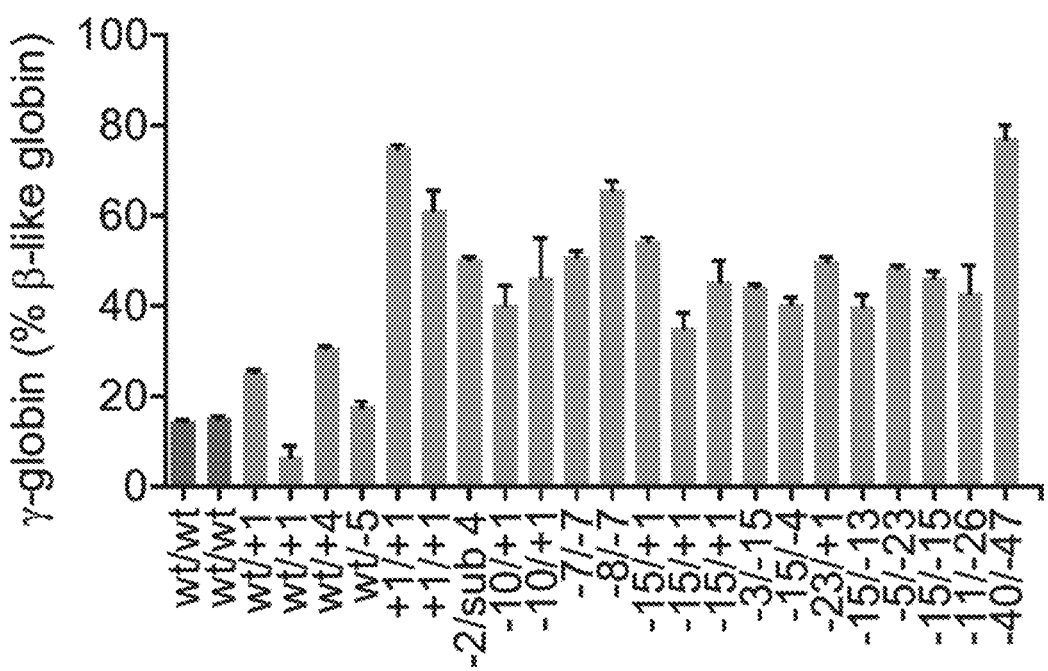
FIG. 8 shows genotyping and β-like globin expression analysis of clonal erythroid cells derived from single CD34+ HSPCs. Error bars indicate standard deviation (n=3 replicates).

We compared a set of 8 MS-sgRNAs targeting the core of the +58 erythroid enhancer of BCL11A in CD34+ HSPCs and observed efficient editing with indel frequencies ranging from 66.1-90.7% (FIG. 6). It was found that sgRNA-1617 editing gave the highest level of γ-globin and HbF induction in erythroid progeny (FIG. 6). This sgRNA cleaves directly within a GATA1 binding motif at the core of the +58 enhancer. Editing of the BCL11A enhancer resulted in reduction in BCL11A transcript expression by 54.6% (data not shown, assessed by RT-qPCR). Also observed was a strong correlation between reduction of BCL11A expression and induction of γ-globin and HbF (FIG. 6). Deep sequencing confirmed the high rate of indels, and showed that the most common mutations were +1 bp insertions, as produced by imprecise nonhomologous-end joining repair (NHEJ), followed by −15 bp and −13 bp deletions, each products of microhomology-mediated end joining (MMEJ) repair (data not shown). Clonal analysis of the erythroid progeny of CD34+ HSPCs edited at the BCL11A enhancer by sgRNA-1617 was conducted. Here, genotype was assessed, globin gene expression by RT-qPCR, and HbF analysis by HPLC (FIG. 8). Clones with biallelic enhancer modifications demonstrated elevated γ-globin mRNA levels (mean 50.8% of total β-like globin, range 35.3-75.1%, as compared to 14.7% in unedited clones) and elevated HbF protein levels (mean 37.6%, range 27.5-46.9%, as compared to 9.1% in unedited clones). Single base insertions at the sgRNA-1617 cleavage site were just as effective as longer deletions at increasing HbF levels, consistent with the hypothesis that mere disruption of a single GATA1 binding motif could be sufficient to impair the function of the +58 enhancer.

Figure 9A:
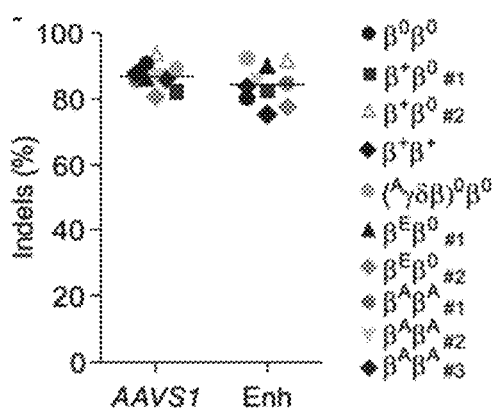
FIG. 9A shows editing efficiency of Cas9:sgRNA RNP targeting AAVS1 or BCL11A DHS h+58 functional core (Enh) with MS-sgRNA-1617 in CD34+ HSPCs from β-thalassemia patients ($\beta^0 \beta^0$, $\beta^+\beta^0$, $\beta^+\beta^+$, $(^A\gamma\delta\beta)^0\beta^0$ and $\beta E\beta 0$) genotypes) as measured by TIDE analysis.
Figure 9C:
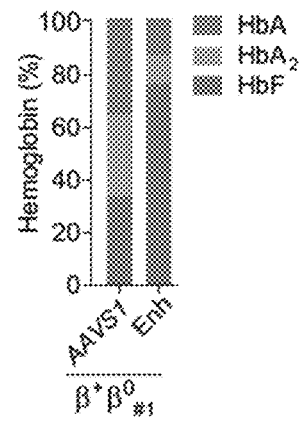
FIGS. 9C and 9D show HbF induction by HPLC analysis in erythroid cells in vitro differentiated from RNP edited CD34+ HSPCs of indicated β-thalassemia β-globin genotype or healthy donors ($\beta^A\beta^A$).
Figure 9B:
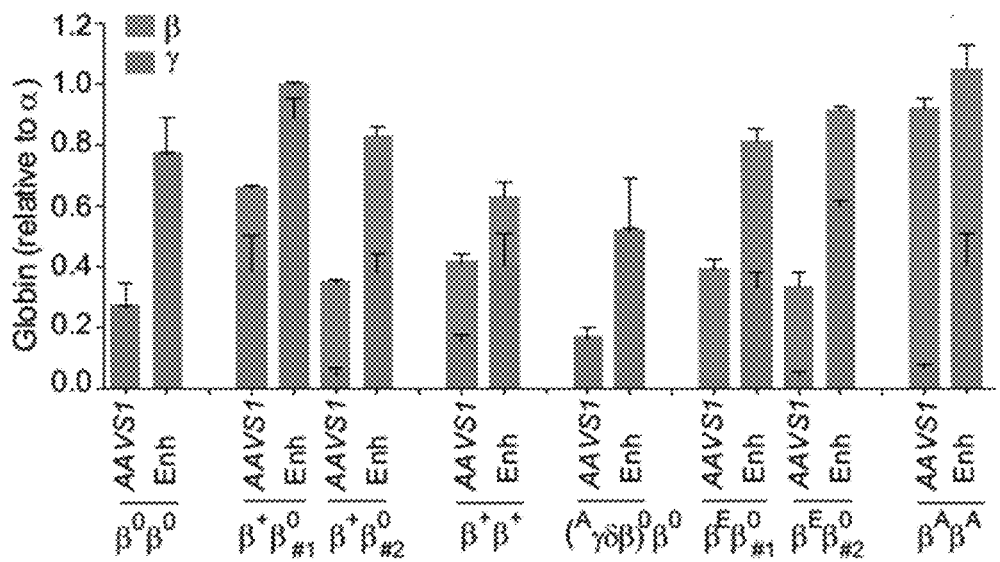
FIG. 9B shows β-like globin expression by RT-qPCR normalized by α-globin in erythroid cells in vitro differentiated from RNP edited CD34+ HSPCs of indicated β-thalassemia β-globin genotype or healthy donors ($\beta^A\beta^A$).
Figure 9D:
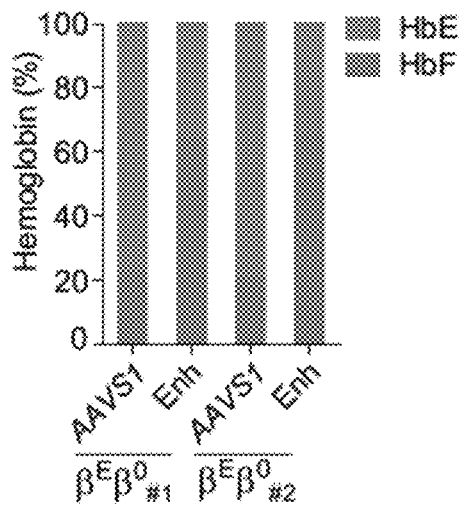

Amelioration of β-thalassemia—This BCL11A enhancer editing approach was tested for clinically meaningful γ-globin induction. CD34+ HSPCs were isolated from patients with β-thalassemia and subjected to BCL11A enhancer editing. Seven patient donors with varying genotypes were included, including $β^0β^0$, $β^+β^0$, $β^+β^+$, $(^{A}γδβ)^0β^0$ and $β^Eβ^0$. The RNP editing rate with MS-sgRNA-1617 was similar to that in HSPCs from healthy controls with a mean of 84.4% indels (range 75.3-92.5%). See FIG. 9A. RNP editing of the AAVS1 locus was performed as a functionally neutral control. In each β-thalassemia donor's BCL11A enhancer edited cells, potent induction of γ-globin was noted, with a mean of 55.6% relative to α-globin (range 33.0-89.0%) (FIG. 9B). In patients with $β^+$ or $β^E$ alleles where there was residual expression of HbA or HbE respectively, substantial induction of HbF upon BCL11A enhancer editing was observed (FIGS. 9C & 9D). Here, clearly therapeutically relevant amelioration of globin chain imbalance, the pathophysiologic underpinning of β-thalassemia, would result in improvement of terminal erythroid maturation. A higher frequency of enucleation of terminal erythroid cells in each of the β-thalassemia samples was noted too, but no effect on enucleation of the healthy donor samples, following BCL11A enhancer editing (data not shown). Characteristic features of thalassemic erythrocytes are their small size (microcytosis) and irregular shape (poikilocytosis). Following BCL11A enhancer editing of the enucleated β-thalassemia erythroid cells, increases in cell size and cell circularity to levels approaching those of healthy donor enucleated erythroid cells were observed (data not shown). Together these data suggest that Cas9 RNP-mediated mutagenesis at a single target site within the BCL11A enhancer in patient-derived CD34+ HSPCs is sufficient to ameliorate globin chain imbalance and erythroid maturation and therefore is a viable therapeutic strategy for β-thalassemia.

Genetic modification of HSCs—The durability of an autologous hematopoietic cell therapy depends on the ability to permanently modify stem cells. To test the impact of BCL11A enhancer editing on the function of HSCs and assess the editing rate within this cell population, edited human CD34+ HSPCs were engrafted into immunodeficient mice. NBSGW mice were utilized as recipients for these transplants since they can support not only myeloid and lymphoid but also erythroid engraftment. Using two separate donors, the recipients of edited and unedited CD34+ HSPCs had similar levels of human cell engraftment within the bone marrow after 16 weeks (data not shown). Moreover, similar degrees of lymphoid, myeloid, and erythroid engraftment occurred in recipients of edited and recipients of unedited cells (data not shown). There was a dose-dependent relationship between cell infusion dose and human cell engraftment. Variability in the fraction of indels in the engrafting cells from edited mice were observed, ranging from 13.8%-85.5% (data not shown). Comparing the indel frequencies in the input cells to the long-term engrafting cells, a mean reduction of 40.9% in indel frequencies was observed. The BCL11A expression in the engrafting bone marrow cells were measured. No reduction in BCL11A transcript levels in edited B-lymphocytes was detected, but 80.0% reduction in edited erythroid cells, consistent with the strict lineage specificity of these enhancer sequences (data not shown). In human erythroid cells from the bone marrow, robust induction of γ-globin was observed, increasing from 1.8% to 46.8% upon BCL11A enhancer editing (data not shown). The edited bone marrow cells were able to support secondary transplantation to a similar level as unedited cells, while maintaining a mean indel frequency of 72.2%, consistent with gene editing of self-renewing HSCs (data not shown).

Amelioration of SCD—The BCL11A enhancer editing strategy was also tested in sickle cell disease (SCD) HSCs. G-CSF mobilization is contraindicated in SCD due to risk of precipitating vaso-occlusion, and bone marrow harvest is morbid and inefficient. The CXCR4 antagonist plerixafor is a promising novel approach to mobilize SCD CD34+ HSPCs to the peripheral blood for autologous HSC therapies. Plerixafor-mobilized peripheral blood CD34+ HSPCs were obtained from a patient with SCD. There were 94.2% indels at the BCL11A enhancer following RNP electroporation of CD34+ HSPCs (data not shown). In vitro erythroid differentiated progeny showed 48.8% γ-globin in edited cells as compared to 3.5% in unedited cells (data not shown). Clonal analysis demonstrated that biallelic indels of the BCL11A enhancer, as short as 1 bp in length, resulted in robust induction of γ-globin (data not shown). Similar human engraftment of edited and unedited SCD cells ware observed (data not shown). Edited SCD cells were competent for lymphoid, myeloid, and erythroid engraftment (data not shown). Similar results were observed when edited cells were infused 1 or 2 days following editing (data not shown). Edited cells showed 95.1% indels after 16 weeks of bone marrow engraftment as compared to 94.2% indels in input cells (data not shown). BCL11A expression in erythroid cells was reduced by 82.0% while it was preserved in B-lymphocytes (data not shown). Edited bone marrow human erythroid cells expressed 57.5% γ-globin as compared to 3.6% in unedited cells (data not shown). The edited bone marrow SCD cells were able to support secondary transplantation to a similar level as unedited SCD cells, while maintaining a mean indel frequency of 98.1%, consistent with gene editing of self-renewing HSCs (data not shown). CD34$^+$ HSPCs were collected from the bone marrow of mice engrafted by SCD and healthy donor cells and subject to in vitro erythroid differentiation. In all cases of BCL11A enhancer editing, HbF levels were elevated (data not shown).

Lack of detectable genotoxicity—One of the major concerns with therapeutic genome editing is the potential for off-target genotoxicity. Therefore, to test the specificity of the RNP sgRNA-1617, CIRCLE-sequencing was performed, a method to define genome-wide target sequences susceptible to RNP cleavage in vitro. Based on this analysis, 20 potential off-target sites wele defined. Amplicon deep sequencing of each of these 20 off-target sites from CD34$^+$ HSPCs edited was performed. No identifiable or detectable off-target sites was observed for each studied Cas9-dependent indel, at the limit of detection of 0.1% allele frequency (data not shown). From the same edited gDNA, 81.0-95.5% on-target indels were observed at the BCL11A enhancer. In addition, amplicon deep sequencing was used to test four additional in silico predicted off-target sites not identified by CIRCLE-seq. No detectable indels was found at any of these sites (data not shown). Finally, targeted deep sequencing of edited CD34$^+$ HSPCs was performed using a clinically approved 95-gene sequencing panel designed to identify recurrent somatically acquired hematologic malignancy associated mutations. Here again, no variant alleles was observed at any of these hematologic malignancy associated loci in the edited HSPCs (data not shown). Together these data indicate the absence of detectable genotoxicity attributable to our BCL11A enhancer editing approach.

Previous experiments of genome editing in human HSPCs have shown variability in editing efficiency, specificity, and persistence in long-term engrafting HSCs. For the hemoglobin disorders, Cas9-mediated approaches have shown limited potency in reversal of hemoglobinopathy pathophysiology or required selection following genome editing. Here, the investigators developed an optimized protocol for selection-free, HSC expansion-free BCL11A enhancer editing using modified synthetic sgRNA, SpCas9 protein. Even 1 bp indels following cleavage at core sequences within the BCL11A erythroid enhancer were sufficient for robust HbF induction. This latter finding is especially relevant in light of our observation that microhomology-mediated gene editing events appear disfavored in HSCs.

The investigators found Cas9-mediated BCL11A enhancer editing to be compatible with the long-term self-renewing and multilineage repopulating function of patient-derived human HSCs. Despite the high efficiency of on-target indels, there was no off-target genotoxicity when delivering Cas9 RNPs. BCL11A enhancer editing proved to be an effective strategy to mitigate globin chain imbalance in β-thalassemia and to prevent deoxyhemoglobin polymerization in SCD. Alternative plausible strategies for genome editing to ameliorate the β-hemoglobinopathies include targeting the β-globin cluster for gene repair or to mimic hereditary persistence of fetal hemoglobin alleles. The efficiency of these homology and microhomology based maneuvers in HSCs in the absence of selection remains to be determined, and in the case of gene repair the clinically relevant delivery of an extrachromosomal donor sequence would be an additional challenge. Ex vivo BCL11A enhancer editing approaching complete allelic disruption appears to be a realistic strategy with existing technology for durable HbF induction for the β-hemoglobinopathies. This HSC editing approach could be adapted for the genetic amelioration of additional blood disorders.

REFERENCES

1. Canver, M. C. et al. BCL11A enhancer dissection by Cas9-mediated in situ saturating mutagenesis. *Nature* 527, 192-197 (2015).
2. GWAS-implicated HbF-associated sequences mark an erythroid enhancer of BCL11A (Sankaran et al, Science 2008; Bauer et al, Science 2013).
3. Smith, E. et al. Strict in vivo specificity of the Bcl11a erythroid enhancer. Blood 128, 2338-2342 (2016).
4. Therapeutic genome editing approach to induce fetal haemoglobin production in patients with sickle-cell disease (Lettre and Bauer, Lancet 2016).
5. Hendel A. et al., Chemically modified guide RNA enhance CRISPR-Cas genome editing in human primary cells. *Nature Biotechnology,* 33, pages 985-989 (2015)

Example 2

Rapid progress in genome editing technologies promises to transform the treatment of disease[1]. However to realize this potential, the efficiency and specificity of genetic modification must be maximized while enabling delivery of genome editing material to patient-derived disease affected tissues under clinically relevant conditions. Blood disorders are particularly favorable candidates for therapeutic genome editing in that ex vivo modification of HSCs could be sufficient for enduring correction of the hematopoietic system[2]. Existing protocols for bone marrow transplant and lentiviral gene therapy may be adapted for such HSC manipulation. The β-hemoglobin disorders sickle cell disease (SCD) and β-thalassemia are severe monogeneic disorders of β-globin (HBB) that comprise the most common Mendelian diseases in the world and continue to exert substantial morbidity and premature mortality. Re-expression of the paralogous γ-globin genes (HBG, $\alpha_2\gamma_2$)[3]. would be a universal strategy to ameliorate these disorders by induction of fetal hemoglobin (HbF, $\alpha_2\gamma_2$)[3]. Previously it was shown that core sequences at the erythroid enhancer of BCL11A are required for repression of HbF in adult-stage erythroid cells but dispensable in non-erythroid cells[4-8]. CRISPR-Cas9 based systems boast easy programming of guide RNA to genomic target[9-11], while Cas9 proteins may be engineered for desired properties[12-15]. Prior efforts to use Cas9 and other programmable nucleases to edit human hematopoietic stem and progenitor cells (HSPCs) have shown variable efficiency, genotoxicity, requirement for HSC selection or expansion prior to infusion, and limited ability to support long-term multilineage reconstitution with persistence of edited alleles[16-19]. Studies described herein have mainly relied on healthy donors as surrogates for patient derived cells. Therefore the feasibility of these approaches to achieve successful editing for the hemoglobin disorders remains uncertain. Herein is it investigated the use of Cas9 in combination with single chimeric guide RNAs (sgRNA) as a ribonucleoprotein (RNP) complex for the ex vivo targeting of the BCL11A erythroid enhancer in HSCs from patients with β-thalassemia and SCD.

Results

Figures 17A, 17B, 17C, 17D:
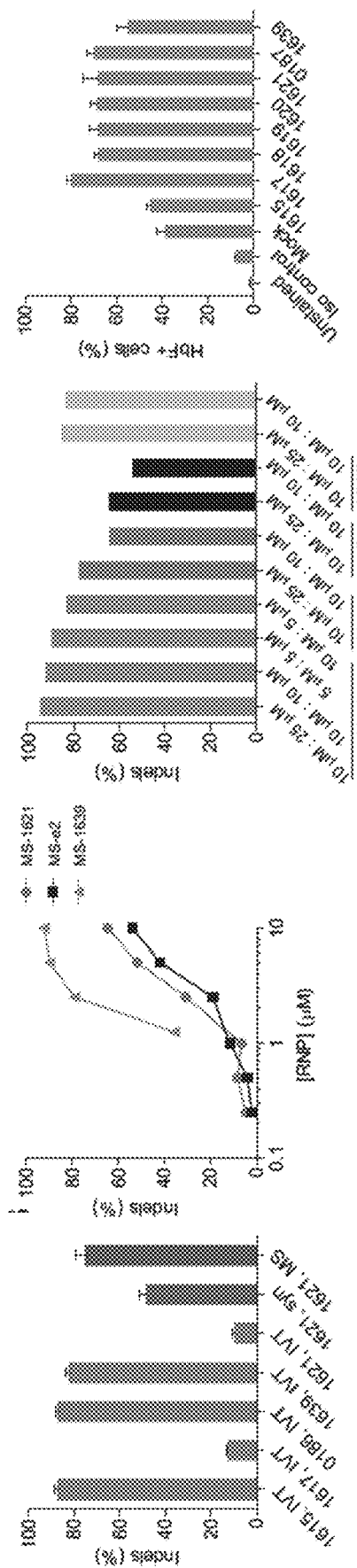
FIG. 17A-17D show Cas9 RNP dose dependent editing of BCL11A enhancer for HbF induction in CD34+ HSPCs.

Identification of a potent and specific RNP complex. Electroporation of Cas9 and sgRNA RNP complexes enables delivery of a transient pulse of genome editing material to human cells[20,21]. Previously lentiviral pooled sgRNA screening was used to identify a set of sgRNAs targeting the core of the +58 erythroid enhancer of BCL11A resulting in potent HbF derepression[5]. In vitro transcription was used to produce sgRNAs targeting the BCL11A enhancer and electroporated RNP complexes to healthy donor CD34+ HSPCs. Variability was found in editing, ranging from 9.5-87.0% indels (FIG. 17A). Of note, several sgRNAs such as sgRNA-1621 and -1617 that were among the top performing in the lentiviral screen context were associated with relatively low indel frequencies. Consistent with prior observations, chemically modified synthetic (MS) sgRNAs was found to produce more efficient editing as compared to in vitro transcribed sgRNAs following RNP electroporation of CD34+ HSPCs[22]. A dose-dependent relationship between RNP concentration and indel frequency was observed and similar editing efficiency at Cas9:sgRNA molar ratios ranging from 1:1 to 1:2.5 (FIG. 17B, 17C).

Figure 10E:
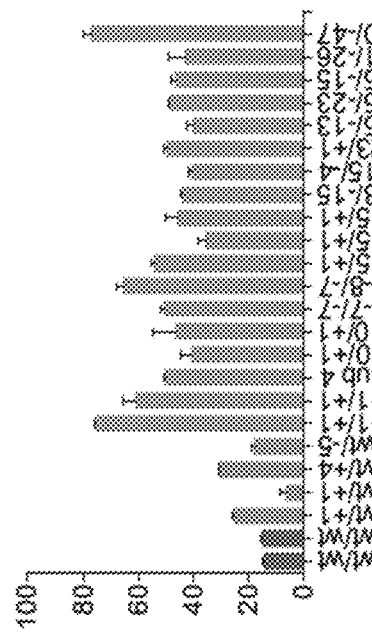
Figure 10G:
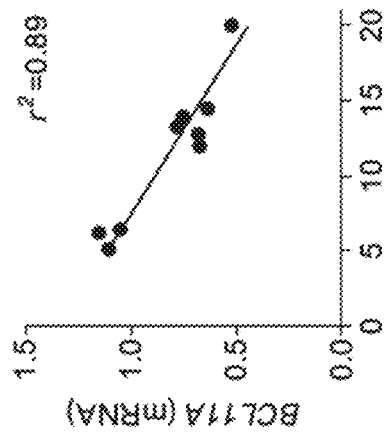
Figure 10F:
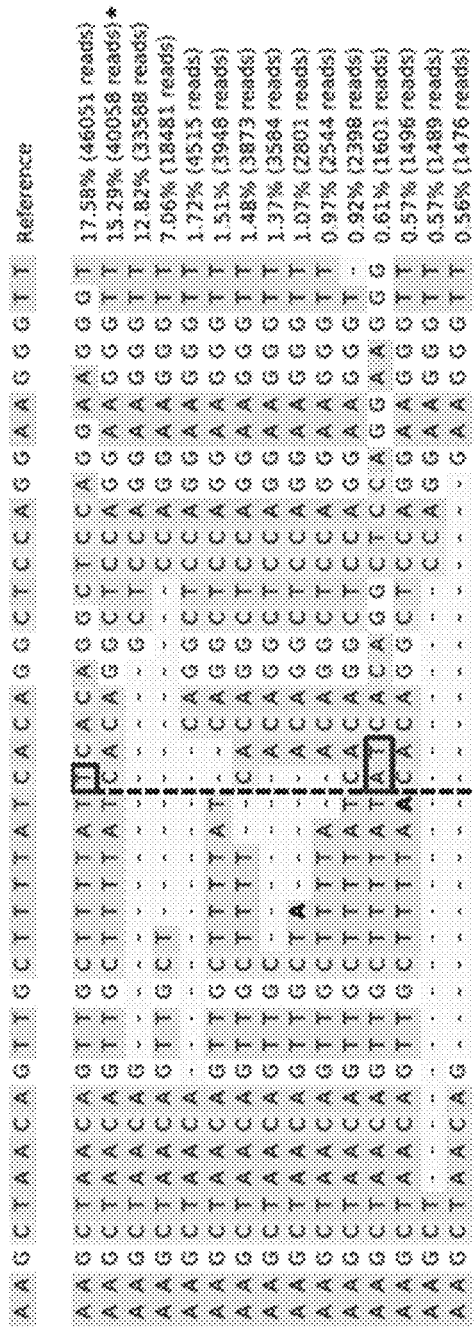
Figure 18A:
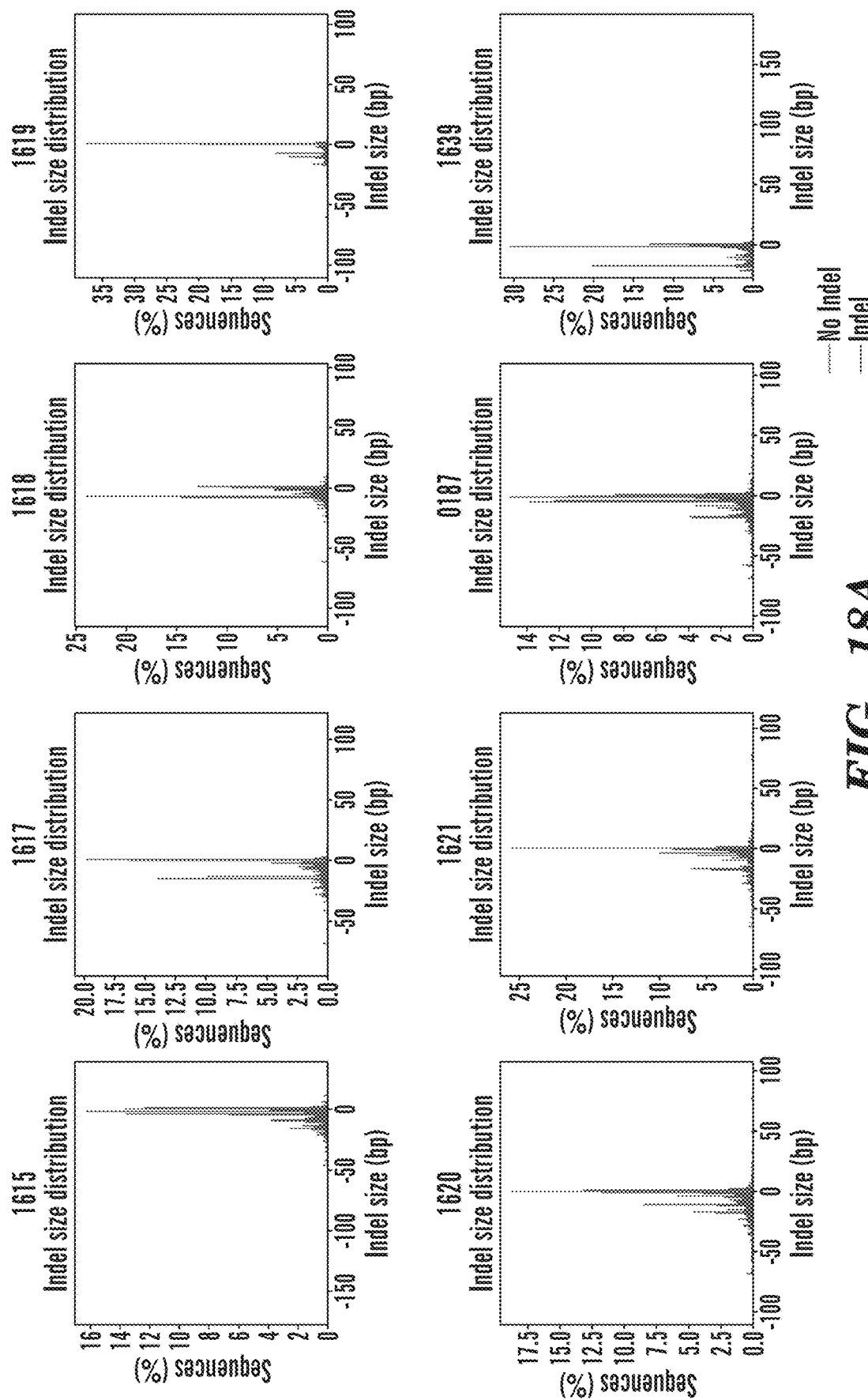
FIG. 18A-18B show indel frequencies from deep sequencing.
Figure 18B:
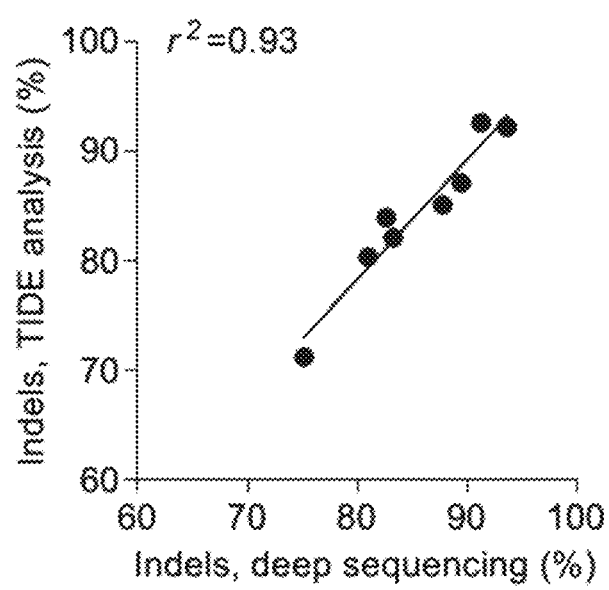

A set of 8 MS-sgRNAs targeting the core of the +58 erythroid enhancer of BCL11A was compared in CD34+ HSPCs and observed efficient editing with indel frequencies ranging from 66.1-90.7% (FIG. 10A, 10B, 18). sgRNA-1617 editing gave the highest level of γ-globin and HbF induction in erythroid progeny (FIG. 10C, 10D, 17D). This sgRNA cleaves directly within a GATA1 binding motif[23] at the core of the +58 enhancer (FIG. 10A). Editing of the BCL11A enhancer resulted in reduction in BCL11A transcript expression by 54.6% (FIG. 19A). A strong correlation was observed between reduction of BCL11A expression and induction of γ-globin and HbF (FIG. 10E, 19A-19C). Deep sequencing confirmed the high rate of indels, and showed that the most common mutations were +1 bp insertions, as produced by imprecise nonhomologous-end joining repair (NHEJ), followed by −15 bp and −13 bp deletions, each products of microhomology-mediated end joining (MMEJ) repair (FIG. 10F, 18). Clonal analysis of the erythroid progeny of CD34+ HSPCs edited at the BCL11A enhancer by sgRNA-1617, assessing genotype, globin gene expression by RT-qPCR, and HbF analysis by HPLC (FIG. 10G, 19D, 19E) was done. Clones with biallelic enhancer modifications demonstrated elevated γ-globin mRNA levels (mean 50.8% of total β-like globin, range 35.3-75.1%, as compared to 14.7% in unedited clones) and elevated HbF protein levels (mean 37.6%, range 27.5-46.9%, as compared to 9.1% in unedited clones). Single base insertions at the sgRNA-1617 cleavage site were just as effective as longer deletions at increasing HbF levels, consistent with the hypothesis that mere disruption of a single GATA1 binding motif could be sufficient to impair the function of the +58 enhancer.

Amelioration of β-thalassemia. It was determined if this BCL11A enhancer editing approach would result in clinically meaningful γ-globin induction. CD34+ HSPCs were isolated from patients with β-thalassemia and subjected them to BCL11A enhancer editing. Seven patient donors with varying genotypes were included, including $β^0β^0$, $β^+β^0$, $β^+β^+$, $(^A γδβ)^0β^0$ and $β^Eβ^0$ (data not shown). It was found that the RNP editing rate with MS-sgRNA-1617 was similar to that in HSPCs from healthy controls with a mean of 84.4% indels (range 75.3-92.5%, FIG. 11A). RNP editing of the AAVS1 locus was performed as a functionally neutral control. In each β-thalassemia donor's BCL11A enhancer edited cells, potent induction of γ-globin was demonstrated, with a mean of 55.6% relative to α-globin (range 33.0-89.0%) (FIG. 11B). In patients with $β^+$ or $β^E$ alleles where there was residual expression of HbA or HbE respectively, substantial induction of HbF upon BCL11A enhancer editing was observed (FIG. 11C, 11D). Without wishing to be bound by a particular theory, it was hypothesized that therapeutically relevant amelioration of globin chain imbalance, the pathophysiologic underpinning of β-thalassemia, would result in improvement of terminal erythroid maturation. A higher frequency of enucleation of terminal erythroid cells in each of the β-thalassemia samples was found, but no effect on enucleation of the healthy donor samples, following BCL11A enhancer editing (FIG. 11E). Characteristic features of thalassemic erythrocytes are their small size (microcytosis) and irregular shape (poikilocytosis). Following BCL11A enhancer editing of the enucleated β-thalassemia erythroid cells, increases in cell size and cell circularity were observed to levels approaching those of healthy donor enucleated erythroid cells (FIG. 11F-11I). Together these data indicate that Cas9 RNP-mediated mutagenesis at a single target site within the BCL11A enhancer in patient-derived CD34+ HSPCs is sufficient to ameliorate globin chain imbalance and erythroid maturation and therefore is a viable therapeutic strategy for β-thalassemia.

Genetic modification of HSCs. The durability of an autologous hematopoietic cell therapy depends on the ability to permanently modify stem cells. To test the impact of BCL11A enhancer editing on the function of HSCs and assess the editing rate within this cell population, edited human CD34+ HSPCs were engrafted into immunodeficient mice. NBSGW mice were utilized as recipients for these transplants since they can support not only myeloid and lymphoid but also erythroid engraftment[24]. Using two separate donors, it was found that the recipients of edited and unedited CD34+ HSPCs had similar levels of human cell engraftment within the bone marrow after 16 weeks (FIG. 12A, data not shown). Moreover, it was found that similar degrees of lymphoid, myeloid, and erythroid engraftment comparing recipients of edited and unedited cells (FIG. 12C, 12D). There was a dose-dependent relationship between cell infusion dose and human cell engraftment. Variability was observed in the fraction of indels in the engrafting cells from edited mice, ranging from 13.8%-85.5% (FIG. 12B). Comparing the indel frequencies in the input cells to the long-term engrafting cells a mean reduction of 40.9% was observed. BCL11A expression was measured in the engrafting bone marrow cells. No reduction in BCL11A transcript levels was found in edited B-lymphocytes, but 80.0% reduction in edited erythroid cells, consistent with the strict lineage specificity of these enhancer sequences (FIG. 12E, 12F). In human erythroid cells from the bone marrow, robust induction of γ-globin was observed, increasing from 1.8% to 46.8% upon BCL11A enhancer editing (FIG. 12G). The edited bone marrow cells were able to support secondary transplantation to a similar level as unedited cells, while maintaining a mean indel frequency of 72.2%, consistent with gene editing of self-renewing HSCs (FIG. 12H, 12I).

Figure 13A:
Figure 13B:
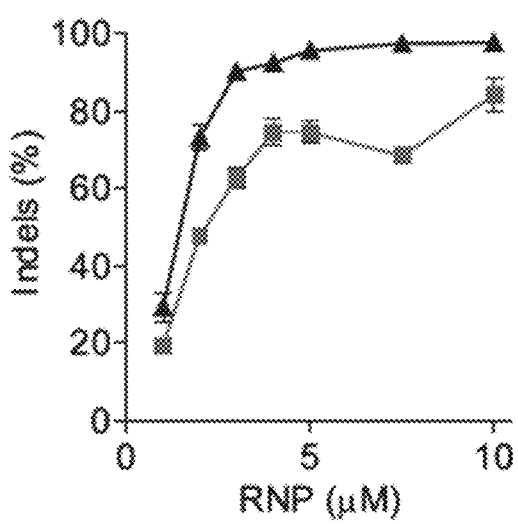
(FIG. 13B) Dose-dependent editing of human BCL11A enhancer with 2×NLS-Cas9 or 3×NLS-Cas9 RNP.
Figure 13C:
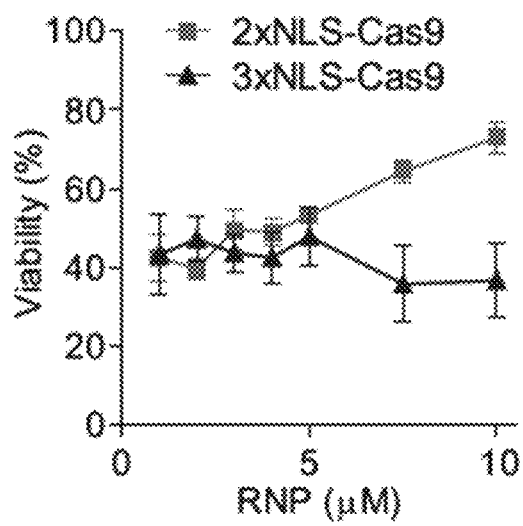
(FIG. 13C) Viability of CD34$^+$ HSPCs after electroporation with 2×NLS-Cas9 and 3×NLS-Cas9.
Figure 13D:
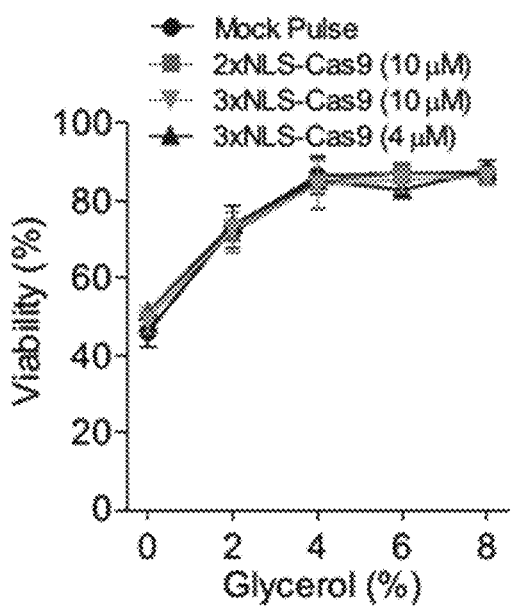
(FIG. 13D) Viability of CD34$^+$ HSPCs after electroporation with RNP and glycerol.
Figure 13E:
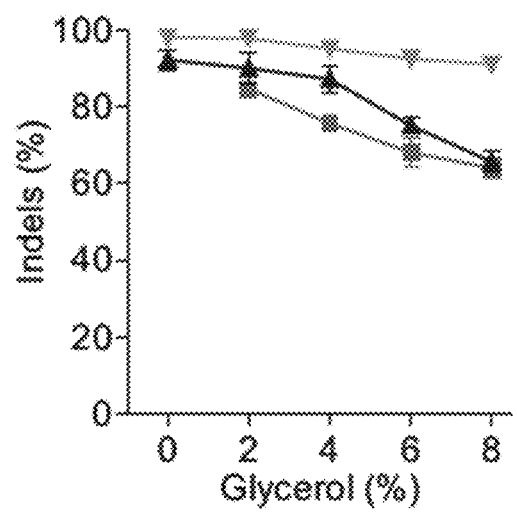
(FIG. 13E) Indel frequencies of CD34$^+$ HSPCs after electroporation with RNP and glycerol. Error bars indicate standard deviation (n=3 replicates).
Figure 13F:
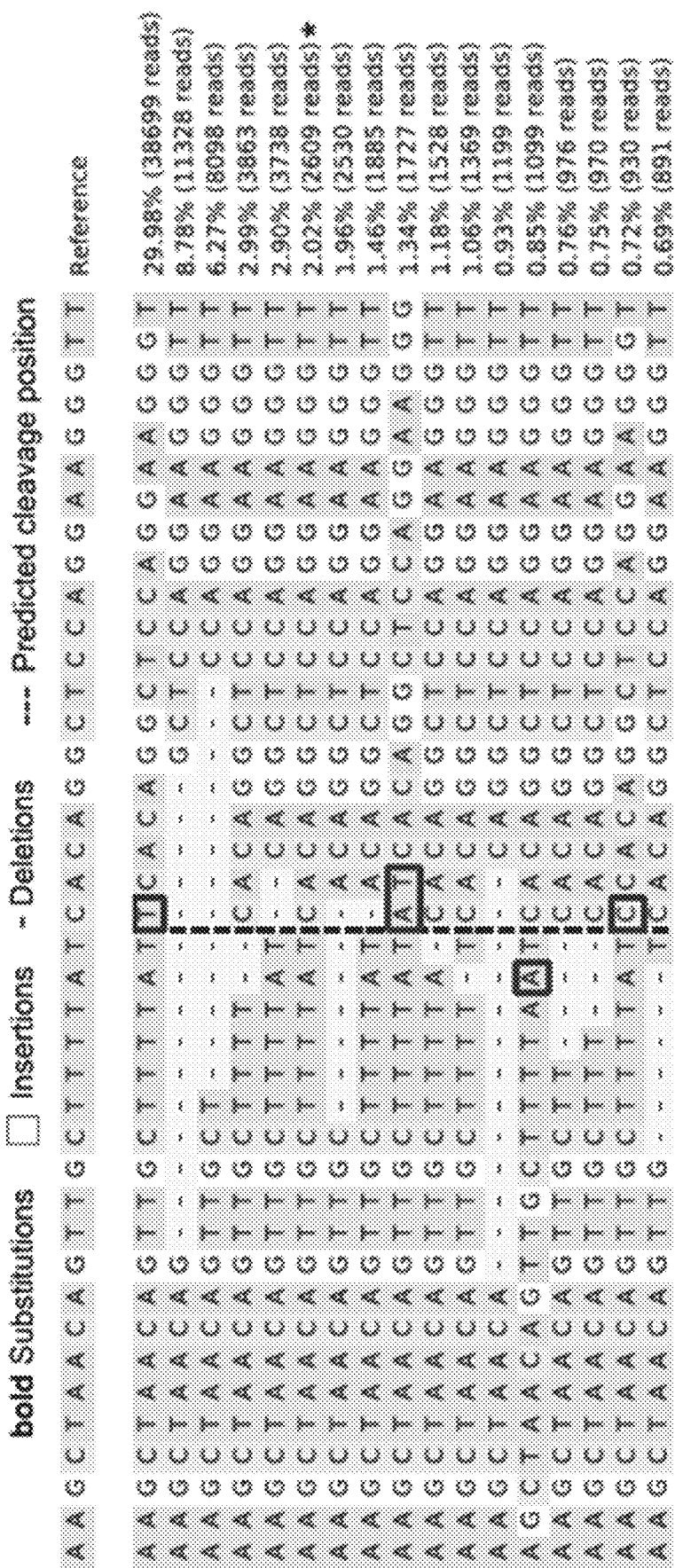
(FIG. 13F) Summary of most frequent indels by deep sequencing following 3×NLS-Cas9 RNP BCL11A enhancer editing of CD34$^+$ HSPCs. Asterisk indicates unedited allele.

Optimized editing conditions. The SpCas9 protein were used in the experiments described above included two SV40 nuclear localization sequences (NLSs) on the C-terminus[25] (subsequently called 2×NLS-Cas9). It was hypothesized that additional orthogonal nuclear localization sequences could improve genome editing efficiency. Ac-Myc NLS was appended to the N-terminus and both SV40 and nucleoplasmin NLSs to the C-terminus of SpCas9 (subsequently called 3×NLS-Cas9) (FIG. 13A). To test this hypothesis, human CD34+ HSPCs were electroporated with BCL11A enhancer targeting RNPs at concentrations ranging from 1-10 μM. Increased indel frequencies was found at all doses with 3×NLS-Cas9 (FIG. 13B). At doses of 5 μM and greater the indel frequency exceeded 95%. It was found that the viability of cells electroporated with 3×NLS-Cas9 was inferior as compared to those receiving 2×NLS-Cas9. However as the dose of 2×NLS-Cas9 decreased, the viability approached that of 3×NLS-Cas9 treated cells (FIG. 13C). It was hypothesized that a component of the diluent for 2×NLS-Cas9 might be protective. The 2×NLS-Cas9 stock was dissolved in 10% glycerol, whereas the 3×NLS-Cas9 stock was not dissolved in glycerol. Cells were electroporated with 3×NLS-Cas9 with a final glycerol concentration ranging from 0 to 8% and found that additional glycerol protected the cells from loss of viability (FIG. 13D). This protective effect was observed with 2×NLS-Cas9, 3×NLS-Cas9, and without Cas9, indicating that glycerol was protective against electroporation-mediated toxicity independent of genome editing (FIG. 13D). Similar protection was observed against electroporation toxicity with glycine, consistent with a possible osmoprotectant effect (FIG. 20A). A slight decrement of editing was observed with increasing doses of glycerol, indicating a balance between maximizing cell viability and genome editing efficiency (FIG. 13E). At concentrations of 2-4% glycerol, only minimal reduction of indels was found but substantially improved cell viability. It was found that 3×NLS-Cas9 RNP electroporation was able to achieve up to 98.1% indels in CD34+ HSPCs (FIG. 13F, 20B, 20C). There was a similar distribution of alleles as with 2×NLS-Cas9 editing, with the +1 bp insertion the most frequent indel, followed by the −15 bp and −13 bp deletions. A similar magnitude of decrease in BCL11A mRNA and protein level was observed during in vitro erythroid maturation with 2×NLS-Cas9 or 3×NLS-Cas9 RNP electroporation, although there was a modest increase in both γ-globin and HbF induction with 3×NLS-Cas9 (p<0.05, FIGS. 13G, 20D, 20E, 20F and 20G).

It was hypothesized that maximizing genome editing efficiency might increase the fraction of indels in long-term engrafting edited HSCs. Furthermore, it was reasoned that erythroid enhancer edited HSCs would show enhanced HbF induction as compared to HSPCs edited in vitro while undergoing erythroid maturation, since in the former case BCL11A expression would be disrupted from the earliest stages of erythropoiesis. RNP electroporation was performed with 3×NLS-Cas9 and BCL11A enhancer MS-sgRNA-1617. Similar human marrow engraftment after 16 weeks with edited and unedited CD34+ HSPCs was observed (FIG. 13H). No difference in human engraftment was observed if cells were infused 0, 1, or 2 days following electroporation (FIG. 21A). Edited cells showed similar capacity for lymphoid, myeloid, and erythroid engraftment (FIG. 13I, 13J, 21B, 21C). Long-term engrafting human cells maintained 96.5% indels, similar to the 98.1% indels observed in the input cells (FIG. 13K, 21D). In the bone marrow, BCL11A expression was preserved in edited B-lymphocytes but reduced by 82.7% in edited erythroid cells (FIG. 13L, 13M). γ-globin was elevated from 2.2% to 70.8% total β-like globin in edited human erythroid cells (FIG. 13N, 23C). Transplant of CD34+ HSPCs electroporated with 3×NLS-Cas9 and MS-sgRNA-1617 and supplemented with 2%, 4% or 6% glycerol also yielded potent human engraftment while maintaining high indel frequencies in the long-term repopulating cells (FIG. 21E-21H).

Figure 14B:
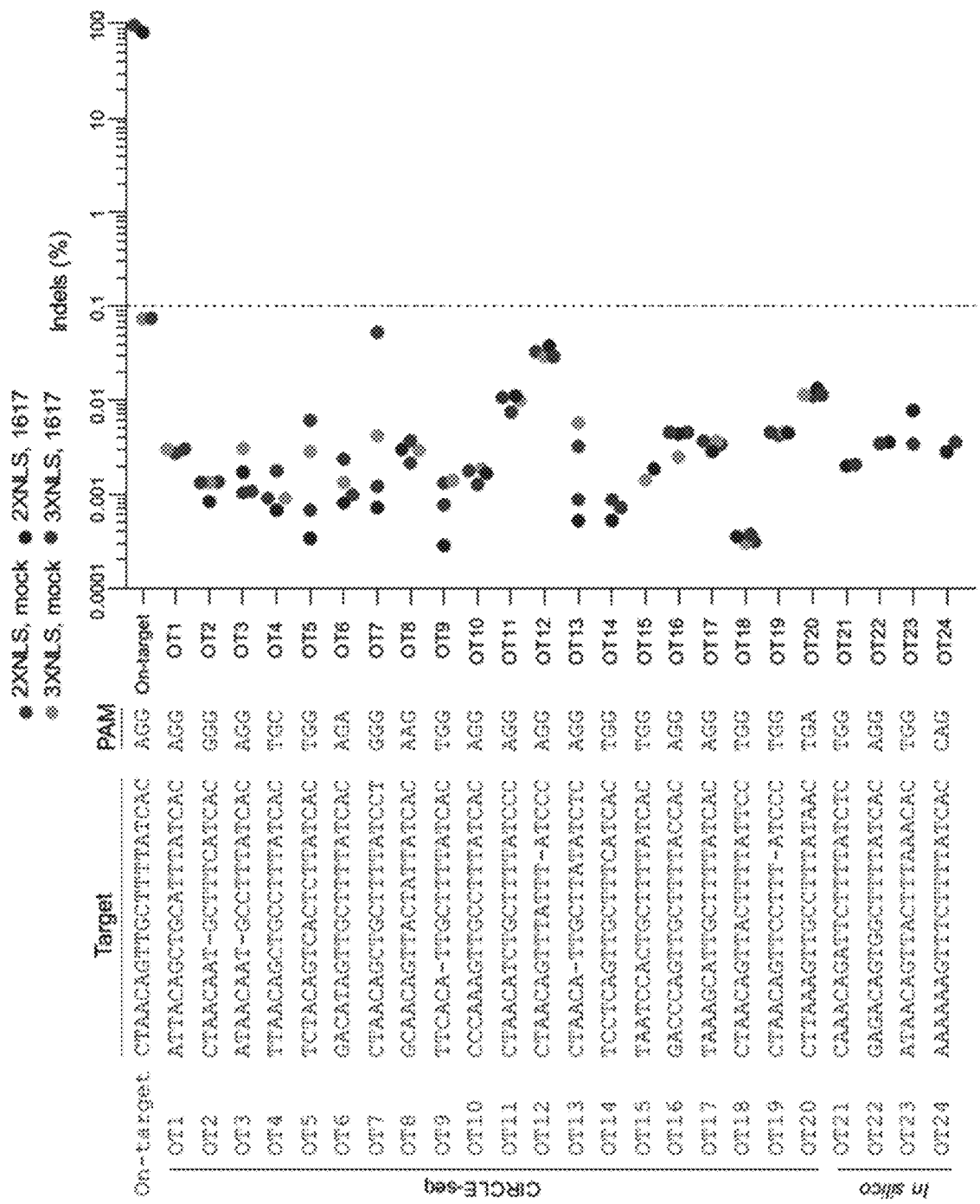

Lack of detectable genotoxicity. One of the major concerns with therapeutic genome editing is the potential for off-target genotoxicity. Therefore, to test the specificity of the RNP sgRNA-1617, CIRCLE-seq was performed, a method to define genome-wide target sequences susceptible to RNP cleavage in vitro[26]. Based on this analysis, 20 potential off-target sites were defined (FIG. 14A, 18). Amplicon deep sequencing of each of these 20 off-target sites was performed from CD34+ HSPCs edited with both 2×NLS-Cas9 and 3×NLS-Cas9. Off-target sites were not identified at observed Cas9-dependent indels, at the limit of detection of 0.1% allele frequency (FIG. 14B). From the same edited gDNA, 81.0-95.5% on-target indels at the BCL11A enhancer was observed. In addition, four additional in silico predicted off-target sites not identified by CIRCLE-seq were tested by amplicon deep sequencing (FIG. 19). Indels were not detected at any of these sites (FIG. 14B). Finally targeted deep sequencing of edited CD34+ HSPCs was performed using a clinically approved 95-gene sequencing panel designed to identify recurrent somatically acquired hematologic malignancy associated mutations[27]. No variant alleles were identified at any of these hematologic malignancy associated loci in the edited HSPCs (FIG. 20). Together these data indicate the absence of detectable genotoxicity attributable to the BCL11A enhancer editing approach described herein.

Figure 15K:
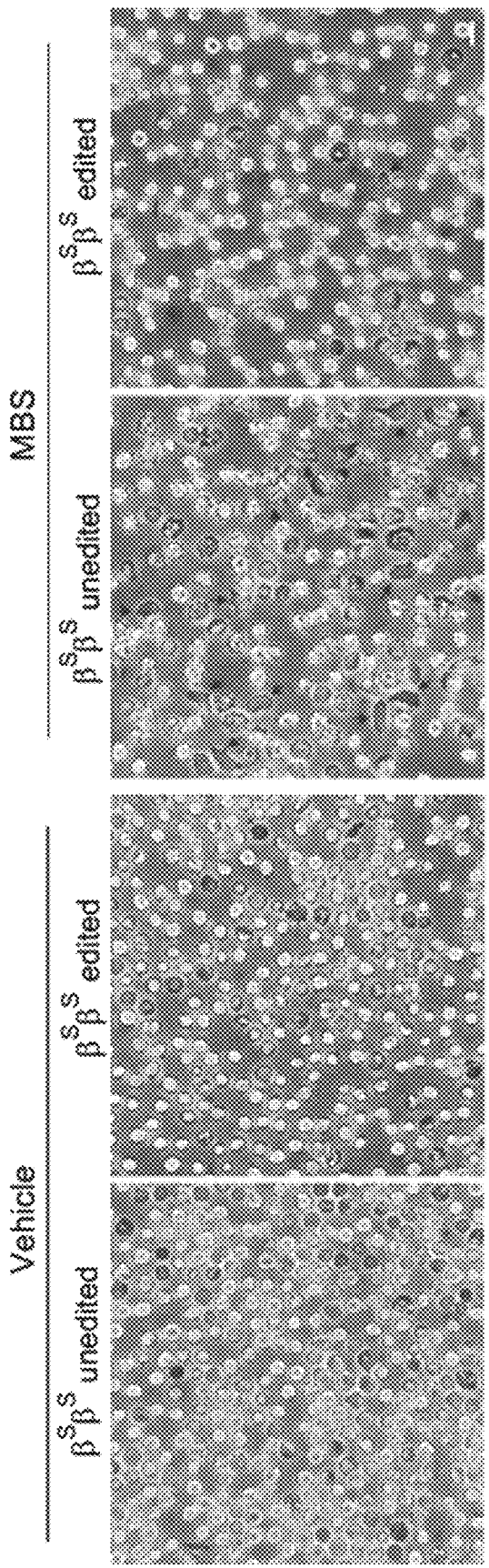
Figure 15L:
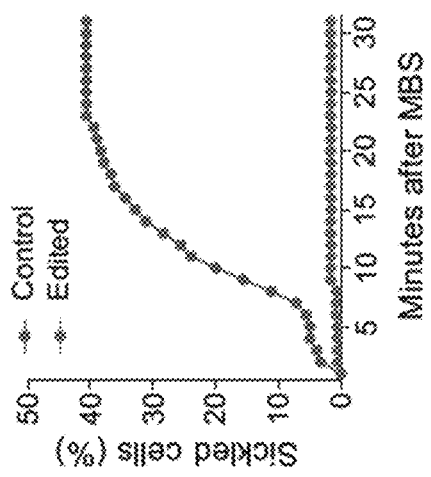
Figure 22D:
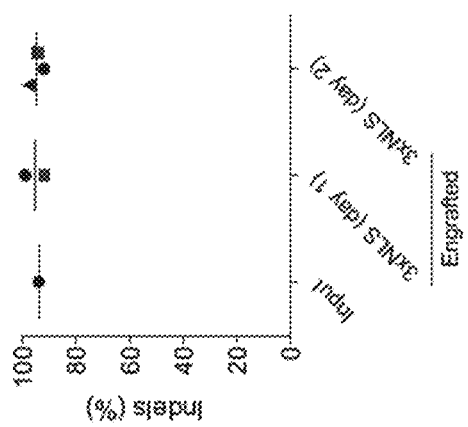
FIG. 22A-22D show editing of BCL11A enhancer in SCD patient ($\beta^S\beta^S$) HSPCs. NBSGW mice were transplanted with 3×NLS-Cas9 RNP with MS-sgRNA-1617 edited $\beta^S\beta^S$ CD34+ HSPCs 24 h (day 1) or 48 h (day 2) after electroporation. BM were collected 16 weeks after transplantation and analyzed by flow cytometry for human cell chimerism (FIG. 22A), multilineage reconstitution (FIG. 22B) or human erythroid cells (FIG. 22C) in BM, as well as the indel frequencies determined by TIDE analysis (FIG. 22D). Error bars indicate standard deviation.
Figure 22C:
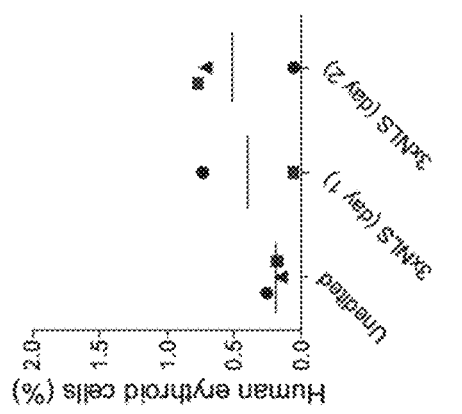
Figure 22B:
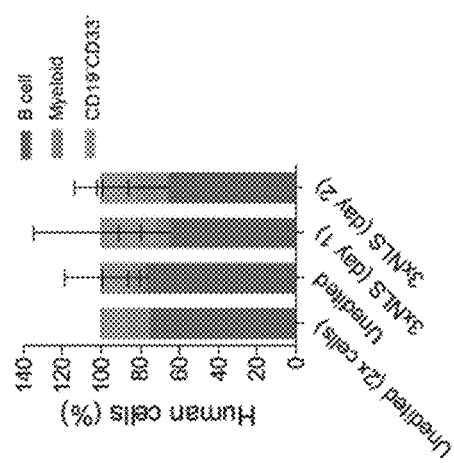
Figure 22A:
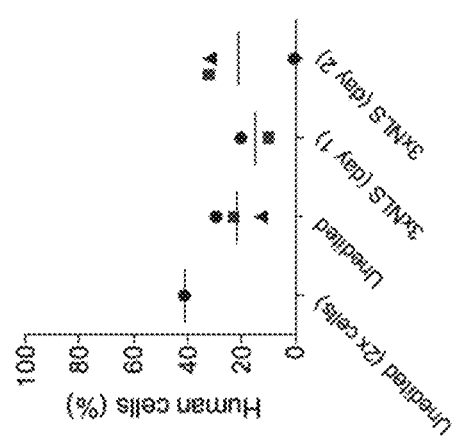

Amelioration of SCD. It was determined if this optimized BCL11A enhancer editing strategy could be effective in sickle cell disease (SCD) HSCs. G-CSF mobilization is contraindicated in SCD due to risk of precipitating vaso-occlusion, and bone marrow harvest is morbid and inefficient[28]. The CXCR4 antagonist plerixafor is a promising novel approach to mobilize SCD CD34+ HSPCs to the peripheral blood for autologous HSC therapies[29-32]. Plerixafor-mobilized peripheral blood CD34+ HSPCs was obtained from a patient with SCD. 94.2% indels at the BCL11A enhancer following RNP electroporation of CD34+ HSPCs was demonstrated (FIG. 15A). In vitro erythroid differentiated progeny showed 48.8% γ-globin in edited cells as compared to 3.5% in unedited cells (FIG. 15B). Clonal analysis demonstrated that biallelic indels of the BCL11A enhancer, as short as 1 bp in length, resulted in robust induction of γ-globin (FIG. 15C, 17). Similar human engraftment of edited and unedited SCD cells were observed (FIG. 15D). Edited SCD cells were competent for lymphoid, myeloid, and erythroid engraftment (FIG. 22B, 22C). Similar results when edited cells were infused 1 or 2 days following editing were observed (FIG. 22A-22D). Edited cells showed 95.1% indels after 16 weeks of bone marrow engraftment as compared to 94.2% indels in input cells (FIG. 15E). BCL11A expression in erythroid cells was reduced by 82.0% while it was preserved in B-lymphocytes (FIG. 15F, 15G). Edited bone marrow human erythroid cells expressed 57.5% γ-globin as compared to 3.6% in unedited cells (FIG. 15H). The edited bone marrow SCD cells were able to support secondary transplantation to a similar level as unedited SCD cells, while maintaining a mean indel frequency of 98.1%, consistent with gene editing of self-renewing HSCs (FIG. 15I, 15J). CD34+ HSPCs were collected from the bone marrow of mice engrafted by SCD and healthy donor cells and subject to in vitro erythroid differentiation. In all cases of BCL11A enhancer editing, HbF levels were elevated (FIG. 16A). In healthy donor cells, HbF levels rose from 4.1% in unedited to 35.9% in 3×NLS-Cas9 RNP edited cells, and in SCD patient cells, HbF levels rose from 13.9% to 47.5%. While unedited SCD enucleated erythroid cells derived from engrafting HSCs demonstrated robust in vitro sickling following sodium metabisulfite (MBS) treatment, edited SCD cells were resistant to sickling (FIG. 15K, 15L).

Figure 24A:
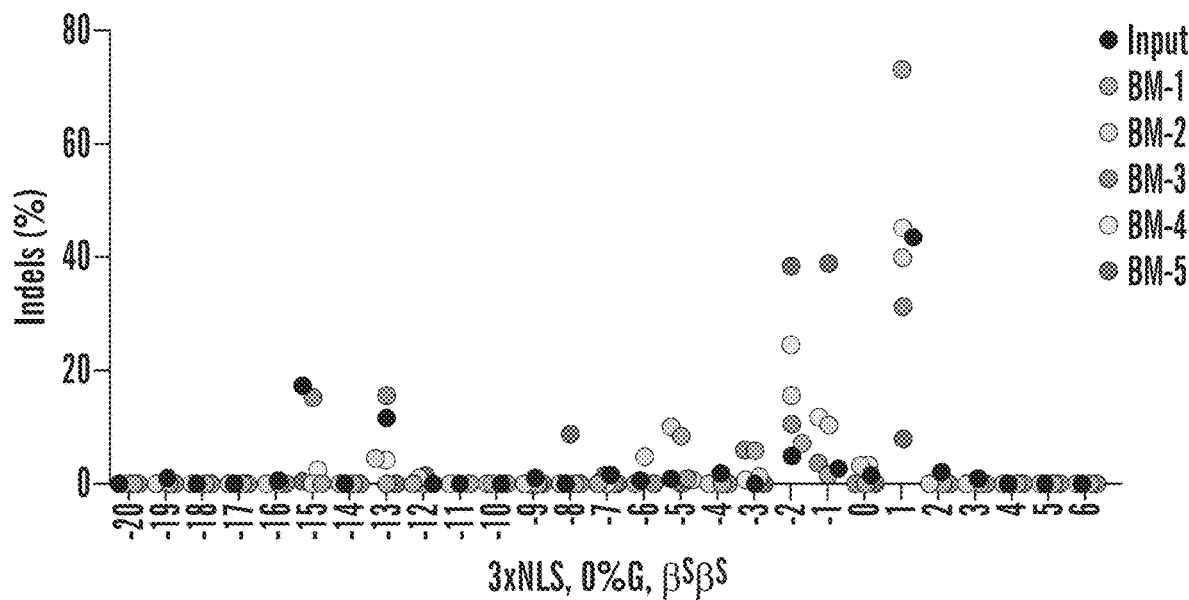
FIG. 24A-24B show indel spectrums of engrafted bone marrow and corresponding input cells. Indel spectrums of engrafted bone marrow (BM) and corresponding input cells from four donors electroporated with 2×NLS-Cas9 or 3×NLS-Cas9 coupled with MS-sgRNA-1617 (FIG. 24A) or -AAVS1 (FIG. 24B) supplemented with different concentration of glycerol (0% G to 6% G).
Figure 24B:
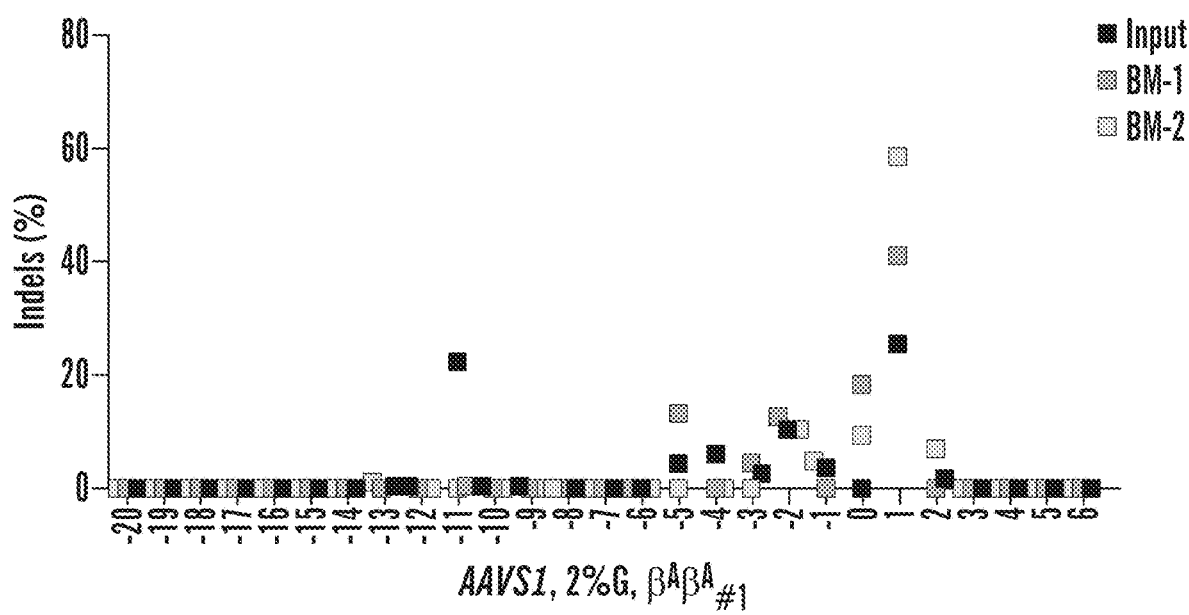
Figure 25:
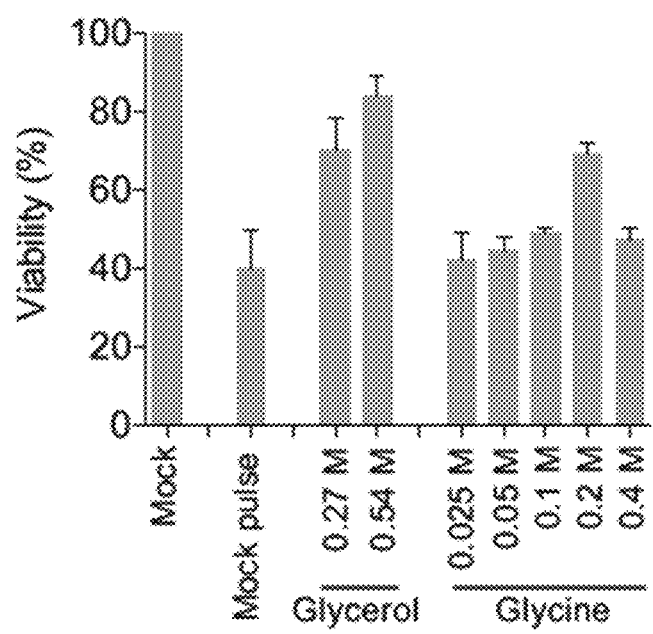
FIG. 25 shows viability of CD34+ HSPCs after electroporation with 2×NLS-Cas9 and 3×NLS-Cas9.

Persistence of NHEJ repaired alleles in HSCs. Erythroid cells differentiated in vitro from the bone marrow of mice engrafted with 3×NLS-Cas9 edited cells showed more potent induction of HbF as compared to 2×NLS-Cas9 edited cells, consistent with greater persistence of edited alleles in long-term repopulating HSCs (FIG. 17A, 23A). Comparing all of the transplant results described herein, a strong correlation ($r^2$=0.91) was observed between the indel frequencies observed in input HSPCs and indel frequencies in human cells engrafting in the bone marrow after 16 weeks (FIG. 16B). These data indicate that maximizing indel frequencies at a target sequence in an input HSPC population is critical to obtain high levels of biallelic modifications within the HSC population. However, when evaluated, the composition of edited alleles found in long-term repopulating cells found a different indel spectrum as compared to that found in the input transplanted HSPCs (FIG. 16C, 24A, 24B). For example, HSPCs edited with 2×NLS-Cas9 in the presence of 2% glycerol showed that the second and third most common deletions were 15 bp and 13 bp deletions, comprising together 25.9% of all alleles (FIG. 16C). These deletions were nearly absent in the long-term engrafted cells, comprising together 1.0% of alleles. The 15-bp and 13-bp deletions were both predicted products of MMEJ repair[33]. These results indicated that NHEJ may be favored relative to MMEJ repair in the long-term repopulating HSC population relative to the bulk HSPC population. Each of the repair alleles were classified, at BCL11A and AAVS1, as originating from NHEJ or MMEJ and compared their abundance in input HSPCs used for transplantation or in the engrafted cells resulting from these transplants. Together these data comprised nine independent transplants conducted with 30 recipient mice across BCL11A and AAVS1. A significant decrease was observed in the fraction of edited alleles repaired by MMEJ (median 24.4% versus 2.9%, p<0.0001) and a concomitant increase in the fraction of edited alleles repaired by NHEJ (median 64.6% versus 85.1%, p<0.005) in engrafted human cells as compared to input HSPCs (FIG. 16D). These results indicate that the types and frequencies of nuclease-initiated editing events observed in bulk HSPCs do not necessarily reflect editing events and rates present within long-term repopulating HSCs.

DISCUSSION

Previous experiments of genome editing in human HSPCs have shown variability in editing efficiency, specificity, and persistence in long-term engrafting HSCs[8,16,17,34-36]. For the hemoglobin disorders, Cas9-mediated approaches have shown limited potency in reversal of hemoglobinopathy pathophysiology or required selection following genome editing[16,17]. Herein is an optimized protocol for selection-free, HSC expansion-free BCL11A enhancer editing using modified synthetic sgRNA, SpCas9 protein with an additional NLS, and reformulated electroporation buffer. Even 1 bp indels following cleavage at core sequences within the BCL11A erythroid enhancer were sufficient for robust HbF induction. This latter finding is especially relevant in light of the observation that microhomology-mediated gene editing events appear disfavored in HSCs, described herein. It is speculated that the relative bias against MMEJ repair in HSCs could be related to the cell-cycle dependence of MMEJ-mediated repair and the relatively quiescent nature of HSCs[37-39]. This observation could have implications for target site choice in therapeutic applications.

Cas9-mediated BCL11A enhancer editing was found to be compatible with the long-term self-renewing and multilineage repopulating function of patient-derived human HSCs. Despite the high efficiency of on-target indels, off-target genotoxicity was not observed when delivering Cas9 RNPs. It is demonstrated herein that BCL11A enhancer editing to be an effective strategy to mitigate globin chain imbalance in β-thalassemia and to prevent deoxyhemoglobin polymerization in SCD. Alternative plausible strategies for genome editing to ameliorate the β-hemoglobinopathies include targeting the β-globin cluster for gene repair or to mimic hereditary persistence of fetal hemoglobin alleles[16,17,35,40-42]. The efficiency of these homology and microhomology based maneuvers in HSCs in the absence of selection remains to be determined, and in the case of gene repair the clinically relevant delivery of an extrachromosomal donor sequence would be an additional challenge. Ex vivo BCL11A enhancer editing approaching complete allelic disruption appears to be a realistic strategy with existing technology for durable HbF induction for the β-hemoglobinopathies. This HSC editing approach could be adapted for the genetic amelioration of additional blood disorders.

REFERENCES

1. Dunbar, C. E. et al. Gene therapy comes of age. *Science* 359, (2018).
2. Hoban, M. D. & Bauer, D. E. A genome editing primer for the hematologist. *Blood* 127, blood-2016-01-678151 (2016).
3. Vinjamur, D. S., Bauer, D. E. & Orkin, S. H. Recent progress in understanding and manipulating haemoglobin switching for the haemoglobinopathies. *British Journal of Haematology* (2017). doi:10.1111/bjh.15038
4. Bauer, D. E. et al. An Erythroid Enhancer of BCL11A Subject to Genetic Variation Determines Fetal Hemoglobin Level. *Science* 342, 253-257 (2013).
5. Canver, M. C. et al. BCL11A enhancer dissection by Cas9-mediated in situ saturating mutagenesis. *Nature* 527, 192-197 (2015).
6. Smith, E. et al. Strict in vivo specificity of the Bcl11a erythroid enhancer. *Blood* 128, 2338-2342 (2016).
7. Vierstra, J. et al. Functional footprinting of regulatory DNA. *Nat. Methods* 12, 927-30 (2015).
8. Chang, K.-H. et al. Long-Term Engraftment and Fetal Globin Induction upon BCL11A Gene Editing in Bone-Marrow-Derived CD34+ Hematopoietic Stem and Progenitor Cells. *Mol. Ther.—Methods Clin. Dev.* 4, 137-148 (2017).
9. Jinek, M. et al. A Programmable Dual-RNA-Guided DNA Endonuclease in Adaptive Bacterial Immunity. *Science* 337, 816-821 (2012).
10. Mali, P. et al. RNA-Guided Human Genome Engineering via Cas9. *Science* 339, 823-6 (2013).
11. Cong, L. et al. Multiplex Genome Engineering Using CRISPR/Cas Systems. *Science* 339, 819-23 (2013).
12. Kleinstiver, B. P. et al. High-fidelity CRISPR-Cas9 nucleases with no detectable genome-wide off-target effects. *Nature* (2016). doi:10.1038/nature16526

13. Kleinstiver, B. P. et al. Engineered CRISPR-Cas9 nucleases with altered PAM specificities. *Nature* 523, 481-5 (2015).
14. Slaymaker, I. M. et al. Rationally engineered Cas9 nucleases with improved specificity. *Science* (2015).
15. Chen, J. S. et al. Enhanced proofreading governs CRISPR-Cas9 targeting accuracy. *Nature* 550, 407-410 (2017).
16. DeWitt, M. A. et al. Selection-free genome editing of the sickle mutation in human adult hematopoietic stem/progenitor cells. *Sci. Transl. Med.* 8, (2016).
17. Dever, D. P. et al. CRISPR/Cas9 β-globin gene targeting in human haematopoietic stem cells. *Nature* 539, 384-389 (2016).
18. Genovese, P. et al. Targeted genome editing in human repopulating haematopoietic stem cells. *Nature* 510, 235-40 (2014).
19. Wang, J. et al. Homology-driven genome editing in hematopoietic stem and progenitor cells using ZFN mRNA and AAV6 donors. *Nat. Biotechnol.* (2015). doi: 10.1038/nbt.3408
20. Kim, S., Kim, D., Cho, S. W., Kim, J. & Kim, J. Highly efficient RNA-guided genome editing in human cells via delivery of purified Cas9 ribonucleoproteins. *Genome Res.* 24, 1012-1019 (2014).
21. Lin, S., Staahl, B., Alla, R. K. & Doudna, J. a. Enhanced homology-directed human genome engineering by controlled timing of CRISPR/Cas9 delivery. *Elife* 3, 1-13 (2014).
22. Hendel, A. et al. Chemically modified guide RNAs enhance CRISPR-Cas genome editing in human primary cells. *Nat. Biotechnol.* (2015). doi:10.1038/nbt.3290
23. Tsai, S.-F. et al. Cloning of cDNA for the major DNA-binding protein of the erythroid lineage through expression in mammalian cells. *Nature* 339, 446-451 (1989).
24. McIntosh, B. E. et al. Nonirradiated NOD,B6.SCID Il2r??-/- kitW41/W41 (NBSGW) mice support multilineage engraftment of human hematopoietic cells. *Stem Cell Reports* 4, 171-180 (2015).
25. Lin, S., Staahl, B., Alla, R. K. & Doudna, J. a. Enhanced homology-directed human genome engineering by controlled timing of CRISPR/Cas9 delivery. *Elife* 3, 1-13 (2014).
26. Tsai, S. Q. et al. CIRCLE-seq: a highly sensitive in vitro screen for genome-wide CRISPR-Cas9 nuclease off-targets. *Nat. Methods* (2017). doi:10.1038/nmeth.4278
27. Kluk, M. J. et al. Validation and Implementation of a Custom Next-Generation Sequencing Clinical Assay for Hematologic Malignancies. *J. Mol. Diagnostics* 18, 507-515 (2016).
28. Fitzhugh, C. D., Hsieh, M. M., Bolan, C. D., Saenz, C. & Tisdale, J. F. Granulocyte colony-stimulating factor (G-CSF) administration in individuals with sickle cell disease: time for a moratorium? *Cytotherapy* 11, 464-471 (2009).
29. Lagresle-Peyrou, C. et al. Plerixafor enables the safe, rapid, efficient mobilization of haematopoietic stem cells in sickle cell disease patients after exchange transfusion. *Haematologica* haematol.2017.184788 (2018). doi: 10.3324/haematol.2017.184788
30. Boulad, F. et al. Safety and efficacy of plerixafor dose escalation for the mobilization of CD34+ hematopoietic progenitor cells in patients with sickle cell disease: interim results. *Haematologica* Epub ahead, (2018).
31. Tisdale, J. F. et al. Successful Plerixafor-Mediated Mobilization, Apheresis, and Lentiviral Vector Transduction of Hematopoietic Stem Cells in Patients with Severe Sickle Cell Disease. *Blood* 130, 990 LP-990 (2017).
32. Esrick, E. B. et al. Successful hematopoietic stem cell mobilization and apheresis collection using plerixafor alone in sickle cell patients. *In submission*. (2018).
33. Bae, S., Kweon, J., Kim, H. S. & Kim, J.-S. Microhomology-based choice of Cas9 nuclease target sites. *Nat. Methods* 11, 705-706 (2014).
34. Genovese, P. et al. Targeted genome editing in human repopulating haematopoietic stem cells. *Nature* 510, 235-40 (2014).
35. Hoban, M. D. et al. Correction of the sickle-cell disease mutation in human hematopoietic stem/progenitor cells. *Blood* 125, 2597-604 (2015).
36. Ravin, S. S. De et al. CRISPR-Cas9 gene repair of hematopoietic stem cells from patients with X-linked chronic granulomatous disease. *Sci. Transl. Med.* 9, 1-10 (2017).
37. Mohrin, M. et al. Hematopoietic stem cell quiescence promotes error-prone DNA repair and mutagenesis. *Cell Stem Cell* 7, 174-185 (2010).
38. Truong, L. N. et al. Microhomology-mediated End Joining and Homologous Recombination share the initial end resection step to repair DNA double-strand breaks in mammalian cells. *Proc. Natl. Acad. Sci.* 110, 7720-7725 (2013).
39. Sfeir, A. & Symington, L. S. Microhomology-Mediated End Joining: A Back-up Survival Mechanism or Dedicated Pathway? *Trends Biochem. Sci.* 40, 701-714 (2015).
40. Traxler, E. A. et al. A genome-editing strategy to treat β-hemoglobinopathies that recapitulates a mutation associated with a benign genetic condition. *Nat. Med.* (2016). doi:10.1038/nm.4170
41. Liu, N. et al. Direct Promoter Repression by BCL11A Controls the Fetal to Adult Hemoglobin Switch Article Direct Promoter Repression by BCL11A Controls the Fetal to Adult Hemoglobin Switch. *Cell* 1-13 (2018). doi:10.1016/j.cell.2018.03.016
42. Martyn, A. G. E., Wienert, B., Yang, L., Shah, M. & Norton, L. J. Title: Natural regulatory mutations elevate fetal globin via disruption of BCL11A or ZBTB7A binding. *Nat. Genet.* (2018). doi:10.1038/s41588-018-0085-0

Table 1 show sgRNA sequences that target the BCL11A enhancer DHS +62, +58, and +55 functional regions, and also the BCL11A exon 2. These sgRNA sequences produced HbF enrichment.

| SEQ ID NO: | Identifer | sgRNA Sequence | PAM | Targeted Site | Coordinate Relative to TSS | Chr2 Genomic Coordinate (hg19) |
|---|---|---|---|---|---|---|
| 1 | BCL_00108_H_D55 | TCTGAGGAGCTAGAGACTTG | NGG | DHS_55 | 54701 | 60725932 |
| 2 | BCL_00096_H_D55 | AGCAAATAGGCTTAGTGTGC | NGG | DHS_55 | 54874 | 60725759 |

-continued

| SEQ ID NO: | Identifer | sgRNA Sequence | PAM | Targeted Site | Coordinate Relative to TSS | Chr2 Genomic Coordinate (hg19) |
|---|---|---|---|---|---|---|
| 3 | BCL_01427_H_D55 | GGCTAAATAATGAATGTCCC | NGG RC | DHS_55 | 54944 | 60725689 |
| 4 | BCL_00093_H_D55 | TCCCTTCCTAGAATTGGCCT | NGG | DHS_55 | 54950 | 60725683 |
| 5 | BCL_00092_H_D55 | TTCCCTTCCTAGAATTGGCC | NGG | DHS_55 | 54951 | 60725682 |
| 6 | BCL_01428_H_D55 | GAATGTCCCAGGCCAATTCT | NGG RC | DHS_55 | 54955 | 60725678 |
| 7 | BCL_00091_H_D55 | CCCACTTCCCTTCCTAGAAT | NGG | DHS_55 | 54956 | 60725677 |
| 8 | BCL_00090_H_D55 | CCTGGTACCAGGAAGGCAAT | NGG | DHS_55 | 54989 | 60725644 |
| 9 | BCL_00089_H_D55 | TCCTGGTACCAGGAAGGCAA | NGG | DHS_55 | 54990 | 60725643 |
| 10 | BCL_00088_H_D55 | GCATCATCCTGGTACCAGGA | NGG | DHS_55 | 54996 | 60725637 |
| 11 | BCL_00087_H_D55 | CATTGCATCATCCTGGTACC | NGG | DHS_55 | 55000 | 60725633 |
| 12 | BCL_00086_H_D55 | CTCCAAGCATTGCATCATCC | NGG | DHS_55 | 55007 | 60725626 |
| 13 | BCL_01438_H_D55 | TACCAGGATGATGCAATGCT | NGG RC | DHS_55 | 55016 | 60725617 |
| 14 | BCL_00085_H_D55 | GGGTGTGCCCTGAGAAGGTG | NGG | DHS_55 | 55040 | 60725593 |
| 15 | BCL_00084_H_D55 | AGGGTGTGCCCTGAGAAGGT | NGG | DHS_55 | 55041 | 60725592 |
| 16 | BCL_00082_H_D55 | TCACAGGGTGTGCCCTGAGA | NGG | DHS_55 | 55045 | 60725588 |
| 17 | BCL_01443_H_D55 | GGCACACCCTGTGATCTTGT | NGG RC | DHS_55 | 55065 | 60725568 |
| 18 | BCL_00073_H_D55 | AGCACACAAGATGCACACCC | NGG | DHS_55 | 55096 | 60725537 |
| 19 | BCL_01448_H_D55 | TGTGCTTGGTCGGCACTGAT | NGG RC | DHS_55 | 55124 | 60725509 |
| 20 | BCL_01449_H_D55 | GTGCTTGGTCGGCACTGATA | NGG RC | DHS_55 | 55125 | 60725508 |
| 21 | BCL_01450_H_D55 | TGCTTGGTCGGCACTGATAG | NGG RC | DHS_55 | 55126 | 60725507 |
| 22 | BCL_01454_H_D55 | GGGTCGCGGTAGGGAGTTGT | NGG RC | DHS_55 | 55146 | 60725487 |
| 23 | BCL_00065_H_D55 | GCCAACAGTGATAACCAGCA | NGG | DHS_55 | 55235 | 60725398 |
| 24 | BCL_00064_H_D55 | TGCCAACAGTGATAACCAGC | NGG | DHS_55 | 55236 | 60725397 |
| 25 | BCL_01461_H_D55 | GCCCTGCTGGTTATCACTGT | NGG RC | DHS_55 | 55245 | 60725388 |
| 26 | BCL_00062_H_D55 | AGCAGCCCTGGGCACAGAAG | NGG | DHS_55 | 55272 | 60725361 |
| 27 | BCL_00058_H_D55 | CCTCTATGTAGACGGGTGTG | NGG | DHS_55 | 55311 | 60725322 |
| 28 | BCL_00057_H_D55 | GGAAGGGCCTCTATGTAGAC | NGG | DHS_55 | 55318 | 60725315 |
| 29 | BCL_00051_H_D55 | GGAGGTGTGGAGGGATAAC | NGG | DHS_55 | 55356 | 60725277 |
| 30 | BCL_00031_H_D55 | CTGGCAGACCCTCAAGAGCA | NGG | DHS_55 | 55444 | 60725189 |
| 31 | BCL_00027_H_D55 | CCCATGGAGGTGGGAGATG | NGG | DHS_55 | 55474 | 60725159 |
| 32 | BCL_01483_H_D55 | GTCATCCTCGGCCAATGAAG | NGG RC | DHS_55 | 55559 | 60725074 |
| 33 | BCL_00012_H_D55 | AAGTGAGCCAGGTGATAGAA | NGG | DHS_55 | 55585 | 60725048 |
| 34 | BCL_00008_H_D55 | TGAAACCAAGCTTCCTCTGC | NGG | DHS_55 | 55612 | 60725021 |

-continued

| SEQ ID NO: | Identifer | sgRNA Sequence | PAM | Targeted Site | Coordinate Relative to TSS | Chr2 Genomic Coordinate (hg19) |
|---|---|---|---|---|---|---|
| 35 | BCL_01495_H_D55 | AGGGAGAAATGAGACAAAAG | NGG RC | DHS_55 | 55700 | 60724933 |
| 36 | BCL_01497_H_D55 | AAGAGGCCACTGAGTCCTTT | NGG RC | DHS_55 | 55717 | 60724916 |
| 37 | BCL_01615_H_D58 | ACTCTTAGACATAACACACC | NGG RC | DHS_58 | 58176 | 60722457 |
| 38 | BCL_01616_H_D58 | CTCTTAGACATAACACACCA | NGG RC | DHS_58 | 58177 | 60722456 |
| 39 | BCL_01617_H_D58 | CTAACAGTTGCTTTTATCAC | NGG RC | DHS_58 | 58232 | 60722401 |
| 40 | BCL_01618_H_D58 | TTGCTTTTATCACAGGCTCC | NGG RC | DHS_58 | 58239 | 60722394 |
| 41 | BCL_01619_H_D58 | TTTTATCACAGGCTCCAGGA | NGG RC | DHS_58 | 58243 | 60722390 |
| 42 | BCL_01620_H_D58 | TTTATCACAGGCTCCAGGAA | NGG RC | DHS_58 | 58244 | 60722389 |
| 43 | BCL_00187_H_D58 | ATCAGAGGCCAAACCCTTCC | NGG | DHS_58 | 58246 | 60722387 |
| 44 | BCL_00188_H_D58 | CTTCAAAGTTGTATTGACCC | NGG | DHS_58 | 58183 | 60722450 |
| 45 | BCL_01621_H_D58 | CACAGGCTCCAGGAAGGGTT | NGG RC | DHS_58 | 58249 | 60722384 |
| 46 | BCL_00186_H_D58 | CACGCCCCCACCCTAATCAG | NGG | DHS_58 | 58261 | 60722372 |
| 47 | BCL_01622_H_D58 | GAAGGGTTTGGCCTCTGATT | NGG RC | DHS_58 | 58261 | 60722372 |
| 48 | BCL_01623_H_D58 | AAGGGTTTGGCCTCTGATTA | NGG RC | DHS_58 | 58262 | 60722371 |
| 49 | BCL_01624_H_D58 | GGTTTGGCCTCTGATTAGGG | NGG RC | DHS_58 | 58265 | 60722368 |
| 50 | BCL_01625_H_D58 | GTTTGGCCTCTGATTAGGGT | NGG RC | DHS_58 | 58266 | 60722367 |
| 51 | BCL_01626_H_D58 | TTTGGCCTCTGATTAGGGTG | NGG RC | DHS_58 | 58267 | 60722366 |
| 52 | BCL_01627_H_D58 | TTGGCCTCTGATTAGGGTGG | NGG RC | DHS_58 | 58268 | 60722365 |
| 53 | BCL_01629_H_D58 | TCTGATTAGGGTGGGGCGT | NGG RC | DHS_58 | 58274 | 60722359 |
| 54 | BCL_01631_H_D58 | ATTAGGGTGGGGCGTGGGT | NGG RC | DHS_58 | 58278 | 60722355 |
| 55 | BCL_01632_H_D58 | TTAGGGTGGGGCGTGGGTG | NGG RC | DHS_58 | 58279 | 60722354 |
| 56 | BCL_01634_H_D58 | TGGGTGGGTAGAAGAGGAC | NGG RC | DHS_58 | 58293 | 60722340 |
| 57 | BCL_00185_H_D58 | GCAAACGGCCACCGATGGAG | NGG | DHS_58 | 58309 | 60722324 |
| 58 | BCL_00184_H_D58 | CCTGGGCAAACGGCCACCGA | NGG | DHS_58 | 58314 | 60722319 |
| 59 | BCL_00183_H_D58 | AAGAGGCCCCCTGGGCAAA | NGG | DHS_58 | 58324 | 60722309 |
| 60 | BCL_01637_H_D58 | CCATCGGTGGCCGTTTGCCC | NGG RC | DHS_58 | 58325 | 60722308 |

-continued

| SEQ ID NO: | Identifer | sgRNA Sequence | PAM | Targeted Site | Coordinate Relative to TSS | Chr2 Genomic Coordinate (hg19) |
|---|---|---|---|---|---|---|
| 61 | BCL_01638_H_D58 | CATCGGTGGCCGTTTGCCCA | NGG RC | DHS_58 | 58326 | 60722307 |
| 62 | BCL_01639_H_D58 | ATCGGTGGCCGTTTGCCCAG | NGG RC | DHS_58 | 58327 | 60722306 |
| 63 | BCL_01640_H_D58 | TCGGTGGCCGTTTGCCCAGG | NGG RC | DHS_58 | 58328 | 60722305 |
| 64 | BCL_01641_H_D58 | CGGTGGCCGTTTGCCCAGGG | NGG RC | DHS_58 | 58329 | 60722304 |
| 65 | BCL_00182_H_D58 | CTTCCGAAAGAGGCCCCCCT | NGG | DHS_58 | 58331 | 60722302 |
| 66 | BCL_00181_H_D58 | CCTTCCGAAAGAGGCCCCCC | NGG | DHS_58 | 58332 | 60722301 |
| 67 | BCL_00160_H_D58 | TCAGGGGAGGCAAGTCAGT | NGG | DHS_58 | 58575 | 60722058 |
| 68 | BCL_00154_H_D58 | AGGGAAAGGGAGAGGAAAA | NGG | DHS_58 | 58612 | 60722021 |
| 69 | BCL_01665_H_D58 | TGTAACTAATAAATACCAGG | NGG RC | DHS_58 | 58706 | 60721927 |
| 70 | BCL_01669_H_D58 | CCAGCTGAAGAAAGAACATT | NGG RC | DHS_58 | 58870 | 60721763 |
| 71 | BCL_00135_H_D58 | CCATCTCCCTAATCTCCAAT | NGG | DHS_58 | 58958 | 60721675 |
| 72 | BCL_00131_H_D58 | TGGGGAGAGAAGAGTGGAAA | NGG | DHS_58 | 59030 | 60721603 |
| 73 | BCL_00130_H_D58 | GGAGTATGGGAGAGAAGAG | NGG | DHS_58 | 59036 | 60721597 |
| 74 | BCL_01684_H_D58 | ACAACCTCCTTGTTTACAGA | NGG RC | DHS_58 | 59129 | 60721504 |
| 75 | BCL_01788_H_D62 | GAGATTTACTCTTGTTGCCC | NGG RC | DHS_62 | 61848 | 60718785 |
| 76 | BCL_01790_H_D62 | TTGCCCGGGCTGGAATGCAA | NGG RC | DHS_62 | 61862 | 60718771 |
| 77 | BCL_00245_H_D62 | GGAGATCGCTTGAACCTGGG | NGG | DHS_62 | 61901 | 60718732 |
| 78 | BCL_00241_H_D62 | CTCAGCTACTCGGGAGGCTG | NGG | DHS_62 | 61926 | 60718707 |
| 79 | BCL_00240_H_D62 | TGTAATCTCAGCTACTCGGG | NGG | DHS_62 | 61932 | 60718701 |
| 80 | BCL_00239_H_D62 | GCCTGTAATCTCAGCTACTC | NGG | DHS_62 | 61935 | 60718698 |
| 81 | BCL_00238_H_D62 | TGCCTGTAATCTCAGCTACT | NGG | DHS_62 | 61936 | 60718697 |
| 82 | BCL_01794_H_D62 | CAGGCATGTATTACCATGCC | NGG RC | DHS_62 | 61964 | 60718669 |
| 83 | BCL_00233_H_D62 | CAGGAGGATCACCTGAGGTC | NGG | DHS_62 | 62037 | 60718596 |
| 84 | BCL_01799_H_D62 | CTCAGGTGATCCTCCTGCCC | NGG RC | DHS_62 | 62054 | 60718579 |
| 85 | BCL_00229_H_D62 | CCCAGCACTTTGGGAGGCCG | NGG | DHS_62 | 62060 | 60718573 |
| 86 | BCL_00228_H_D62 | TCCCAGCACTTTGGGAGGCC | NGG | DHS_62 | 62061 | 60718572 |
| 87 | BCL_00227_H_D62 | ATCCCAGCACTTTGGGAGGC | NGG | DHS_62 | 62062 | 60718571 |
| 88 | BCL_00225_H_D62 | ACCTGTAATCCCAGCACTTT | NGG | DHS_62 | 62069 | 60718564 |
| 89 | BCL_01800_H_D62 | GCCCCGGCCTCCCAAAGTGC | NGG RC | DHS_62 | 62070 | 60718563 |
| 90 | BCL_01801_H_D62 | CCCCGGCCTCCCAAAGTGCT | NGG RC | DHS_62 | 62071 | 60718562 |
| 91 | BCL_01825_H_D62 | ATTTGCTCTTCTCCAGGGTG | NGG RC | DHS_62 | 62469 | 60718164 |

| SEQ ID NO: | Identifer | sgRNA Sequence | PAM | Targeted Site | Coordinate Relative to TSS | Chr2 Genomic Coordinate (hg19) |
|---|---|---|---|---|---|---|
| 92 | BCL_00210_H_D62 | TAAACAGCCACCCCACACCC | NGG | DHS_62 | 62470 | 60718163 |
| 93 | BCL_01826_H_D62 | TTTGCTCTTCTCCAGGGTGT | NGG RC | DHS_62 | 62470 | 60718163 |
| 94 | BCL_01828_H_D62 | CTCTTCTCCAGGGTGTGGGG | NGG RC | DHS_62 | 62474 | 60718159 |
| 95 | BCL_01829_H_D62 | TGTGGGGTGGCTGTTTAAAG | NGG RC | DHS_62 | 62487 | 60718146 |
| 96 | BCL_01831_H_D62 | GGGTGGCTGTTTAAAGAGGG | NGG RC | DHS_62 | 62491 | 60718142 |
| 97 | BCL_01833_H_D62 | AGTTCAAGTAGATATCAGAA | NGG RC | DHS_62 | 62580 | 60718053 |
| 98 | BCL_01834_H_D62 | TATCAGAAGGGAACTGTTTG | NGG RC | DHS_62 | 62592 | 60718041 |
| 99 | BCL_02015_H_exon2 | AAGAATGGCTTCAAGAGGCT | NGG RC | exon2 | 7218 | 60773415 |
| 100 | BCL_02014_H_exon2 | TCTGTAAGAATGGCTTCAAG | NGG RC | exon2 | 7223 | 60773410 |
| 101 | BCL_00248_H_exon2 | ACAGATGATGAACCAGACCA | NGG | exon2 | 7224 | 60773409 |
| 102 | BCL_00249_H_exon2 | TGAACCAGACCACGGCCCGT | NGG | exon2 | 7232 | 60773401 |
| 103 | BCL_00250_H_exon2 | GAACCAGACCACGGCCCGTT | NGG | exon2 | 7233 | 60773400 |
| 104 | BCL_00251_H_exon2 | GGCCCGTTGGGAGCTCCAGA | NGG | exon2 | 7245 | 60773388 |
| 105 | BCL_00252_H_exon2 | GCCCGTTGGGAGCTCCAGAA | NGG | exon2 | 7246 | 60773387 |
| 106 | BCL_00253_H_exon2 | CCCGTTGGGAGCTCCAGAAG | NGG | exon2 | 7247 | 60773386 |
| 107 | BCL_02011_H_exon2 | CTGGAGCTCCCAACGGGCCG | NGG RC | exon2 | 7258 | 60773375 |
| 108 | BCL_02010_H_exon2 | CCCCTTCTGGAGCTCCCAAC | NGG RC | exon2 | 7264 | 60773369 |
| 109 | BCL_02009_H_exon2 | TCCCCTTCTGGAGCTCCCAA | NGG RC | exon2 | 7265 | 60773368 |
| 110 | BCL_00254_H_exon2 | GATCATGACCTCCTCACCTG | NGG | exon2 | 7269 | 60773364 |
| 111 | BCL_00255_H_exon2 | ATCATGACCTCCTCACCTGT | NGG | exon2 | 7270 | 60773363 |
| 112 | BCL_02008_H_exon2 | AGGAGGTCATGATCCCCTTC | NGG RC | exon2 | 7277 | 60773356 |
| 113 | BCL_02007_H_exon2 | GCACTGCCCACAGGTGAGG | NGG RC | exon2 | 7294 | 60773339 |
| 114 | BCL_00256_H_exon2 | GTGCCAGATGAACTTCCCAT | NGG | exon2 | 7295 | 60773338 |
| 115 | BCL_00257_H_exon2 | TGCCAGATGAACTTCCCATT | NGG | exon2 | 7296 | 60773337 |
| 116 | BCL_00258_H_exon2 | GCCAGATGAACTTCCCATTG | NGG | exon2 | 7297 | 60773336 |
| 117 | BCL_02006_H_exon2 | TCTGGCACTGCCCACAGGTG | NGG RC | exon2 | 7297 | 60773336 |
| 118 | BCL_00259_H_exon2 | CCAGATGAACTTCCCATTGG | NGG | exon2 | 7298 | 60773335 |
| 119 | BCL_02005_H_exon2 | GTTCATCTGGCACTGCCCAC | NGG RC | exon2 | 7302 | 60773331 |
| 120 | BCL_02004_H_exon2 | CCCCCAATGGGAAGTTCATC | NGG RC | exon2 | 7315 | 60773318 |

| SEQ ID NO: | Identifer | sgRNA Sequence | PAM | Targeted Site | Coordinate Relative to TSS | Chr2 Genomic Coordinate (hg19) |
|---|---|---|---|---|---|---|
| 121 | BCL_02003_H_exon2 | AAATAAGAATGTCCCCCAAT | NGG RC | exon2 | 7327 | 60773306 |
| 122 | BCL_02002_H_exon2 | AAAATAAGAATGTCCCCCAA | NGG RC | exon2 | 7328 | 60773305 |
| 123 | BCL_00261_H_exon2 | CACAAACGGAAACAATGCAA | NGG | exon2 | 7341 | 60773292 |
| 124 | BCL_00262_H_exon2 | CCTCTGCTTAGAAAAAGCTG | NGG | exon2 | 7367 | 60773266 |
| 125 | BCL_02001_H_exon2 | CCACAGCTTTTTCTAAGCAG | NGG RC | exon2 | 7384 | 60773249 |
| 126 | BCL_02000_H_exon2 | TCGATTGGTGAAGGGGAAGG | NGG RC | exon2 | 7412 | 60773221 |
| 127 | BCL_01999_H_exon2 | ATCTCGATTGGTGAAGGGGA | NGG RC | exon2 | 7415 | 60773218 |
| 128 | BCL_01998_H_exon2 | TTTCATCTCGATTGGTGAAG | NGG RC | exon2 | 7419 | 60773214 |
| 129 | BCL_00263_H_exon2 | GAAAAAAGCATCCAATCCCG | NGG | exon2 | 7421 | 60773212 |
| 130 | BCL_00264_H_exon2 | AAAAGCATCCAATCCCGTGG | NGG | exon2 | 7424 | 60773209 |
| 131 | BCL_00265_H_exon2 | GCATCCAATCCCGTGGAGGT | NGG | exon2 | 7428 | 60773205 |
| 132 | BCL_00266_H_exon2 | TCCCGTGGAGGTTGGCATCC | NGG | exon2 | 7436 | 60773197 |
| 133 | BCL_00267_H_exon2 | TGGCATCCAGGTCACGCCAG | NGG | exon2 | 7448 | 60773185 |
| 134 | BCL_01994_H_exon2 | GATGCCAACCTCCACGGGAT | NGG RC | exon2 | 7449 | 60773184 |
| 135 | BCL_01993_H_exon2 | ACCTGGATGCCAACCTCCAC | NGG RC | exon2 | 7454 | 60773179 |
| 136 | BCL_01992_H_exon2 | GACCTGGATGCCAACCTCCA | NGG RC | exon2 | 7455 | 60773178 |
| 137 | BCL_01991_H_exon2 | CGTCATCCTCTGGCGTGACC | NGG RC | exon2 | 7471 | 60773162 |
| 138 | BCL_01990_H_exon2 | GATAAACAATCGTCATCCTC | NGG RC | exon2 | 7481 | 60773152 |
| 139 | BCL_01989_H_exon2 | CTGCTATGTGTTCCTGTTTG | NGG RC | exon2 | 7525 | 60773108 |

Table 2 show subset of sgRNA sequences from Table 1 that target DHS 58+ functional region

| Seq ID No | sgRNA | 20-nt protospacer sequence |
|---|---|---|
| 37 | 1615 | ACTCTTAGACATAACACACC |
| 38 | 1616 | CTCTTAGACATAACACACCA |
| 39 | 1617 | CTAACAGTTGCTTTTATCAC |
| 40 | 1618 | TTGCTTTTATCACAGGCTCC |
| 41 | 1619 | TTTTATCACAGGCTCCAGGA |
| 42 | 1620 | TTTATCACAGGCTCCAGGAA |

-continued

| Seq ID No | sgRNA | 20-nt protospacer sequence |
|---|---|---|
| 43 | 0187 | ATCAGAGGCCAAACCCTTCC |
| 44 | 0188 | CTTCAAAGTTGTATTGACCC |
| 45 | 1621 | CACAGGCTCCAGGAAGGGTT |
| 46 | 0186 | CACGCCCCACCCTAATCAG |
| 47 | 1622 | GAAGGGTTTGGCCTCTGATT |
| 48 | 1623 | AAGGGTTTGGCCTCTGATTA |
| 50 | 1625 | GTTTGGCCTCTGATTAGGGT |
| 51 | 1626 | TTTGGCCTCTGATTAGGGTG |
| 52 | 1627 | TTGGCCTCTGATTAGGGTGG |
| 53 | 1629 | TCTGATTAGGGTGGGGGCGT |
| 54 | 1631 | ATTAGGGTGGGGGCGTGGGT |
| 55 | 1632 | TTAGGGTGGGGCGTGGGTG |
| 56 | 1634 | TGGGTGGGGTAGAAGAGGAC |

-continued

| Seq ID No | sgRNA | 20-nt protospacer sequence |
|---|---|---|
| 57 | 0185 | GCAAACGGCCACCGATGGAG |
| 62 | 1639 | ATCGGTGGCCGTTTGCCCAG |

Table 3 show HBB genotype of β-thalassemia patients.

| Simplified genotype | Genotype |
|---|---|
| β⁰β⁰ | Homozygous codon 44 (-C) TCC > TC- frameshift β⁰ thalassemia mutation |
| β⁺β⁰#1 | IVSII-745 C > G; codon 44 (-C) TCC > TC- |
| β⁺β⁰#2 | IVS I-110 G > A; codon 39 CAG > TAG or Gln39Term |
| β⁺β⁺ | Homozygous IVS-I-5 G > C |
| (ᴬγδβ)⁰β⁰ | Large Chinese (ᴬγδβ)⁰ deletion; codon 41/42 (--CTTT) |
| βᴱβ⁰#1 | Codon 26 (G > A; GAG > AAG; Glu > Lys) hemoglobin E; codon 71/72 +A frameshift β⁰ thalassemia mutation |
| βᴱβ⁰#2 | Codon 26 (G > A; GAG > AAG; Glu > Lys) hemoglobin E; p.Ser72fsX2 |

Table 4 show primers used in the Example section.

| Primers fA3:B19s for in vitro transcription of sgRNAs. Protospacer sequence in red. | |
|---|---|
| IVT-1615-F | TAATACGACTCACTATAGGGACTCTTAGACATAACACACCGTTTTAGAGCTAGAA (SEQ ID NO: 140) |
| IVT-1616-F | TAATACGACTCACTATAGGGCTCTTAGACATAACACACCAGTTTTAGAGCTAGAA (SEQ ID NO: 141) |
| IVT-1617-F | TAATACGACTCACTATAGGGTACAGAGCCCCAGTCCTGGAGTTTTAGAGCTAGAA (SEQ ID NO: 142) |
| IVT-1618-F | TAATACGACTCACTATAGGGTTGCTTTTATCACAGGCTCCGTTTTAGAGCTAGAA (SEQ ID NO: 143) |
| IVT-1619-F | TAATACGACTCACTATAGGGTTTTATCACAGGCTCCAGGAGTTTTAGAGCTAGAA (SEQ ID NO: 144) |
| IVT-1620-F | TAATACGACTCACTATAGGGTTTATCACAGGCTCCAGGAAGTTTTAGAGCTAGAA (SEQ ID NO: 145) |
| IVT-0186-F | TAATACGACTCACTATAGGGCACGCCCCACCCTAATCAGGTTTTAGAGCTAGAA (SEQ ID NO: 146) |
| IVT-0187-F | TAATACGACTCACTATAGGGATCAGAGGCCAAACCCTTCCGTTTTAGAGCTAGAA (SEQ ID NO: 147) |
| IVT-1621-F | TAATACGACTCACTATAGGGCACAGGCTCCAGGAAGGGTTGTTTTAGAGCTAGAA (SEQ ID NO: 148) |
| IVT-1622-F | TAATACGACTCACTATAGGGGAAGGGTTTGGCCTCTGATTGTTTTAGAGCTAGAA (SEQ ID NO: 149) |
| IVT-1623-F | TAATACGACTCACTATAGGGAAGGGTTTGGCCTCTGATTAGTTTTAGAGCTAGAA (SEQ ID NO: 150) |
| IVT-1625-F | TAATACGACTCACTATAGGGGTTTGGCCTCTGATTAGGGTGTTTTAGAGCTAGAA (SEQ ID NO: 151) |

| | Primers fA3:B19s for in vitro transcription of sgRNAs. |
|---|---|
| | Protospacer sequence in red. |
| IVT-1626-F | TAATACGACTCACTATAGGGTTTGGCCTCTGATTAGGGTGGTTTTAGAGCTAGAA (SEQ ID NO: 152) |
| IVT-1627-F | TAATACGACTCACTATAGGGTTGGCCTCTGATTAGGGTGGGTTTTAGAGCTAGAA (SEQ ID NO: 153) |
| IVT-1629-F | TAATACGACTCACTATAGGGTCTGATTAGGGTGGGGGCGTGTTTTAGAGCTAGAA (SEQ ID NO: 154) |
| IVT-1631-F | TAATACGACTCACTATAGGGATTAGGGTGGGGGCGTGGGTGTTTTAGAGCTAGAA (SEQ ID NO: 155) |
| IVT-1632-F | TAATACGACTCACTATAGGGTTAGGGTGGGGGCGTGGGTGGTTTTAGAGCTAGAA (SEQ ID NO: 156) |
| IVT-1634-F | TAATACGACTCACTATAGGGTGGGTGGGGTAGAAGAGGACGTTTTAGAGCTAGAA (SEQ ID NO: 157) |
| IVT-0185-F | TAATACGACTCACTATAGGGGCAAACGGCCACCGATGGAGGTTTTAGAGCTAGAA (SEQ ID NO: 158) |
| IVT-1639-F | TAATACGACTCACTATAGGGATCGGTGGCCGTTTGCCCAGGTTTTAGAGCTAGAA (SEQ ID NO: 159) |
| IVT-AAVS1-F | TAATACGACTCACTATAGGGCTCCCTCCCAGGATCCTCTCGTTTTAGAGCTAGAA (SEQ ID NO: 160) |
| IVT-sg-R | AAAAAAGCACCGACTCGGTG (SEQ ID NO: 161) |
| | Primers for TIDE analysis. |
| 58 enh-1F | GAGAGTGCAGACAGGGGAAG (SEQ ID NO: 161) |
| 58 enh-1R | ACCCTGGAAAACAGCCTGAC (SEQ ID NO: 162) |
| 58 enh-2F | CACACGGCATGGCATACAAA (SEQ ID NO: 163) |
| 58 enh-2R | CACCCTGGAAAACAGCCTGA (SEQ ID NO: 164) |
| AAVS1-1F | CACCTTATATTCCCAGGGCCG (SEQ ID NO: 165) |
| AAVS1-1R | CCTAGGACGCACCATTCTCAC (SEQ ID NO: 166) |
| AAVS1-2F | ATTGGGTCTAACCCCCACCT (SEQ ID NO: 167) |
| AAVS1-2R | TCAGTGAAACGCACCAGACA (SEQ ID NO: 168) |
| Primers for RT-qPCR. | |
| BCL11A_RT_e1/e2_114F | AACCCCAGCACTTAAGCAAA (SEQ ID NO: 169) |
| BCL11A_RT_e1/e2_114R | GGAGGTCATGATCCCCTTCT (SEQ ID NO: 170) |
| HBA_RT_F | GCCCTGGAGAGGATGTTC (SEQ ID NO: 171) |
| HBA_RT_R | TTCTTGCCGTGGCCCTTA (SEQ ID NO: 172) |
| HBB_RT_F | CAGTGCAGGCTGCCTATC (SEQ ID NO: 173) |
| HBB_RT_R | ATACTTGTGGGCCAGGGCAT (SEQ ID NO: 174) |
| HBG_RT_F | TGGGTCATTTCACAGAGGAG (SEQ ID NO: 175) |
| HBG_RT_R | CATCTTCCACATTCACCTTGC (SEQ ID NO: 176) |
| GAPDH_RT_125_F | ACCCAGAAGACTGTGGATGG (SEQ ID NO: 177) |
| GAPDH_RT_125_R | TTCAGCTCAGGGATGACCTT (SEQ ID NO: 178) |
| hCAT_RT90_e8_F | CTTCGACCCAAGCAACATGC (SEQ ID NO: 179) |
| hCAT_RT90_e8_R | CGGTGAGTGTCAGGATAGGC (SEQ ID NO: 180) |

-continued

| Primers fA3:B19s for in vitro transcription of sgRNAs. |
| --- |
| Protospacer sequence in red. |

| Primers for deep sequencing | |
| --- | --- |
| 58 enh_seq_1F | GCCAGAAAAGAGATATGGCATC (SEQ ID NO: 181) |
| 58 enh_seq_1R | AGAGAGCCTTCCGAAAGAGG (SEQ ID NO: 182) |
| OT1_seq_F | GTTCTCTCTTCTTCCTGACAGTG (SEQ ID NO: 183) |
| OT1_seq_R | GAGGTCCCTATGAAAAGATGGCT (SEQ ID NO: 184) |
| OT2_seq_F | GTTGAATGCCAAGTGCCCAA (SEQ ID NO: 185) |
| OT2_seq_R | GGTCTCAGTTCAGCCCCTTC (SEQ ID NO: 186) |
| OT3_seq_F | TGAACAATATTGCCTTTTGTGCT (SEQ ID NO: 187) |
| OT3_seq_R | ATGCTGCTGTAAGGCACTGT (SEQ ID NO: 188) |
| OT4_seq_F | TCCATAAAACAATGTTGAGGTGGG (SEQ ID NO: 189) |
| OT4_seq_R | GTCCTCCAGTTGATCCTGAAGT (SEQ ID NO: 190) |
| OT5_seq_F | ATCCAGGGGCTTTGAGATTGA (SEQ ID NO: 191) |
| OT5_seq_R | TCTCCATCCCCGTTGTTAAGTGA (SEQ ID NO: 192) |
| OT6_seq_F | CACACACAAAGCCCTTCTGC (SEQ ID NO: 193) |
| OT6_seq_R | CACCATATCCAGCCTGTCGG (SEQ ID NO: 194) |
| OT7_seq_F | CTCTGGAAAGCAGGGACCAT (SEQ ID NO: 195) |
| OT7_seq_R | GCATGCTAACCAGCACACTG (SEQ ID NO: 196) |
| OT8_seq_F | ACAGAGCTGGGCCAATAACC (SEQ ID NO: 197) |
| OT8_seq_R | TGTTCACATGGGAAAGCCTCA (SEQ ID NO: 198) |
| OT9_seq_F | GCTTGTGTGCGTGTATGGAA (SEQ ID NO: 199) |
| OT9_seq_R | GTAGCACACTAATACATGGAAATGA (SEQ ID NO: 200) |
| OT10_seq_F | TAAGATCCAAACACCCAATCACG (SEQ ID NO: 201) |
| OT10_seq_R | AGTCTTCAGCTGGTGATTTCAGG (SEQ ID NO: 202) |
| OT11_seq_F | GTACCATTCCTCCAACTAAGGCA (SEQ ID NO: 203) |
| OT11_seq_R | CTAAGTTCTTCCACCTCGAGTCAT (SEQ ID NO: 204) |
| OT12_seq_F | AGCTGAGATCACACCACTGC (SEQ ID NO: 205) |
| OT12_seq_R | TCTAGCCCCTGGTAACCTCC (SEQ ID NO: 206) |
| OT13_seq_F | ACAGAAGATGAATAGCGGAACA (SEQ ID NO: 207) |
| OT13_seq_R | TAGTGACGCGAATAGCCCTG (SEQ ID NO: 208) |
| OT14_seq_F | ATCAGCCTGGATCCCTACCC (SEQ ID NO: 209) |
| OT14_seq_R | ACCTGAGATTCCTCTGGGCT (SEQ ID NO: 210) |
| OT15_seq_F | TCTGTTTCATGGTGATGCTTGA (SEQ ID NO: 211) |
| OT15_seq_R | ACAATTTTTCACTCTTGGTACTCTT (SEQ ID NO: 212) |
| OT16_seq_F | TCTCTCCTTAGATTTCTTCATGTCT (SEQ ID NO: 213) |
| OT16_seq_R | CAGAACAAAGGCACAGCCAC (SEQ ID NO: 214) |
| OT17_seq_F | ACAGAATGCTATGAGAGACGTT (SEQ ID NO: 215) |
| OT17_seq_R | GGTAGGAAAAACGCAGAAAGA (SEQ ID NO: 216) |

| Primers fA3:B19s for in vitro transcription of sgRNAs. Protospacer sequence in red. | |
|---|---|
| OT18_seq_F | CATGACTTGGTGAAGCCCCT (SEQ ID NO: 217) |
| OT18_seq_R | ATTTGGGCCACCAACTTAGG (SEQ ID NO: 218) |
| OT19_seq_F | GTGTAGTGGAGGAGACAGACAA (SEQ ID NO: 219) |
| OT19_seq_R | TTTCAAACTTGCCAGACCCCA (SEQ ID NO: 220) |
| OT20_seq_F | GTTCCCAGCATCCCAAAAGAAC (SEQ ID NO: 221) |
| OT20_seq_R | GGAGGCTCTGAGAGAATGAGG (SEQ ID NO: 222) |
| OT21_seq_F | GATGTGTTCAATGCAATGGAGATTA (SEQ ID NO: 223) |
| OT21_seq_R | GGCTGCCTCTCATTCTCTTGTA (SEQ ID NO: 224) |
| OT22_seq_F | AGAGTCCAATAAATTGAGGTTTCAC (SEQ ID NO: 225) |
| OT22_seq_R | ATAACTCCATTCCGGGAGCC (SEQ ID NO: 226) |
| OT23_seq_F | CAGGGCCTCACTTTTGCCTC (SEQ ID NO: 227) |
| OT23_seq_R | TGACTGCATATCCATGCACCAT (SEQ ID NO: 228) |
| OT24_seq_F | CAGCTGAGGCTACTGCTGTT (SEQ ID NO: 229) |
| OT24_seq_R | TCTTCTGTTCACTCTTTGGCT (SEQ ID NO: 230) |

What is claimed is:

1. A method of increasing gene editing efficiency following electroporation, the method comprising electroporating a cell with a ribonucleoprotein (RNP) complex comprising a DNA-targeting endonuclease Cas (CRISPR-associated) protein and a modified synthetic nucleic acid molecule having a sequence selected from SEQ ID NOS: 37, 38, 39, 40, 41, 42, 43, 44, 45, 46, 47, 48, 50, 51, 52, 53, 54, 55, 56, 57, and 62 in a solution comprising 2%-4% glycerol.

2. The method of claim 1, wherein the modification is located at one or more terminal nucleotides in synthetic nucleic acid molecule.

3. The method of claim 2, wherein the modification is selected from the group consisting of 2'-O-methyl 3'phosphorothioate (MS), 2'-O-methyl-3'-phosphonoacetate (MP), 2'-0-Ci-4alkyl, 2'-H, 2'-0-Ci.3alkyl-0-Ci.3alkyl, 2'-F, 2'-NH2, 2'-arabino, 2'-F-arabino, 4'-thioribosyl, 2-thioU, 2-thioC, 4-thioU, 6-thioG, 2-aminoA, 2-aminopurine, pseudouracil, hypoxanthine, 7-deazaguanine, 7-deaza-8-azaguanine, 7-deazaadenine, 7-deaza-8-azaadenine, 5-methylC, 5-methylU, 5-hydroxymethylcytosine, 5-hydroxymethyluracil, 5,6-dehydrouracil, 5-propynylcytosine, 5-propynyluracil, 5-ethynylcytosine, 5-ethynyluracil, 5-allylU, 5-allylC, 5-aminoallyl-uracil, 5-aminoallyl-cytosine, an abasic nucleotide ("abN"), Z, P, UNA, isoC, isoG, 5-methyl-pyrimidine, x(A,G,C,T) and y(A,G,C,T), a phosphorothioate internucleotide linkage, a phosphonoacetate internucleotide linkage, a thiophosphonoacetate internucleotide linkage, a methylphosphonate internucleotide linkage, a boranophosphonate internucleotide linkage, a phosphorodithioate internucleotide linkage, 4'-thioribosyl nucleotide, a locked nucleic acid ("LNA") nucleotide, an unlocked nucleic acid ("ULNA") nucleotide, an alkyl spacer, a heteroalkyl (N, O, S) spacer, a 5'- and/or 3'-alkyl terminated nucleotide, a Unicap, a 5'-terminal cap known from nature, an xRNA base (analogous to "xDNA" base), an yRNA base (analogous to "yDNA" base), a PEG substituent, and a conjugated linker to a dye or non-fluorescent label (or tag).

4. The method of claim 1, wherein the glycerol is selected from the group consisting of: purified glycerol, unpurified glycerol, naturally occurring glycerol, and synthetic glycerol.

5. The method of claim 1, wherein the cell is selected from the group consisting of: a pluripotent stem cell, an induced pluripotent stem cell, a progenitor cell, a somatic cell, a differentiated cell.

6. The method of claim 1, wherein the cell is a hematopoietic progenitor cell.

7. The method of claim 1, wherein the solution comprising 2%-4% glycerol increases the on-target indel frequency following electroporation as compared to electroporation in a solution that does not comprise glycerol.

8. The method of claim 7, wherein on-target indel frequency is increased at least 50%, 60%, 70%, 80%, 90% or more.

9. The method of claim 7, wherein indel frequency is at least 95%, 96%, 97%, 98%, 99% or more.

* * * * *